United States Patent
Yamamoto et al.

(10) Patent No.: US 6,737,425 B1
(45) Date of Patent: May 18, 2004

(54) N,N-SUBSTITUTED CYCLIC AMINE DERIVATIVES

(75) Inventors: Noboru Yamamoto, Ibaraki (JP); Makoto Komatsu, Kanagawa (JP); Yuichi Suzuki, Ibaraki (JP); Koki Kawano, Ibaraki (JP); Teiji Kimura, Ibaraki (JP); Koichi Ito, Chiba (JP); Satoshi Nagato, Chiba (JP); Yoshihiko Norimine, Ibaraki (JP); Tetsuhiro Niidome, Ibaraki (JP); Tetsuyuki Teramoto, Brookline, MA (US); Yoichi Iimura, Ibaraki (JP); Shinji Hatakeyama, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/743,358

(22) PCT Filed: Jul. 21, 1999

(86) PCT No.: PCT/JP99/03900
§ 371 (c)(1),
(2), (4) Date: Jan. 29, 2001

(87) PCT Pub. No.: WO00/05210
PCT Pub. Date: Feb. 3, 2000

(30) Foreign Application Priority Data

Jul. 21, 1998 (JP) .......... 10-205709
Oct. 1, 1998 (JP) .......... 10-280103

(51) Int. Cl.[7] .......... A61K 31/497; A61P 9/10; C07D 295/00; C07D 243/08
(52) U.S. Cl. .......... 514/252.12; 514/218; 514/252.14; 514/255.06; 544/358; 544/359; 544/399; 544/403; 540/575
(58) Field of Search .......... 514/218, 252.14, 514/252.12, 255.06; 544/358, 359, 399, 403; 540/575

(56) References Cited

FOREIGN PATENT DOCUMENTS

| DE | A14404249 | 8/1995 |
|---|---|---|
| EP | 0441226 A1 | 8/1991 |
| EP | 0 617 032 A1 | 9/1994 |
| EP | 0 255 134 A2 | 2/1998 |
| EP | 1 167 348 A1 | 1/2002 |
| GB | 1174880 | 12/1969 |
| HU | 217 619 B | 9/1991 |
| JP | 262167762 | 7/1987 |
| JP | 2-83375 | 3/1990 |
| JP | 5-97673 | 4/1993 |
| JP | 5213879 | 8/1993 |
| JP | A1095758 | 4/1998 |
| WO | WO9013539 | 11/1990 |

OTHER PUBLICATIONS

Laguerre et al., Eur. J. Med. Chem., vol. 25, pp. 351–359, (1990).
Butora et al., Collect. Czech. Chem. Commun., vol. 57, pp. 1967–1981, (1992).
Carceller et al., J. Med. Chem., vol. 35, pp. 4118–4134, (1992).

*Primary Examiner*—Richard L. Raymond
*Assistant Examiner*—Tamthom N. Truong
(74) *Attorney, Agent, or Firm*—Birch, Stewart, Kolasch & Birch, LLP

(57) ABSTRACT

The invention provides an N,N-substituted cyclic amine compound represented by the following formula (VIII):

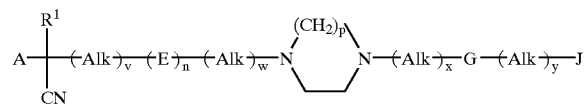

(VIII)

wherein A represents an aryl group etc.; E represents a group represented by the formula —CO— or a group represented by the formula —CHOH—; G represents an oxygen atom etc.; J represents an aryl group which may be substituted; $R^1$ represents a lower alkyl group etc.; Alk represents a linear or branched lower alkylene group; n, v, w, x and y are independent of each other and each represents 0 or 1; and p represents 2 or 3, or a pharmacologically acceptable salt thereof. The compound of the present invention or a salt thereof is effective to treat a disease against which calcium antagonism is effective. The disease may include acute ischemic stroke, cerebral apoplexy, cerebral infarction, head trauma, cerebral nerve cell death, Alzheimer disease, Parkinson disease, amyotrophic lateral sclerosis, Huntington disease, cerebral circulatory metabolism disturbance, cerebral function disturbance, pain, spasm, schizophrenia, migraine, epilepsy, maniac-depressive psychosis, nerve degenerative diseases, cerebral ischemia, AIDS dementia complications, edema, anxiety disorder (generalized anxiety disorder) and diabetic neuropathy.

16 Claims, 5 Drawing Sheets

N,N-SUBSTITUTED CYCLIC AMINE DERIVATIVES

This application is the national phase under 35 U.S.C. §371 of PCT International Application No. PCT/JP99/03900 which has an International filing date of Jul. 21, 1999, which designated the United States of America.

INDUSTRIAL FIELD OF THE APPLICATION

The present invention relates to novel N,N-substituted cyclic amine compounds useful as a calcium antagonist, particularly as a nerve-selective calcium antagonist, specifically as an agent for treating and improving the diseases against which an inhibitory action on P/Q type calcium channels or an inhibitory action on N type calcium channels is effective, more specifically as an agent for inhibiting the death of nerve cells or for protecting cerebral nerve cells, and further specifically as an agent for treating and improving nerve diseases, and most specifically as an agent for preventing, treating or improving acute ischemic stroke, cerebral apoplexy, cerebral infarction, head trauma, cerebral nerve cell death, Alzheimer disease, Parkinson disease, amyotrophic lateral sclerosis, Huntington disease, cerebral circulatory metabolism disturbance, cerebral function disturbance, pain, spasm, schizophrenia, migraine, epilepsy, maniac-depressive psychosis, nerve degenerative diseases, cerebral ischemia, AIDS dementia complications, edema, anxiety disorder (generalized anxiety disorder) and diabetic neuropathy.

BACKGROUND OF THE INVENTION

In Japan, the number of patients with cerebral apoplexy is about 1.4 million or more per year, and the medical expenses therefor are estimated to be about two billion yen. Cerebral apoplexy is the second cause of death next to malignant tumor and is the biggest cause for bedridden man often suffering from severe secondary diseases. A key to the treatment of cerebral apoplexy is to deal with the acute stage, and the treatment at the acute stage influences the life and function prognosis of the patient and significantly influences secondary diseases.

For the purpose of improving blood stream, several drugs such as ozagrel sodium (thromboxane synthase inhibitor), argatroban (anti-thrombin agent) as an agent for treatment of chronic arterial occlusion, t-PA (alteplase: tissue plasminogen activator which should be used within 3 hours after the onset) as thrombolytic agent etc. are now approved of, or in off lavel use.

In the treatment with these drugs, the following complicated techniques and cautious judgement based on adequate knowledge and experience by a medical specialist are required.

(1) In the case of thrombus-type cerebral infarction, respiratory control, blood pressure control and blood transfusion control are first conducted.

(2) Blood gas and blood pressure are periodically measured.

(3) At the acute stage, reactive high blood pressure is observed, but if complications in the heart and kidney are not observed, treatment for decreasing blood pressure is not conducted.

(4) Then, in the early-acute stage case with no low absorption range observed in CT, the thrombus-lytic agent "urokinase" is used.

(5) In the case where these agents are not applicable or in the case where 24 hours or more has elapsed after the onset, "ozagrel sodium" is administered. Or "argatroban" is administered. However, argatroban is not applicable to lacuna infarction.

(6) To prevent the development of cerebral edema, "glycerin" or "mannitol" is administered at a suitable dosage.

However, the therapeutic effects of the drugs used heretofore are not satisfactory and further there is the danger that bleeding is often accompanied by their pharmacological effect.

Accordingly, there is the problem that it is difficult for those except of skilled medical specialists to use these drugs.

JP 62-167762-A (EP 229623), JP 2-506694-A (WO 90/13539), DE 4404249, JP 10-95758-A (EP 805147) etc. disclose compounds having piperazine compounds being completely different in structure from the N,N-substituted cyclic amine compounds of the present invention.

BRIEF SUMMARY OF THE INVENTION

The present inventors sought a highly safe drug, which causes no bleeding, and is highly effective in treating and improving the acute ischemic stroke against which no useful drugs have been developed. The inventors focused their attention on nerve-selective, voltage-dependent calcium channel antagonist which directly acts on nerve cells to prevent the development of infarction volume, and they made extensive studies thereon.

As a result, they have found that novel N,N-substituted cyclic amine compounds having the following formula, or pharmacologically acceptable salts thereof, possess an excellent action on inhibition of the death of nerve cells and on protection of cerebral nerve cells, based on inhibitory action on P/Q type calcuim channels or N-type calcium channels. These N,N-substituted cyclic amine compounds are superior in safety and can solve the problems described above, and the present invention has been thereby completed.

DETAILED DESCRIPTION OF THE INVENTION

The N,N-substituted cyclic amine compounds according to the present invention are represented by the following formula (VIII):

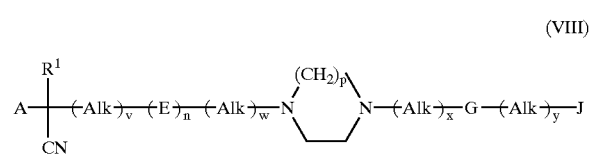

(VIII)

wherein

A represents an aryl group which may be substituted, a heteroaryl group which may be substituted, an aralkyl group which may be substituted or a heteroaryl alkyl group which may be substituted;

E represents a group represented by the formula —CO— or a group represented by the formula —CHOH—;

G represents an oxygen atom, a sulfur atom, and a group represented by the formula —NR$^{10}$— (wherein R$^{10}$ represents a hydrogen atom, a lower alkyl group, a lower cycloalkyl, a lower acyl group or a lower alkyl sulfonyl group), a group represented by the formula —CO—, a group represented by —COO—, a group represented by the formula —OOC—, a group represented by the formula —CONR$^{11}$— (wherein R$^{11}$ represents a hydrogen atom or a lower alkyl group), a group represented by the formula —$NR^{12}CO$— (wherein $R^{12}$ represents a hydrogen atom or a lower alkyl group), a group represented by the formula —SO—, a group represented by the formula —$SO_2$—, a group represented by the formula —$SONR^{13}$— (wherein $R^{13}$ represents a hydrogen atom or a lower alkyl group) a group represented by the formula —$NR^{14}SO$— (wherein $R^{14}$ represents a hydrogen atom or a lower alkyl group), a group represented by the formula —$SO_2NR^{15}$— (wherein $R^{15}$ represents a hydrogen atom or a lower alkyl group), a group represented by the formula —$NR^{16}SO_2$— (wherein $R^{16}$ represents a hydrogen atom or a lower alkyl group), a group represented by the formula >C=N—$OR^{17}$ (wherein $R^{17}$ represents a hydrogen atom or a lower alkyl group), a group represented by the formula —NHCONH—, a group represented by the formula —NHCSNH—, a group represented by the formula —C(=NH)NH—, a group represented by the formula —NHC(=NH)—, a group represented by the formula —OCOS—, a group represented by the formula —SCOO—, a group represented by the formula —OCOO—, a group represented by the formula —NHCOO—, a group represented by the formula —OCONH—, a group represented by the formula —CO($CH_2$)$_s$O—, a group represented by the formula —CHOH— or a group represented by the formula —CHOH($CH_2$)$_s$O— (wherein s represents 0 or an integer of 1 to 6);

J represents an aryl group which may be substituted or a heteroaryl group which may be substituted;

$R^1$ represents a hydrogen atom, a halogen atom, a hydroxy group, a lower alkyl group, a lower alkenyl group, a lower alkynyl group, a lower cycloalkyl group, a hydroxy lower alkyl group, a lower alkoxyalkyl group, a cyano-lower alkyl group, a halogenated lower alkyl group, an optionally N-substituted amino-lower alkyl group, a group represented by the formula —$NR^{18}R^{19}$ (wherein $R^{18}$ and $R^{19}$ may be the same as or different from each other and each represents a hydrogen atom or a lower alkyl group), an aralkyl group, a morpholinyl group, a thiomorpholinyl group, a piperidyl group, a pyrrolidinyl group or a piperazinyl group;

Alk represents a linear or branched lower alkylene group; and n, v, w, x and y are independent of each other and each represents 0 or 1, and p represents 2 or 3.

The invention includes a pharmacologically acceptable salt of the compound.

Herein, particular examples of the aryl group which may be substituted are phenyl group, naphthyl group etc., or those further substituted with at least one of, for example, a halogen atom, a hydroxy group, a lower alkyl group, a lower alkoxy group, a lower alkoxycarbonyl group, a hydroxy lower alkyl group, a halogenated lower alkyl group, a hydroxy iminoalkyl group, a cyano group, a nitro group, an optionally N-substituted amino group, an optionally N-substituted carbamoyl group, an optionally N-substituted sulfamoyl group, a lower thioalkoxy group, a lower acyl group, an aromatic acyl group etc.

Particular examples of the heteroaryl group which may be substituted are pyridyl group, pyrazinyl group, pyrimidinyl group, pyrrolyl group, imidazolyl group, pyrazolyl group, quinolyl group, isoquinolyl group, quinazolinyl group, phthaladinyl group, quinoxalinyl group, cinnolynyl group, furyl group, thienyl group, thiazolyl gorup etc., or those further substituted.

Particular examples of the aralkyl group which may be substituted are a lower alkyl group substituted with an aryl group, such as benzyl group, phenethyl group, phenylpropyl group, naphthylmethyl group, naphthylethyl group, naphthylpropyl group etc., or that having the aryl group further substituted.

Particular examples of the heteroaryl alkyl group which may be substituted are a lower alkyl group substituted with a heteroaryl group, for example, pyridylmethyl group, pyrazinylmethyl group, pyrimidinylmethyl group, pyrrolylmethyl group, imidazolylmethyl group, pyrazolylmethyl group, quinolylmethyl group, isoquinolylmethyl group, furfuryl group, thienylmethyl group, thiazolylmethyl group etc., or that having the heteroaryl group further substituted.

Particular examples of the halogen atom are fluorine atom, chlorine atom, bromine atom or iodine atom.

Particular examples of the lower alkyl group are linear or branched alkyl groups having 1 to 6 carbon atoms, such as methyl group, ethyl group, n-propyl group, i-propyl group, n-butyl group, i-butyl group, t-butyl group, n-pentyl group, i-pentyl group, t-pentyl group, neopentyl group, hexyl group etc.

Particular examples of the lower alkenyl group are groups derived from linear or branched alkenes having 2 to 6 carbon atoms, such as vinyl group ($CH_2$=CH—), 1-propenyl group ($CH_3$CH=CH—), allyl group ($CH_2$=$CHCH_2$—), isopropenyl ($CH_2$=C($CH_3$)—) etc.

Particular examples of the lower alkynyl group are groups derived from linear or branched alkynes having 2 to 6 carbon atoms, such as ethynyl group, 1-propynyl group, 2-propynyl group etc.

Particular examples of the lower cycloalkyl group are cyclic alkyl groups having 3 to 8 carbon atoms such as cyclopropyl group, cyclobutyl group, cyclopentyl group, cyclohexyl group, cycloheptyl group, cyclooctyl group etc.

Particular examples of the hydroxy lower alkyl group are a group having one or more hydroxy groups bonded to the above-mentioned lower alkyl group, such as a hydroxymethyl group, a hydroxyethyl group, 2,3-dihydroxypropyl group etc.

Particular examples of the cyano-lower alkyl group are a group having one or more cyano groups bonded to the above-mentioned lower alkyl group, such as a cyanomethyl group, a cyanoethyl group, a cyanopropyl group etc.

Particular examples of the halogenated lower alkyl group are a group having one or more halogen atoms, which may be the same as or different from each other, bonded to the above-mentioned lower alkyl group, such as fluoromethyl group, difluoromethyl group, trifluoromethyl group, chloromethyl group, 1-fluoroethyl group, 2-fluoroethyl group, 1,1-difluoroethyl group, 1,2-difluoroethyl group, 2,2-difluoroethyl group, 2,2,2-trifluoroethyl group etc.

Particular examples of the lower alkoxy group are a group having the above-mentioned lower alkyl group bonded to an oxygen atom, specifically, a linear or branched alkoxy group such as methoxy group, ethoxy group, n-propoxy group, i-propoxy, n-butoxy group, i-butoxy group, t-butoxy group, pentyloxy group, hexyloxy group etc.

Particular examples of the lower acyl group are a linear or branched acyl group derived from fatty acid having 1 to 6 carbon atoms, such as formyl group, acetyl group, propionyl group, butyryl group, isobutyryl group, valeryl group, isovaleryl group, pivaloyl group, hexanoyl group etc.

Particular examples of the amino group which may be substituted are an amino which may be N-substituted by a lower alkyl group, a lower acyl group, a lower alkyl sulfonyl group etc., and the case in which the nitrogen atom is part of a cyclic amine is included. Specifically, an amino group (—NH$_2$), methylamino group (—NHCH$_3$), dimethylamino group (—N(CH$_3$)$_2$), ethylamino group (—NHC$_2$H$_5$), diethylamino group (—N(C$_2$H$_5$)$_2$), methylethylamino group (—N(CH$_3$)C$_2$H$_5$), acetamide group (CH$_3$CONH—), propionamide group (C$_2$H$_5$CONH—), methanesulfonamide group (CH$_3$SO$_2$NH—), ethanesulfonamide group (C$_2$H$_5$SO$_2$NH—), pyrrolidinyl group, pyrazolinyl group, piperidyl group, piperazinyl group, 4-morpholinyl group, 4-thiomorpholinyl group etc. may be proposed.

Particular examples of the carbamoyl group which may be substituted are a carbamoyl group which may be N-substituted by a lower alkyl group etc., and the case in which the nitrogen atom is part of a cyclic amine is included. Specifically, carbamoyl group (—CONH$_2$), N-methylcarbamoyl group (—CONHCH$_3$), N,N-dimethylcarbamoyl group (—CON(CH$_3$)$_2$), N-ethylcarbamoyl group (—CONHC$_2$H$_5$), N,N-diethylcarbamoyl group (—CON(C$_2$H$_5$)$_2$), N-methyl-N-ethylcarbamoyl group (—CON(CH$_3$)C$_2$H$_5$), 1-pyrrolidinylcarbonyl group, 1-pyrazolylcarbonyl group, 1-piperidylcarbonyl group, 1-piperazinylcarbonyl group, 4-morpholinylcarbonyl group, 4-thiomorpholinylcarbonyl group etc. may be proposed.

Particular examples of the sulfamoyl group which may be substituted are a sulfamoyl group which may be N-substituted by a lower alkyl group etc., and the case in which the nitrogen atom is part of a cyclic amine is included. Specifically, sulfamoyl group (—SO$_2$NH$_2$), N-methylsulfamoyl group (—SO$_2$NHCH$_3$), N,N-dimethylsulfamoyl group (—SO$_2$N(CH$_3$)$_2$), N-ethylsulfamoyl group (—SO$_2$NHC$_2$H$_5$), N,N-diethylsulfamoyl group (—SO$_2$N(C$_2$H$_5$)$_2$), N-methyl-N-ethylsulfamoyl group (—SO$_2$N(CH$_3$)C$_2$H$_5$), 1-pyrrolidinylsulfonyl group, 1-pyrazolinylsulfonyl group, 1-piperidylsulfonyl group, 1-piperazinylsulfonyl group, 4-morpholinylsulfonyl group, 4-thiomorpholinylsulfonyl group etc. may be proposed.

Particular examples of the lower thioalkoxy group are a group having the above-mentioned lower alkyl group bonded to a sulfur atom, such as methylthiogroup (—SCH$_3$), ethylthio group (—SC$_2$H$_5$) etc.

Particular examples of the lower alkylene group are a divalent group derived from a linear or branched alkane having 1 to 6 carbon atoms, such as methylene group (—CH$_2$—), ethylene group (—CH$_2$CH$_2$—), ethylidene group (—CH(CH$_3$)—), trimethylene group (—CH$_2$CH$_2$CH$_2$—), isopropylidene group (—C(CH$_3$)$_2$—), propylene group (—CH(CH$_3$)CH$_2$—), tetramethylene group (—CH$_2$CH$_2$CH$_2$CH$_2$—), 1,2-butylene group (—CH(C$_2$H$_5$)CH$_2$—), 1,3-butylene group (—CH(CH$_3$)CH$_2$CH$_2$—), 2,3-butylene group (—CH(CH$_3$)CH(CH$_3$)—), isobutylene group (—C(CH$_3$)$_2$CH$_2$—) etc. Moreover, the bonding position (right-handed or left-handed) of the unsymmetrical alkylene group is not limited.

Particular examples of the lower alkoxy carbonyl group are a carbonyl group substituted by the above-mentioned lower alkoxy group, such as methoxy carbonyl group, ethoxy carbonyl group etc.

Particular examples of the lower thioalkoxy group are a group having the above-mentioned lower alkyl group bonded to a sulfur atom, such as methyl thio group, ethyl thio group, propyl thio group etc.

Particular examples of the lower alkyl sulfonyl group are a group having the above-mentioned lower alkyl group bonded to a sulfonyl group, such as methane sulfonyl group, ethane sulfonyl group, propane sulfonyl group etc.

When $R^{20}$ groups or $R^{21}$ groups are bonded by themselves to form an alicyclic ring, particular examples of this group are an alicyclic condensed phenyl group such as indanyl group, tetralinyl group etc., or a group in which the alicyclic group or phenyl group is further substituted.

When $R^{20}$ groups or $R^{21}$ groups are bonded by themselves to form a hetero ring, particular examples of this ring are a hetero ring condensed with phenyl group, such as benzofuranyl group, chromanyl group, isochromanyl group, indolynyl group, isoindolynyl group, teterhydroquinolyl group, tetrahydroisoquinolyl group, or groups in which the hetero ring or phenyl group is further substituted.

When $R^{20}$ groups or $R^{21}$ groups are bonded by themselves to form an alkylene dioxy group, particular examples of this group are methylene dioxy phenyl group, ethylene dioxy phenyl group, or groups in which the phenyl group is further substituted.

Herein, particular examples of the aryl group which may be substituted are phenyl group, naphthyl group etc., or groups having these groups further substituted.

Particular examples of the heteroaryl group which may be substituted are pyridyl group, pyrazinyl group, pyrimidinyl group, pyrrolyl group, imidazolyl group, pyrazolyl group, quinolyl group, isoquinolyl group, quinazolinyl group, phthaladinyl group, quinoxalinyl group, cinnolynyl group, furyl group, thienyl group, thiazolyl group etc., or groups having these groups further substituted.

Particular examples of the aralkyl group which may be substituted are a lower alkyl group substituted with an aryl group, such as benzyl group, phenethyl group, phenyl propyl group, naphthyl methyl group, naphthyl ethyl group, naphthyl propyl group etc., or groups having the aryl group further substituted.

Particular examples of the heteroaryl alkyl group which may be substituted are a lower alkyl group substituted with a heteroaryl group, for example, pyridyl methyl group, pyrazinyl methyl group, pyrimidinyl methyl group, pyrrolyl methyl group, imidazolyl methyl group, pyrazolyl methyl group, quinolyl methyl group, isoquinolyl methyl group, furfuryl group, thienyl methyl group, thiazolyl methyl group etc., or groups having the heteroaryl group further substituted.

Particular examples of the lower alkyl group are $C_1$ to $C_6$ alkyl groups, such as methyl group, ethyl group, n-propyl group, i-propyl group, n-butyl group, i-butyl group, t-butyl group, pentyl group, hexyl group etc.

Particular examples of the lower cycloalkyl group are $C_3$ to $C_8$ cycloalkyl groups, such as cyclopropyl group, cyclobutyl group, cyclopentyl group, cyclohexyl group, cycloheptyl group, cyclooctyl group etc.

Herein, particular examples of the halogen atom are fluorine atom, chlorine atom, bromine atom or iodine atom.

Particular examples of the lower alkoxy group are a group having the above-mentioned lower alkyl group bonded to an oxygen atom, such as methoxy group, ethoxy group, propoxy group etc.

Particular examples of the amino group which may be substituted are an amino group or a group wherein 1 or 2 hydrogen atoms in the amino group is substituted by lower alkyl group etc., such as methyl amino group, ethyl amino group, dimethyl amino group, diethyl amino group, methyl ethyl amino group etc.

Particular examples of the lower alkoxy carbonyl group are a carbonyl group substituted by the above-mentioned lower alkoxy group, such as methoxy carbonyl group, ethoxy carbonyl group etc.

Particular examples of the lower thioalkoxy group are a group having the above-mentioned lower alkyl group bonded to a sulfur atom, such as methyl thio group, ethyl thio group, propyl thio group etc.

Particular examples of the lower alkyl sulfonyl group are a group having the above-mentioned lower alkyl group bonded to a sulfonyl group, such as methane sulfonyl group, ethane sulfonyl group, propane sulfonyl group etc.

Particular examples of the lower acyl group are a group having the above-mentioned lower alkyl group bonded to a carbonyl group, such as acetyl group, propionyl group, butyroyl group etc.

When $R^{20}$ groups or $R^{21}$ groups are bonded to form an alicyclic ring, particular examples of this group are an alicyclic condensed phenyl group such as indanyl group, tetralinyl group etc., or the group in which alicyclic group or phenyl group is further substituted.

When $R^{20}$ groups or $R^{21}$ groups are bonded to form a hetero ring, particular examples of this ring are a hetero ring condensed with phenyl group, such as benzofuranyl group, chromanyl group, isochromanyl group, indolynyl group, isoindolynyl group, teterhydroquinolyl group, tetrahydroisoquinolyl group, or groups in which the hetero ring or phenyl group is further substituted.

When $R^{20}$ groups or $R^{21}$ groups are bonded to form an alkylene dioxy group, particular examples of this group are methylene dioxy phenyl group, ethylene dioxy phenyl group, or groups in which the phenyl group is further substituted.

The invention includes as an embodiment an N,N-substituted cyclic amine compound (I) represented by the following formula (I):

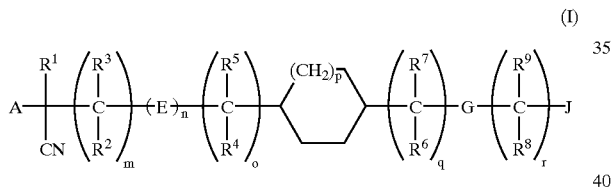

wherein
A represents an aryl group which may be substituted, a heteroaryl group which may be substituted, an aralkyl group which may be substituted or a heteroaryl alkyl group which may be substituted;

E represents a group represented by the formula —CO— or a group represented by the formula —CHOH—;

G represents an oxygen atom, a sulfur atom, and a group represented by the formula —NR$^{10}$— (wherein R$^{10}$ represents a hydrogen atom, a lower alkyl group, a lower acyl group or a lower alkyl sulfonyl group), a group represented by the formula —CO—, a group represented by —COO—, a group represented by the formula —OOC—, a group represented by the formula —CONR$^{11}$— (wherein R$^{11}$ represents a hydrogen atom or a lower alkyl group) a group represented by the formula —NR$^{12}$CO— (wherein R$^{12}$ represents a hydrogen atom or a lower alkyl group), a group represented by the formula —SO—, a group represented by the formula —SO$_2$—, a group represented by the formula —SONR$^{13}$— (wherein R$^{13}$ represents a hydrogen atom or a lower alkyl group) a group represented by the formula —NR$^{14}$SO— (wherein R$^{14}$ represents a hydrogen atom or a lower alkyl group), a group represented by the formula —SO$_2$NR$^{15}$— (wherein R$^{15}$ represents a hydrogen atom or a lower alkyl group), a group represented by the formula —NR$^{16}$SO$_2$— (wherein R$^{16}$ represents a hydrogen atom or a lower alkyl group), a group represented by the formula >C=N—OR$^{17}$ (wherein R$^{17}$ represents a hydrogen atom or a lower alkyl group), a group represented by the formula —NHCONH—, a group represented by the formula —NHCSNH—, a group represented by the formula —C(=NH)NH—, a group represented by the formula —NHC(=NH)—, a group represented by the formula —OCOS—, a group represented by the formula —SCOO—, a group represented by the formula —OCOO—, a group represented by the formula —NHCOO—, a group represented by the formula —OCONH—, a group represented by the formula —CO(CH$_2$)$_s$O—, a group represented by the formula —CHOH— or a group represented by the formula —CHOH(CH$_2$)$_s$O— (wherein s is 0 or an integer of 1 to 6);

J represents an aryl group which may be substituted or a heteroaryl group which may be substituted;

R$^1$ represents a lower alkyl group, a lower cycloalkyl group, a group represented by the formula —NR$^{18}$R$^{19}$ (wherein R$^{18}$ and R$^{19}$ may be the same or different from each other and each represents a hydrogen atom or a lower alkyl group), a morpholinyl group, a thiomorpholinyl group, a piperidyl group, a pyrrolidnyl group or a piperazinyl group;

R$^2$, R$^3$, R$^4$, R$^5$, R$^6$, R$^7$, R$^8$ and R$^9$ may be the same or different from each other and each represents a hydrogen atom or a lower alkyl group; and m, o, q, and r may be the same or different from each other and each represents 0 or an integer of 1 to 6, n is 0 or 1, and p is 2 or 3.

Next, the invention includes as an embodiment an N,N-substituted cyclic amine compound (II) represented by the following formula (II):

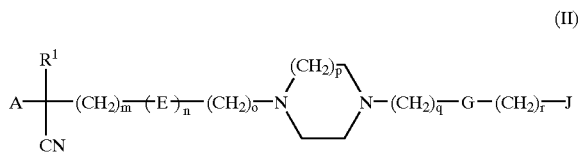

wherein A, E, G, J, R$^1$, m, n, o, p, q and r have the same meanings as defined above.

Next, the invention includes as an embodiment an N,N-substituted cyclic amine compound (III) represented by the following formula (III):

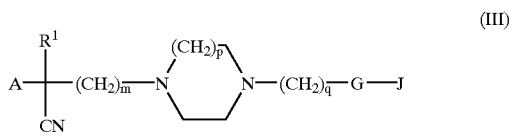

wherein A, G, J, R$^1$, m, p and q have the same meanings as defined above.

Finally, the invention includes as an embodiment an N,N-substituted cyclic amine compound (IV) represented by the following formula (IV):

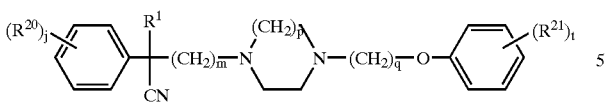

(IV)

wherein
R[1], m, p, and q have the same meanings as defined above; R[20] and R[12] are the same or different from each other and each represents a hydrogen atom, a halogen atom, a hydroxy group, a mercapto group, a lower alkyl group, a lower alkoxy group, a hydroxymethyl group, a nitro group, an amino group which may be substituted, a cyano group, a carboxyl group, a lower alkoxy carbonyl group, a lower thioalkoxy group, a lower alkyl sulfonyl group, a lower acyl group, a halogenated lower alkyl group, an aryl group which may be substituted, a heteroaryl group which may be substituted, an aryloxy group, an aralkyloxy group, a lower alkoxycarbonylalkoxy group or a hydroxy lower alkoxy group, and R[20] groups or R[21] groups may form an alicyclic group which may be substituted, or a heterocyclic group or alkylene dioxy group which may be substituted; and j and t may be the same or different from each other and each represents 0 or an integer of 1 to 5.

The N,N-substituted cyclic amine compounds (VIII) and those having formulas (I) to (IV) according to the present invention contain 1 or more asymmetric carbon atoms in the molecule, so their optical isomers or meso forms can exist, but the present invention is not limited. The present invention encompasses any of the optical isomers, meso forms and racemates of these compounds. Further, these include not only anhydrides but also hydrates and polymorphs.

When producing the optically active substances, optically active starting materials can be used for asymmetric synthesis, or racemates can be optically resolved by column chromatography or crystallization.

The pharmacologically acceptable salts in the present invention are not limited insofar as they form salts with the N,N-substituted cyclic amine compounds (VIII) and (I) to (IV) of the present invention, and particular examples are inorganic acid addition salts such as hydrochloride, sulfate, nitrate, hydrobromate, hydriodate, perchlorate, phosphate etc., organic acid addition salts such as oxalate, maleate, fumarate, succinate etc., sulfonic acid addition salts such as methane sulfonate, ethane sulfonate, benzene sulfonate, p-toluene sulfonate, camphor sulfonate, and amino acid addition salts, among which hydrochloride and oxalate are preferable.

More specific examples of the N,N-substituted amine compounds (VIII) and (I) to (IV) according to the present invention include the following compounds which are not intended to limit the present invention:

(1) 1-[(4-cyano-5-methyl-4-phenyl)hexyl]-4-[2-(4-fluorophenoxy)ethyl]piperazine
(2) 1-[(4-cyano-5-methyl-4-phenyl)hexyl]-4-[3-(4-fluorophenoxy)propyl]piperazine
(3) 1-[(4-cyano-5-methyl-4-phenyl)hexyl]-4-[2-(4-fluorophenoxy)ethyl]homopiperazine
(4) 1-[(3-cyano-4-methyl-3-phenyl)pentyl]-4-[2-(4-fluorophenoxy)ethyl]homopiperazine
(5) 1-[(3-cyano-4-methyl-3-phenyl)pentyl]-4-[3-(4-fluorophenoxy)propyl]piperazine
(6) 1-[(4-cyano-5-methyl-4-phenyl)hexyl]-4-(4-phenoxybutyl)piperazine
(7) 1-[(4-cyano-5-methyl-4-phenyl)hexyl]-4-[2-phenoxyethyl]piperazine
(8) 1-[(4-cyano-5-methyl-4-phenyl)hexyl]-4-[2-(4-nitrophenoxy)ethyl]piperazine
(9) 1-[4-cyano-5-methyl-4-(4-methylphenyl)hexyl]-4-[2-(4-fluorophenoxy)ethyl]piperazine
(10) 1-[4-cyano-5-methyl-4-(4-chlorophenyl)hexyl]-4-[2-(4-fluorophenoxy)ethyl]piperazine
(11) 1-[4-cyano-5-methyl-4-(4-methoxyphenyl)hexyl]-4-[2-(4-fluorophenoxy)ethyl]piperazine
(12) 1-[4-cyano-5-methyl-4-(4-carbomethoxyphenyl)hexyl]-4-[2-(4-fluorophenoxy)ethyl]piperazine
(13) 1-[4-cyano-5-methyl-4-(4-hydroxymethylphenyl)hexyl]-4-[2-(4-fluorophenoxy)ethyl]piperazine
(14) 1-[4-cyano-5-methyl-4-(4-hydroxyiminomethylphenyl)hexyl]-4-[2-(4-fluorophenoxy)ethyl]piperazine
(15) 1-[4-cyano-5-methyl-4-(4-cyanophenyl)hexyl]-4-[2-(4-fluorophenoxy)ethyl]piperazine
(16) 1-[4-cyano-5-methyl-4-(4-nitrophenyl)hexyl]-4-[2-(4-fluorophenoxy)ethyl]piperazine
(17) 1-[4-cyano-5-methyl-4-(4-aminophenyl)hexyl]-4-[2-(4-fluorophenoxy)ethyl]piperazine
(18) 1-[4-cyano-5-methyl-4-(4-acetamidophenyl)hexyl]-4-[2-(4-fluorophenoxy)ethyl]piperazine
(19) 1-[4-cyano-5-methyl-4-(4-dimethylaminophenyl)hexyl]-4-[2-(4-fluorophenoxy)ethyl]piperazine
(20) 1-{[4-cyano-5-methyl-4-(2-thienyl)hexyl]}-4-[2-(4-fluorophenoxy)ethyl]piperazine
(21) 1-{[4-cyano-5-methyl-4-(3-pyridyl)hexyl]}-4-[2-(4-fluorophenoxy)ethyl]piperazine
(22) 1-{[4-cyano-5-methyl-4-(2-fluorophenyl)hexyl]}-4-[2-(4-fluorophenoxy)ethyl]piperazine
(23) 1-{[4-cyano-5-methyl-4-(3-fluorophenyl)hexyl]}-4-[2-(4-fluorophenoxy)ethyl]piperazine
(24) 1-{[4-cyano-5-methyl-4-(4-fluorophenyl)hexyl]}-4-[2-(4-fluorophenoxy)ethyl]piperazine
(25) 1-[(3-cyano-4-methyl-3-phenyl)pentyl]-4-[2-(4-fluorophenoxy)ethyl]piperazine
(26) 1-[(4-cyano-4-phenyl)pentyl]-4-[2-(4-fluorophenoxy)ethyl]piperazine
(27) 1-[(4-cyano-4-phenyl)heptyl]-4-[2-(4-fluorophenoxy)ethyl]piperazine
(28) 1-[(4-cyano-4-phenyl)hexyl]-4-[2-(4-fluorophenoxy)ethyl]piperazine
(29) 1-[(4-cyano-4-phenyl)octyl]-4-[2-(4-fluorophenoxy)ethyl]piperazine
(30) 1-[(4-cyano-6-methyl-4-phenyl)heptyl]-4-[2-(4-fluorophenoxy)ethyl]piperazine
(31) 1-[(4-cyano-5-methyl-4-phenyl)hexyl]-4-[2-(2-fluorophenoxy)ethyl]piperazine
(32) 1-[(4-cyano-5-methyl-4-phenyl)hexyl]-4-[2-(3-fluorophenoxy)ethyl]piperazine
(33) 1-[(4-cyano-5-methyl-4-phenyl)hexyl]-4-[3-(4-fluorophenoxy)pentyl]piperazine
(34) 1-[(4-cyano-5-methyl-4-phenyl)heptyl]-4-[3-(4-fluorophenoxy)ethyl]piperazine
(35) 1-[(4-cyano-5-methyl-4-phenyl)hexyl]-4-[2-(3,4-difluorophenoxy)ethyl]piperazine
(36) 1-[(4-cyano-5-methyl-4-phenyl)hexyl]-4-[2-(4-chlorophenoxy)ethyl]piperazine
(37) 1-{[4-cyano-5-methyl-4-(3,4-dichlorophenyl)hexyl]}-4-[2-(4-fluorophenoxy)ethyl]piperazine

(38) 1-[(4-cyano-4-cyclohexyl-4-phenyl)butyl]-4-[2-(4-fluorophenoxy)ethyl]piperazine

(39) 1-[(4-cyano-5-methyl-4-phenyl)hexyl]-4-[2-(4-methoxyphenoxy)ethyl]piperazine

(40) 1-[(4-cyano-5-methyl-4-phenyl)hexyl]-4-[2-(2,3-dimethoxyphenoxy)ethyl]piperazine

(41) 1-[(4-cyano-5-methyl-4-phenyl)hexyl]-4-[2-(3,4-dimethoxyphenoxy)ethyl]piperazine

(42) 1-[(4-cyano-5-methyl-4-phenyl)hexyl]-4-[2-(4-aminophenoxy)ethyl]piperazine

(43) 1-[(4-cyano-5-methyl-4-phenyl)hexyl]-4-[2-(4-dimethylaminophenoxy)ethyl]piperazine

(44) 1-[(4-cyano-5-methyl-4-phenyl)hexyl]-4-[2-(4-acetamidophenoxy)ethyl]piperazine

(45) 1-[(4-cyano-5-methyl-4-phenyl)hexyl]-4-[2-(4-methylthiophenoxy)ethyl]piperazine

(46) 1-[(4-cyano-5-methyl-4-phenyl)hexyl]-4-[2-(2-cyanophenoxy)ethyl]piperazine

(47) 1-[(4-cyano-5-methyl-4-phenyl)hexyl]-4-[2-(4-cyanophenoxy)ethyl]piperazine

(48) 1-[(4-cyano-5-methyl-4-phenyl)hexyl]-4-[2-(benzyloxy)ethyl]piperazine

(49) 1-[(4-cyano-5-methyl-4-phenyl)hexyl]-4-[2-(4-fluorophenylthio)ethyl]piperazine

(50) 1-[(4-cyano-5-methyl-4-phenyl)hexyl]-4-[2-(4-fluorophenylsulfonyl)ethyl]piperazine

(51) 1-[(4-cyano-5-methyl-4-phenyl)hexyl]-4-[2-(4-fluorophenylamino)ethyl]piperazine

(52) 1-[(4-cyano-5-methyl-4-phenyl)hexyl]-4-{2-[N-(4-fluorophenyl)-N-methylamino]ethyl}piperazine

(53) 1-[(4-cyano-5-methyl-4-phenyl)hexyl]-4-{2-[N-(4-fluorophenyl)-N-acetylamino]ethyl}piperazine

(54) 1-[(4-cyano-5-methyl-4-phenyl)hexyl]-4-{2-[N-(4-fluorophenyl)-N-methanesulfonylamino]ethyl}piperazine

(55) 1-[(4-cyano-5-methyl-4-phenyl)hexyl]-4-[2-(benzylamino)ethyl]piperazine

(56) 1-[(4-cyano-5-methyl-4-phenyl)hexyl]-4-[2-(N-acetyl-N-benzylamino)ethyl]piperazine

(57) 1-[(4-cyano-5-methyl-4-phenyl)hexyl]-4-[2-(N-methanesulfonyl-N-benzylamino)ethyl]piperazine

(58) 1-[(4-cyano-5-methyl-4-phenyl)hexyl]-4-[2-(N-benzyl-N-isopropylamino)ethyl]piperazine

(59) 1-[(4-cyano-5-methyl-4-phenyl)hexyl]-4-[2-(4-fluorobenzoyl)ethyl]piperazine

(60) 1-[(4-cyano-5-methyl-4-phenyl)hexyl]-4-[3-hydroxy-3-(4-fluorophenyl)propyl]piperazine

(61) 1-[(4-cyano-5-methyl-4-phenyl)hexyl]-4-[2-(4-fluorophenoxy)acetyl]piperazine

(62) 1-[(4-cyano-5-methyl-4-phenyl)hexyl]-4-[2-hydroxy-3-(4-fluorophenoxy)propyl]piperazine

(63) 1-[(4-cyano-5-methyl-4-phenyl)hexyl]-4-[2-(4-fluorophenylaminocarbonyl)ethyl]piperazine

(64) 1-[(4-cyano-5-methyl-4-phenyl)hexyl]-4-[2-(4-fluorobenzoylamino)ethyl]piperazine

(65) 1-[(4-cyano-5-methyl-4-phenyl)hexyl]-4-[N-(4-fluorophenyl)carbamoylmethyl]piperazine

(66) 1-[(4-cyano-5-methyl-4-phenyl)hexyl]-4-[2-(4-fluorobenzenesulfonylamino)ethyl]piperazine

(67) 1-[(4-cyano-5-methyl-4-phenyl)hexyl]-4-{2-[N-(4-fluorophenyl)sulfamoyl]ethyl}piperazine

(68) 1-[(4-cyano-5-methyl-4-phenyl)hexyl]-4-{2-[N-(4-fluorophenyl)-N-methylsulfamoyl]ethyl}piperazine

(69) 1-[(4-cyano-5-methyl-4-phenyl)hexyl]-4-[2-(N-methyl-4-fluorobenzenesulfonylamino)ethyl]piperazine

(70) 1-[(4-cyano-5-methyl-4-phenyl)hexyl]-4-{2-[(4-fluorophenylthio)carbonyloxy]ethyl}piperazine

(71) 1-[(4-cyano-5-methyl-4-phenyl)hexyl]-4-[2-(2-pyridyloxy)ethyl]piperazine

(72) 1-(3-cyclohexyl-3-cyano-3-phenyl)propionyl-4-[2-(4-fluorophenoxy)ethyl]piperazine

(73) 1-(2-hydroxy-4-cyano-5-methyl-4-phenyl)hexyl-4-[2-(4-fluorophenoxy)ethyl]piperazine

(74) 1-[(4-cyano-5-methyl-4-phenyl)hexyl]-4-[2-(2-benzylphenoxy)ethyl]piperazine

(75) 1-[(4-cyano-5-hydroxy-5-methyl-4-phenyl)hexyl]-4-[2-(4-fluorophenoxy)ethyl]piperazine

(76) 1-[5-(4-cyano-5-methyl-4-phenyl)hexenyl]-4-[2-(4-fluorophenoxy)ethyl]piperazine

(77) 1-[4-cyano-5-methyl-4-(4-hydroxyphenyl)hexyl]-4-[2-(4-fluorophenoxy)ethyl]piperazine

(78) 1-[(4-cyano-5-methyl-4-phenyl)hexyl]-4-[2-(2-hydroxy-4-fluorophenoxy)ethyl]piperazine

(79) 1-[(4-cyano-4-fluoro-4-phenyl)butyl]-4-[2-(4-fluorophenoxy)ethyl]piperazine

(80) 1-[(4-Cyano-5-methyl-4-phenyl)hexyl]-4-[2-(2-ethoxycarbonylmethoxy-4-fluorophenoxy)ethyl]piperazine

(81) 1-[(4-cyano-5-methyl-4-phenyl)hexyl]-4-[2-(2-hydroxyethoxy-4-fluorophenoxy)ethyl]piperazine

(82) 1-[(4-cyano-5-methyl-4-phenyl)hexyl]-4-[2-(2-methoxy-4-fluorophenoxy)ethyl]piperazine

(83) 1-[(4-cyano-5-methyl-4-phenyl)hexyl]-4-[2-(N-isopropylanilino)ethyl]piperazine

(84) 1-[(4-cyano-5-methyl-4-phenyl)hexyl]-4-[2-(N-cyclohexylanilino)ethyl]piperazine

(85) 1-[(4-cyano-5-methyl-4-phenyl)hexyl]-4-{2-[N-methyl(4-isopropylanilino)ethyl]}piperazine

(86) 1-[(4-cyano-5-methyl-4-phenyl)hexyl]-4-{2-[N-methyl(3-isopropylanilino)ethyl]}piperazine

(87) 1-[(4-cyano-5-methyl-4-phenyl)hexyl]-4-{2-[N-methyl(2-isopropylanilino)ethyl]}piperazine

(88) 1-[(4-cyano-5-methyl-4-phenyl)hexyl]-4-{2-[3,4-(methylenedioxy)phenoxy]ethyl}piperazine

(89) Synthesis of 1-[(4-cyano-5-methyl-4-phenyl)hexyl]-4-[2-(6-quinolyloxy)ethyl]piperazine

(90) 1-[(4-cyano-5-methyl-4-phenyl)hexyl]-4-[2-(5-isoquinolyloxy)ethyl]piperazine

(91) 1-[{2-(5-cyano-6-methyl-5-phenyl)heptyl}]-4-[2-(4-fluorophenoxy)ethyl]piperazine

(92) 1-{[4-(7-cyano-8-methyl-7-phenyl)nonyl]}-4-[2-(4-fluorophenoxy)ethyl]piperazine

(93) 1-[(4-cyano-5-methyl-4-phenyl)hexyl]-4-[2-(4-pyridyloxy)ethyl]piperazine

(94) 1-[(4-cyano-5-methyl-4-phenyl)hexyl]-4-[2-(3-pyridyloxy)ethyl]piperazine

(95) 1-[(4-cyano-5-methyl-4-phenyl)hexyl]-4-[2-(5-quinolyloxy)ethyl]piperazine

(96) 1-[(4-cyano-5-methyl-4-phenyl)hexyl]-4-[2-(4-trifluoromethylphenoxy)ethyl]piperazine

(97) 1-[(4-cyano-5-methyl-4-phenyl)hexyl]-4-[2-(1-naphthyloxy)ethyl]piperazine

(98) 1-[(4-cyano-5-methyl-4-phenyl)hexyl]-4-[2-ethyl-2-(4-fluorophenoxy)ethyl]piperazine

(99) 1-[(4-cyano-5-methyl-4-phenyl)hexyl]-4-[2-(4-quinazolinyloxy)ethyl]piperazine (100) 1-[(4-cyano-5-methyl-4-phenyl)hexyl]-4-{2-[4-(3-pyridyl)phenoxy]ethyl}piperazine (101) 1-[(4-cyano-5-methyl-4-phenyl)hexyl]-4-{2-[3-(3-pyridyl)phenoxy]ethyl}piperazine (102) 1-[(4-cyano-5-methyl-4-phenyl)hexyl]-4-[2-(4-bromophenoxy)ethyl]piperazine (103) 1-[(4-cyano-5-methyl-4-phenyl)hexyl]-4-[2-(3-bromophenoxy)ethyl]piperazine (104) 1-[(4-cyano-5-methyl-4-phenyl)hexyl]-4-[2-(2-bromophenoxy)ethyl]piperazine (105) 1-[(4-Cyano-5-methyl-4-phenyl)hexyl]-4-{2-[4-(imidazol-1-yl)phenoxy]ethyl}piperazine (106) 1-[(4-cyano-5-methyl-4-phenyl)hexyl]-4-[2-(2-pyrimidinyloxy)ethyl]piperazine (107) 1-[(4-cyano-5-methyl-4-phenyl)hexyl]-4-{2-[2-(3-pyridyl)phenoxy]ethyl}piperazine (108) 1-[4-cyano-5-methyl-4-(2-cyano-5-thienyl)hexyl]-4-[2-(4-fluorophenoxy)ethyl]piperazine (109) 1-[4-cyano-5-methyl-4-(2-cyano-5-thienyl)hexyl]-4-[2-(3-fluorophenoxy)ethyl]piperazine (110) 1-[4-cyano-5-methyl-4-(2-thienyl)hexyl]-4-[2-(3-fluorophenoxy)ethyl]piperazine (111) 1-[(4-cyano-5-methyl-4-phenyl)hexyl]-4-{2-[3-(3-thienyl)phenoxy]ethyl}piperazine (112) 1-[(4-cyano-5-methyl-4-phenyl)hexyl]-4-{2-[2-(6-methyl-2-pyridyl)vinylphenoxy]ethyl}piperazine (113) 1-[(4-cyano-5-methyl-4-phenyl)hexyl]-4-[2-(3-cyanophenoxy)ethyl]piperazine (114) 1-[(4-cyano-5-methyl-4-phenyl)hexyl]-4-[2-(3-phenylphenoxy)ethyl]piperazine (115) 1-[(4-cyano-5-methyl-4-phenyl)hexyl]-4-{2-[3-(2-cyanovinyl)phenoxy]ethyl}piperazine (116) 1-[(4-cyano-5-methyl-4-phenyl)hexanoyl]-4-[2-(4-fluorophenoxy)ethyl]piperazine and (117) 1-[(4-cyano-4-phenyl)butyl]-4-[2-(4-fluorophenoxy)ethyl]piperazine.

The compounds of the present invention have extremely high $LD_{50}$ and extremely high safety.

Among the above compounds of the present invention, for example, compounds of (1), (9), (10), (11), (20), (22), (23), (24), (36), (52), (75), (76), (79), (86), (88), (92), (95), (104), (107), (109) and (116) are preferable from the viewpoin of a pharmacological activity and safety.

Next, the process for producing the N,N-substituted cyclic amine compounds according to the present invention is not limited, and for example it can be produced in the following manner.

(1) Production of N,N-Substituted Cylic Amine Compound (VIII) Where w>2 and the Left Side-chain is Methyl Group In this case, aldehyde compound (IX) and cyclic amine (X) can be reacted in the presence of a reducing agent according to conventional reductive amination, for example a method described in shin Jikken Kagaku Koza 14-III, page 1373, published by Maruzen K. K. This reaction is shown in the following chemical scheme:

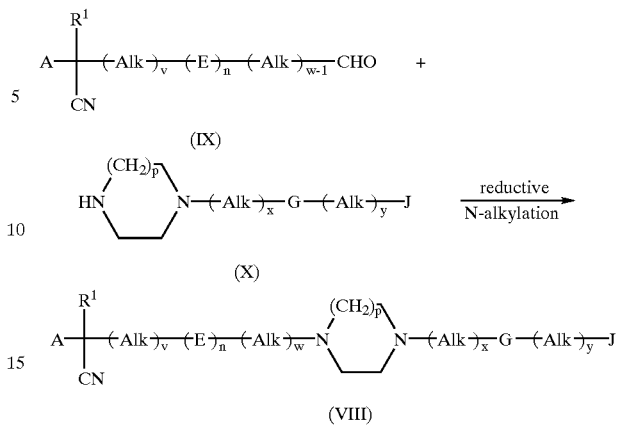

wherein A, E, G, J, Alk, $R^1$, v, n, w, x, y and p have the same meanings as defined above.

Here in, the reducing agent is not limited insofar as it is conventionally used for reductive N-alkylation, and preferable examples include sodium triacetoxy borohydride, sodium cyano borohydride, sodium borohydride, lithium aluminum hydride etc.

(2) Production of N,N-Substituted Cylic Amine Compound (VIII) Where w>2 and the Left Terminal is Methylene Group In a method other than (1), the desired compound can be synthesized by adding active alkyl compound (XII) to cyclic amine (XI) in the presence of a base. This reaction is shown in the following reaction scheme:

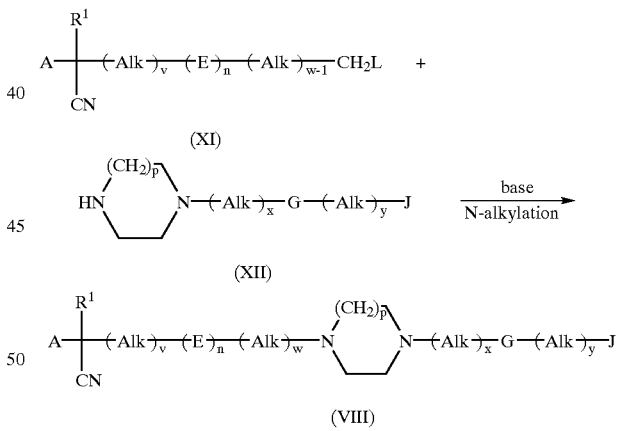

wherein A, E, G, J, Alk, $R^1$, v, n, w, x, y and p have the same meanings as defined above. L is a leaving group such as halogen atom, methane sulfonyloxy group etc.

(3) Prodiirctin of N,N-Substituted Cyclic Amine Compound (I) Where o>2 and Terminal $R^4=R^5=H$ In this case, aldehyde compound (V) and cyclic amine (VI) can be reacted in the presence of a reducing agent according to conventional reductive amination, for example a method described in Shin Jikken Kagaku Koza 14-III, page 1373, published by Maruzen K. K. This reaction is shown in the following chemical scheme:

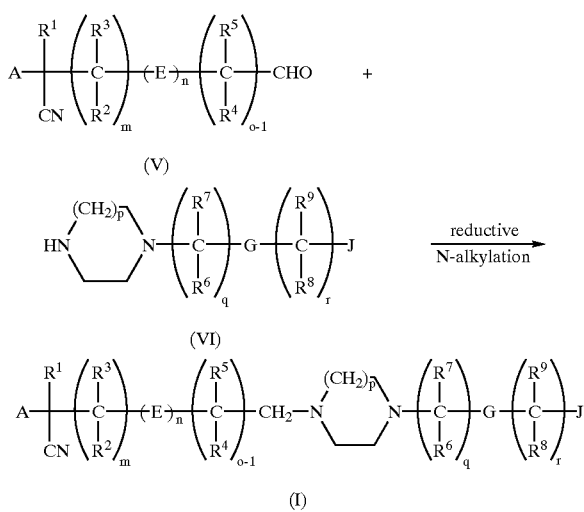

wherein A, E, G, J, $R^1$, $R^2$, $R^3$, $R^4$, $R^5$, $R^6$, $R^7$, $R^8$, $R^9$, m, n, o, p, q and r have the same meanings as defined above.

Herein, the reducing agent is not limited insofar as it is conventionally used for reductive N-alkylation, and preferable examples include sodium triacetoxy borohydride, sodium cyano borohydride, sodium borohydride, lithium aluminum hydride etc.

(4) Production of N,N-Substituted Cyclic Amine Compound (I) Where o>2 and Terminal $R^4$=$R^5$=H In a method other than (3), the desired compound can be synthesized by adding active alkyl compound (VII) to cyclic amine (VI) in the presence of a base. This reaction is shown in the following reaction scheme:

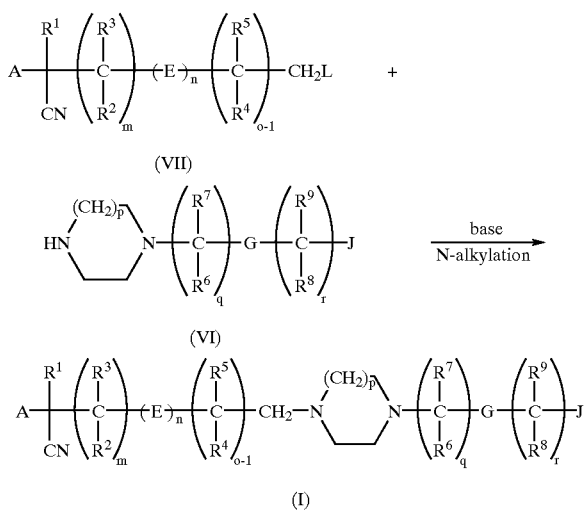

wherein A, E, G, J, $R^1$, $R^2$, $R^3$, $R^4$, $R^5$, $R^6$, $R^7$, $R^8$, $R^9$, m, n, o, p, q, and r have the same meanings as defined above. L is a leaving group such as halogen atom, methane sulfonyloxy group etc.

The administration form of the compounds of the present invention include e.g. oral pharmaceutical preparations such as powder, fine granule, granule, tablet, coated tablet and capsule, external application such as ointments, plaster and suppository, as well as injection. For pharmaceutical composition manufacturing, conventional pharmaceutical carriers can be used in a usual manner.

That is, for production of oral pharmaceutical composition, N,N-substituted cyclic amine compounds or pharmacologically acceptable salts thereof and fillers, and as necessary binders, disintegrators, lubricants, coloring agents, taste and odor correctives etc. mixed and formed in a usual manner to form powder, fine granule, granule, tablet, coated tablet, capsule etc.

The fillers include e.g. milk sugar, corn starch, white sugar, glucose, mannitol, sorbit, crystalline cellulose, silicon dioxide etc.; the binders include e.g. polyvinyl alcohol, polyvinyl ether, methyl cellulose, ethyl cellulose, gum arabic, tragacanth, gelatin, shellac, hydroxypropyl methyl cellulose, hydroxypropyl cellulose, polyvinyl pyrrolidone, polypropylene glycol-polyoxyethylene block polymers, meglumine etc.; the disintegrators include e.g. starch, agar, gelatin powder, crystalline cellulose, calcium carbonate, sodium bicarbonate, calcium citrate, dextrin, pectin, carboxymethyl cellulose calcium etc.; the lubricants include e.g. magnesium stearate, talc, polyethylene glycol, silica, hardened vegetable oil; the coloring agents include those approved to be added to pharmaceutical composition; and the taste and odor correctives include cocoa powder, menthol, aromatic powder, peppermint oil, camphor, cinnamon powder. These tablets and granules may be coated with sugar-coatings or any other materials as necessary.

For production of pharmaceutical composition for injection, pH adjustors, dissolution agents, isotonicity-imparting agents etc. and as necessary dissolution assistants, stabilizers etc. are added to the N,N-substituted cyclic amine compounds or pharmacologically acceptable salts thereof, to manufacture pharmaceutical composition in a usual manner.

The method of producing the pharmaceutical composition for external application is not limited, and these can be produced in a usual manner. That is, the base starting materials used in pharmaceutical manufacturing may be various starting materials conventionally used in pharmaceutical compositions, non-pharmaceutical compositions, cosmetics etc.

Specifically, the base starting materials include e.g. raw materials such as animal and vegetable oil, mineral oil, ester oil, waxes, higher alcohols, fatty acids, silicon oil, surfactants, phospholipids, alcohols, polyols, water-soluble polymers, clays and minerals, purified water etc., and as necessary, pH adjustors, antioxidants, chelating agents, preservatives, anti-fungus agents, coloring agents, perfumes etc., but the base starting materials for external application according to the present invention are not limited to those enumerated above. Further, components having differentiation-inducing action, blood stream promoters, disinfectants, anti-inflammatory agents, cell activators, vitamins, amino acids, humectants, keratin-lytic agent etc. can also be incorporated. The amount of these base starting materials is usually determined as an amount used in producing preparations for external application.

In the present invention, the clinical dosage of the N,N-substituted cyclic amine compounds or pharmacologically acceptable salts thereof is not limited, and the dosage varies depending on conditions, severity, age, complications etc. and on the type of salt and administration route. This dosage is in the range of usually 0.01 to 1000 mg, preferably 0.1 to 500 mg, and more preferably 0.5 to 100 mg per day for an adult, and it is administered orally, intravenously, as suppository or percutaneously.

Hereinafter, the excellent pharmacological effects of the compounds of the present invention are mentioned as the effects of the invention.

For example, the following literatures describe that compounds having an inhibitory action on N type or P/Q type calcium channels can serve as an agent for inhibiting the death of nerve cells or for protecting cerebral nerve cells, an agent for treating or improving nervous diseases, an agent for treating or improving acute ischemic stroke, head trauma, death of nerve cells, Alzheimer disease, cerebral circulatory metabolism disturbance, cerebral function disturbance or pain, an anti-spasm agent, an agent for treating or improving schizophrenia and an agent for preventing, treating or improving migraine, epilepsy, maniac-depressive psychosis, nerve degenerative diseases (Parkinson disease, Alzheimer disease, amyotrophic lateral sclerosis, Huntington disease) cerebral ischemia, epilepsy, head trauma, AIDS dementia complications, edema, anxiety disorder (generalized anxiety disorder) and diabetic neuropathy.

(1) Acute ischemia stroke: Annj. Rev. Physiol., 52, 543–559, 1990.

(2) Head trauma: SCRIP, No. 2203, 24, 1997.

(3) Ischemia—death of cerebral nerve cells: Advances in Pharmacology, 22, 271–297, 1991.

(4) Alzheimer disease: Trends in Neuroscience, 16, 409, 1993.

(5) Cerebral circulatory metabolism disturbance: Nichiyakurishi, 85, 323–328, 1985.

(6) Cerebral function disturbance: Acta Neurol. Scand., 78:2, 14–200, 1998.

(7) Analgesic: Drug of the Future, 23 (2), 152–160, 1998.

(8) Cerebral ischemia, migraine, epilepsy, maniac-depressive psychosis: CasopisLekau Ceskych., 130 (22–23), 625–630, 1991.

(9) Nerve degenerative diseases (Parkinson disease, Alzheimer disease, amyotrophic lateral sclerosis, Huntington disease), cerebral ischemia, epilepsy, head trauma, and AIDS dementia complications: Revista de Neurologia., 24 (134), 1199–1209, 1996.

Further, for example, the following literatures describe that compounds having an inhibitory action on N type or P/Q type calcium channels can serve as an agent for preventing, treating or improving edema, anxiety disorder (generalized anxiety disorder), schizophrenia, diabetic neuropathy and migraine.

(10) Edema: Brain Research, 776, 140–145, 1997.

(11) Anxiety disorder (generalized anxiety disorder), schizophrenia: Jyunkanseigyo (Circulation Control), 14 (2), 139–145, 1993.

(12) Diabetic neuropathy: Shinkeinaika (Neurological Medicine), 50, 423–428, 1999.

(13) Migraine: Neurology, 50 (4), 1105–1110, 1998.

Accordingly the invention provides a calcium antagonist comprising the N,N-substituted cyclic amine compounds or a pharmacologically acceptable salt thereof; a nerve-selective calcium antagonist comprising the N,N-substituted cyclic amine compounds or a pharmacologically acceptable salt thereof; an agent for preventing, treating and improving the diseases against which an inhibitory action on P/Q type calcium channel is effective, comprising the N,N-substituted cyclic amine compounds or a pharmacologically acceptable salt thereof; an agent for preventing, treating and improving the diseases against which an inhibitory action on N type calcium channel is effective, comprising the N,N-substituted cyclic amine compounds or a pharmacologically acceptable salt thereof; an agent for inhibiting the death of nerve cells or for protecting brain nerve cells, comprising the N,N-substituted cyclic amine compounds or a pharmacologically acceptable salt thereof; an agent for preventing, treating or improving a nerve disease, comprising the N,N-substituted cyclic amine compounds or a pharmacologically acceptable salt thereof wherein the nerve cell disease may be one disease selected from the group consisting of acute ischemic stroke, cerebral apoplexy, cerebral infarction, head trauma, cerebral nerve cell death, Alzheimer disease, Parkinson disease, amyotrophic lateral sclerosis, Huntington disease, cerebral circulatory metabolism disturbance, cerebral function disturbance, pain, spasm, schizophrenia, migraine, epilepsy, maniac-depressive psychosis, nerve degenerative diseases, cerebral ischemia, AIDS dementia complications, edema, anxiety disorder (generalized anxiety disorder) and diabetic neuropathy; and a calcium antagonist composition comprising a pharmacologically effective amount of the N,N-substituted cyclic amine compounds or a pharmacologically acceptable salt thereof and a pharmacologically acceptable carrier.

Moreover the present invention provides a method of treating a disease against which calcium antagonism is effective, which comprises administering a pharmacologically effective amount of the N,N-substituted cyclic amine compounds or a pharmacologically acceptable salt thereof to a patient suffering from the disease; and use of the N,N-substituted cyclic amine compounds or a pharmacologically acceptable salt thereof for manufacturing calcium antagonist.

PHARMACOLOGICAL EXPERIMENTAL EXAMPLE 1

Figure 1:
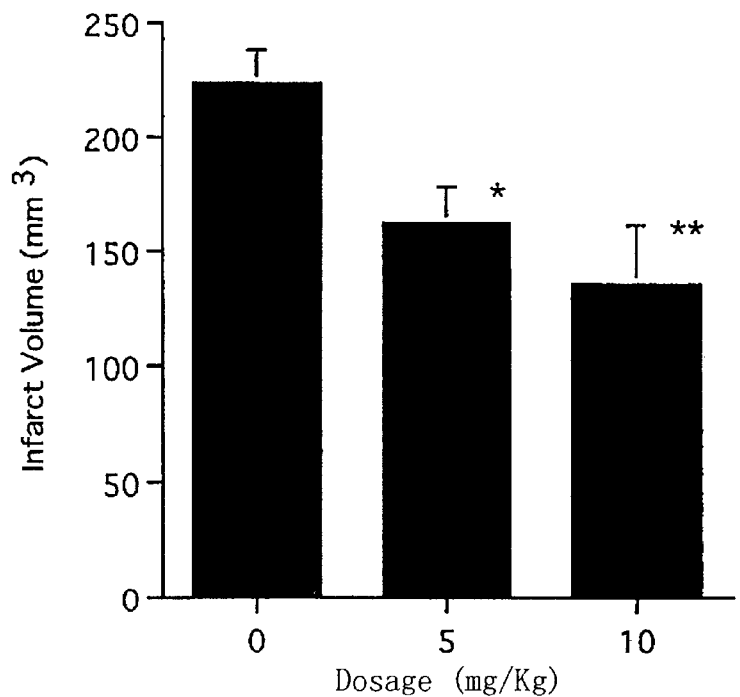
FIG. 1 is a graph showing effect of reducing infarct volume of the compound of the present invention (i.v.) in a rat model with occlusion in the middle cerebral artery (represented by Mean±SE).

Measurement of Voltage-dependent Calcium Channel Activity by the use of a Fluorescent Pigment (fura 2)

(1) Relationship Between Model and Disease

At present, the "glutamic acid-Ca hypothesis" is regarded as the most important as the mechanism of brain infarction (the death of nerve cells due to ischemia). That is, if cerebral blood stream is reduced, anaerobic glycolysis occurs and ATP in cerebral tissues is exhausted. Because of this energy exhaustion, an intracellular and extracellular ion concentration gradient cannot be maintained to generate depolarization. In pre-synapses, voltage-dependent calcium channels are activated due to the depolarization, and excessive release of glutamic acid is induced. In post-synapses, voltage-dependent calcium channels are activated due to the depolarization, and intracellular $Ca^{2+}$ levels are increased, while excessively released glutamic acid stimulates glutamic acid receptors to increase intracellular $Ca^{2+}$ levels. As a result, a wide variety of $Ca^{2+}$-dependent enzymes such as calpain and phospholipase are activated to induce the death of nerve cells. Out of this flowchart, the inflow of $Ca^{2+}$ inpre-synapses can be evaluated in this experiment system.

(2) Preparation of Cerebral Cortex Synaptosome

Cerebral cortex synaptosome was prepared in the following method in accordance with Neuropharmacology, 32 (11), 1195–1202, 1993.

Cerebral cortexes were removed from cut rat brains and disrupted roughly with scissors. These were introduced into a homogenizer, homogenized in 0.3 M saccharose and centrifuged at 4° C. (1,500 g×10 min). The resulting supernatant was further centrifuged at 4° C. (10,000 g×20 min). The resulting precipitates were suspended in 0.3 M saccharose. The suspension was layered on 0.8 M saccharose and centrifuged (10,000 g×30 min.). The resulting precipitates were suspended in solution A (118 mM NaCl, 4.6 mM KCl, 1 mM $CaCl_2$, 1 mM $MgCl_2$, 1.2 mM $Na_2HPO_4$, 10 mM D-glucose, 20 mM HEPES-NaOH pH 7.4, 0.1% BSA) to give cerebral cortex synaptosome.

(3) Inhibitory Action on Calcium Channels

4 μM fura 2/AM (Dojin Ltd.) was suspended in solution A to prepare a loading solution. To the synaptosome solution prepared in the method described above was added an equal volume of the loading solution, and the mixture was incubated for 40 minutes at room temperature. After incubation, the loading solution was removed by centrifugation, and the sample was further washed twice with solution A. Solution A containing the compound of the present invention was added thereto and incubated for 10 minutes at room temperature. 1/10 volume of solution B (122.6 mM $KCl_2$, 1 mM $CaCl_2$, 1 mM $MgCl_2$, 1.2 mM $Na_2HPO_4$, 10 mM D-glucose, 20 mM HEPES-NaOH pH 7.4, 0.1% BSA) was added thereto to stimulate the calcium channels. Intracellular calcium ion levels were determined by measurement at 2 wavelengths of 340 nm and 380 nm with ARUGUS-FDSS (Hamamatsu Pothonics Co., Ltd.), and the $IC_{50}$ of each compound was determined.

As comparative and control compound, verapamil hydrochloride was used.

| Example | $IC_{50}$ (μM) |
|---|---|
| 1 | 5.9 |
| 2 | 4 |
| 3 | 4.8 |
| 4 | 5.7 |
| 5 | 7.7 |
| 6 | 2.7 |
| 7 | 8.9 |
| 8 | 4.2 |
| 9 | 3.5 |
| 10 | 3.2 |
| 11 | 4.8 |
| 12 | 8.1 |
| 14 | 8.7 |
| 15 | 9.8 |
| 16 | 4.8 |
| 17 | >16 |
| 19 | 6 |
| 20 | 5.5 |
| 22 | 5.4 |
| 23 | 4.3 |
| 24 | 3.9 |
| 25 | 9.7 |
| 27 | 4.6 |
| 28 | 7.2 |
| 29 | 4 |
| 30 | 2.9 |
| 31 | 9.3 |
| 32 | 6.2 |
| 33 | 3.4 |
| 34 | 3.8 |
| 35 | 5.2 |
| 36 | 3.4 |
| 37 | 2.7 |
| 38 | 4 |
| 39 | 9.6 |
| 40 | 10 |
| 43 | 13 |
| 45 | 4.6 |
| 46 | 16 |
| 47 | 13 |
| 48 | 8.4 |
| 49 | 4.8 |
| 51 | 7.5 |
| 52 | 3.8 |
| 56 | 16 |
| 59 | 12 |
| 60 | 10 |
| 61 | 11 |
| 62 | 8.8 |
| 63 | 7.4 |
| 65 | >16 |
| 66 | 8.2 |
| 67 | 10 |
| 68 | 8.7 |
| 69 | 9.2 |
| 70 | 3.8 |
| 71 | >16 |
| 75 | 4.5 |
| 76 | 5.8 |
| 77 | 7.5 |
| 78 | 15 |
| 79 | 3.3 |
| 80 | 3.8 |
| Control | >16 |
| 81 | >16 |
| 82 | 5.0 |
| 83 | 13 |
| 84 | 6.0 |
| 85 | 16 |
| 86 | 4.3 |
| 87 | >16 |
| 88 | 4.9 |
| 89 | 2.7 |
| 90 | 2.6 |
| 91 | 2.1 |
| 92 | 1.8 |
| 93 | 2.4 |
| 94 | 6.1 |
| 95 | 11 |
| 96 | 5.4 |
| 97 | 3.9 |
| 98 | >16 |
| 99 | >16 |
| 100 | >16 |
| 101 | 9.2 |
| 102 | 2.7 |
| 103 | 2.5 |
| 104 | 2.2 |
| 105 | >16 |
| 106 | 7.0 |
| 107 | 4.1 |

-continued

| Example | IC$_{50}$ ($\mu$M) |
|---|---|
| 108 | 3.3 |
| 109 | 3.3 |
| 110 | 3.5 |
| 111 | >16 |
| 112 | >16 |
| 113 | 4.5 |
| 114 | 6.8 |
| 115 | 5.8 |
| 116 | 5.5 |
| 117 | 3.2 |
| 118 | 6.4 |
| 119 | 7.7 |
| 120 | 4.1 |
| 121 | 6.8 |
| 122 | 12 |

Control: verapamil hydrochloride

PHARMACOLOGICAL TEST EXAMPLE 2

Inhibitory Activity on Glutamic Acid Release (1) Relationship Between Model and Disease This experimental system is considered to be an experimental system in which the release of glutamic acid in pre-synapses in the flow-chart of the "glutamic acid-Ca hypothesis" can be evaluated.

(2) Preparation of Rat Cerebral Cortex Slices

Cerebral cortexes were isolated from SD strain male rats (8-week-old) and used to prepare 300 $\mu$m×300 $\mu$m slices by use of a slice chopper. The prepared slices were incubated at 37° C. for 30 minutes in solution C (120 mM NaCl, 4 mM KCl, 10 mM MgSO$_4$, 16 mM NaHCO$_3$, 10 mM glucose, 1 mM NaH$_2$PO$_4$, 10 mM HEPES-NaOH pH 7.4) in the presence of 95% O$_2$/5% CO$_2$. Thereafter, solution C was exchanged with fresh one, followed by further incubation for 30 minutes.

(3) Glutamic Acid Release by Stimulation with High-conc. KCl

The cerebral cortex slices were incubated in a 24-wells plate for cell culture according to a multi-well method (Brain Res., 402, 255–263, 1987), and the release of glutamic acid was induced with 50 mM KCl. Solution D (120 mM NaCl, 4 mM KCl, 1.2 mM CaCl$_2$, 1 mM MgSO$_4$, 16 mM NaHCO$_3$, 10 mM glucose, 1 mM NaH$_2$PO$_4$, 10 mM HEPES-NaOH pH 7.4) was aerated with 95% O$_2$/5% CO$_2$ and kept at 37° C. and used in this experiment. 50 mM KCl containing the same total amount of K$^+$ and Na$^+$ was prepared. Slices corresponding to 1 to 2 mg protein were placed on an upper cup provided with a mesh at the bottom, and 1.3 ml solution C or 50 mM KCl solution was introduced into a lower well, and the upper cup was transferred to a new well. 20 minutes before and 5 minutes after reaction was intiated, the the test compound was added to solution D or 50 mM KCl.

(4) Quantification Glutamic Acid

Glutamic acid was quantified by HPLC using fluorescent etor (Ex. 330 nm Em. 45 nm). The eluting solvent used was prepared by diluting 150 ml sodium citrate buffer for automatic amino acid analysis (Wako Pure Chemical Industries) 10-fold with distilled water, then adding MgCl$_2$ thereto at the final concentration of 50 mM, and further diluting it twice with acetonitrile. The flow rate was 2.0 ml/min. The column used was Asahipak (ES-502N Denko, K. K.). The glutamic acid was converted into a derivative by addition, to 50 $\mu$l sample, of 50 $\mu$l deriving agent (10 mg o-phthalaldehyde/500 $\mu$l MeOH, 10 $\mu$l b-mercaptopropionic acid, 0.15 M sodium borate buffer pH 9.5, 100 $\mu$l) followed by stirring (Neuroscience Lett., 96, 202–206, 1989).

(5) Results

| Examples | IC$_{50}$ ($\mu$M) |
|---|---|
| 1 | 3.5 |
| 9 | 2.4 |
| 10 | 2 |
| 11 | 3.8 |
| 20 | 1.9 |
| 22 | 4.1 |
| 23 | 2.5 |
| 24 | 2.4 |
| 36 | 4.2 |
| 52 | 2.9 |
| 75 | 2.9 |
| 76 | 3.9 |
| 79 | 5.9 |

Hereinafter, reduction of infarct volume in a rat model with occlusion in the middle cerebral artery, and the antalgic action on mice in a formalin test were tested with the compound of the present invention to demonstrate its in vivo effects of the invention.

PHARMACOLOGICAL EXPERIMENTAL EXAMPLE 3

Effect (I) of Reducing Infarct Volume in a Rat Model with Occlusion in the Middle Cerebral Artery (1) Background Intracellular calcium ion plays an important role in exhibiting various cellular functions. However, if intracellular calcium ion level is raised excessively, cellular disturbance is induced (references, and so forth, 1 and 2). For example, nerve cell disturbance induced by excitatory amino acids generated upon cerebral ischemia causes an excessive increase in intracellular calcium ion level (3, 4). Upon occurrence of local cerebral ischemia, the mechanism of maintaining membrane potential is destroyed by the increased excitatory amino acids (3), and depolarization of the membrane is thereby induced (5), and the inflow of calcium ion into cells via voltage-dependent calcium channels is increased (6, 7). From the foregoing, it is suggested that the hypothesis that the death of nerve cells is based on the excitatory toxicity of excitatory amino acids is correlated with the hypothesis that the death of nerve cells is based on the increase of intracellular calcium ion, and that the activation of voltage-dependent calcium channel contributes to induction of the death of nerve cells (8).

From electro-physiological and pharmacological studies, the voltage-dependent calcium channels present in nerve cells are classified into 6 subtypes (T, L, N, P, Q and R types) (9).

Among these, N, P and Q types play an important role in liberating glutamic acid from synaptosomes in rat cerebral cortex (10, 11).

Accordingly, the protective effect of the typical compound of the present invention on nerve cells against disturbance induced upon occurrence of local cerebral ischemia in a rat model with occlusion in the middle cerebral artery was evaluated.

(2) Experimental Method 2-1) Preparation of Sample

The compound in Example 1 was selected as the typical example of the compound of the present invention, and this sample was dissolved in 5.28% mannitol to be adjusted to a dosage of 5 or 10 mg/kg/h just before use. The concentration of the sample was calculated on the basis of the average weight of animals, as shown in the following example. The average weight was determined by measuring the weights of all animals to be used in the experiment.

Example) In the case of 10 mg/kg/h
Sample concentration=10 mgxaverage weight (kg)/volume (0.616 ml) administered per hour 2-2) Preparation of a Nylon Embolus For occlusion in the middle cerebral artery, an embolus prepared from nylon yarn of 4-0 monofilament (Ethicon, Inc., Somerville, N.J., USA) was used. The end of the nylon embolus was previously rounded with flame, and it was cut into fragments of 25 mm in length, and each fragment was marked at a position 17 mm apart from the end with an oil-based felt pen.

2-3) Implantation of a Catheter for Intravenous Administration

Implantation of a catheter for intravenous administration (Atom venous catheter 3Fr, Atom Medical Co., Ltd., Tokyo) was conducted under anesthesia with 70% laughing gas-2% halothane. The catheter filled with physiological saline was inserted through the thigh vein in the left leg.

2-4) Occlusion in the Middle Cerebral Artery

Occlusion in the middle cerebral artery was conducted in accordance with the method of Longa et al. (12). Just after the catheter was implanted, the operation was conducted under anesthesia with 70% laughing gas-2% halothane. A rat was allowed to lie on the back and the cervical region was cut open under a stereoscopic microscope for operation, and the part where the common carotid artery at the right side branched into the external carotid artery and the internal carotid artery was confirmed. The external carotid artery was cut at the peripheral side, and the nylon embolus was inserted through the end of the cut external carotid artery into the internal carotid artery. The embolus was inserted until the position 17 mm apart from the end of the embolus reached the point where the external carotid artery was joined to the internal carotid artery, and the embolus was fixed. To initiate blood stream again, the nylon embolus was removed 2 hours after the middle cerebral artery was occluded.

2-5) Selection of Animals with Ischemia Symptoms

Thirty minutes after the middle cerebral artery was occluded, each rat was raised by holding the tail, and a rat clearly having hemiplegia in the foreleg (paralysis in the foreleg at the opposite side to the produced occlusion) was selected as an example where the middle cerebral artery was occluded to successfully cause ischemia conditions, and this selected animal was subjected to the experiment.

2-6) Medium and Sample Administration

The rat showing hemiplegia 30 minutes after the middle cerebral artery was occluded was placed in a cage with a unit for controlling body temperature, and the rat had a probe for monitoring body temperature fixed to the rectum. Then, a syringe containing a medium or a sample was attached to the catheter for intravenous administration, and half (0.31 ml) of the dosage to be infused for 1 hour was intravenously administered for 1 minute. Thereafter, the medium or the sample was administered continuously for 6 hours at a rate of 0.616 ml/h by the use of a syringe pump for infusion (Razel Scientific Instruments, Inc., Stamford, Conn., USA). During administration and for 2 hours after administration was finished, the temperature of the rectum was maintained in the range of 37.0 to 38.5° C. in a system for controlling body temperature. After the body temperature control was finished, the animal was returned to the cage and maintained for 1 day in a breeding room.

2-7) Measurement of Infarct Volume

Staining of Cerebral Slices with TTC

Twenty four hours after the middle cerebral artery was occluded, the head was cut off from the rat and the brain was taken out. Blood adhered thereto was washed out in ice-cooled physiological saline. The brain from which the bulb for smelling had been removed was sliced at 2 mm intervals from the end (6 slices in total), and each slice was placed in 2% TTC solution such that the rear of the brain faced upward. TTC was dissolved in physiological saline when used. The sample was left at room temperature for at least 1 hour in the TTC solution and then measured for the infarct area.

Calculation of Infarct Volume

The upper face (the rear of the brain) of each slice was used for calculation of the infarct area. An image of the cerebral slice was input into a computer (PM7500/100, Apple Japan, Tokyo) by the use of an image scanner (CCD color camera, Sankei, Tokyo). The cerebral cortex infarct area in the image was determined using image analysis software (NIH image ver. 1.60, National Institutes of Health, USA). The infarct volume from one animal was calculated as the total ($mm^3$) of 6 slices by multiplying the infarct area ($mm^2$) in each slice by 2 (mm) which is the thickness of the slice.

2-8) Data Analysis

The infarct volume ($mm^3$) in the cerebral cortex was expressed in mean±standard error. The statistical significance between the medium control group and each sample group was analyzed by Dunnett multiple comparative test, and 5% of both the sides was regarded as level of significance. The dosage reactivity was analyzed by regression analysis, and 5% of one side was regarded as level of significance.

(3) Results

After the middle cerebral artery was occluded for 2 hours by the nylon embolus, the nylon embolus was removed to initiate blood stream again, and 24 hours after the middle cerebral artery was occluded, the infarct volume was measured. The results are shown in the table below and in FIG. 1 (*; $p<0.05$, **; $p<0.01$).

Infarct volume ($mm^3$) in the cerebral cortex 24 hours after the middle cerebral artery was occluded

|  | Mean | Standard Error | Number of Animals |
| --- | --- | --- | --- |
| Control | 224.06 | 14.41 | 14 |
| 5 mg/kg | 162.17 | 16.30 | 14 |
| 10 mg/kg | 135.50 | 26.21 | 8 |

The infarct volume in the cerebral cortex in the control group was 224.1±14.4 $mm^3$. By intravenously administering the compound of the present invention at a dosage of 5 or 10 mg/kg/h 30 minutes after the middle cerebral artery was occluded, the infarct volume in the cerebral cortex was reduced to 28% (162.2±16.3 $mm^3$; $p<0.05$) and 40% (135.5±26.2 $mm^3$; $p<0.01$) respectively. As a result of regression analysis, it was recognized that the action of the compound of the present invention on reduction of infarct volume was dose-dependent.

(4) Summary

As described above, the compound of the present invention inhibits the inflow, induced by high KCl levels, of calcium ion into synaptosomes in the rat cerebral cortex, and inhibits the liberation of glutamic acid from slices of the rat cerebral cortex. Further, in the present experiment, the compound of the present invention has a protective action on nerve cells against disturbance caused by local cerebral ischemia, and upon administration 30 minutes after generation of ischemia, the compound of the present invention exhibits the significant effect of reducing the infarct volume, thus clarifying the effectiveness of the compound against human cerebral apoplexy by post treatment.

These results are also supported by the reports (13, 14) that SNX-111 (CAS registration No. 107452-89-1) i.e. an inhibitor peptide for N-type calcium channels serves for protection against the liberation of glutamic acid from the cerebral cortex and against the subsequent disturbance of nerve cells, in a rat model with local cerebral ischemia, and also by the report (15) that ω-agatoxin IVA i.e. an inhibitor peptide for P/Q type channels has a protective action on nerve cells in a rat model with local cerebral ischemia.

(5) References (1) Schanne, F. A. X., Kane, A. B., Young, E. E., Farber, J. L. Calcium dependence of toxic cell death: a final common pathway. Science 206: 700–702 (1979).

(2) Kristian, T., Siesjo, B. K. Calcium in ischemic cell death. Stroke 29: 705–718 (1998).

(3) Graham, S. H., Shiraisi, K., Panter, S. S., Simon, R. P., Faden, A. I. Changes in extracellular amino acid neurotransmitters produced by focal cerebral ischemia. Neurosci. Lett. 110: 124–130 (1990).

(4) Rothman, S. M., Olney, J. W. Glutamate and the pathophysiology of hypoxic-ischemic brain damage. Ann. Neurol. 19: 105–111 (1986).

(5) Siesjo, B. K., Bengtsson, F. Calciuminfluxes, calcium antagonists, and calcium-related pathology in brain ischemia, hypoglycemia, and spreading depression: A unifying hypothesis. J. Cereb. Blood Flow Metab. 9: 127–140 (1989).

(6) Mayer, M. L., Miller, R. J. Excitatory amino acid receptors, second messengers and regulation of intracellular $Ca^{2+}$ in mammalian neurons. Trends Pharmacol. Sci. 11: 254–260 (1990).

(7) Osuga, H., Hakim, A. M. Relationship between extracellular glutamate concentration and voltage-sensitive calcium channel function in focal cerebral ischemia in the rat. J. Cereb. Blood Flow Metab. 16: 629–636 (1996).

(8) Choi, D. W. Calcium-mediated neurotoxicity: Relationship to specific channel types and role in ischemic damage. Trends Neurosci. 11: 465–469 (1988).

(9) Randall, A. D., Tsien, R. W. Pharmacological dessection of multiple types of $Ca^{2+}$ channel currents in rat cerebellar granule neurons. J. Neurosci. 15: 2995–3012 (1995).

(10) Turner, T. J., Dunlap, K. Pharmacological characterization of presynaptic calcium channels using subsecond biochemical measurements of synaptosomal neurosecretion. Neuropharmacology 34: 1469–1478 (1995).

(11) Maubecin, V. A., Sanchez, V. N., Rosato Siri, M. D., Cherksey, B. D., Sugimori, K., Llinas, R., Uchitel, O. D. Pharmacological characterization of the voltage-dependent $Ca^{2+}$ channels present in synaptosomes from rat and chicken central nervous system. J. Neurochem. 64: 2544–2551 (1995).

(12) Longa, E. Z., Weinstein, P. R., Carlson, S., Cummins, R. Reversible middle cerebral artery occlusion without craniectomy in rats. Stroke 20: 84–91 (1989).

(13) Bowersox, S. S., Singh, T., Luther, R. R. Selective blockade of N-type voltage-sensitive calcium channels protects against brain injury after transient focal ischemia in rats, Brain Res. 747: 343–347 (1997).

(14) Takizawa, S., Matsushima, K., Fujita, H., Nanri, K., Ogawa, S., Shinohara, Y. A selective N-type calcium channel antagonist reduces extracellular glutamate release and infarct volume in focal cerebral ischemia. J. Cereb. Blood flow Metab. 15: 611–618 (1995).

(15) Asakura, K., Matsuo, Y., Kanemasa, T., Ninomiya, M. P/Q-type $Ca^{2+}$ channel blocker ω-agatoxin IVA protect against brain injury after focal ischemia in rats. Brain Res. 7760: 140–145 (1997).

PHARMACOLOGICAL EXPERIMENTAL
EXAMPLE 4

Effect (II) of Reducing Infarct volume in a Rat Model with Occlusion in the Middle Cerebral Artery The typical example of the compound of the present invention (the compound in Example 1) was compared with compounds disclosed in JP 8-508037-A (WO 94/25469, U.S. Pat. No. 5,750,525), which have affinity for AMPA receptors and is effective against cellular necrosis after ischemia in anoxia and hypocalcemia.

Hereinafter, only different features in the experimental method are described.

(2) Experimental Method 2-1) Preparation of the Sample a) Typical Example of the Compound of the Present Invention (The Compound in Example 1)

The compound of the present invention was dissolved in physiological saline to be adjusted to a dosage of 10 or 20 mg/kg/h just before use.

b) Control Compound (JP 8-508037-A, Example 6)

Chemical name: {[3,4-Dihydro-7-(4-morpholinyl)-2,3-dioxo-6-(trifluoromethyl)-1-(2H)-quinoxalinyl] methyl}phosphonic acid (CAS registration number: 161605-73-8)

General name: MPQX, ZK200775

The control compound was dissolved in physiological saline to be adjusted to a dosage of 3 mg/kg/h just before use.

2-4) Occlusion in the Middle Cerebral Artery

Occlusion in the middle cerebral artery was conducted according to the method described above. However, the middle cerebral artery was permanently occluded without removing the nylon embolus.

2-6) Medium and Sample Administration a) Compound of the Present Invention

Two hours after the middle cerebral artery was occluded, a syringe containing the medium or the sample (10 or 20 mg/kg/h) was attached to a catheter for intravenous administration, and half (0.31 ml) of the dosage to be infused for 1 hour was intravenously administered for 1 minute. Thereafter, the medium or the sample was administered continuously for 6 hours at a rate of 0.616 ml/h by the use of a syringe pump for infusion. During administration and for 2 hours after administration was finished, the temperature of the rectum was maintained in the range of 37.0 to 38.5° C. in a system for controlling body temperature. After the body temperature control was finished, the animal was returned to a cage and maintained for 1 day in a breeding room.

b) Control Compound

Two hours after the middle cerebral artery was occluded, a syringe containing the medium or the sample (3 mg/kg/h) was attached to a catheter for intravenous administration, and the medium or the sample was administered continuously for 6 hours at a rate of 0.616 ml/h by means of the syringe pump for infusion. During administration and for 2 hours after administration was finished, the temperature of the rectum was maintained in the range of 37.0 to 38.5° C. in the system for controlling body temperature. After the body temperature control was finished, the animal was returned to a cage and maintained for 1 day in a breeding room.

(3) Results

The middle cerebral artery was permanently occluded by the nylon embolus, and the infarct volume was measured 24 hours after the occlusion was conducted.

a) Compound of the Present Invention

The infarct volume in the cerebral cortex from the control group was 307.2±13.3 mm (n=7). As a result of intravenous administration of the compound of the present invention at a dosage of 10 or 20 mg/kg/h two hours after the middle cerebral artery was occluded, the infarct volume in the cerebral cortex was reduced to 260.7±13.1 mm$^3$ (n=8) and 215.4±21.3 mm$^3$ (n=7) respectively in a dose-dependent manner, and the infarct volume in the 20 mg/kg/h administration group was statistically significantly lower ($p<0.01$) than that of the control group. The degrees of reduction of the infarct volume by the compound of the present invention at dosages of 10 and 20 mg/kg/h were 15% and 30% respectively.

Figure 2:
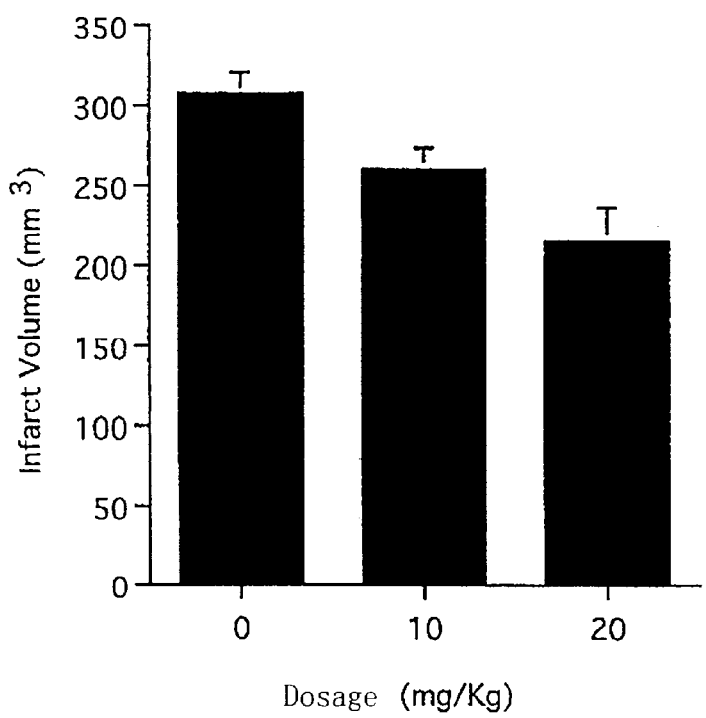
FIG. 2 is a graph showing effect of reducing infarct volume of the compound of the present invention (i.v.) in a rat model with occlusion in the middle cerebral artery (represented by Mean±SE).

The results are shown in the table below and in FIG. 2. Infarct volume (mm$^3$) in the cerebral cortex 24 hours after the middle cerebral artery was occluded

|  | Mean | Standard Error | Number of Animals |
| --- | --- | --- | --- |
| Control | 307.2 | 13.3 | 7 |
| 10 mg/kg | 260.7 | 13.1 | 8 |
| 20 mg/kg | 215.4 | 21.3 | 7 | b) Control Group

The infarct volume in the cerebral cortex from the control group was 294.9±12.6 mm$^3$ (n=9). Although the control compound was intravenously administered at a dosage of 3 mg/kg/h two hours after the middle cerebral artery was occluded, the infarct volume in the cerebral cortex was 284.9±10.9 mm$^3$ (n=11), so there was no difference from the control group.

Figure 3:
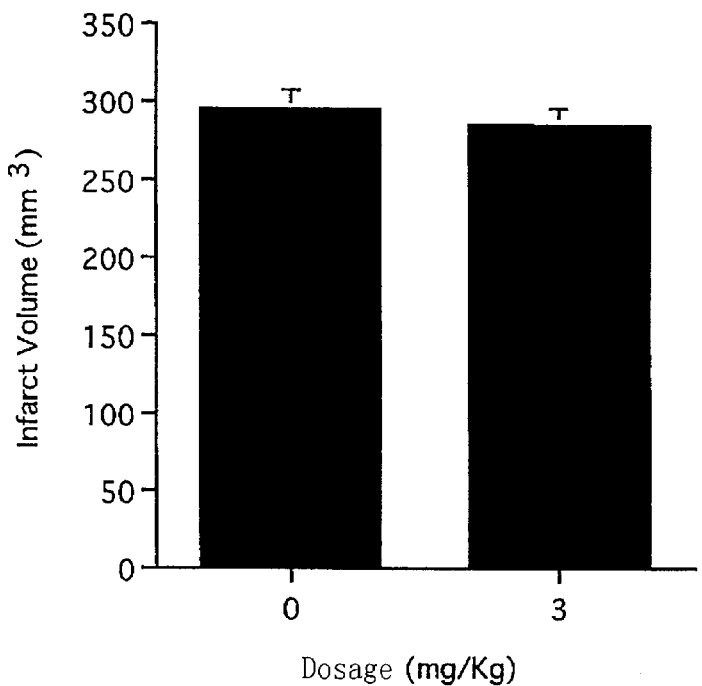
FIG. 3 is a graph showing effect of reducing infarct volume of control compound (i.v.) in a rat model with occlusion in the middle cerebral artery (represented by Mean±SE).

The results are shown in the table below and in FIG. 3. Infarct volume (mm$^3$) in the cerebral cortex 24 hours after the middle cerebral artery was occluded

|  | Mean | Standard Error | Number of Animals |
| --- | --- | --- | --- |
| Control | 294.9 | 12.6 | 9 |
| 3 mg/kg | 284.9 | 10.9 | 11 |

From the results described above, it is evident that the compound of the present invention has the superior effect to that of the control compound.

PHARMACOLOGICAL EXPERIMENT EXAMPLE 5

Antalgic Effect (I) on Mice in a Formalin Test (1) Background

N-type calcium channel that is one of nerve-specific calcium channels is inhibited selectively by a low-molecular peptide SNX-111. In a formalin test as one of analgesic tests, it is reported that SNX-111 has an antalgic action when administered into spinal cord (1, 2).

The antalgic action of the typical example of the compound of the present invention (Example 1) when intravenously administered was examined in the formalin test using mice (3).

(2) Method 2-1) Experimental Animals ddy Mice (male, 4-week-old) purchased from Nippon SLC Ltd. were used in the experiment.

The mice were maintained preliminarily for 4 days (conditions: room temperature, 23±1° C.; humidity, 55±5%; a cycle of bright and dark conditions at 12-hour intervals) A group consisting of about 20 animals was accommodated and maintained in a 20-mouse polycarbonate cage in which wood chip bedding (white flakes) (Charles River Co., Ltd., Tokyo) were placed. In the morning of the day on which the experiment was conducted, the cage was transferred to a laboratory (room temperature, 23° C.; humidity, 35%).

The animals were satiated with MR (Oriental Yeast Co., Ltd.) and free watered with tap water 2-2) Test Compound As the typical example of the compound of the present invention, the compound in Example 1 was used as the test compound.

2-3) Preparation of the Sample 20.4 mg of the test compound was weighed, and 10.2 ml of 5.28% mannitol was added thereto to prepare 2 mg/ml (20 mg/kg) solution. Then, 3.8 ml of 5.28% mannitol was added to 3.8 ml of the 2 mg/ml solution to prepare 1 mg/ml (10 mg/kg) solution. Finally, 2.5 ml of 5.28% mannitol was added to 2.5 ml of the 1 mg/ml solution to prepare 0.5 mg/ml (5 mg/kg) solution. This test compound was weighed and prepared on the day when the experiment was conducted.

2-4) Preparation of the Reagent

30 µl of commercial 35.0 to 38.0% formaldehyde was added to 970 µl physiological saline. The resulting solution was used as 3% formalin. Because the indicated purity of this commercial formaldehyde is 35.0 to 38.0%, the 3% formalin presently prepared and used is accurately 2.84 to 3.08% formalin.

2-5) Grouping, Number of Animals, and Dosage

The treatment group in this test consisted of 4 groups in total, that is, a control group, a 5 mg/kg test compound administration group, a 10 mg/kg administration group, and a 20 mg/kg administration group, and each group consisted of 5 animals.

The control group was given 0.1 ml of 5.28% mannitol per 10 g of the body weight. The test compound was administered at each concentration (0.5 mg/ml, 1 mg/ml, and 2 mg/ml) in an volume of 0.1 ml per 10 g of the body weight into the 5 mg/kg group, 10 mg/kg group and 20 mg/kg group, respectively.

2-6) Test Method 5.28% mannitol was administered via the tail vein into each group given the compound of the present invention or into the control group, and the animals were placed in a transparent plastic observation cage. 5 minutes later, 20 µl of 3% formalin was subcutaneously administered into the bottom of the left hind leg of each mouse. The duration of the behavior of mouse's licking the left hind leg after administration of formalin was measured for 5 minutes and used as an indication of pain. The duration was expressed in second.

2-7) Statistical Test

In the significant test, parametric one-way layout analysis of variance was conducted and then Dunnet-type multiple comparison was made (*: 0.01<p<0.05, **: p<0.01, vs. the control group). For the test, a statistical analysis assistant system with SAS 6.12 (SAS Institute Japan Ltd., Tokyo) integrated in it was used.

(3) Results

Figure 4:
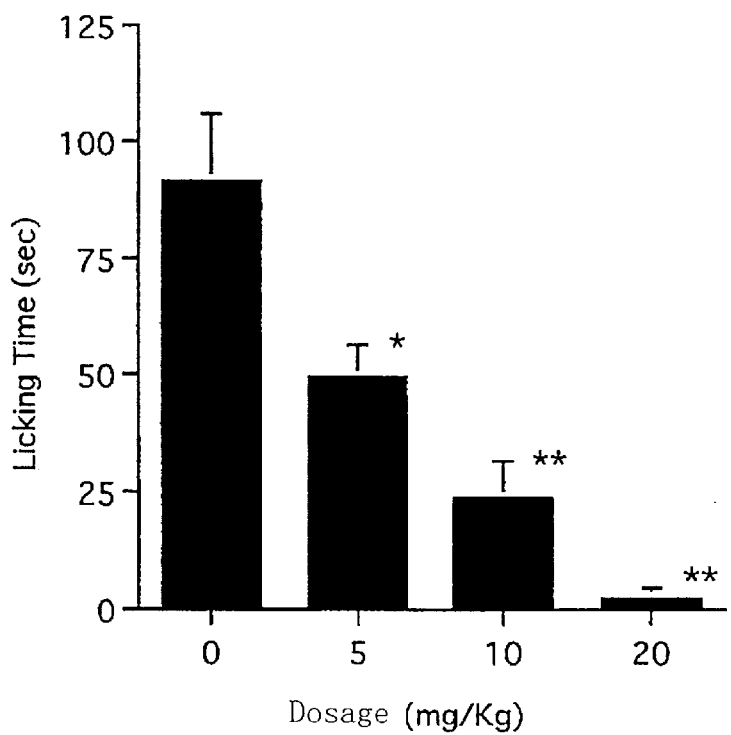
FIG. 4 is a graph showing antalgic effect of the compound of the present invention (i.v.) on mice in a formalin test (represented by Mean±SE)

The effect of the compound of the present invention in the formalin test was expressed in terms of average left hind leg-licking time (sec.) and standard error (see FIG. 4).

|  | Mean | Standard Error | Number of Animals |
| --- | --- | --- | --- |
| Control | 91.4 | 14.5 | 5 |
| 5 mg/kg | 49.4 | 6.8 | 5 |
| 10 mg/kg | 23.6 | 7.9 | 5 |
| 20 mg/kg | 2.2 | 2.2 | 5 |

As is evident from the above results, the groups given the compound of the present invention at dosages 5 mg/kg, 10 mg/kg and 20 mg/kg indicated a statistically significant reduction in licking time as compared to that of the control group.

Similar to N-type calcium channel inhibitor SNX-111, the compound of the present invention i.e. a nerve-specific calcium channel inhibitor exhibits an antalgic action in the formalin test, so it is evident that the compound of the present invention is useful as an agent for treating and improving acute pain.

(4) References (1) Annika B. Malmberg, and Tony L. Yaksh (1994) Voltage-Sensitive Calcium Channels in Spinal Nociceptive Processing: Blockade of N- and P-Type Channels Inhibits Formalin-Induced Nociception. The Journal of Neuroscience 14 (8): 4882–4890.

(2) S. Scott Bowersox, Theresa Gadbois, Tejinder Singh, Mark Pettus, Yong-Xiang Wang and Robert R. Luther (1996) Selective N-type Neuronal Voltage-Sensitive Calcium Channel Blocker, SNX-111, Produces Spinal Antinociception in Rat Models of Acute, Persistent and Neuropathic Pain. The Journal of pharmacology and Experimental Therapeutics 279 (3): 1243–1249.

(3) Hunskaar S, Fasmer O B and Hole K (1985) Formalin test in mice, a useful technique for evaluating mild analgesics. Journal of Neuroscience Methods 14 (1): 69–76.

PHARMACOLOGICAL EXPERIMENT EXAMPLE 6

Antalgic Effect (II) on Mice in a Formalin Test

The typical example of the compound of the present invention (the compound in Example 1) was compared with morphine and indomethacin in the same manner as in Pharmacological Experimental Example 5 above.

Hereinafter, only different features in the experimental method are described.

(2) Experimental Method 2-1) Preparation of the Sample a) Typical Example of the Compound of the Present Invention (the Compound in Example 1)

20.4 mg of the compound of the present invention was weighed, and 10.2 ml of 5.28% mannitol was added thereto to prepare 2 mg/ml (20 mg/kg) solution. Then, 3.8 ml of 5.28% mannitol was added to 3.8 ml of the 2 mg/ml solution to prepare 1 mg/ml (10 mg/kg) solution. Finally, 2.5 ml of 5.28% mannitol was added to 2.5 ml of the 1 mg/ml solution to prepare 0.5 mg/ml (5 mg/kg) solution. The test compound was weighed and prepared on the day when the experiment was conducted.

b) Control Compounds b-1) Morphine 17.0 mg of morphine purchased as a reagent was weighed, and 5.67 ml physiological saline was added thereto to form 3 mg/ml (30 mg/kg) solution. Then, 2.6 ml physiological saline was added to 1.3 ml of the 3 mg/ml solution to prepare 1 mg/ml (10 mg/kg) solution. Finally, 2.1 ml physiological saline was added to 0.9 ml of the 1 mg/ml solution to prepare 0.3 mg/ml (3 mg/kg) solution. The test compound was weighed and prepared on the day when the experiment was conducted.

b-2) Indomethacin 12.9 mg of indomethacin purchased as a reagent was weighed, and 12.9 ml of 0.5% methyl cellulose (MC) was added thereto to form 1 mg/ml (10 mg/kg) suspension. Then, 2.24 ml of 0.5% MC was added to 0.96 ml of the 1 mg/ml suspension to prepare 0.3 mg/ml (3 mg/kg) suspension. Finally, 1.6 ml of 0.5% MC was added to 0.8 ml of the 0.3 mg/ml suspension to prepare 0.1 mg/ml (1 mg/kg) suspension. The test compound was weighed and prepared on the day when the experiment was conducted.

2-5) Grouping, Number of Animals, and Dosage a) Compound of the Present Invention The treatment group by the compound of the present invention consisted of 4 groups in total, that is, a control group, a 5 mg/kg compound administration group, a 10 mg/kg compound administration group, and a 20 mg/kg compound administration group, and each group consisted of 5 animals.

The control group was given 0.1 ml of 5.28% mannitol per 10 g of the body weight via the tail vein. The compound of the present invention was administered via the tail vein at each concentration (0.5 mg/ml, 1 mg/ml, and 2 mg/ml) in an volume of 0.1 ml per 10 g of the body weight into the 5 mg/kg group, 10 mg/kg group and 20 mg/kg group, respectively.

b-1) Morphine

The treatment group by morphine consisted of 4 groups in total, that is, a control group, a 3 mg/kg morphine administration group, a 10 mg/kg morphine administration group, and a 30 mg/kg morphine administration group, and each group consisted of 5 animals.

The control group was orally given 0.1 ml of physiological saline per 10 g of the body weight. Morphine was orally administered at each concentration (0.3 mg/ml, 1 mg/ml, and 3 mg/ml) in a volume of 0.1 ml per 10 g of the body weight into the 3 mg/kg group, 10 mg/kg group and 30 mg/kg group, respectively.

b-2) Indomethacin

The treatment group by indomethacin consisted of 4 groups in total, that is, a control group, a 1 mg/kg indomethacin administration group, a 3 mg/kg indomethacin administration group, and a 10 mg/kg indomethacin administration group, and each group consisted of 5 animals.

The control group was orally given 0.1 ml of 0.5% MC per 10 g of the body weight. Indomethacin was orally administered at each concentration (0.1 mg/ml, 0.3 mg/l, and 1 mg/ml) in a volume of 0.1 ml per 10 g of the body weight into the 1 mg/kg group, 3 mg/kg group and 10 mg/kg group, respectively.

2-6) Test Method a) Compound of the Present Invention 5.28% mannitol was administered via the tail vein into each group given the compound of the present invention or into the control group, and the animals were placed in a transparent plastic observation cage. 5 minutes later, 20 μl of 3% formalin was subcutaneously administered into the bottom of the left hind leg of each mouse. The duration of the behavior of mouse's licking the left hind leg after administration of formalin was measured for 5 minutes and used as an indication of pain. The duration was expressed in second.

b-1) Morphine

Physiological saline was orally administered into each morphine group or the control group, and the animals were placed in a transparent plastic observation cage. 30 minutes later, 20 μl of 3% formalin was subcutaneously administered into the bottom of the left hind leg of each mouse. The subsequent steps are the same as in the test method of the compound of the present invention.

b-2) Indomethacin 0.5% MC was orally administered into each indomethacin group or the control group, and the animals were placed in a transparent plastic observation cage. 90 minutes later, 20 μl of 3% formalin was subcutaneously administered into the bottom of the left hind leg of each mouse. The subsequent steps are the same as in the test method of the compound of the present invention.

(3) Results

Figure 5:
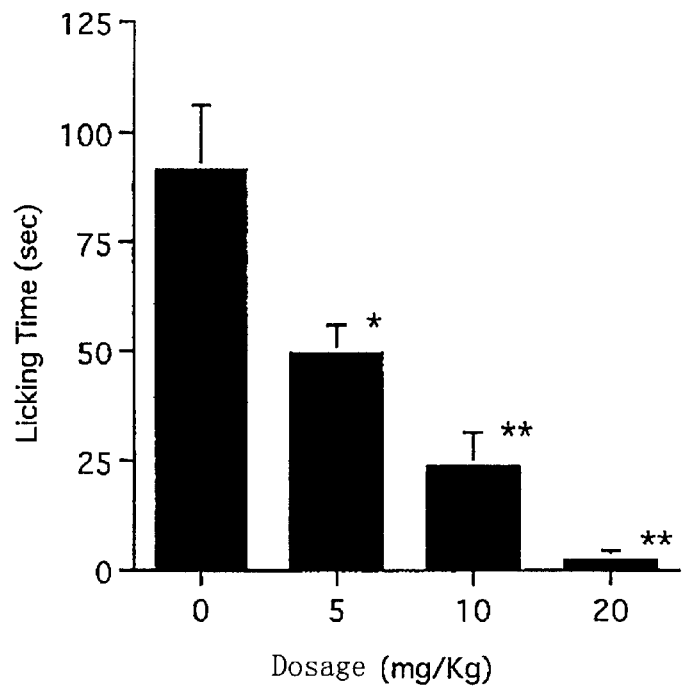
FIG. 5 is a graph showing antalgic effect of the compound of the present invention (i.v.) on mice in a formalin test (represented by Mean±SE).

The effect of the compound of the present invention in the formalin test was expressed in terms of average left hind leg-licking time (sec.) and standard error, as follows.

a) Action of the Compound of the Present Invention on the Formalin Test (see FIG. 5).

Figure 6:
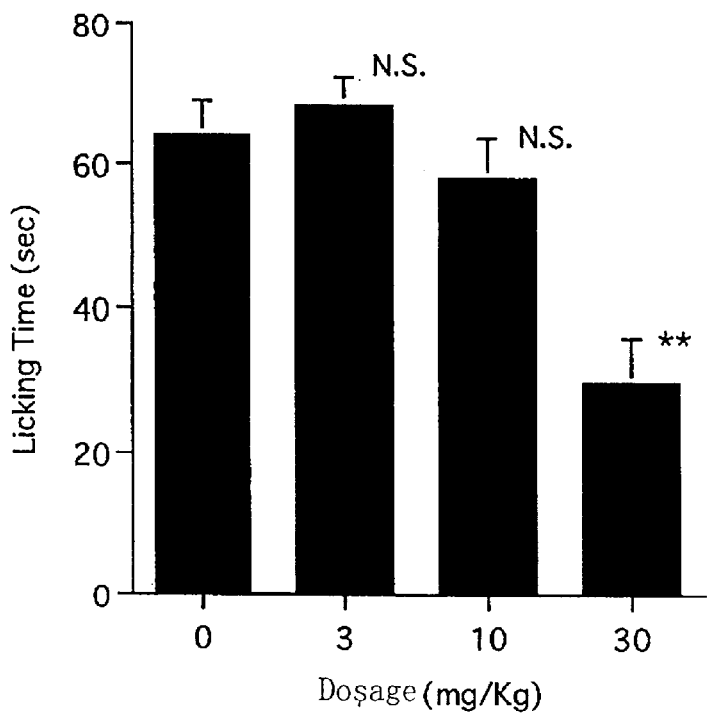
FIG. 6 is a graph showing antalgic effect of morphine (p.o.) on mice in a formalin test (represented by Mean±SE).

|  | Mean | Standard Error | Number of Animals |
| --- | --- | --- | --- |
| Control | 91.4 | 14.5 | 5 |
| 5 mg/kg | 49.4 | 6.8 | 5 |
| 10 mg/kg | 23.6 | 7.9 | 5 |
| 20 mg/kg | 2.2 | 2.2 | 5 | b-1) Action of Morphine on the Formalin Test (see FIG. 6).

Figure 7:
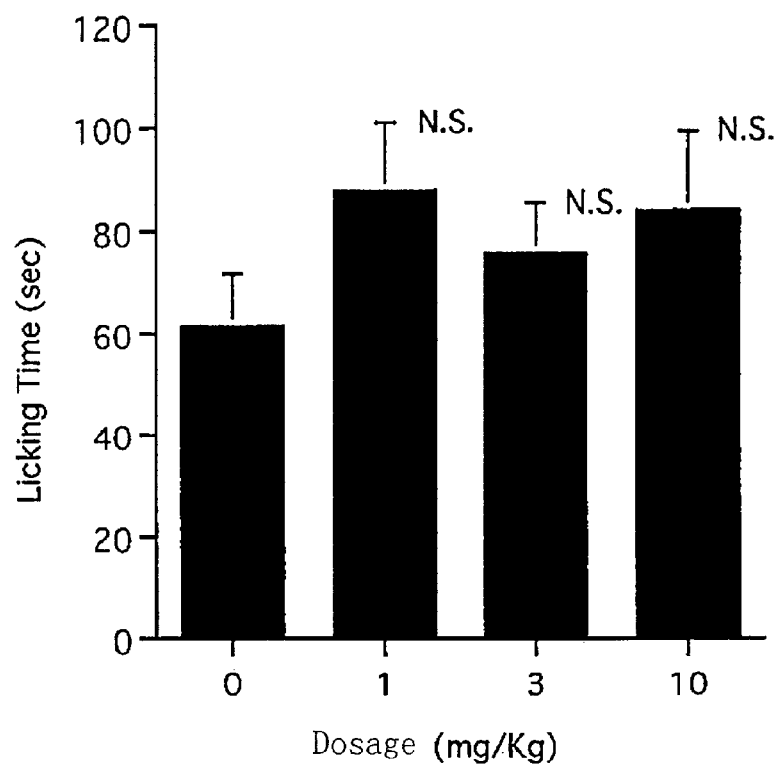
FIG. 7 is a graph showing antalgic effect of indomethacin (p.o.) on mice in a formalin test (represented by Mean±SE).

|  | Mean | Standard Error | Number of Animals |
| --- | --- | --- | --- |
| Control | 64.0 | 4.9 | 5 |
| 3 mg/kg | 68.2 | 4.0 | 5 |
| 10 mg/kg | 58.0 | 5.6 | 5 |
| 30 mg/kg | 29.6 | 6.2 | 5 | b-2) Action of Indomethacin on the Formalin Test (see FIG. 7).

|  | Mean | Standard Error | Number of Animals |
| --- | --- | --- | --- |
| Control | 61.4 | 10.4 | 5 |
| 1 mg/kg | 87.8 | 13.2 | 5 |
| 3 mg/kg | 75.8 | 9.8 | 5 |
| 10 mg/kg | 84.0 | 15.0 | 5 |

From the above experimental results, it is evident that indomethacin does not have any effect, while the compound of the present invention has an excellent effect similar to that of morphine.

Hereinafter, Preparatory Examples of the starting materials in the present invention are specifically described below, but aldehyde compound and piperazine compound, such as 2-(1-methylethyl)-5-oxo-2-phenyl pentane nitrile etc. can be synthesized according to the following literatures:

(1) Compt. Rend., 256, 702 (1963).

(2) Compt. Rend., 256, 2632 (1963)

(3) Collect. Czech. Chem. Commun., 57, 1967 (1992).

PREPARATORY EXAMPLES

Preparatory Example 1

Synthesis of 1-[2-(4-Fluorophenoxy)ethyl]piperazine

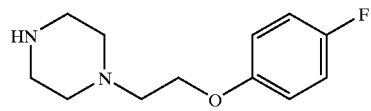

1-Benzyl piperazine (8.3 g) and 2-(4-fluorophenoxy)ethyl bromide (10.3 g) were dissolved in acetonitrile (100 ml), and Potassium carbonate (6.51 g) was added thereto, and the mixture was stirred overnight at 70 to 80° C. The organic layer was partitioned by adding aqueous saturated sodium bicarbonate and ethyl acetate, washed with water and brine, dried over sodium sulfate anhydrous, and evaporated. The residue was purified by silica gel column chromatography (hexane/ethyl acetate system) to give a colorless oil (12.3 g). The resulting colorless oil (12.3 g) was dissolved in methanol (120 ml), and 10% palladium hydroxide/carbon was added thereto followed by overnight stirring in a hydrogen atmosphere. The reaction solution was filtered and evaporated, whereby the title compound (7.7 g, 73%) was obtained as a pale yellow oil.

Free Compound;

$^1$H-NMR (400 MHz, CDCl$_3$); δ (ppm) 2.55 (br, 4H), 2.78 (t, J=6 Hz, 2H), 2.92 (br-t, J=4.8 Hz, 4H), 4.07 (t, J=6 Hz, 2H), 6.81–6.88 (m, 2H), 6.93–7.00 (m, 2H).

Preparatory Example 2

Synthesis of 1-(2-Phenoxyethyl)piperazine

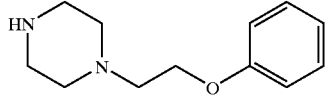

Piperazine (2.15 g) and 2-phenoxyethyl bromide (1.00 g) were dissolved in tetrahydrofuran (30 ml), and the mixture was stirred at 40 to 60° C. for 36 hours. The reaction solution was evaporated, and aqueous saturated sodium bicarbonate and diethyl ether were added to the residue, and the aqueous layer was partitioned. Methylene chloride was added to the aqueous layer, and the organic layer was partitioned. The organic layer was dried over sodium sulfate anhydrous and evaporated, whereby the title compound (664 mg, 65%) was obtained.

Free Compound;

$^1$H-NMR (400 MHz, CDCl$_3$); δ (ppm) 2.56 (br, 4H), 2.80 (t, J=6 Hz, 2H), 2.92 (br-t, J=4.8 Hz, 4H), 4.12 (t, J=6 Hz, 2H), 6.88–6.98 (m, 3H), 7.26–7.32 (m, 2H).

Preparatory Example 3

Synthesis of 1-[2-(4-Fluorophenoxy)propyl]piperazine

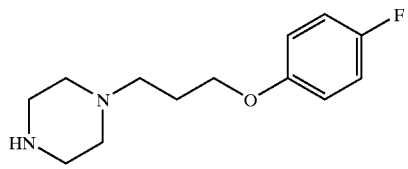

1-Formyl piperazine (2.8 g) and 2-(4-fluorophenoxy)propyl chloride (4.7 g) were dissolved in dimethylformamide (60 ml), and sodium iodide (3.2 g) and triethylamine (4.4 ml) were added thereto, and the mixture was stirred overnight at 50 to 70° C. The organic layer was partitioned by adding water and ethyl acetate, washed with brine, dried over sodium sulfate anhydrous, and evaporated. The residue was purified by Cromatorex NH silica gel column chromatography (ethyl acetate). The resulting yellow oil (12.3 g) was dissolved in methanol (20 ml), and 5N aqueous sodium hydroxide (10 ml) was added thereto and then stirred for 1 hour under reflux. The reaction mixture was evaporated, then the organic layer was partitioned by adding water and ethyl acetate, washed with brine, and dried over sodium sulfate anhydrous. The residue obtained by evaporation was purified by Cromatorex NH silica gel column chromatography (ethyl acetate/methanol system), whereby the title compound (2.2 g, 38%) was obtained as a pale yellow oil.
Free Compound;
$^1$H-NMR (400 MHz, CDCl$_3$); δ (ppm) 1.93 (quintet, 7.2 Hz, 2H), 2.41 (br, 4H), 2.47 (t, J=7.2 Hz, 2H), 2.87 (br-t, J=5.0 Hz, 4H), 3.94 (t, J=7.2 Hz, 2H), 6.79–6.85 (m, 2H), 6.90–6.97 (m, 2H).

Preparatory Example 4

Synthesis of 1-(4-Phenoxybutyl)piperazine

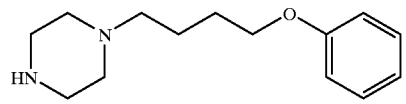

tert-Butyl-1-piperazine carboxylate (1.0 g) and 4-phenoxybutyl chloride (991 mg) were dissolved in acetonitrile (50 ml), and triethylamine (1.5 ml) and sodium iodide (160 mg) were added thereto, and the mixture was stirred overnight at 50 to 70° C. After concentration, the organic layer was partitioned by adding water and ethyl acetate, washed with brine, dried over sodium sulfate anhydrous, and evaporated. The resulting residue was purified by Cromatorex NH silica gel column chromatography (hexane/ethyl acetate system) to give a colorless oil (222 mg). This colorless oil (222 mg) was dissolved in dichloromethane (10 ml), and trifluoroacetic acid (1 ml) was added thereto, and the mixture was stirred overnight at room temperature. The organic layer was partitioned by adding aqueous saturated sodium bicarbonate and dichloromethane to the reaction mixture and dried over sodium sulfate anhydrous. The residue was evaporated, whereby the title compound (190 mg, 15%) was obtained as a pale yellow oil.
Free Compound;
$^1$H-NMR (400 MHz, CDCl$_3$); δ (ppm) 1.63–1.72 (m, 2H), 1.76–1.86 (m, 2H), 2.38–2.43 (m, 2H), 2.43–2.52 (br, 4H), 2.92–2.98 (m, 4H), 3.96–4.00 (m, 2H), 6.87–6.96 (m, 3H), 7.25–7.30 (m, 2H).

Further, the following compounds were synthesized according to Preparatory Examples 1 to 4.

Preparatory Example 5

1-[2-(4-Florophenoxy)ethyl]piperazine

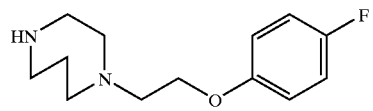

Free Compound;
$^1$H-NMR (400 MHz, CDCl$_3$); δ (ppm) 1.70–1.82 (m, 3H), 2.78–2.88 (m, 4H), 2.90–3.00 (m, 6H), 4.03 (t, J=6 Hz), 6.81–6.87 (m, 2H), 6.93–7.00 (m, 2H).

Preparatory Example 6

1-[2-(4-Nitrophenoxy)ethyl]piperazine

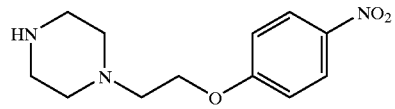

Free Compound;
$^1$H-NMR (400 MHz, CDCl$_3$); δ (ppm) 2.35 (br-s, 4H), 2.62 (t, J=5.8 Hz, 2H), 2.65–2.75 (m, 4H), 4.00 (t, J=5.8 Hz, 2H), 6.76 (d, J=9.2 Hz, 2H), 7.95 (d, J=9.2 Hz, 2H).

Similarly, 1-[4-(phenoxy)butyl]piperazine was also obtained.

Hereinafter, the present invention is described in more detail by reference to Examples, which however are not intended to limit the present invention.

EXAMPLES

Example 1

Synthesis of 1-[(4-Cyano-5-methyl-4-phenyl)hexyl]-4-[2-(4-fluorophenoxy)ethyl]piperazine

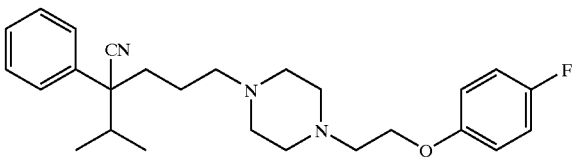

2-(1-Methylethyl)-5-oxo-2-phenyl pentane nitrile (100 mg), 1-[2-(4-fluorophenyl)ethyl]piperazine (104 mg) and acetic acid (0.13 ml) were dissolved in dichloromethane (8.0 ml), and sodium triacetoxy borohydride (196 mg) was added thereto, and the mixture was stirred overnight at room temperature. The organic layer was partitioned by adding aqueous saturated sodium bicarbonate and dichloromethane, washed with water, and dried over sodium sulfate anhydrous. The residue obtained by evaporation was purified by Cromatorex NH silica gel column chromatography (hexane/ethyl acetate system) to give the title compound (168 mg, 86%) as a colorless oil. 4 N hydrogen chloride/ethyl acetate solution was added to a methanol solution containing this free compound (168 mg). After stirred for 10 minutes, the solvent was evaporated, whereby the hydrochloride (190 mg) of the title compound was obtained.

Free Compound;

¹H-NMR (400 MHz, CDCl₃); δ (ppm) 0.77 (d, J=6.8 Hz, 3H), 1.05–1.17 (m, 1H), 1.20 (d, J=6.8 Hz, 3H), 1.50–1.60 (m, 1H), 1.88 (dt, J=4.4 Hz, 12.4 Hz, 1H), 2.06–2.19 (m, 2H), 2.24–2.30 (m, 2H), 2.30–2.43 (m, 4H), 2.46–2.62 (m, 4H), 2.77 (t, J=5.8 Hz, 2H), 4.04 (t, J=5.8 Hz, 2H), 6.80–6.85 (m, 2H), 6.91–6.99 (m, 2H), 7.25–7.32 (m, 1H), 7.32–7.40 (m, 4H).

Hydrochloride;

¹H-NMR (400 MHz, DMSO-d₆); δ (ppm) 0.68 (d, J=6.6 Hz, 3H), 1.11 (d, J=6.6 Hz, 3H), 1.22–1.34 (m, 1H), 1.58–1.62 (m, 1H), 2.06–2.30 (m, 3H), 3.00–3.25 (m, 2H), 3.30–3.80 (m, 10H), 4.36 (br-s, 2H), 6.98–7.07 (m, 2H), 7.11–7.20 (m, 2H), 7.32–7.40 (m, 1H), 7.40–7.50 (m, 4H).

ESI-Mass; 424 (MH+).

Example 2

Synthesis of 1-[(4-Cyano-5-methyl-4-phenyl)hexyl]-4-[3-(4-fluorophenoxy)propyl]piperazine

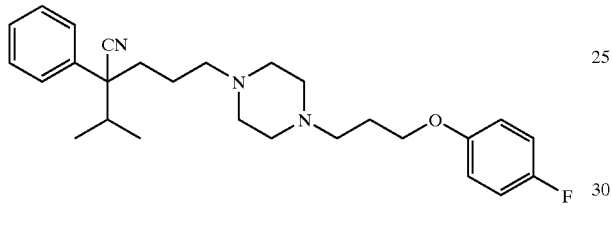

The title compound (196 mg, 99%) was obtained as a colorless oil from 2-(1-methylethyl)-5-oxo-2-phenyl pentane nitrile (100 mg) and 1-[3-(4-fluorophenyl)propyl] piperazine (111 mg) in the same manner as in Example 1. This free compound (194 mg) was treated in the same manner as in Example 1 to give the hydrochloride (196 mg) of the title compound.

Free Compound;

¹H-NMR (400 MHz, CDCl₃); δ (ppm) 0.77 (d, J=6.8 Hz, 3H), 1.05–1.19 (m, 1H), 1.20 (d, J=6.8 Hz, 3H), 1.84–2.00 (m, 3H), 2.07–2.18 (m, 2H), 2.23–2.55 (m, 13H), 3.92–3.99 (m, 2H), 6.79–6.85 (m, 2H), 6.91–6.99 (m, 2H), 7.25–7.32 (m, 1H), 7.32–7.40 (m, 4H).

Hydrochloride;

¹H-NMR (400 MHz, DMSO-d₆); δ (ppm) 0.67 (d, J=6.6 Hz, 3H), 1.11 (d, J=6.6 Hz, 3H), 1.22–1.34 (m, 1H), 1.56–1.72 (m, 1H), 2.06–2.28 (m, 5H), 3.00–3.95 (m, 12H), 4.00–4.10 (m, 2H), 6.92–7.01 (m, 2H), 7.10–7.18 (m, 2H), 7.33–7.42 (m, 1H), 7.42–7.48 (m, 4H).

ESI-Mass; 438 (MH+).

Example 3

Synthesis of 1-[(4-Cyano-5-methyl-4-phenyl)hexyl]-4-[2-(4-fluorophenoxy)ethyl]piperazine

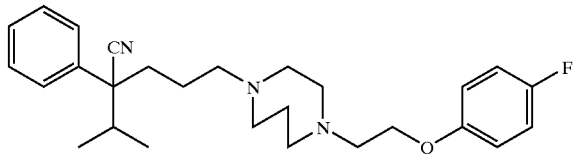

The title compound (166 mg, 82%) was obtained as a colorless oil from 2-(1-methylethyl)-5-oxo-2-phenyl pentane nitrile (100 mg) and 1-[2-(4-fluorophenyl)ethyl] homopiperazine (111 mg) in the same manner as in Example 1. This free compound (166 mg) was treated in the same manner as in Example 1 to give the hydrochloride (169 mg) of the title compound.

Free Compound;

¹H-NMR (400 MHz, CDCl₃); δ (ppm) 0.77 (d, J=6.8 Hz, 3H), 1.02–1.16 (m, 1H), 1.19 (d, J=6.8 Hz, 3H), 1.46–1.57 (m, 1H), 1.70–1.77 (m, 2H), 1.88 (dt, J=4.4 Hz, 12.4 Hz, 1H), 2.06–2.19 (m, 2H), 2.33–2.45 (m, 2H), 2.53–2.57 (m, 4H), 2.74–2.81 (m, 4H), 2.92 (t, J=6.2 Hz, 2H), 4.00 (t, J=6.2 Hz, 2H), 6.80–6.86 (m, 2H), 6.92–7.00 (m, 2H), 7.26–7.33 (m, 1H), 7.33–7.40 (m, 4H).

Hydrochloride;

¹H-NMR (400 MHz, DMSO-d₆); δ (ppm) 0.67 (d, J=6.6 Hz, 3H), 1.11 (d, J=6.6 Hz, 3H), 1.18–1.22 (m, 1H), 1.55–1.70 (m, 1H), 2.06–2.28 (m, 5H), 3.00–3.20 (m, 2H), 3.20–3.70 (m, 8H), 3.70–3.96 (m, 2H), 4.30–4.40 (m, 2H), 6.98–7.05 (m, 2H), 7.11–7.20 (m, 2H), 7.33–7.40 (m, 1H), 7.40–7.50 (m, 4H).

ESI-Mass; 438 (MH+).

Example 4

Synthesis of 1-[(3-Cyano-4-methyl-3-phenyl)pentyl]-4-[2-(4-fluorophenoxy)ethyl]homopiperazine

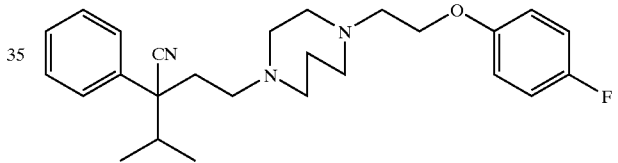

The title compound (85 mg, 57%) was obtained as a colorless oil from 2-(1-methylethyl)-4-oxo-2-phenyl butyronitrile (70 mg) and 1-[2-(4-fluorophenyl)ethyl] homopiperazine (83 mg) in the same manner as in Example 1. This free compound (85 mg) was treated in the same manner as in Example 1 to give the hydrochloride (88 mg) of the title compound.

Free Compound;

¹H-NMR (400 MHz, CDCl₃); δ (ppm) 0.77 (d, J=6.8 Hz, 3H), 1.20 (d, J=6.8 Hz, 3H), 1.70–1.77 (m, 2H), 1.99–2.15 (m, 3H), 2.30–2.37 (m, 1H), 2.45–2.90 (m, 9H), 2.90 (t, J=6.2 Hz, 2H), 3.99 (t, J=6.2 Hz, 2H), 6.80–6.86 (m, 2H), 6.93–7.00 (m, 2H), 7.28–7.33 (m, 1H), 7.33–7.40 (m, 4H).

Hydrochloride;

¹H-NMR (400 MHz, DMSO-d₆); δ (ppm) 0.68 (d, J=6.6 Hz, 3H), 1.13 (d, J=6.6 Hz, 3H), 1.26 (m, 1H), 2.10–2.34 (m, 3H), 2.51–2.25 (m, 2H), 3.00–3.45 (m, 6H), 3.45–3.67 (m, 3H), 3.67–3.39 (m, 2H), 4.30–4.43 (m, 2H), 7.00–7.07 (m, 2H), 7.12–7.20 (m, 2H), 7.36–7.44 (m, 1H), 7.44–7.51 (m, 4H).

ESI-Mass; 424 (MH+).

Example 5

Synthesis of 1-[(3-Cyano-4-methyl-3-phenyl)pentyl]-4-[3-(4-fluorophenoxy)propyl]piperazine

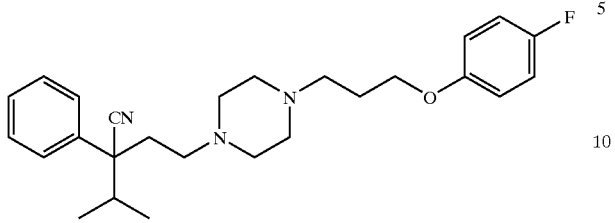

The title compound (95 mg, 64%) was obtained as a colorless oil from 2-(1-methylethyl)-4-oxo-2-phenyl butyronitrile (70 mg) and 1-[3-(4-fluorophenoxy)propyl] piperazine (83 mg) in the same manner as in Example 1. This free compound (94 mg) was treated in the same manner as in Example 1 to give the hydrochloride (97 mg) of the title compound.

Free Compound;
$^1$H-NMR (400 MHz, CDCl$_3$); δ (ppm) 0.77 (d, J=6.6 Hz, 3H), 1.20 (d, J=6.6 Hz, 3H), 1.88–2.16 (m, 5H), 2.30–2.57 (m, 12H), 3.92–4.00 (m, 2H), 6.78–6.85 (m, 2H), 6.92–6.98 (m, 2H), 7.28–7.34 (m, 1H), 7.36–7.40 (m, 4H).

Hydrochloride;
$^1$H-NMR (400 MHz, DMSO-d$_6$); δ (ppm) 0.68 (d, J=6.6 Hz, 3H), 1.13 (d, J=6.6 Hz, 3H), 2.10–2.28 (m, 4H), 2.57–2.70 (m, 2H), 3.00–3.90 (m, 11H), 4.00–4.10 (m, 2H), 6.93–7.00 (m, 2H), 7.10–7.17 (m, 2H), 7.37–7.44 (m, 1H), 7.46–7.50 (m, 4H).

ESI-Mass; 424 (MH+).

Example 6

Synthesis of 1-[(4-Cyano-5-methyl-4-phenyl)hexyl]-4-(4-phenoxybutyl)piperazine

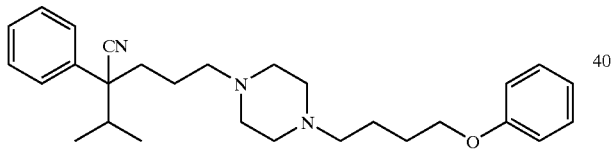

The title compound (135 mg, 96%) was obtained as a colorless oil from 2-(1-methylethyl)-5-oxo-2-phenyl pentane nitrile (70 mg) and 1-(4-phenoxypropyl)piperazine (76 mg) in the same manner as in Example 1. This free compound (135 mg) was treated in the same manner as in Example 1 to give the hydrochloride (140 mg) of the title compound.

Free Compound;
$^1$H-NMR (400 MHz, CDCl$_3$); δ (ppm) 0.78 (d, J=6.6 Hz, 3H), 1.05–1.17 (m, 2H), 1.20 (d, J=6.6 Hz, 3H), 1.24–1.28 (m, 1H), 1.50–1.58 (m, 1H), 1.61–1.69 (m, 1H), 1.73–1.82 (m, 2H), 1.88 (dt, J=4.4 Hz, 12.4 Hz, 1H), 2.05–2.18 (m, 2H), 2.20–2.50 (m, 11H), 3.96 (t, J=6.4 Hz, 2H), 6.88 (d, J=7.2 Hz, 2H), 6.92 (t, J=7.2 Hz, 1H), 7.23–7.40 (m, 3H), 7.44–7.49 (m, 4H).

Hydrochloride;
$^1$H-NMR (400 MHz, DMSO-d$_6$); δ (ppm) 0.67 (d, J=6.6 Hz, 3H), 1.11 (d, J=6.6 Hz, 3H), 1.20–1.33 (m, 1H), 1.55–1.95 (m, 4H), 2.00–2.30 (m, 3H), 2.95–3.25 (m, 4H), 3.25–3.85 (m, 9H), 3.98 (t, J=6 Hz, 2H), 6.85–6.97 (m, 3H), 7.28 (br-t, J=8 Hz, 2H), 7.34–7.40 (m, 1H), 7.40–7.48 (m, 4H).

ESI-Mass; 434 (MH+).

Example 7

Synthesis of 1-[(4-Cyano-5-methyl-4-phenyl)hexyl]-4-(2-phenoxyethyl)piperazine

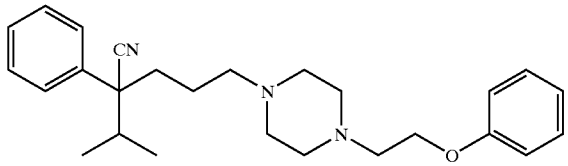

The title compound (520 mg, 64%) was obtained as a colorless oil from 2-(1-methylethyl)-5-oxo-2-phenyl pentane nitrile (429 mg) and 1-(2-phenoxyethyl)piperazine (644 mg) in the same manner as in Example 1. This free compound (510 mg) was treated in the same manner as in Example 1 to give the hydrochloride (600 mg) of the title compound.

Free Compound;
$^1$H-NMR (400 MHz, CDCl$_3$); δ (ppm) 0.77 (d, J=6.8 Hz, 3H), 1.02–1.16 (m, 1H), 1.20 (d, J=6.8 Hz, 3H), 1.50–1.61 (m, 1H), 1.88 (dt, J=4.4, 12.4 Hz, 1H), 2.08–2.18 (m, 2H), 2.27 (br-t, J=7.6 Hz, 2H), 2.30–2.46 (m, 4H), 2.46–2.70 (m, 4H), 2.78 (t, J=5.8 Hz, 2H), 4.08 (t, J=5.8 Hz, 2H), 6.88–6.95 (m, 3H), 7.24–7.30 (m, 3H), 7.32–7.38 (m, 4H).

Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.16–1.30 (m, 1H), 1.55–1.65 (m, 1H), 2.05–2.25 (m, 3H), 2.90–3.65 (m, 12H), 4.20–4.40 (m, 2H), 6.69–6.99 (m, 3H), 7.29–7.33 (m, 2H), 7.36–7.40 (m, 1H), 7.41–7.48 (m, 4H).

ESI-Mass; 406 (MH+).

Example 8

Synthesis of 1-[(4-Cyano-5-methyl-4-phenyl)hexyl]-4-[2-(4-nitrophenoxy)ethyl]piperazine

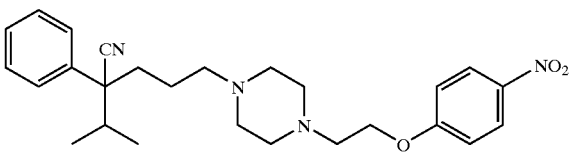

The title compound (1.19 g, 71%) was obtained as a yellow oil from 2-(1-methylethyl)-5-oxo-2-phenyl pentane nitrile (800 mg) and 1-[2-(4-nitrophenoxy)ethyl]piperazine (1.40 g) in the same manner as in Example 1. This free compound (225 mg) was treated in the same manner as in Example 1 to give the hydrochloride (255 mg) of the title compound.

Free Compound;
$^1$H-NMR (400 MHz, CDCl$_3$); δ (ppm) 0.77 (d, J=6.4 Hz, 3H), 1.05–1.18 (m, 1H), 1.20 (d, J=6.4 Hz, 3H), 1.45–1.60 (m, 1H), 1.88 (dt, J=5.0, 13.0 Hz, 1H), 2.08–2.20 (m, 2H), 2.28 (br-t, J=7.5 Hz, 2H), 2.30–2.45 (m, 4H), 2.50–2.62 (m, 4H), 2.82 (t, J=5.8 Hz, 2H), 4.17 (t, J=5.8 Hz, 2H), 6.94–6.96 (m, 2H), 7.26–7.31 (m, 1H), 7.36–7.37 (m, 4H), 8.18–8.20 (m, 2H).

Hydrochloride;
$^1$H-NMR (400 MHz, DMSO-d$_6$): δ (ppm) 0.67 (d, J=6.8 Hz, 3H), 1.12 (d, J=6.8 Hz, 3H), 1.20–1.33 (m, 1H), 1.56–1.70 (m, 1H), 2.05–2.25 (m, 3H), 3.00–3.80 (m, 12H), 4.45–4.60 (m, 2H), 7.18–7.24 (m, 2H), 7.34–7.41 (m, 1H), 7.43–7.49 (m, 4H), 8.22–8.28 (m, 2H).
ESI-Mass; 451 (MH+).

Example 9

Synthesis of 1-[4-Cyano-5-methyl-4-(4-methylphenyl)hexyl]-4-[2-(4-fluorophenoxy)ethyl]piperazine

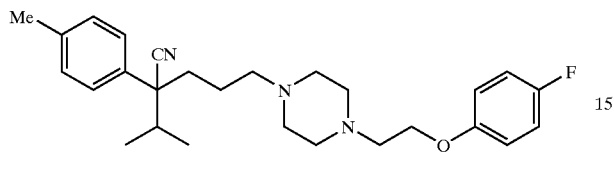

The title compound (376 mg, 59%) was obtained as a colorless oil from 2-(1-methylethyl)-5-oxo-2-(4-methylphenyl)pentane nitrile (334 mg) and 1-[2-(4-fluorophenoxy)ethyl]piperazine (360 mg) in the same manner as in Example 1. This free compound (42 mg) was treated in the same manner as in Example 1 to give the hydrochloride (49 mg) of the title compound.
Free Compound;
$^1$H-NMR (400 MHz, CDCl$_3$); δ (ppm) 0.77 (d, J=6.8 Hz, 3H), 1.06–1.17 (m, 1H), 1.18 (d, J=6.8 Hz, 3H), 1.48–1.61 (m, 1H), 1.85 (dt, J=4.4, 12.5 Hz, 1H), 2.03–2.16 (m, 2H), 2.27 (t, J=7.1 Hz, 2H), 2.30–2.45 (m, 4H), 2.34 (s, 3H), 2.45–2.65 (m, 4H), 2.77 (t, J=5.8 Hz, 2H), 4.04 (t, J=5.8 Hz, 2H), 6.81–6.85 (m, 2H), 6.92–6.98 (m, 2H), 7.15 (d, J=8.4 Hz, 2H), 7.23 (d, J=8.4 Hz, 2H).
Hydrochloride;
$^1$H-NMR (400 MHz, D$_2$O); δ (ppm) 0.60 (d, J=6.6 Hz, 3H), 1.01 (d, J=6.6 Hz, 3H), 1.18–1.32 (m, 1H), 1.52–1.65 (m, 1H), 1.86–1.96 (m, 1H), 2.06–2.17 (m, 2H), 2.20 (s, 3H), 2.90–3.00 (m, 1H), 3.04–3.13 (m, 1H), 3.22–3.48 (m, 10H), 4.18 (t, J=4.9 Hz, 2H), 6.82–6.87 (m, 2H), 6.92–6.99 (m, 2H), 7.18 (d, J=8.2 Hz, 2H), 7.23 (d, J=8.2 Hz, 2H).
ESI-Mass; 438 (MH+).

Example 10

Synthesis of 1-[4-Cyano-5-methyl-4-(4-chlorophenyl)hexyl]-4-[2-(4-fluorophenoxy)ethyl]piperazine

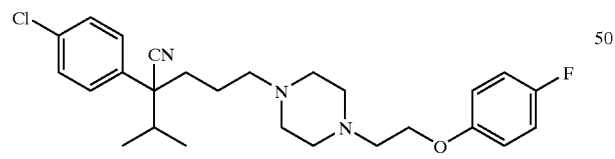

The title compound (599 mg, 63%) was obtained as a colorless oil from 2-(1-methylethyl)-5-oxo-2-(4-chlorophenyl)pentane nitrile (496 mg) and 1-[2-(4-fluorophenoxy)ethyl]piperazine (490 mg) in the same manner as in Example 1. This free compound (46 mg) was treated in the same manner as in Example 1 to give the hydrochloride (53 mg) of the title compound.
Free Compound;
$^1$H-NMR (400 MHz, CDCl$_3$); δ (ppm) 0.77 (d, J=6.8 Hz, 3H), 1.13–1.16 (m, 1H), 1.19 (d, J=6.8 Hz, 3H), 1.48–1.61 (m, 1H), 1.84 (dt, J=4.4, 12.5 Hz, 1H), 2.03–2.19 (m, 2H), 2.28 (t, J=7.1 Hz, 2H), 2.30–2.46 (m, 4H), 2.46–2.64 (m, 4H), 2.77 (t, J=5.8 Hz, 2H), 4.04 (t, J=5.8 Hz, 2H), 6.81–6.85 (m, 2H), 6.93–6.98 (m, 2H), 7.30 (d, J=8.6 Hz, 2H), 7.34 (d, J=8.6 Hz, 2H).
Hydrochloride;
$^1$H-NMR (400 MHz, D$_2$O); δ (ppm) 0.60 (d, J=6.6 Hz, 3H), 1.02 (d, J=6.6 Hz, 3H), 1.18–1.30 (m, 1H), 1.54–1.67 (m, 1H), 1.87–1.96 (m, 1H), 2.06–2.20 (m, 2H), 2.95–3.05 (m, 1H), 3.08–3.17 (m, 1H), 3.32–3.58 (m, 10H), 4.20 (t, J=4.9 Hz, 2H), 6.82–6.87 (m, 2H), 6.93–6.98 (m, 2H), 7.30 (d, J=8.8 Hz, 2H), 7.36 (d, J=8.8 Hz, 2H).
ESI-Mass; 458 (MH+).

Example 11

Synthesis of 1-[4-Cyano-5-methyl-4-(4-methoxyphenyl)hexyl]-4-[2-(4-fluorophenoxy)ethyl]piperazine

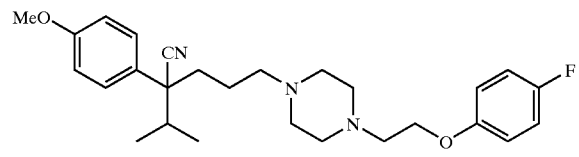

The title compound (404 mg, 62%) was obtained as a colorless oil from 2-(1-methylethyl)-5-oxo-2-(4-methoxyphenyl)pentane nitrile (345 mg) and 1-[2-(4-fluorophenoxy)ethyl]piperazine (350 mg) in the same manner as in Example 1. This free compound (59 mg) was treated in the same manner as in Example 1 to give the hydrochloride (68 mg) of the title compound.
Free Compound;
$^1$H-NMR (400 MHz, CDCl$_3$); δ (ppm) 0.77 (d, J=6.8 Hz, 3H), 1.07–1.19 (m, 1H), 1.18 (d, J=6.8 Hz, 3H), 1.48–1.61 (m, 1H), 1.77–1.87 (m, 1H), 2.03–2.15 (m, 2H), 2.28 (t, J=7.1 Hz, 2H), 2.30–2.46 (m, 4H), 2.46–2.65 (m, 4H), 2.77 (t, J=5.8 Hz, 2H), 3.81 (s, 3H), 4.04 (t, J=5.8 Hz, 2H), 6.81–6.85 (m, 2H), 6.88 (d, J=9.0 Hz, 2H), 6.93–6.97 (m, 2H), 7.26 (d, J=9.0 Hz, 2H).
Hydrochloride;
$^1$H-NMR (400 MHz, D$_2$O); δ (ppm) 0.60 (d, J=6.6 Hz, 3H), 1.00 (d, J=6.6 Hz, 3H), 1.21–1.35 (m, 1H), 1.54–1.68 (m, 1H), 1.83–1.96 (m, 1H), 2.02–2.19 (m, 2H), 2.97–3.09 (m, 1H), 3.12–3.21 (m, 1H), 3.35–3.67 (m, 10H), 3.70 (s, 3H), 4.23 (br-t, J=4.9 Hz, 2H), 6.82–6.87 (m, 2H), 6.90–6.99 (m, 3H), 7.27 (d, J=8.8 Hz, 2H).
ESI-Mass; 454 (MH+).

Example 12

Synthesis of 1-[4-Cyano-5-methyl-4-(4-carbomethoxyphenyl)hexyl]-4-[2-(4-fluorophenoxy)ethyl]piperazine

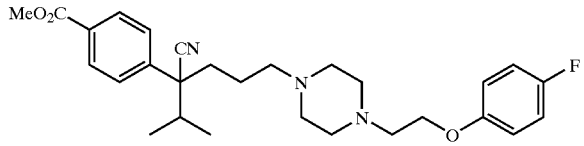

The title compound (74 mg, 71%) was obtained as a colorless oil from 2-(1-methylethyl)-5-oxo-2-(4-carbomethoxyphenyl)pentane nitrile (59 mg) and 1-[2-(4-fluorophenoxy)ethyl]piperazine (53 mg) in the same manner as in Example 1. This free compound (10 mg) was treated in the same manner as in Example 1 to give the hydrochloride (11 mg) of the title compound.

Free Compound;

$^1$H-NMR (400 MHz, CDCl$_3$); δ (ppm) 0.76 (d, J=6.8 Hz, 3H), 1.10–1.13 (m, 1H), 1.22 (d, J=6.8 Hz, 3H), 1.49–1.62 (m, 1H), 1.91 (dt, J=4.4, 12.5 Hz, 1H), 2.09–2.24 (m, 2H), 2.27 (t, J=7.1 Hz, 2H), 2.27–2.46 (m, 4H), 2.46–2.70 (m, 4H), 2.77 (t, J=5.8 Hz, 2H), 3.93 (s, 3H), 4.04 (t, J=5.8 Hz, 2H), 6.81–6.85 (m, 2H), 6.93–6.98 (m, 2H), 7.46 (d, J=8.2 Hz, 2H), 8.04 (d, J=8.2 Hz, 2H).

Hydrochloride;

$^1$H-NMR (400 MHz, D$_2$O); δ (ppm) 0.60 (d, J=6.6 Hz, 3H), 1.05 (d, J=6.6 Hz, 3H), 1.18–1.29 (m, 1H), 1.55–1.70 (m, 1H), 1.94–2.04 (m, 1H), 2.12–2.25 (m, 2H), 2.99–3.10 (m, 1H), 3.11–3.22 (m, 1H), 3.35–3.68 (m, 10H), 3.80 (s, 3H), 4.22 (br-t, J=4.9 Hz, 2H), 6.82–6.87 (m, 2H), 6.93–6.99 (m, 2H), 7.48 (d, J=8.4 Hz, 2H), 7.94 (d, J=8.4 Hz, 2H).

ESI-Mass; 482 (MH+).

Example 13

Synthesis of 1-[4-Cyano-5-methyl-4-(4-hydroxymethylphenyl)hexyl]-4-[2-(4-fluorophenoxy)ethyl]piperazine

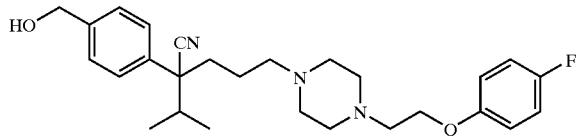

Lithium borohydride (3 mg) was added to a tetrahydrofuran solution (2 ml) containing the 1-[4-cyano-5-methyl-4-(4-carbomethoxyphenyl)hexyl]-4-[2-(4-fluorophenoxy) ethyl]piperazine (64 mg) obtained in Example 12, and the mixture was heated under reflux for 3 hours. The reaction mixture was cooled to room temperature, then 1 N hydrochloric acid (1 ml) was added thereto, and the mixture was stirred at room temperature for 10 minutes. The organic layer was partitioned by adding aqueous saturated sodium bicarbonate and ethyl acetate, washed with water, and dried over sodium sulfate anhydrous. The residue obtained by evaporation was purified by Cromatorex NH silica gel column chromatography (hexane/ethyl acetate system) to give the title compound (57 mg, 95%) as a colorless oil. 4 N hydrogen chloride/ethyl acetate solution was added at room temperature to a solution of this free compound (27 mg) in methanol. The solution was stirred for 10 minutes, and then the solvent was evaporated, whereby the hydrochloride (31 mg) of the title compound was obtained.

Free Compound;

$^1$H-NMR (400 MHz, CDCl$_3$); δ (ppm) 0.77 (d, J=6.8 Hz, 3H), 1.05–1.18 (m, 1H), 1.19 (d, J=6.8 Hz, 3H), 1.49–1.62 (m, 1H), 1.87 (dt, J=4.4, 12.5 Hz, 1H), 2.07–2.20 (m, 2H), 2.27 (t, J=7.1 Hz, 2H), 2.29–2.44 (m, 4H), 2.46–2.61 (m, 4H), 2.76 (t, J=5.8 Hz, 2H), 4.03 (t, J=5.8 Hz, 2H), 4.69 (s, 2H), 4.70–4.72 (m, 1H), 6.79–6.85 (m, 2H), 6.92–6.98 (m, 2H), 7.33–7.40 (br-s, 4H).

Hydrochloride;

$^1$H-NMR (400 MHz, D$_2$O); δ (ppm) 0.60 (d, J=6.6 Hz, 3H), 1.03 (d, J=6.6 Hz, 3H), 1.17–1.31 (m, 1H), 1.53–1.68 (m, 1H), 1.89–1.99 (m, 1H), 2.09–2.20 (m, 2H), 2.93–3.02 (m, 1H), 3.06–3.15 (m, 1H), 3.24–3.54 (m, 10H), 4.19 (t, J=4.9 Hz, 2H), 4.51 (s, 2H), 6.82–6.87 (m, 2H), 6.93–6.99 (m, 2H), 7.32 (d, J=8.8 Hz, 2H), 7.34 (d, J=8.8 Hz, 2H).

ESI-Mass; 454 (MH+).

Example 14

Synthesis of 1-[4-Cyano-5-methyl-4-(4-hydroxyiminomethylphenyl)hexyl]-4-[2-(4-fluorophenoxy)ethyl]piperazine

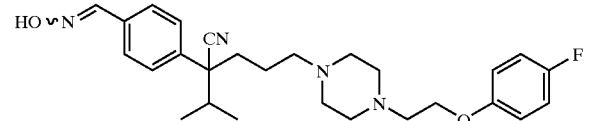

DMSO (0.5 ml), triethylamine (0.5 ml) and sulfur trioxide pyridine (31 mg) was added to the 1-[4-cyano-5-methyl-4-(4-hydroxymethylphenyl)hexyl]-4-[2-(4-fluorophenoxy) ethyl]piperazine obtained in Example 13, and the mixture was stirred at room temperature for 30 minutes. Brine and ether were added to the reaction mixture, and the organic layer was partitioned, dried over sodium sulfate anhydrous, and evaporated. The resulting residue was dissolved in ethanol (2 ml), then hydroxylamine hydrochloride (7 mg) and sodium acetate (9 mg) were added thereto, and the mixture was stirred at room temperature for 12 hours. Aqueous saturated sodium bicarbonate and ethyl acetate were added to the reaction mixture, and the organic layer was partitioned, washed with water, dried over sodium sulfate anhydrous, and evaporated. The resulting residue was purified by silica gel column chromatography (toluene/acetone system) to give the title compound (23 mg, 74%) as a colorless oil. 4 N hydrogen chloride/ethyl acetate solution was added at room temperature to a solution of this free compound (8 mg) in methanol. The reaction mixture was stirred for 10 minutes, and then the solvent was evaporated, whereby the hydrochloride (9 mg) of the title compound was obtained.

Free Compound;

$^1$H-NMR (400 MHz, CDCl$_3$); δ (ppm) 0.77 (d, J=6.8 Hz, 3H), 1.19 (d, J=6.8 Hz, 3H), 1.20–1.31 (m, 1H), 1.55–1.70 (m, 1H), 1.92 (dt, J=4.4, 12.5 Hz, 1H), 2.04–2.20 (m, 2H), 2.38–2.45 (m, 2H), 2.48–2.66 (m, 4H), 2.66–2.82 (m, 4H), 2.85 (t, J=5.8 Hz, 2H), 4.08 (t, J=5.8 Hz, 2H), 6.79–6.84 (m, 2H), 6.92–6.97 (m, 2H), 7.37 (d, J=8.4 Hz, 2H), 7.50 (d, J=8.4 Hz, 2H), 8.06 (s, 1H).

Hydrochloride;

$^1$H-NMR (400 MHz, D$_2$O); δ (ppm) 0.61 (d, J=6.6 Hz, 3H), 1.04 (d, J=6.6 Hz, 3H), 1.17–1.31 (m, 1H), 1.53–1.68 (m, 1H), 1.90–2.00 (m, 1H), 2.10–2.23 (m, 2H), 2.91–3.01 (m, 1H), 3.04–3.14 (m, 1H), 3.22–3.46 (m, 10H), 4.18 (t, J=4.9 Hz, 2H), 6.82–6.87 (m, 2H), 6.92–6.99 (m, 2H), 7.40 (d, J=8.2 Hz, 2H), 7.56 (d, J=8.2 Hz, 2H), 8.13 (s, 1H).

ESI-Mass; 467 (MH+).

Example 15

Synthesis of 1-[4-Cyano-5-methyl-4-(4-cyanonphenyl)hexyl]-4-[2-(4-fluorophenoxy)ethyl]piperazine

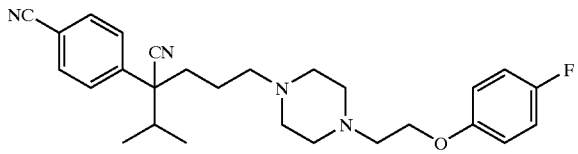

Carbonyl diimidazole (26 mg) was added to the solution of the 1-[(4-cyano-5-methyl-4-(4-hydroxyiminomethylphenyl)hexyl]-4-[2-(4-fluorophenoxy)ethyl]piperazine (15 mg) obtained in Example 14 in tetrahydrofuran (2 ml), and then stirred at 50° C. for 12 hours. Brine and ethyl acetate were added to the reaction mixture, and the organic layer was partitioned, washed with water, dried over sodium sulfate anhydrous, and evaporated. The resulting residue was purified by silica gel column chromatography (toluene/acetone system) to give the title compound (9 mg, 63%) as a colorless oil. 4 N hydrogen chloride/ethyl acetate solution was added at room temperature to a solution of this free compound (9 mg) in methanol. The reaction mixture was stirred for 10 minutes, and then the solvent was evaporated, whereby the hydrochloride (10 mg) of the title compound was obtained.

Free Compound;
$^1$H-NMR (400 MHz, CDCl$_3$); δ (ppm) 0.77 (d, J=6.8 Hz, 3H), 0.96–1.10 (m, 1H), 1.22 (d, J=6.8 Hz, 3H), 1.49–1.63 (m, 1H), 1.89 (dt, J=4.4, 12.5 Hz, 1H), 2.07–2.25 (m, 2H), 2.30 (t, J=7.0 Hz, 2H), 2.32–2.46 (m, 4H), 2.46–2.65 (m, 4H), 2.78 (t, J=5.8 Hz, 2H), 4.05 (t, J=5.8 Hz, 2H), 6.81–6.85 (m, 2H), 6.93–6.98 (m, 2H), 7.52 (d, J=8.6 Hz, 2H), 7.69 (d, J=8.6 Hz, 2H).

Hydrochloride;
$^1$H-NMR (400 MHz, D$_2$O); δ (ppm) 0.59 (d, J=6.6 Hz, 3H), 1.04 (d, J=6.6 Hz, 3H), 1.11–1.26 (m, 1H), 1.54–1.69 (m, 1H), 1.93–2.03 (m, 1H), 2.10–2.24 (m, 2H), 2.98–3.08 (m, 1H), 3.09–3.20 (m, 1H), 3.31–3.60 (m, 10H), 4.21 (t, J=4.9 Hz, 2H), 6.82–6.87 (m, 2H), 6.92–6.99 (m, 2H), 7.51 (d, J=8.4 Hz, 2H), 7.72 (d, J=8.4 Hz, 2H).

ESI-Mass; 449 (MH+).

Example 16

Synthesis of 1-[4-Cyano-5-methyl-4-(4-nitrophenyl)hexyl]-4-[2-(4-fluorophenoxy)ethyl]piperazine

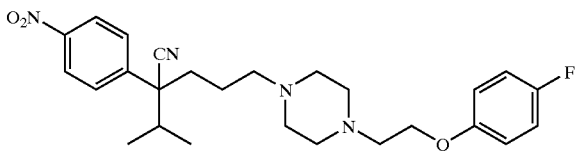

The title compound (356 mg, 90%) was obtained as a colorless oil from 2-(1-methylethyl)-5-oxo-2-(4-nitrophenyl)pentane nitrile (219 mg) and 1-[2-(4-fluorophenoxy)ethyl]piperazine (210 mg) in the same manner as in Example 1. The free compound (44 mg) thereof was treated in the same manner as in Example 1 to give the hydrochloride (50 mg) of the title compound.

Free Compound;
$^1$H-NMR (400 MHz, CDCl$_3$); δ (ppm) 0.78 (d, J=6.8 Hz, 3H), 0.96–1.10 (m, 1H), 1.24 (d, J=6.8 Hz, 3H), 1.50–1.63 (m, 1H), 1.92 (dt, J=4.4, 12.5 Hz, 1H), 2.11–2.26 (m, 2H), 2.28 (t, J=7.1 Hz, 2H), 2.30–2.44 (m, 4H), 2.46–2.66 (m, 4H), 2.77 (t, J=5.8 Hz, 2H), 4.04 (t, J=5.8 Hz, 2H), 6.80–6.85 (m, 2H), 6.93–6.98 (m, 2H), 7.58 (d, J=9.0 Hz, 2H), 8.25 (d, J=9.0 Hz, 2H).

Hydrochloride;
$^1$H-NMR (400 MHz, D$_2$O); δ (ppm) 0.61 (d, J=6.6 Hz, 3H), 1.05 (d, J=6.6 Hz, 3H), 1.15–1.30 (m, 1H), 1.57–1.72 (m, 1H), 1.96–2.06 (m, 1H), 2.17–2.28 (m, 2H), 3.03–3.12 (m, 1H), 3.13–3.24 (m, 1H), 3.35–3.65 (m, 10H), 4.22 (br-t, J=4.9 Hz, 2H), 6.82–6.87 (m, 2H), 6.92–6.99 (m, 2H), 7.58 (d, J=8.8 Hz, 2H), 8.18 (d, J=8.8 Hz, 2H).

ESI-Mass; 469 (MH+).

Example 17

Synthesis of 1-[4-Cyano-5-methyl-4-(4-aminophenyl)hexyl]-4-[2-(4-fluorophenoxy)ethyl]piperazine

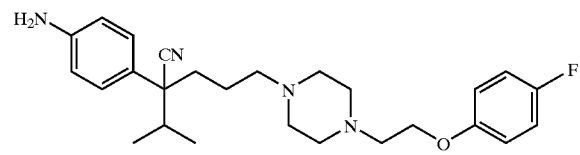

10% palladium/carbon (10 mg) was added to an ethyl acetate solution (5 ml) containing the 1-[(4-cyano-5-methyl-4-(4-nitrophenyl)hexyl]-4-[2-(4-fluorophenoxy)ethyl]piperazine (312 mg) obtained in Example 16, and then stirred for 5 hours at room temperature under a hydrogen gas stream. The reaction mixture was filtered, and the filtrate was evaporated. The residue was purified by Cromatorex NH silica gel column chromatography (hexane/ethyl acetate system) whereby the title compound (87 mg, 30%) was obtained as a colorless oil. A 4 N hydrogen chloride/ethyl acetate solution was added to a solution of this free compound (26 mg) in methanol. After the reaction mixture was stirred for 10 minutes, the solvent was evaporated, whereby the hydrochloride (32 mg) of the title compound was obtained.

Free Compound;
$^1$H-NMR (400 MHz, CDCl$_3$); δ (ppm) 0.78 (d, J=6.8 Hz, 3H), 1.16 (d, J=6.8 Hz, 3H), 1.47–1.61 (m, 1H), 1.77–1.85 (m, 2H), 1.99–2.14 (m, 2H), 2.28 (t, J=7.1 Hz, 2H), 2.30–2.45 (m, 4H), 2.46–2.67 (m, 4H), 2.77 (t, J=5.8 Hz, 2H), 3.68 (br-s, 2H), 4.04 (t, J=5.8 Hz, 2H), 6.66 (d, J=8.4 Hz, 2H), 6.81–6.85 (m, 2H), 6.92–6.98 (m, 2H), 7.11 (d, J=8.4 Hz, 2H).

Hydrochloride;
$^1$H-NMR (400 MHz, D$_2$O); δ (ppm) 0.59 (d, J=6.6 Hz, 3H), 1.02 (d, J=6.6 Hz, 3H), 1.19–1.31 (m, 1H), 1.56–1.69 (m, 1H), 1.93–2.04 (m, 1H), 2.09–2.23 (m, 2H), 3.04–3.14 (m, 1H), 3.15–3.24 (m, 1H), 3.39–3.72 (m, 10H), 4.24 (br-t, J=4.9 Hz, 2H), 6.83–6.87 (m, 2H), 6.93–6.99 (m, 2H), 7.35 (d, J=8.6 Hz, 2H), 7.48 (d, J=8.6 Hz, 2H).

ESI-Mass; 439 (MH+).

Example 18

Synthesis of 1-[4-Cyano-5-methyl-4-(4-acetamidophenyl)hexyl]-4-[2-(4-fluorophenoxy)ethyl]piperazine

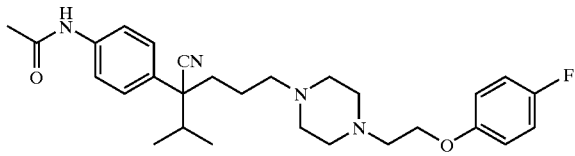

Acetic acid anhydride (1 ml) was added to a pyridine solution (2 ml) containing the 1-[4-cyano-5-methyl-4-(4-aminophenyl)hexyl]-4-[2-(4-fluorophenoxy)ethyl]piperazine (15 mg) obtained in Example 17, and then stirred at room temperature for 12 hours. The reaction mixture was evaporated, and the residue was purified by silica gel column chromatography (toluene/acetone system), whereby the title compound (15 mg, 91%) was obtained as a colorless oil. A 4 N hydrogen chloride/ethyl acetate solution was added to a solution of the free compound (15 mg) thereof in methanol. After the reaction mixture was stirred for 10 minutes, the solvent was evaporated, whereby the hydrochloride (17 mg) of the title compound was obtained.

Free Compound;
$^1$H-NMR (400 MHz, CDCl$_3$); δ (ppm) 0.77 (d, J=6.8 Hz, 3H), 1.10–1.22 (m, 1H), 1.18 (d, J=6.8 Hz, 3H), 1.49–1.63 (m, 1H), 1.87 (dt, J=4.0, 12.8 Hz, 1H), 2.03–2.17 (m, 2H), 2.19 (s, 3H), 2.35 (t, J=7.1 Hz, 2H), 2.38–2.54 (m, 4H), 2.55–2.75 (m, 4H), 2.81 (t, J=5.8 Hz, 2H), 4.06 (t, J=5.8 Hz, 2H), 6.79–6.85 (m, 2H), 6.93–6.99 (m, 2H), 7.29 (br-s, 1H), 7.31 (d, J=8.4 Hz, 2H), 7.52 (d, J=8.4 Hz, 2H).

Hydrochloride;
$^1$H-NMR (400 MHz, D$_2$O); δ (ppm) 0.61 (d, J=6.6 Hz, 3H), 1.03 (d, J=6.6 Hz, 3H), 1.20–1.35 (m, 1H), 1.54–1.69 (m, 1H), 1.86–1.99 (m, 1H), 2.03 (s, 3H), 2.05–2.22 (m, 2H), 2.96–3.06 (m, 1H), 3.08–3.20 (m, 1H), 3.33–3.59 (m, 10H), 4.21 (br-t, J=4.9 Hz, 2H), 6.83–6.88 (m, 2H), 6.94–7.00 (m, 2H), 7.33 (d, J=9.0 Hz, 2H), 7.36 (d, J=9.0 Hz, 2H).

ESI-Mass; 481 (MH+).

Example 19

Synthesis of 1-[4-Cyano-5-methyl-4-(4-dimethylaminophenyl)hexyl]-4-[2-(4-fluorophenoxy)ethyl]piperazine

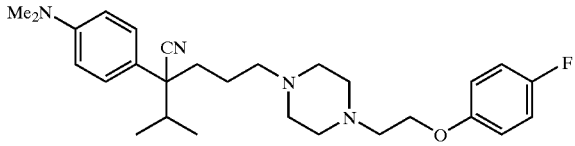

p-Formaldehyde (30 mg) and sodium cyano borohydride (30 mg) were added to an acetic acid (2 ml) solution containing the 1-[4-cyano-5-methyl-4-(4-aminophenyl)hexyl]-4-[2-(4-fluorophenoxy)ethyl]piperazine (21 mg) obtained in Example 17, and then stirred at room temperature for 12 hours. The reaction mixture was evaporated, and the organic layer was partitioned by adding aqueous saturated sodium bicarbonate and ethyl acetate. The organic layer was washed with water, dried over sodium sulfate anhydrous, and evaporated. The residue was purified by Cromatorex NH silica gel column chromatography (hexane/ethyl acetate system), whereby the title compound (12 mg, 56%) was obtained as a colorless oil. A 4 N hydrogen chloride/ethyl acetate solution was added to a solution of this free compound (12 mg) in methanol. After the reaction mixture was stirred for 10 minutes, the solvent was evaporated, whereby the hydrochloride (14 mg) of the title compound was obtained.

Free Compound;
$^1$H-NMR (400 MHz, CDCl$_3$); δ (ppm) 0.79 (d, J=6.8 Hz, 3H), 1.16 (d, J=6.8 Hz, 3H), 1.17–1.24 (m, 1H), 1.49–1.62 (m, 1H), 1.82 (dt, J=4.0, 12.8 Hz, 1H), 1.99–2.14 (m, 2H), 2.28 (t, J=7.1 Hz, 2H), 2.30–2.47 (m, 4H), 2.47–2.65 (m, 4H), 2.77 (t, J=5.8 Hz, 2H), 2.95 (s, 6H), 4.04 (t, J=5.8 Hz, 2H), 6.68 (d, J=9.0 Hz, 2H), 6.80–6.85 (m, 2H), 6.92–6.98 (m, 2H), 7.19 (d, J=9.0 Hz, 2H).

Hydrochloride;
$^1$H-NMR (400 MHz, D$_2$O); δ (ppm) 0.59 (d, J=6.6 Hz, 3H), 1.03 (d, J=6.6 Hz, 3H), 1.17–1.30 (m, 1H), 1.55–1.70 (m, 1H), 1.94–2.05 (m, 1H), 2.10–2.25 (m, 2H), 3.01–3.22 (m, 2H), 3.17 (s, 3H), 3.34–3.60 (m, 10H), 4.22 (br-t, J=4.9 Hz, 2H), 6.83–6.88 (m, 2H), 6.94–6.99 (m, 2H), 7.55 (br-s, 4H).

ESI-Mass; 467 (MH+).

Example 20

Synthesis of 1-{[4-Cyano-5-methyl-4-(2-thienyl)hexyl]}-4-[2-(4-fluorophenoxy)ethyl]piperazine The title compound (293 mg, 50%) was obtained as a yellow oil in the same manner as in Example 1 from 2-(1-methylethyl)-5-oxo-2-(2-thienyl)pentane nitrile (300 mg) synthesized from 2-thiophene acetonitrile, and 1-[2-(4-fluorophenoxy)ethyl]piperazine (305 mg). This free compound (293 mg) was treated in the same manner as in Example 1 to give the hydrochloride (220 mg) of the title compound.

Free Compound;
$^1$H-NMR (400 MHz, CDCl$_3$); δ (ppm) 0.90 (d, J=6.8 Hz, 3H), 1.18 (d, J=6.8 Hz, 3H), 1.23–1.38 (m, 1H), 1.57–1.70 (m, 1H), 1.77 (dt, J=4.0 Hz, 12.0 Hz, 2H), 2.00–2.10 (m, 1H), 2.11–2.20 (m, 1H), 2.26–2.35 (m, 2H), 2.35–2.49 (m, 4H), 2.49–2.66 (m, 4H), 2.78 (t, J=5.8 Hz, 2H), 4.04 (t, J=5.8 Hz, 2H), 6.80–6.86 (m, 2H), 6.92–6.99 (m, 3H), 7.11 (dd, J=1.2 Hz, 3.6 Hz, 1H), 7.24–7.27 (m, 1H).

Hydrochloride;
$^1$H-NMR (400 MHz, DMSO-d$_6$); δ (ppm) 0.80 (d, J=6.8 Hz, 3H), 1.07 (d, J=6.8 Hz, 3H), 1.40–1.55 (m, 1H), 1.66–1.82 (m, 1H), 1.87–1.99 (m, 1H), 2.06–2.30 (m, 2H), 3.00–4.0 (m, 12H), 4.34 (br-s, 2H), 6.98–7. 08 (m, 3H), 7.10–7.18 (m, 3H), 7.57 (dd, J=1.2 Hz, 4.8 Hz, 1H).

ESI-Mass; 430 (MH+).

Example 21

Synthesis of 1-{[4-Cyano-5-methyl-4-(3-pyridyl)hexyl]}-4-[2-(4-fluorophenoxy)ethyl]piperazine

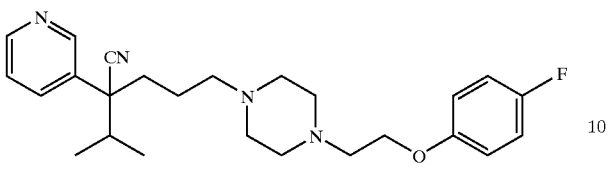

The title compound (325 mg, 54%) was obtained as a colorless oil in the same manner as in Example 1 from 2-(1-methylethyl)-5-oxo-2-(3-pyridyl)pentane nitrile (300 mg) synthesized from 3-pyridyl acetonitrile, and 1-[2-(4-fluorophenoxy)ethyl]piperazine (311 mg). This free compound (325 mg) was treated in the same manner as in Example 1 to give the hydrochloride (300 mg) of the title compound.

Free Compound;
$^1$H-NMR (400 MHz, CDCl$_3$); δ (ppm) 0.81 (d, J=6.8 Hz, 3H), 1.05–1.18 (m, 1H), 1.22 (d, J=6.8 Hz, 3H), 1.52–1.65 (m, 1H), 1.89–1.99 (m, 1H), 2.10–2.24 (m, 2H), 2.25–2.32 (m, 2H), 2.32–2.46 (m, 4H), 2.46–2.64 (m, 4H), 2.77 (t, J=5.8 Hz, 2H), 4.04 (t, J=5.8 Hz, 2H), 6.80–6.86 (m, 2H), 6.92–6.99 (m, 2H), 7.30–7.36 (m, 1H), 7.70–7.75 (m, 1H), 8.55–8.59 (m, 1H), 8.63–8.67 (m, 1H).

Hydrochloride;
$^1$H-NMR (400 MHz, DMSO-d$_6$); δ (ppm) 0.69 (d, J=6.86 Hz, 3H), 1.11 (d, J=6.8 Hz, 3H), 1.22–1.39 (m, 1H), 1.60–1.73 (m, 1H), 2.17–2.40 (m, 3H), 2.95–3.85 (m, 12H), 4.31–4.42 (m, 2H), 6.97–7.06 (m, 2H), 7.09–7.18 (m, 2H), 7.84–7.92 (m, 1H), 8.28–8.36 (m, 1H), 8.78–8.88 (m, 2H).

ESI-Mass; 425 (MH+).

Example 22

Synthesis of 1-{[4-Cyano-5-methyl-4-(2-fluorophenyl)hexyl]}-4-[2-(4-fluorophenoxy)ethyl]piperazine

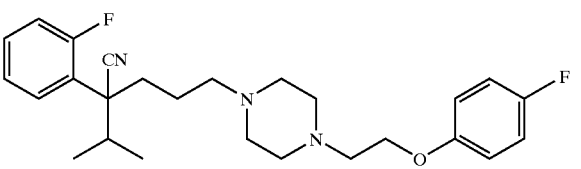

The title compound (67 mg, 12%) was obtained as a colorless oil in the same manner as in Example 1 from 2-(1-methylethyl)-5-oxo-2-(2-fluorophenyl)pentane nitrile (290 mg) synthesized from 2-fluorophenyl acetonitrile, and 1-[2-(4-fluorophenoxy)ethyl]piperazine (278 mg). This free compound (67 mg) was treated in the same manner as in Example 1 to give the hydrochloride (60 mg) of the title compound.

Free Compound;
$^1$H-NMR (400 MHz, CDCl$_3$); δ (ppm) 0.80 (d, J=6.8 Hz, 3H), 1.04–1.18 (m, 1H), 1.22 (d, J=6.8 Hz, 3H), 1.51–1.64 (m, 1H), 2.02–2.13 (m, 1H), 2.15–2.66 (m, 12H), 2.77 (t, J=5.8 Hz, 2H), 4.04 (t, J=5.8 Hz, 2H), 6.79–6.86 (m, 2H), 6.91–6.99 (m, 2H), 6.99–7.06 (m, 1H), 7.12–7.18 (m, 1H), 7.26–7.34 (m, 1H), 7.55–7.62 (m, 1H).

Hydrochloride;
$^1$H-NMR (400 MHz, DMSO-d$_6$); δ (ppm) 0.73 (d, J=6.8 Hz, 3H), 1.11 (d, J=6.8 Hz, 3H), 1.20–1.39 (m, 1H), 1.57–1.73 (m, 1H), 2.08–2.20 (m, 2H), 2.30–2.42 (m, 1H), 3.30–3.75 (m, 12H), 4.29 (br-s, 2H), 6.97–7.03 (m, 2H), 7.10–7.17 (m, 2H), 7.24–7.32 (m, 2H), 7.42–7.53 (m, 2H).

ESI-Mass; 424 (MH+).

Example 23

Synthesis of 1-[{4-Cyano-5-methyl-4-(3-flourophenyl)hexyl]}-4-[2-(4-fluorophenoxy)ethyl]piperazine

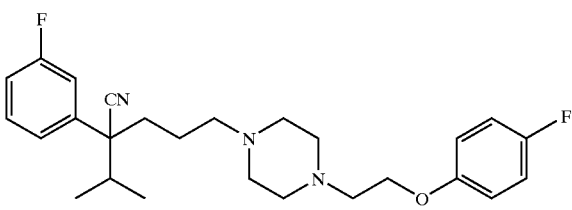

The title compound (258 mg, 45%) was obtained as a colorless oil in the same manner as in Example 1 from 2-(1-methylethyl)-5-oxo-2-(3-fluorophenyl)pentane nitrile (300 mg) synthesized from 3-fluorophenyl acetonitrile and 1-[2-(4-fluorophenoxy)ethyl]piperazine (289 mg). The free compound (258 mg) thereof was treated in the same manner as in Example 1 to give the hydrochloride (80 mg) of the title compound.

Free Compound;
$^1$H-NMR (400 MHz, CDCl$_3$); δ (ppm) 0.79 (d, J=6.8 Hz, 3H), 1.04–1.17 (m, 1H), 1.20 (d, J=6.8 Hz, 3H), 1.50–1.60 (m, 1H), 1.85 (dt, J=4.4 Hz, 13.6 Hz, 1H), 2.03–2.20 (m, 2H), 2.22–2.31 (m, 2H), 2.31–2.46 (m, 4H), 2.46–2.66 (m, 4H), 2.77 (t, J=6.0 Hz, 2H), 4.04 (t, J=6.0 Hz, 2H), 6.80–6.85 (m, 2H), 6.92–7.04 (m, 3H), 7.05–7.10 (m, 1H), 7.16–7.20 (m, 1H), 7.30–7.37 (m, 1H).

Hydrochloride;
$^1$H-NMR (400 MHz, DMSO-d$_6$); δ (ppm) 0.66 (d, J=6.8 Hz, 3H), 1.10 (d, J=6.8 Hz, 3H), 1.15–1.30 (m, 1H), 1.52–1.68 (m, 1H), 2.0–2.27 (m, 3H), 3.30–3.75 (m, 12H), 4.28 (br-s, 2H), 6.96–7.03 (m, 2H), 7.10–7.17 (m, 2H), 7.27–7.24 (m, 1H), 7.24–7.32 (m, 2H), 7.46–7.53 (m, 1H).

ESI-Mass; 424 (MH+).

Example 24

Synthesis of 1-{[4-Cyano-5-methyl-4-(4-fluorophenyl)hexyl]}-4-[2-(4-fluorophenoxy)ethyl]piperazine

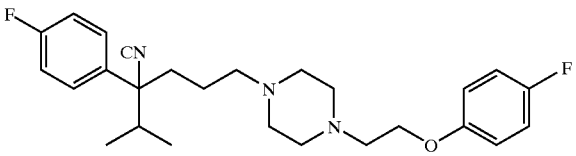

The title compound (78 mg, 17%) was obtained as a colorless oil in the same manner as in Example 1 from 2-(1-methylethyl)-5-oxo-2-(4-fluorophenyl)pentane nitrile (242 mg) synthesized from 4-fluorophenyl acetonitrile and 1-[2-(4-fluorophenoxy)ethyl]piperazine (233 mg). This free compound (78 mg) was treated in the same manner as in Example 1 to give the hydrochloride (62 mg) of the title compound.

Free Compound;

$^1$H-NMR (400 MHz, CDCl$_3$); δ (ppm) 0.771 (d, J=6.8 Hz, 3H), 1.02–1.18 (m, 1H), 1.19 (d, J=6.8 Hz, 3H), 1.48–1.62 (m, 1H), 1.80–1.89 (m, 1H), 2.02–2.19 (m, 2H), 2.23–2.31 (m, 2H), 2.31–2.46 (m, 4H), 2.46–2.66 (m, 4H), 2.77 (t, J=5.8 Hz, 2H), 4.04 (t, J=5.8 Hz, 2H), 6.79–6.86 (m, 2H), 6.93–6.99 (m, 2H), 7.02–7.09 (m, 2H), 7.31–7.37 (m, 2H).
Hydrochloride;

$^1$H-NMR (400 MHz, DMSO-d$_6$); δ (ppm) 0.66 (d, J=6.8 Hz, 3H), 1.09 (d, J=6.8 Hz, 3H), 1.15–1.30 (m, 1H), 1.50–1.67 (m, 1H), 2.00–2.22 (m, 3H), 2.95–3.80 (m, 12H), 4.30–(br-s, 2H), 6.97–7.03 (m, 2H), 7.10–7.17 (m, 2H), 7.24–7.31 (m, 2H), 7.43–7.49 (m, 2H).

ESI-Mass; 424 (MH+).

Example 25

Synthesis of 1-[(3-Cyano-4-methyl-3-phenyl)pentyl]-4-[2-(4-fluourophenoxy)ethyl]piperazine

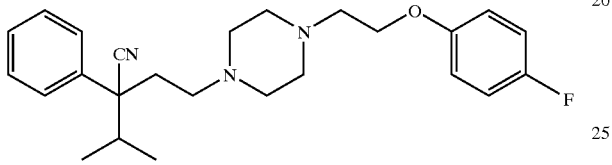

The free compound (0.17 g, 78%) of the title compound was obtained as a colorless oil from 2-(1-methylethyl)-4-oxo-2-phenyl butyronitrile (0.12 g) and 1-[2-(4-fluorophenoxy)ethyl]piperazine (0.12 g) in the same manner as in Example 1.
Free Compound;

$^1$H-NMR (400 MHz, CDCl$_3$); δ (ppm) 0.78 (d, J=6.8 Hz, 3H), 1.21 (d, J=6.8 Hz, 3H), 1.95–2.16 (m, 3H), 2.32–2.48 (m, 6H), 2.48–2.62 (m, 4H), 2.77 (t, J=6.0 Hz, 2H), 4.03 (t, J=6.0 Hz, 2H), 6.79–6.85 (m, 2H), 6.92–6.98 (m, 2H), 7.26–7.34 (m, 1H), 7.34–7.40 (m, 4H).

The above free compound (0.17 g) was treated in a usual manner to give the hydrochloride (0.18 g) of the title compound.
Hydrochloride;

$^1$H-NMR (400 MHz, DMSO-d$_6$); δ (ppm) 0.66 (d, J=6.8 Hz, 3H), 1.11 (d, J=6.8 Hz, 3H), 2.18–2.26 (m, 1H), 2.54–2.68 (m, 2H), 3.40–3.80 (m, 12H), 4.32 (br-s, 2H), 6.96–7.03 (m, 2H), 7.10–7.18 (m, 2H), 7.34–7.42 (m, 1H), 7.42–7.48 (m, 4H).

ESI-Mass; 410 (MH+).

Example 26

Synthesis of 1-[(4-Cyano-4-phenyl)pentyl]-4-[2-(4-fluorophenoxy)ethyl]piperazine

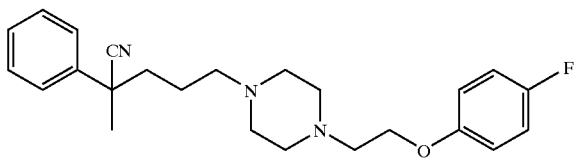

The free compound (0.35 g, 83%) of the title compound was obtained as a colorless oil from 2-methyl-5-oxo-2-phenyl pentane nitrile (0.22 g) and 1-[2-(4-fluorophenoxy)ethyl]piperazine (0.24 g) in the same manner as in Example 1.
Free Compound;

$^1$H-NMR (400 MHz, CDCl$_3$); δ (ppm) 1.33–1.45 (m, 1H), 1.60–1.70 (m, 1H), 1.72 (s, 3H), 1.91–2.00 (m, 2H), 2.30 (t, J=6.8 Hz, 3H), 2.41 (br-s, 4H), 2.57 (br-s, 4H), 2.78 (t, J=6.0 Hz, 2H), 4.04 (t, J=6.0 Hz, 2H), 6.80–6.86 (m, 2H), 6.92–6.99 (m, 2H), 7.27–7.33 (m, 1H), 7.35–7.45 (m, 4H).

The above free compound (0.35 g) was treated in a usual manner to give the hydrochloride (0.37 g) of the title compound.

Hydrochloride;

$^1$H-NMR (400 MHz, DMSO-d$_6$); δ (ppm) 1.48–1.50 (m, 1H), 1.68 (s, 3H), 1.72–1.86 (m, 1H), 1.95–2.05 (m, 2H), 3.04–3.18 (m, 1H), 3.20–3.80 (m, 11H), 4.33 (br-s, 2H), 6.97–7.04 (m, 2H), 7.10–7.18 (m, 2H), 7.33–7.37 (m, 1H), 7.40–7.51 (m, 4H).

ESI-Mass; 396 (MH+).

Example 27

Synthesis of 1-[(4-Cyano-4-phenyl)heptyl]-4-[2-(4-fluorophenoxy)ethyl]piperazine

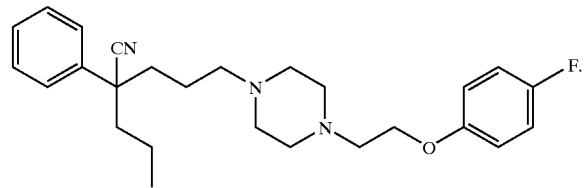

The free compound (0.35 g, 83%) of the title compound was obtained as a colorless oil from 5-oxo-2-phenyl-2-propyl pentane nitrile (0.22 g) and 1-[2-(4-fluorophenoxy)ethyl]piperazine (0.24 g) in the same manner as in Example 1.

Free Compound;

$^1$H-NMR (400 MHz, CDCl$_3$); δ (ppm) 0.87 (t, J=7.2 Hz, 3H), 1.06–1.20 (m, 1H), 1.22–1.33 (m, 1H), 1.42–1.54 (m, 1H), 1.60–1.72 (m, 1H), 1.80–2.05 (m, 4H), 2.28 (t, J=7.2 Hz, 2H), 2.39 (br-s, 4H), 2.56 (br-s, 4H), 2.77 (t, J=6.0 Hz, 2H), 4.04 (t, J=6.0 Hz, 2H), 6.80–6.86 (m, 2H), 6.92–6.99 (m, 2H), 7.26–7.32 (m, 1H), 7.34–7.40 (m, 4H).

The above free compound (0.35 g) was treated in a usual manner to give the hydrochloride (0.37 g) of the title compound.

Hydrochloride;

$^1$H-NMR (400 MHz, DMSO-d$_6$); δ (ppm) 0.82 (t, J=7.2 Hz, 3H), 0.92–1.05 (m, 1H), 1.24–1.37 (m, 1H), 1.37–1.50 (m, 1H), 1.70–1.85 (m, 1H), 1.85–1.98 (m, 2H), 1.98–2.10 (m, 2H), 3.00–3.18 (m, 2H), 3.20–3.80 (m, 10H), 4.33 (br-s, 2H), 6.97–7.04 (m, 2H), 7.10–7.17 (m, 2H), 7.31–7.38 (m, 1H), 7.39–7.47 (m, 4H).

ESI-Mass; 424 (MH+).

Example 28

Synthesis of 1-[(4-Cyano-4-phenyl)hexyl]-4-[2-(4-fluorophenoxy)ethyl]piperazine

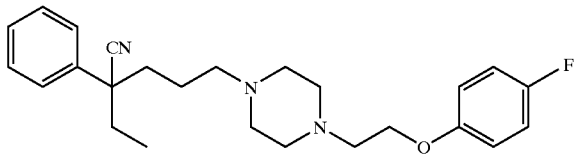

The free compound (0.20 g, 83%) of the title compound was obtained as a colorless oil from 5-oxo-2-ethyl-2-phenyl pentane nitrile (0.13 g) and 1-[2-(4-fluorophenoxy)ethyl]piperazine (0.13 g) in the same manner as in Example 1.
Free Compound;
$^1$H-NMR (400 MHz, CDCl$_3$); δ (ppm) 0.90 (t, J=7.2 Hz, 3H), 1.23–1.34 (m, 1H), 1.59–1.71 (m, 1H), 1.88–2.09 (m, 4H), 2.28 (t, J=7.2 Hz, 2H), 2.39 (br-s, 4H), 2.56 (br-s, 4H), 2.77 (t, J=6.0 Hz, 2H), 4.04 (t, J=6.0 Hz, 2H), 6.80–6.86 (m, 2H), 6.92–6.99 (m, 2H), 7.27–7.33 (m, 1H), 7.34–7.40 (m, 4H).

The above free base compound (0.20 g) was treated in a usual manner to give the hydrochloride (0.14 g) of the title compound.
Hydrochloride;
$^1$H-NMR (400 MHz, DMSO-d$_6$); δ (ppm) 0.77 (t, J=7.2 Hz, 3H), 1.38–1.52 (m, 1H), 1.70–1.84 (m, 1H), 1.90–2.10 (m, 4H), 3.00–3.24 (m, 2H), 3.24–3.80 (m, 10H), 4.35 (br-s, 2H), 6.98–7.04 (m, 2H), 7.10–7.17 (m, 2H), 7.32–7.38 (m, 1H), 7.39–7.47 (m, 4H).
ESI-Mass; 410 (MH+).

Example 29

Synthesis of 1-[(4-Cyano-4-phenyl)octyl]-4-[2-(4-fluorophenoxy)ethyl]piperazine

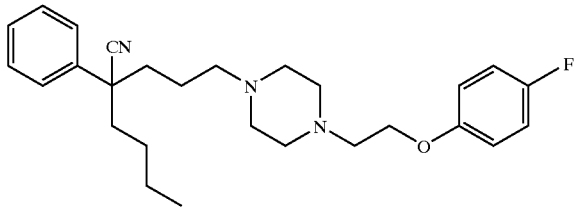

The free compound (0.22 g, 81%) of the title compound was obtained as a colorless oil from 2-butyl-5-oxo-2-phenyl pentane nitrile (0.16 g) and 1-[2-(4-fluorophenoxy)ethyl]piperazine (0.14 g) in the same manner as in Example 1.
Free Compound;
$^1$H-NMR (400 MHz, CDCl$_3$); δ (ppm) 0.84 (t, J=7.2 Hz, 3H), 1.03–1.14 (m, 1H), 1.20–1.36 (m, 3H), 1.37–1.50 (m, 1H), 1.58–1.62 (m, 1H), 1.83–2.06 (m, 4H), 2.28 (t, J=7.2 Hz, 2H), 2.39 (br-s, 4H), 2.56 (br-s, 4H), 2.77 (t, J=6.0 Hz, 2H), 4.04 (t, J=6.0 Hz, 2H), 6.80–6.86 (m, 2H), 6.92–6.99 (m, 2H), 7.27–7.33 (m, 1H), 7.34–7.41 (m, 4H).

The above free compound (0.22 g) was treated in a usual manner to give the hydrochloride (0.22 g) of the title compound.
Hydrochloride;
$^1$H-NMR (400 MHz, DMSO-d$_6$) (ppm) 0.78 (t, J=7.2 Hz, 3H), 0.88–1.00 (m, 1H), 1.17–1.34 (m, 3H), 1.35–1.49 (m, 1H), 1.70–1.83 (m, 1H), 1.90–2.08 (m, 4H), 2.98–3.20 (m, 2H), 3.20–3.80 (m, 10H), 4.32 (br-s, 2H), 6.97–7.03 (m, 2H), 7.10–7.17 (m, 2H) 7.31–7.38 (m, 1H), 7.40–7.47 (m, 4H).
ESI-Mass; 438 (MH+).

Example 30

Synthesis of 1-[(4-Cyano-6-methyl-4-phenyl) hepthyl]-4-[2-(4-fluorophenoxy)ethyl]piperazine

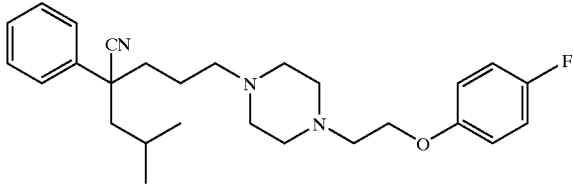

The free compound (0.23 g, 85%) of the title compound was obtained as a colorless oil from 2-(2-methylpropyl)-5-oxo-2-phenyl pentane nitrile (0.15 g) and 1-[2-(4-fluorophenoxy)ethyl]piperazine (0.14 g) in the same manner as Example 1.
Free Compound;
$^1$H-NMR (400 MHz, CDCl$_3$); δ (ppm) 0.67 (d, J=6.4 Hz, 3H), 0.87–0.94 (m, 1H), 0.98 (d, J=6.4 Hz, 3H), 1.14–1.30 (m, 1H), 1.55–1.72 (m, 2H), 1.84–2.05 (m, 3H), 2.26 (t, J=7.2 Hz, 2H), 2.38 (br-s, 4H), 2.77 (t, J=6.0 Hz, 2H), 4.04 (t, J=6.0 Hz, 2H), 6.80–6.86 (m, 2H), 6.92–6.99 (m, 2H), 7.26–7.32 (m, 1H), 7.43–7.43 (m, 4H).

The above free compound (0.23 g) was treated in a usual manner to give the hydrochloride (0.21 g) of the title compound.
Hydrochloride;
$^1$H-NMR (400 MHz, DMSO-d$_6$); δ (ppm) 0.62 (d, J=6.4 Hz, 3H), 0.90 (d, J=6.4 Hz, 3H), 1.33–1.48 (m, 2H), 1.33–2.10 (m, 5H), 2.97–3.18 (m, 2H), 3.20–3.80 (m, 10H), 4.38 (br-s, 2H), 6.97–7.04 (m, 2H), 7.10–7.17 (m, 2H), 7.31–7.37 (m, 1H), 7.40–7.50 (m, 4H).
ESI-Mass; 438 (MH+).

Example 31

Synthesis of 1-[(4-Cyano-5-methyl-4-phenyl)hexyl]-4-[2-(2-(fluorophenoxy)ethyl]piperazine

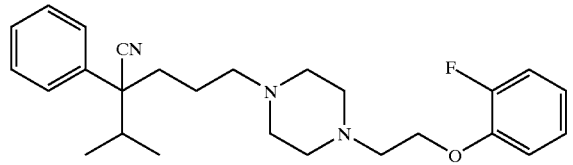

The free compound (100 mg, 26%) of the title compound was obtained as a colorless oil from 1-[(4-cyano-5-methyl-4-phenyl)hexyl]-4-(2-hydroxyethyl)piperazine (300 mg), 2-fluorophenol (408 mg), triphenyl phosphine (263 mg) and 40% azodicarboxylic acid diethyl ester/toluene solution (480 mg) in the same manner as in Example 36-2.
Free Compound;
$^1$H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.49–1.61 (m, 1H), 1.89 (dt, J=4.4, 13.6 Hz, 1H), 2.06–2.19 (m, 2H), 2.24–2.30 (m, 2H), 2.30–2.45 (m, 4H), 2.45–2.66 (m, 4H), 2.82 (t, J=6.0 Hz, 2H), 4.15 (t, J=6.0 Hz, 2H), 6.86–6.92 (m, 1H), 6.92–6.98 (m, 1H), 7.01–7.09 (m, 2H), 7.26–7.32 (m, 1H), 7.33–7.38 (m, 4H).

The above free compound (100 mg) was treated in a usual manner to give the hydrochloride (117 mg) of the title compound.
Hydrochloride;
$^1$H-NMR (400 MHz, DMSO-$d_6$); δ (ppm) 0.67 (d, J=6.8 Hz, 3H), 1.12 (d, J=6.8 Hz, 3H), 1.16–1.30 (m, 1H), 1.54–1.68 (m, 1H), 2.03–2.28 (m, 3H), 2.90–3.70 (m, 12H), 4.30–4.44 (m, 2H), 6.95–7.03 (m, 1H), 7.12–7.27 (m, 3H), 7.33–7.40 (m, 1H), 7.41–7.49 (m, 4H).
ESI-Mass; 424 (MH+).

Example 32

Synthesis of 1-[(4-Cyano-5-methyl-4-phenyl)hexyl]-4-[2-(3-fluorophenoxy)ethyl]piperazine The free compound (204 mg, 53%) of the title compound was obtained as a colorless oil from 1-[(4-cyano-5-methyl-4-phenyl)hexyl]-4-(2-hydroxyethyl)piperazine (300 mg), 3-fluorophenol (408 mg), triphenyl phosphine (263 mg) and 40% azodicarboxylic acid diethyl ester/toluene solution (480 mg) in the same manner as in Example 36-2.
Free Compound;
$^1$H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.49–1.61 (m, 1H), 1.88 (dt, J=4.4, 12.4 Hz, 1H), 2.08–2.18 (m, 2H), 2.23–2.30 (m, 2H), 2.30–2.45 (m, 4H), 2.45–2.65 (m, 4H), 2.78 (t, J=5.8 Hz, 2H), 4.06 (t, J=5.8 Hz, 2H), 6.58–6.70 (m, 3H), 7.17–7.23 (m, 1H), 7.26–7.32 (m, 1H), 7.33–7.38 (m, 4H).

The above free compound (204 mg) was treated in a usual manner to give the hydrochloride (234 mg) of the title compound.
Hydrochloride;
$^1$H-NMR (400 MHz, DMSO-$d_6$); δ (ppm) 0.67 (d, J=6.4 Hz, 3H), 1.12 (d, J=6.4 Hz, 3H), 1.16–1.30 (m, 1H), 1.52–1.68 (m, 1H), 2.00–2.30 (m, 3H), 3.00–3.70 (m, 12H), 4.20–4.40 (m, 2H), 6.78–6.90 (m, 3H), 7.30–7.39 (m, 2H), 7.42–7.48 (m, 4H).
ESI-Mass; 424 (MH+).

Example 33

Synthesis of 1-[(4-Cyano-5-methyl-4-phenyl)hexyl]-4-[-3-(4-fluorophenoxy)ethyl]piperazine 33-1) 1-[5-(4-Fluorophenoxy)pentyl]piperazine

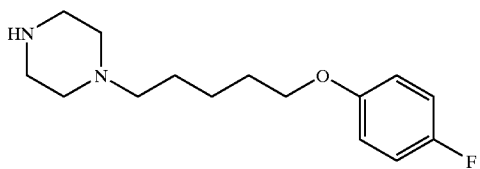

The free compound (1.94 g, 92%) of the title compound was obtained as a colorless oil from t-butyl-1-piperazine carboxylate (1.07 g) and 4-fluorophenoxypentyl iodide (1.61 g) in the same manner as in Preparatory Example 4.
Free Compound;
$^1$H-NMR (400 MHz, CDCl$_3$); δ (ppm) 1.50–1.90 (m, 10H), 2.34–2.50 (m, 4H), 2.90–2.96 (m, 2H), 3.88–3.96 (m, 2H), 6.79–6.85 (m, 12H), 6.93–6.99 (m, 2H).

33-2) 1-[(4-Cyano-5-methyl-4-phenyl)hexyl]-4-[3-(4-fluorophenoxy)pentyl]piperazine

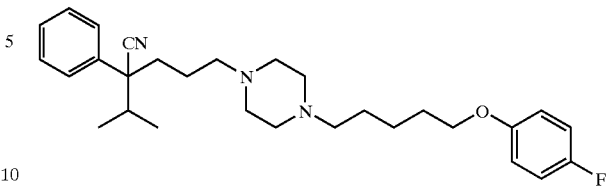

The free compound (177 mg, 89%) of the title compound was obtained as a colorless oil from 2-(1-methylethyl)-5-oxo-2-phenyl pentane nitrile (92 mg) and 1-[3-(4-fluorophenyl)pentyl]piperazine (114 mg) in the same manner as in Example 1.
Free Compound;
$^1$H-NMR (400 MHz, CDCl$_3$); δ (ppm) 0.78 (d, J=6.6 Hz, 3H), 1.05–1.20 (m, 1H), 1.20 (d, J=6.6 Hz, 3H), 1.40–1.90 (m, 10H), 2.05–2.20 (m, 2H), 2.20–2.50 (m, 10H), 3.85–3.40 (m, 2H), 6.75–6.85 (m, 2H), 6.90–7.00 (m, 2H), 7.25–7.40 (m, 5H).

The above free compound (175 mg) was treated in a usual manner to give the hydrochloride (160 mg) of the title compound.
Hydrochloride;
$^1$H-NMR (400 MHz, DMSO-$d_6$); δ (ppm) 0.65 (d, J=6.6 Hz, 3H), 1.09 (d, J=6.6 Hz, 3H), 1.20–1.35 (m, 1H), 1.40–1.60 (m, 2H), 1.60–1.80 (m, 6H), 2.00–2.25 (m, 2H), 3.00–3.20 (m, 2H), 3.20–3.80 (m, 10H), 3.90–4.00 (m, 2H), 6.86–6.96 (m, 2H), 7.00–7.11 (m, 2H), 7.30–7.46 (m, 5H).
ESI-Mass; 466 (MH+).

Example 34

Synthesis of 1-[(4-Cyano-5-methyl-4-phenyl)hexyl]-4-[3-(4-fluorophenoxy)ethyl]piperazine

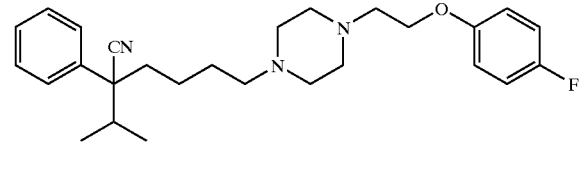

The free compound (54 mg, 2.9%) of the title compound was obtained as a colorless oil from 2-(1-methylethyl)-5-oxo-2-phenyl hexane nitrile (928 mg) and 1-[3-(4-fluorophenyl)ethyl]piperazine (104 mg) in the same manner as in Example 1.
Free Compound;
$^1$H-NMR (400 MHz, CDCl$_3$); δ (ppm) 0.77 (d, J=6.4 Hz, 3H), 0.90–1.00 (m, 1H), 1.19 (d, J=6.4 Hz, 3H), 1.32–1.42 (m, 1H), 1.45–1.52 (m, 1H), 1.80–1.90 (m, 1H), 2.05–2.20 (m, 2H), 2.20–2.27 (m, 2H), 2.30–2.50 (m, 4H), 2.50–2.65 (m, 4H), 2.78 (t, J=6.0 Hz, 2H), 4.05 (t, J=6.0 Hz, 2H), 6.80–6.85 (m, 2H), 6.90–7.00 (m, 2H), 7.28–7.32 (m, 1H), 7.32–7.40 (m, 4H).

This free compound (54 mg) was treated in a usual manner to give the hydrochloride (40 mg) of the title compound.
Hydrochloride;
$^1$H-NMR (400 MHz, DMSO-$d_6$); δ (ppm) 0.66 (d, J=6.4 Hz, 3H), 0.83 (m, 1H), 1.13 (d, J=6.4 Hz, 3H), 1.15–1.30 (m, 1H), 1.55–1.75 (m, 1H), 2.00–2.30 (m, 3H), 2.95–3.10 (m, 1H), 3.30–3.80 (m, 4H), 4.34 (m, 2H), 6.95–7.05 (m, 2H), 7.10–7.20 (m, 2H), 7.30–7.40 (m, 2H), 7.40–7.50 (m, 4H).
ESI-Mass; 438 (MH+).

Example 35

Synthesis of 1-[(4-Cyano-5-methyl-4-phenyl)hexyl]-4-[2-(3,4-difluorophenoxy)ethyl]piperazine

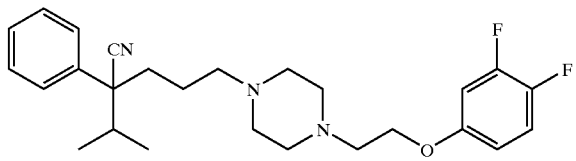

The free compound (96 mg, 24%) of the title compound was obtained as a colorless oil from 1-[(4-cyano-5-methyl-4-phenyl)hexyl]-4-(2-hydroxyethyl)piperazine (300 mg), 3,4-difluorophenol (360 mg), triphenyl phosphine (290 mg) and 40% azodicarboxylic acid diethyl ester/toluene solution (440 mg) in the same manner as in Example 36-2.
Free Compound;
$^1$H-NMR (400 MHz, CDCl$_3$); δ (ppm) 0.77 (d, J=6.8 Hz, 3H), 1.04–1.18 (m, 1H), 1.20 (d, J=6.8 Hz, 3H), 1.48–1.61 (m, 1H), 1.88 (dt, J=4.4, 13.6 Hz, 1H), 2.08–2.18 (m, 2H), 2.27 (br-t, J=7.6 Hz, 2H), 2.30–2.46 (m, 4H), 2.46–2.62 (m, 4H), 2.76 (t, J=5.8 Hz, 2H), 4.01 (t, J=5.8 Hz, 2H), 6.55–6.60 (m, 1H), 6.68–6.74 (m, 1H), 7.00–7.07 (m, 1H), 7.26–7.31 (m, 1H), 7.34–7.38 (m, 4H).

The above free compound (96 mg) was treated in a usual manner to give the hydrochloride (110 mg) of the title compound.
Hydrochloride;
$^1$H-NMR (400 MHz, DMSO-d$_6$); δ (ppm) 0.67 (d, J=6.8 Hz, 3H), 1.11 (d, J=6.8 Hz, 3H), 1.17–1.33 (m, 1H), 1.54–1.70 (m, 1H), 2.05–2.25 (m, 3H), 3.00–3.80 (m, 12H), 4.25–4.40 (m, 2H), 6.81–6.87 (m, 1H), 7.12–7.20 (m, 1H), 7.34–7.42 (m, 2H), 7.42–7.49 (m, 4H).
ESI-Mass; 422 (MH+).

Example 36

Synthesis of 1-[(4-Cyano-5-methyl-4-phenyl)hexyl]-4-[2-(4-chlorophenoxy)ethyl]piperazine

36-1) 1-[(4-Cyano-5-methyl-4-phenyl)hexyl]-4-(2-hydroxyethyl)piperazine

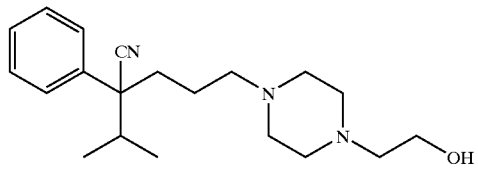

The free compound (1.06 g, 75%)of the title compound was obtained as a colorless oil from 2-(1-methylethyl)-5-oxo-2-phenyl pentane nitrile (1.00 g) and 1-piperazine ethanol (1.21 g) in the same manner as in Example 1.
Free Compound;
$^1$H-NMR (400 MHz, CDCl$_3$); δ (ppm) 0.77 (d, J=6.8 Hz, 3H), 1.06–1.20 (m, 1H), 1.20 (d, J=6.8 Hz, 3H), 1.49–1.63 (m, 1H), 1.88 (dt, J=4.4 Hz, 12.8 Hz, 1H), 2.08–2.19 (m, 2H), 2.22–2.30 (m, 2H), 2.30–2.41 (m, 4H), 2.41–2.55 (m, 4H), 2.52 (t, J=5.8 Hz, 2H), 3.57 (t, J=5.8 Hz, 2H), 7.26–7.32 (m, 1H), 7.34–7.39 (m, 4H).
ESI-Mass 330 (MH+).

36-2) 1-[(4-Cyano-5-methyl-4-phenyl)hexyl]-4-[2-(4-chlorophenoxy)ethyl]piperazine

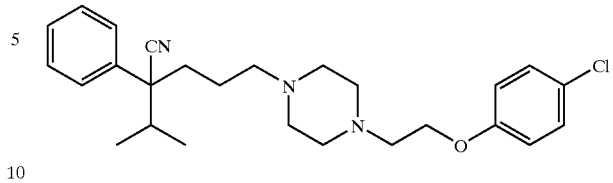

1-[(4-Cyano-5-methyl-4-phenyl)hexyl]-4-(2-hydroxyethyl)piperazine (500 mg), 4-chlorophenol (390 mg) and triphenyl phosphine (796 mg) were dissolved in tetrahydrofuran (15.0 ml), then a solution of 40% azodicarboxylic acid diethyl ester/toluene solution (529 mg) in tetrahydrofuran (5 ml) was added thereto, and the mixture was stirred at room temperature overnight. The reaction mixture was evaporated, and the residue was purified by Cromatorex NH silica gel column chromatography (hexane/ethyl acetate system), whereby the free compound (47 mg, 7%) of the title compound was obtained as a colorless oil.
Free Compound;
$^1$H-NMR (400 MHz, CDCl$_3$); δ (ppm) 0.77 (d, J=6.8 Hz, 3H), 1.04–1.19 (m, 1H), 1.20 (d, J=6.8 Hz, 3H), 1.50–1.65 (m, 1H), 1.88 (dt, J=4.4, 12.8 Hz, 1H), 2.08–2.18 (m, 2H), 2.27 (br-t, J=7.2 Hz, 2H), 2.30–2.43 (m, 4H), 2.50–2.62 (m, 4H), 2.77 (t, J=6.0 Hz, 2H), 4.04 (t, J=6.0 Hz, 2H), 6.80–6.84 (m, 2H), 7.19–7.23 (m, 2H), 7.25–7.31 (m, 1H), 7.33–7.38 (m, 4H).

The above free compound (47 mg) was treated in a usual manner to give the hydrochloride (54 mg) of the title compound.
Hydrochloride;
$^1$H-NMR (400 MHz, DMSO-d$_6$); δ (ppm) 0.67 (d, J=6.8 Hz, 3H), 1.11 (d, J=6.8 Hz, 3H), 1.30–1.45 (m, 1H), 1.59–1.72 (m, 1H), 2.08–2.25 (m, 3H), 3.00–4.35 (m, 12H), 4.38–4.49 (m, 2H), 7.07–7.34 (m, 2H), 7.34–7.40 (m, 3H), 7.42–7.48 (m, 4H).
ESI-Mass; 440 (MH+).

Example 37

Synthesis of 1-{[4-Cyano-5-methyl-4-(3,4-dichlorophenyl)hexyl]}-4-[2-(4-fluorophenoxy)ethyl]piperazine

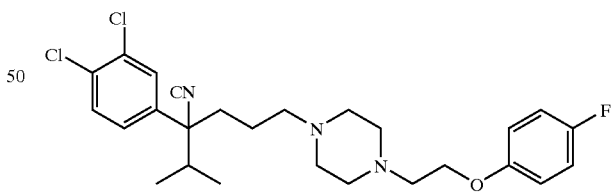

The title compound (390 mg, 68%) was obtained as a colorless oil in the same manner as in Example 1 from 2-(1-methylethyl)-5-oxo-2-(3,4-dichlorophenyl)pentane nitrile (330 mg) synthesized from 3,4-dichlorophenyl acetonitrile, and 1-[2-(4-fluorophenoxy)ethyl]piperazine (312 mg).
Free Compound;
$^1$H-NMR (400 MHz, CDCl$_3$); δ (ppm) 0.79 (d, J=6.8 Hz, 3H), 1.02–1.15 (m, 1H), 1.20 (d, J=6.8 Hz, 3H), 1.49–1.65 (m, 1H), 1.78–89 (m, 1H), 2.02–2.20 (m, 2H), 2.22–2.48 (m, 6H), 2.48–2.66 (m, 4H), 2.78 (t, J=5.8 Hz, 2H), 4.04 (t, J=5.8

Hz, 2H), 6.80–6.86 (m, 2H), 6.92–6.99 (m, 2H), 7.23 (dd, J=2 Hz, 8.4 Hz, 1H), 7.43–7.48 (m, 2H).

The above free compound (390 mg) was treated in a usual manner to give the hydrochloride (348 mg) of the title compound.
Hydrochloride;
$^1$H-NMR (400 MHz, DMSO-d$_6$); δ (ppm) 0.66 (d, J=6.6 Hz, 3H), 1.10 (d, J=6.6 Hz, 3H), 1.16–1.30 (m, 1H), 1.531–1.68 (m, 1H), 2.02–2.30 (m, 3H), 2.97–3.74 (m, 12H), 4.24–4.38 (br-s, 2H), 6.97–7.03 (m, 2H), 7.10–7.17 (m, 2H), 7.41–7.46 (m, 1H), 7.66 (d, J=2.20 Hz, 1H), 7.72 (d, J=8.42 Hz, 1H).
ESI-Mass; 492 (MH+).

Example 38

Synthesis of 1-[(4-Cyano-4-cyclohexyl-4-phenyl) hexyl]-4-[2-(4-fluorophenoxy)ethyl]piperazine

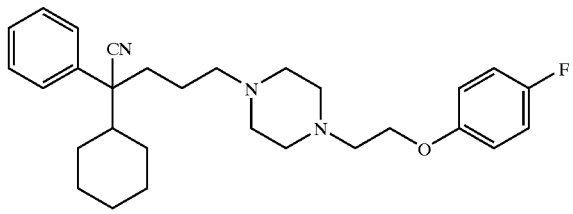

The free compound (0.17 g, 67%) of the title compound was obtained as a colorless oil from 2-cyclohexyl-5-oxo-2-phenyl pentane nitrile (0.16 g) and 1-[2-(4-fluorophenoxy)ethyl]piperazine (0.12 g) in the same manner as in Example 1.
Free Compound;
$^1$H-NMR (400 MHz, CDCl$_3$); δ (ppm) 0.99–1.18 (m, 4H), 1.18–1.34 (m, 3H), 1.48–1.77 (m, 4H), 1.82–1.92 (m, 2H), 2.05–2.23 (m, 2H), 2.27 (t, J=6.8 Hz, 2H), 2.36 (br-s, 4H), 2.55 (br-s, 4H), 2.77 (t, J=6.0 Hz, 2H), 4.04 (t, J=6.0 Hz, 2H), 6.79–6.86 (m, 2H), 6.92–6.99 (m, 2H), 7.26–7.32 (m, 1H), 7.33–7.39 (m, 4H).

The above free compound (0.17 g) was treated in a usual manner to give the hydrochloride (0.19 g) of the title compound.
Hydrochloride;
$^1$H-NMR (400 MHz, DMSO-d$_6$); δ (ppm) 0.80–0.92 (m, 1H), 0.96–1.34 (m, 6H), 1.52–1.68 (m, 3H), 1.72–1.87 (m, 2H), 2.00–2.23 (m, 3H), 2.97–3.23 (m, 2H), 3.24–3.80 (m, 10H), 4.34 (br-s, 2H), 6.97–7.04 (m, 2H), 7.10–7.17 (m, 2H), 7.31–7.38 (m, 1H), 7.39–7.47 (m, 4H).
ESI-Mass; 464 (MH+).

Example 39

Synthesis of 1-[(4-Cyano-5-methyl-4-phenyl)hexyl]-4-[2-(4-methoxyphenoxy)ethyl]piperazine

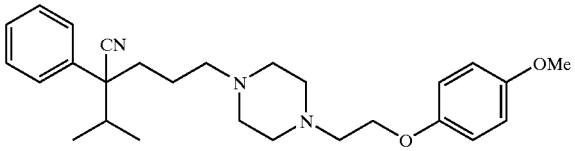

The free compound (877 mg, 85%) of the title compound was obtained as a colorless oil from 1-[(4-cyano-5-methyl-4-phenyl)hexyl]-4-(2-hydroxyethyl)piperazine (780 mg), 4-methoxyphenol (1.18 g), triphenyl phosphine (680 mg) and 40% diazocarboxylic acid diethyl ester/toluene solution (1.24 g) in the same manner as in Example 36-2.
Free Compound;
$^1$H-NMR (400 MHz, CDCl$_3$); δ (ppm) 0.77 (d, J=6.8 Hz, 3H), 1.06–1.18 (m, 1H), 1.20 (d, J=6.8 Hz, 3H), 1.50–1.65 (m, 1H), 1.88 (dt, J=4.4, 13.6 Hz, 1H), 2.07–2.20 (m, 2H), 2.27 (br-t, J=7.2 Hz, 2H), 2.30–2.46 (m, 4H), 2.46–2.65 (m, 4H), 2.76 (t, J=5.8 Hz, 2H), 3.76 (s, 3H), 4.03 (t, J=5.8 Hz, 2H), 6.79–6.86 (m, 4H), 7.26–7.32 (m, 1H), 7.34–7.40 (m, 4H).

The above free compound (877 mg) was treated in a usual manner to give the hydrochloride (995 mg) of the title compound.
Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.15–1.30 (m, 1H), 1.55–1.67 (m, 1H), 2.03–2.27 (m, 3H), 2.96–3.85 (m, 12H), 3.70 (s, 3H), 4.16–4.33 (m, 2H), 6.85–6.96 (m, 4H), 7.34–7.41 (m, 1H), 7.42–7.49 (m, 4H).
ESI-Mass; 436 (MH+).

Example 40

Synthesis of 1-[(4-Cyano-5-methyl-4-phenyl)hexyl]-4-[2-(2,3-dimethoxyphenoxy)ethyl]piperazine

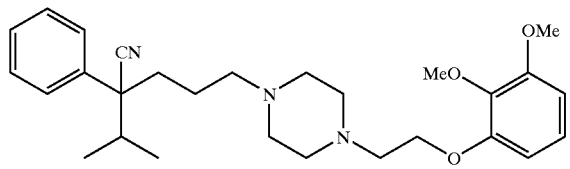

The free compound (112 mg, 26%) of the title compound was obtained as a colorless oil from 1-[(4-cyclo-5-methyl-4-phenyl)hexyl]-4-(2-hydroxyethyl)piperazine (300 mg), 2,3-dimethoxyphenol (720 mg), triphenyl phosphine (290 mg) and 40% azodicarboxylic acid diethyl ester/toluene solution (440 mg) in the same manner as in Example 36-2.
Free Compound;
$^1$H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.50–1.61 (m, 1H), 1.89 (dt, J=4.4, 13.6 Hz, 1H), 2.08–2.18 (m, 2H), 2.24–2.30 (m, 2H), 2.30–2.44 (m, 4H), 2.48–2.68 (m, 4H), 2.81 (t, J=6.0 Hz, 2H), 3.83 (s, 3H), 3.85 (s, 3H), 4.10–4.15 (m, 2H), 6.56 (dd, J=1.2, 8.4 Hz, 1H), 6.57 (dd, J=1.2, 8.4 Hz, 1H), 6.95 (dd, J=8.4, 8.4 Hz, 1H), 7.26–7.31 (m, 1H), 7.34–7.38 (m, 4H).

The above free compound (112 mg) was treated in a usual manner to give the hydrochloride (129 mg) of the title compound.
Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.20–1.32 (m, 1H), 1.57–1.71 (m, 1H), 2.05–2.26 (m, 3H), 3.00–3.90 (m, 12H), 3.68 (s, 3H), 3.78 (s, 3H), 4.26–4.42 (m, 2H), 6.68–6.74 (m, 2H), 7.01 (t, J=8.4 Hz, 1H), 7.34–7.40 (m, 1H), 7.43–7.49 (m, 4H).
ESI-Mass; 466 (MH+).

Example 41

Synthesis of 1-[(4-Cyano-5-methyl-4-phenyl)hexyl]-4-[2-(3,4-dimethoxyphenoxy)ethyl]piperazine

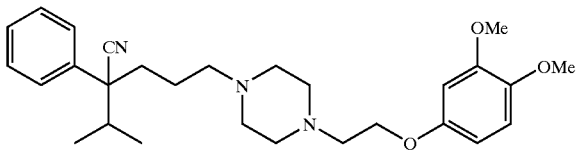

The free compound (104 mg, 25%) of the title compound was obtained as a colorless oil from 1-[(4-cyano-5-methyl-4-phenyl)hexyl]-4-(2-hydroxyethyl)piperazine (300 mg), 3,4-dimethoxyphenol (720 mg), triphenyl phosphine (290 mg) and 40% azodicarboxylic acid diethyl ester/toluene solution (440 mg) in the same manner as in Example 36-2.
Free Compound;
$^1$H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.50–1.61 (m, 1H), 1.88 (dt, J=4.4, 13.6 Hz, 1H), 2.08–2.19 (m, 2H), 2.28 (br-t, J=7.2 Hz, 2H), 2.30–2.46 (m, 4H), 2.46–2.65 (m, 4H), 2.77 (t, J=5.8 Hz, 2H), 3.83 (s, 3H), 3.85 (s, 3H), 4.03 (t, J=5.8 Hz, 2H), 6.38 (dd, J=2.8, 8.8 Hz, 1H), 6.53 (d, J=2.8 Hz, 1H), 6.76 (d, J=8.8 Hz, 1H), 7.26–7.31 (m, 1H), 7.32–7.38 (m, 4H).

The above free compound (104 mg) was treated in a usual manner to give the hydrochloride (119 mg) of the title compound.
Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.15–1.32 (m, 1H), 1.55–1.68 (m, 1H), 2.03–2.27 (m, 3H), 3.00–3.85 (m, 12H), 3.69 (s, 3H), 3.74 (s, 3H), 4.20–4.35 (m, 2H), 6.48 (br-dd, J=2.8, 8.8 Hz, 1H), 6.63 (br-d, J=2.8 Hz, 1H), 6.86 (d, J=8.8 Hz, 1H), 7.34–7.40 (m, 1H), 7.42–7.50 (m, 4H).

ESI-Mass; 466 (MH+).

Example 42

Synthesis of 1-[(4-Cyano-5-methyl-4-phenyl)hexyl]-4-[2-(4-aminophenoxy)ethyl]piperazine

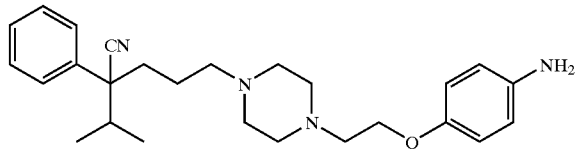

In a hydrogen atmosphere, 1-[(4-cyano-5-methyl-4-phenyl)hexyl]-4-[2-(4-nitrophenoxy)ethyl]piperazine (925 mg) was dissolved in methanol (20 ml), then 10% Pd-C (90 mg) was added thereto, and the mixture was stirred overnight at room temperature. After 10% Pd-C was removed by filtration, the filtrate was evaporated, whereby the free compound (840 mg, 97%) of the title compound was obtained as a yellow oil.
Free Compound;
$^1$H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.50–1.62 (m, 1H), 1.88 (dt, J=4.4, 12.8 Hz, 1H), 2.08–2.18 (m, 2H), 2.27 (br-t, J=7.2 Hz, 2H), 2.30–2.45 (m, 4H), 2.45–2.65 (m, 4H), 2.74 (t, J=6.0 Hz, 2H), 3.42 (br-s, 2H), 4.01 (t, J=6.0 Hz, 2H), 6.61–6.65 (m, 2H), 6.71–6.76 (m, 2H), 7.25–7.32 (m, 1H), 7.33–7.39 (m, 4H).

This free compound (272 mg) was treated in the same manner as in Example 1 to give the hydrochloride (332 mg) of the title compound.

Hydrochloride;
$^1$H-NMR (400 MHz, DMSO-d$_6$); δ (ppm) 0.67 (d, J=6.8 Hz, 3H), 1.11 (d, J=6.8 Hz, 3H), 1.15–1.32 (m, 1H), 1.55–1.70 (m, 1H), 2.06–2.25 (m, 3H), 2.97–3.75 (m, 14H), 4.30–4.42 (m, 2H), 7.07–7.13 (m, 2H), 7.32–7.40 (m, 3H), 7.43–7.48 (m, 4H).

ESI-Mass; 421 (MH+).

Example 43

Synthesis of 1-[(4-Cyano-5-methyl-4-phenyl)hexyl]-4-[2-(4-dimethylaminophenoxy)ethyl]piperazine

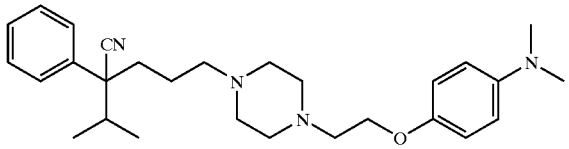

1-[(4-Cyano-5-methyl-4-phenyl)hexyl]-4-[2-(4-aminophenoxy)ethyl]piperazine (243 mg) was dissolved in acetonitrile (5.0 ml) and 37% aqueous formaldehyde (1.0 ml), and sodium cyano borohydride (153 mg) and glacial acetic acid (0.2 ml) were added thereto, and the mixture was stirred overnight at room temperature. The organic layer was partitioned by adding aqueous saturated sodium bicarbonate and ethyl acetate, washed with water, and dried over sodium sulfate anhydrous, and after the drying agent was removed by filtration, the filtrate was evaporated, and the residue was purified by Cromatorex NH silica gel column chromatography (hexane/ethyl acetate system) to give the free compound (210 mg, 81%) of the title compound as a colorless oil.

Free Compound;

$^1$H-NMR (400 MHz, CDCl$_3$); δ (ppm) 0.77 (d, J=6.8 Hz, 3H), 1.03–1.20 (m, 1H), 1.20 (d, J=6.8 Hz, 3H), 1.50–1.65 (m, 1H), 1.88 (dt, J=4.4, 12.4 Hz, 1H), 2.06–2.19 (m, 2H), 2.19–2.30 (m, 2H), 2.30–2.45 (m, 4H), 2.45–2.65 (m, 4H), 2.75 (t, J=5.8 Hz, 2H), 4.03 (t, J=5.8 Hz, 2H), 6.70–6.75 (m, 2H), 6.80–6.85 (m, 2H), 7.25–7.31 (m, 1H), 7.32–7.38 (m, 4H).

The above free compound (210 mg) was treated in a usual manner to give the hydrochloride (260 mg) of the title compound.

Hydrochloride;

$^1$H-NMR (400 MHz, DMSO-d$_6$); δ (ppm) 0.67 (d, J=6.8 Hz, 3H), 1.11 (d, J=6.8 Hz, 3H), 1.18–1.35 (m, 1H), 1.55–1.72 (m, 1H), 2.02–2.26 (m, 3H), 3.07 (s, 6H), 3.00–3.90 (m, 12H), 4.30–4.50 (m, 2H), 7.10–7.20 (m, 2H), 7.32–7.48 (m, 5H), 7.62–7.84 (m, 2H).

ESI-Mass; 449 (MH+).

Example 44

Synthesis of 1-[(4-Cyano-5-methyl-4-phenyl)hexyl]-4-[2-(4-actamidophenoxy)ethyl]piperazine

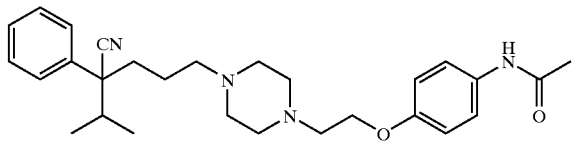

1-[(4-Cyano-5-methyl-4-phenyl)hexyl]-4-[2-(4-aminophenoxy)ethyl]piperazine (261 mg) was dissolved in acetic acid anhydride (2 ml) and pyridine (2 ml), and the mixture was stirred overnight at room temperature. The organic layer was partitioned by adding water and ethyl acetate, washed with water, and dried over sodium sulfate anhydrous, and after the drying agent was removed by filtration, the filtrate was evaporated. The residue was purified by Cromatorex NH silica gel column chromatography (hexane/ethyl acetate system) to give the free compound (2 mg, 1%) of the title compound as a colorless oil.

Free Compound;
$^1$H-NMR (400 MHz, CDCl$_3$); δ (ppm) 0.77 (d, J=6.8 Hz, 3H), 1.06–1.19 (m, 1H), 1.20 (d, J=6.8 Hz, 3H), 1.50–1.62 (m, 1H), 1.89 (dt, J=4.4, 12.4 Hz, 1H), 2.07–2.21 (m, 2H), 2.15 (s, 3H), 2.28 (br-t, J=7.2 Hz, 2H), 2.30–2.46 (m, 4H), 2.46–2.65 (m, 4H), 2.77 (t, J=6.0 Hz, 2H), 4.06 (t, J=6.0 Hz, 2H), 6.82–6.88 (m, 2H), 7.09 (br-s, 1H), 7.25–7.32 (m, 1H), 7.32–7.41 (m, 6H).

The above free compound (2 mg) was treated in a usual manner to give the hydrochloride (2 mg) of the title compound as an amorphous.

Hydrochloride;
$^1$H-NMR (400 MHz, CD$_3$OD); δ (ppm) 0.74 (d, J=6.8 Hz, 3H), 1.21 (d, J=6.8 Hz, 3H), 1.30–1.50 (m, 1H), 1.70–1.90 (m, 1H), 2.05–2.35 (m, 3H), 2.08 (s, 3H), 3.10–4.15 (m, 12H), 4.30–4.50 (m, 2H), 6.97 (br-d, J=8.8 Hz, 2H), 7.30–7.38 (m, 1H), 7.39–7.50 (m, 7H).

ESI-Mass; 463 (MH+).

Example 45

Synthesis of 1-[(4-Cyano-5-methyl-4-phenyl)hexyl]-4-[2-(4-methylthiophenoxy)ethyl]piperazine

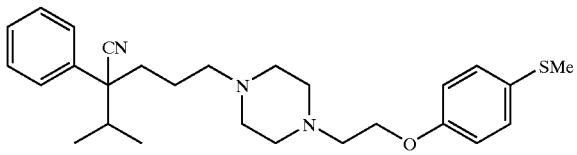

The free compound (122 mg, 30% of the title compound was obtained as a colorless oil from 1-[(4-cyano-5-methyl-4-phenyl)hexyl]-4-(2-hydroxyethyl)piperazine (300 mg), 4-methylthiophenol (430 mg), triphenyl phosphine (290 mg) and 40% azodicarboxylic acid diethyl ester/toluene solution (440 mg) in the same manner as in Example 36-2.

Free Compound;
$^1$H-NMR (400 MHz, CDCl$_3$); δ (ppm) 0.77 (d, J=6.8 Hz, 3H), 1.04–1.18 (m, 1H), 1.20 (d, J=6.8 Hz, 3H), 1.50–1.61 (m, 1H), 1.88 (dt, J=4.4, 13.2 Hz, 1H), 2.08–2.18 (m, 2H), 2.24–2.30 (m, 2H), 2.30–2.43 (m, 4H), 2.44 (s, 3H), 2.46–2.65 (m, 4H), 2.77 (t, J=5.8 Hz, 2H), 4.06 (t, J=5.8 Hz, 2H), 6.82–6.86 (m, 2H), 7.23–7.31 (m, 3H), 7.33–7.39 (m, 4H).

The above free compound (122 mg) was treated in a usual manner to give the hydrochloride (141 mg) of the title compound.

Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.16–1.30 (m, 1H), 1.54–1.67 (m, 1H), 2.03–2.26 (m, 3H), 2.42 (s, 3H), 2.95–3.80 (m, 12H), 4.20–4.36 (m, 2H), 6.93–6.99 (m, 2H), 7.23–7.28 (m, 2H), 7.34–7.40 (m, 1H), 7.41–7.48 (m, 4H).

ESI-Mass; 452 (MH+).

Example 46

Synthesis of 1-[(4-Cyano-5-methyl-4-phenyl)hexyl]-4-[2-(2-cyanophenoxy)ethyl]piperazine 46-1) 2-(2-Cyanophenoxy)ethylpiperazine

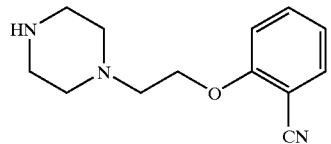

1-Formyl-4-(2-hydroxyethyl)piperazine (4.95 g) was dissolved in tetrahydrofuran (100 ml), then triphenyl phosphine (10.14 g) and 2-cyanophenol (3.57 g) were added thereto, and 40% azodicarboxylic acid diethyl ester/toluene solution (13.5 ml) was added dropwise thereto, and the title compound (1.60 g) was obtained in the same manner as in Example 47-1).

$^1$H-NMR (400 MHz, CDCl$_3$); δ (ppm) 2.48–2.67 (m, 4H), 2.86–2.97 (m, 6H), 4.22 (t, J=5.8 Hz, 2H), 6.94–7.04 (m, 2H), 7.49–7.57 (m, 2H).

46-2) 1-[(4-Cyano-5-methyl-4-phenyl)hexyl]-4-[2-(2-cyanophenoxy)ethyl]piperazine

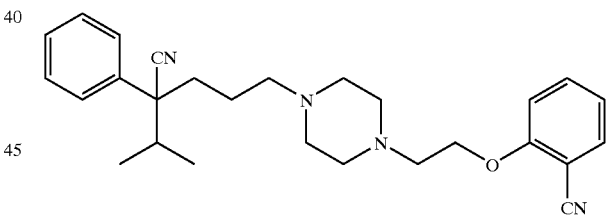

2-(1-Methylethyl)-5-oxo-2-phenyl pentane nitrile (150 mg), 1-[2-(4-cyanophenoxy)ethyl]piperazine (200 mg), and acetic acid (0.10 ml) were dissolved in dichloromethane (15 ml), then sodium triacetoxy borohydride (200 mg) was added thereto, and the mixture was stirred overnight at room temperature. The reaction mixture was poured into aqueous saturated sodium bicarbonate, extracted with dichloromethane, washed with water and brine, dried, and evaporated. The residue was purified by Cromatorex NH silica gel column chromatography (hexane/ethyl acetate system) to give the free compound of the title compound as an oil.

Free Compound;
$^1$H-NMR (400 MHz, CDCl$_3$); δ (ppm) 0.77 (d, J=6.8 Hz, 3H), 1.20 (d, J=6.8 Hz, 3H), 1.25–1.27 (m, 1H), 1.90–2.26 (m, 4H), 2.26–3.01 (m, 12H), 4.20–4.30 (m, 2H), 6.93–7.05 (m, 2H), 7.25–7.34 (m, 1H), 7.36–7.40 (m, 4H), 7.49–7.58 (m, 2H).

The above free compound was dissolved in methanol, and 4 N hydrogen chloride/ethyl acetate solution was added thereto. The solvent and excess hydrogen chloride were evaporated, and the product was recrystallized from methanol/ether to give the hydrochloride (168 mg) of the title compound.

Hydrochloride;
¹H-NMR (400 MHz, DMSO-d$_6$); δ (ppm) 0.68 (d, J=6.6 Hz, 3H), 1.11 (d, J=6.6 Hz, 3H), 1.16–1.32 (m, 1H), 1.57–1.60 (m, 1H), 2.06–2.30 (m, 3H), 3.00–3.70 (m, 14H), 4.51 (brs, 2H), 7.12–7.18 (m, 1H), 7.27–7.31 (m, 1H), 7.33–7.40 (m, 1H), 7.43–7.48 (m, 4H), 7.67–7.73 (m, 1H), 7.75–7.79 (m, 1H).
ESI-Mass; 431 (MH+).

Example 47

Synthesis of 1-[(4-Cyano-5-methyl-4-phenyl)hexyl]-4-[2-(4-cyanophenoxy)ethyl]piperazine 47-1) 2-(4-Cyanophenoxy)ethylpiperazine

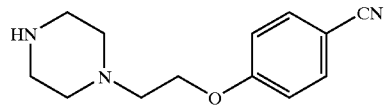

1-Formyl-4-(2-hydroxyethyl)piperazine (1.65 g) synthesized according to Tetrahedron Letters, 26 (31), 3703–3706, was dissolved in tetrahydrofuran (30 ml), then triphenyl phosphine (3.38 g) and 4-cyanophenol (1.19 g) wereadded thereto, and 40% azodicarboxylic acid diethyl ester/toluene solution (4.5 ml) was added dropwise thereto at room temperature. After stirred for 4 hours, the reaction mixture was poured into water and extracted with ethyl acetate and then with diluted hydrochloric acid successively. The extract was basified with 2 N sodium hydroxide, then extracted with ethyl acetate, washed with water, dried, and evaporated. It was dissolved in methanol, and 4 N hydrogen chloride/ethyl acetate was added thereto, and the mixture was left overnight at room temperature. Ether was added to the reaction mixture, and the resulting crystals were filtered off to give the hydrochloride (1.72 g) of the title compound. This product was dissolved in methanol, then basified with aqueous sodium hydroxide, extracted with ethyl acetate, washed with water, dried, and evaporated to give the title compound (0.92 g).

¹H-NMR (400 MHz, CDCl$_3$); δ (ppm) 2.45–2.60 (m, 4H), 2.81 (t, J=5.8 Hz, 2H), 2.91 (t, J=5.8 Hz, 4H), 4.17 (t, J=5.8 Hz, 2H), 6.96 (d, J=7.7 Hz, 2H), 7.59 (d, J=7.7 Hz, 2H).

47-2) 1-[(4-Cyano-5-methyl-4-phenyl)hexyl]-4-[2-(4-cyanophenoxy)ethyl]piperazine

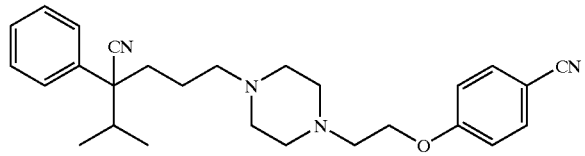

2-(1-Methylethyl)-5-oxo-2-phenyl pentane nitrile (150 mg), 1-[2-(4-cyanophenoxy)ethyl]piperazine (200 mg), and acetic acid (0.10 ml) were dissolved in dichloromethane (15 ml), then sodium triacetoxy borohydride (200 mg) was added thereto, and the mixture was stirred overnight at room temperature. The reaction mixture was poured into aqueous saturated sodium bicarbonate, extracted with dichloromethane, washed with water and brine, and dried. After evaporating, the residue was purified by Cromatorex NH silica gel column chromatography (hexane/ethyl acetate system) to give the free compound of the title compound as an oil.

Free Compound;
¹H-NMR (400 MHz, CDCl$_3$); δ (ppm) 0.77 (d, J=6.8 Hz, 3H), 1.20 (d, J=6.8 Hz, 3H), 1.25–1.27 (m, 1H), 1.90–2.26 (m, 4H), 2.26–3.01 (m, 12H), 4.08–4.23 (m, 2H), 6.91–6.96 (m, 2H), 7.27–7.34 (m, 1H), 7.35–7.40 (m, 4H), 7.56–7.61 (m, 2H).

The above free compound was dissolved in methanol, and 4 N hydrogen chloride/ethyl acetate solution was added thereto. The solvent and excess hydrogen chloride were evaporated to give the hydrochloride (134 mg) of the title compound as an amorphous.

Hydrochloride;
¹H-NMR (400 MHz, DMSO-d$_6$); δ (ppm) 0.67 (d, J=6.6 Hz, 3H), 1.11 (d, J=6.6 Hz, 3H), 1.20–1.32 (m, 1H), 1.57–1.67 (m, 1H), 2.05–2.26 (m, 3H), 2.98–3.82 (m, 14H), 4.45 (br-s, 2H), 7.14–7.19 (m, 2H), 7.34–7.40 (m, 1H), 7.42–7.47 (m, 4H), 7.79–7.84 (m, 2H).
ESI-Mass; 431 (MH+).

Example 48

Synthesis of 1-[(4-Cyano-5-methyl-4-phenyl)hexyl]-4-[2-(benzyloxy)ethyl]piperazine

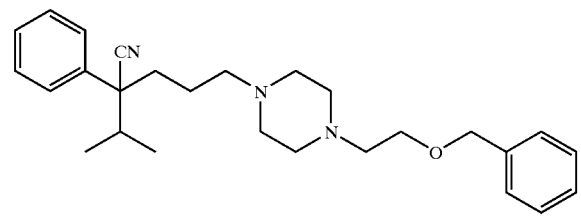

1-[(4-Cyano-5-methyl-4-phenyl)hexyl]-4-(2-hydroxyethyl)piperazine (442 mg) was dissolved in tetrahydrofuran (10 ml), then sodium hydride (54 mg) was added thereto, and after the mixture was stirred for 15 minutes at room temperature, benzyl bromide (250 mg) was added thereto, and the mixture was further stirred for 3 hours at room temperature. The organic layer was partitioned by adding water and ethyl acetate, washed with water, and dried over sodium sulfate anhydrous, and after the drying agent was removed by filtration, the filtrate was evaporated, and the residue was purified by Cromatorex NH silica gel column chromatography (hexane/ethyl acetate system) to give the free compound (270 mg, 48%) of the title compound as a colorless oil.

Free Compound;
¹H-NMR (400 MHz, CDCl$_3$); δ (ppm) 0.77 (d, J=6.8 Hz, 3H), 1.05–1.18 (m, 1H), 1.20 (d, J=6.8 Hz, 3H), 1.50–1.62 (m, 1H), 1.88 (dt, J=4.4, 12.8 Hz, 1H), 2.07–2.18 (m, 2H), 2.20–2.30 (m, 2H), 2.30–2.41 (m, 4H), 2.41–2.55 (m, 4H), 2.59 (t, J=5.8 Hz, 2H), 3.56 (t, J=5.8 Hz, 2H), 4.52 (s, 2H), 7.26–7.39 (m, 10H).

The above free compound (270 mg) was treated in a usual manner to give the hydrochloride (315 mg) of the title compound.

Hydrochloride;
¹H-NMR (400 MHz, DMSO-d$_6$); δ (ppm) 0.67 (d, J=6.8 Hz, 3H), 1.12 (d, J=6.8 Hz, 3H), 1.15–1.30 (m, 1H), 1.55–1.68 (m, 1H), 2.00–2.37 (m, 3H), 3.00–3.70 (m, 12H), 3.70–3.86 (m, 2H), 4.52 (s, 2H), 7.28–7.34 (m, 1H), 7.34–7.39 (m, 5H), 7.42–7.48 (m, 4H).

ESI-Mass; 420 (MH+).

Example 49

Synthesis of 1-[(4-Cyano-5-methyl-4-phenyl)hexyl]-4-[2-(4-fluorophenylthio)ethyl]piperazine 49-1) 2-Chloroethyl 4-fluorophenyl Sulfide

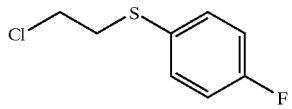

According to J.O.C., 58, 4506, 1993, the title compound (10.9 g, 98%) was obtained as a yellow oil from 4-fluorothiophenol (7.4 g) and 1,2-dichloroethane (58 ml).

$^1$H-NMR (400 MHz, CDCl$_3$); δ (ppm) 3.16 (t, J=8 Hz, 2H), 3.58 (t, J=8 Hz, 2H), 7.03 (t, J=8.8 Hz, 2H), 7.41 (dd, J=5 Hz, 8.8 Hz, 2H).

49-2) 1-[2-(4-Fluorophenylthio)ethyl]piperazine and S-(4-fluorophenyl)thiocarbonate 1-(1-piperazinyl) ethyl

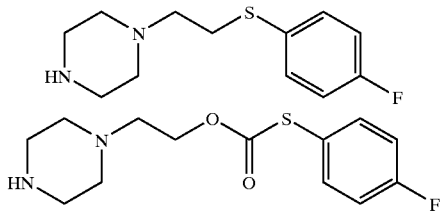

2-chloroethyl 4-fluorophenyl sulfide (2.556 g), N-(t-butoxycarbonyl)piperazine (2.686 g) and triethylamine (2 ml) were dissolved in tetrahydrofuran (30 ml) and stirred overnight at room temperature. The reaction mixture was diluted with ethyl acetate, washed with water, dried, and evaporated. The residue was dissolved in ethanol (20 ml), then 5 N HCl (10 ml) was added thereto, and the mixture was stirred at 50° C. for 1 hour. The reaction mixture was evaporated, basified with 5 N aqueous NaOH, and extracted with ethyl acetate, and the organic layer was washed with water, dried, and evaporated. The residue was purified by Cromatorex NH silica gel column chromatography (hexane/ethyl acetate system) to give the title compounds (138 mg, 4% and 159 mg, 4%) respectively as colorless oil.

(1) 1-[2-(4-Fluorophenylthio)ethyl]piperazine $^1$H-NMR (400 MHz, CDCl$_3$); δ (ppm) 2.38–2.48 (br-s, 4H), 2.58 (t, J=7.6 Hz, 2H), 2.88 (t, J=5 Hz, 4H), 3.00 (t, J=7.6 Hz, 2H), 6.98 (t, J=8.4 Hz, 2H), 6.99 (dd, J=5.2 Hz, 8.4 Hz, 2H).

(2) S-(4-Fluorophenyl)thiocarbonate 1-(1-Piperazinyl)ethyl $^1$H-NMR (400 MHz, CDCl$_3$); δ (ppm) 2.72–2.88 (br-s, 4H), 3.11 (t, J=6.8 Hz, 2H), 3.30–3.48 (m, 4H), 4.23 (t, J=6.8 Hz, 2H), 7.39–7.43 (m, 2H).

49-3) 1-[(4-Cyano-5-methyl-4-phenyl)hexyl]-4-[2-(4-fluorophenylthio)ethyl]piperazine

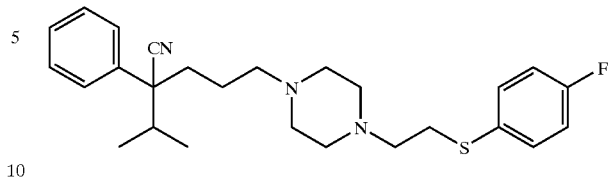

The free compound (205 mg, 82%) of the title compound was obtained as a colorless oil from 2-(1-methylethyl)-5-oxo-2-phenyl pentane nitrile (124 mg) and 1-[2-(4-fluorophenylthio)ethyl]piperazine (138 mg) in the same manner as in Example 1.

Free Compound;

$^1$H-NMR (400 MHz, CDCl$_3$); δ (ppm) 0.77 (d, J=6.8 Hz, 3H), 1.04–1.16 (m, 1H), 1.19 (d, J=6.4 Hz, 3H), 1.48–1.60 (m, 1H), 1.87 (dt, J=4.4 Hz, 12.8 Hz, 1H), 2.07–2.17 (m, 2H), 2.21–2.52 (m, 12H), 2.54–2.58 (m, 2H), 2.95–2.99 (m, 2H), 6.98 (t, J=8.6 Hz, 2H), 7.26–7.38 (m, 7H).

The above free compound was treated in a usual manner to give the hydrochloride (181 mg) of the title compound.

Hydrochloride;

$^1$H-NMR (400 MHz, DMSO-d$_6$); δ (ppm) 0.65 (d, J=6.8 Hz, 3H), 1.09 (d, J=6.8 Hz, 3H), 1.18–1.32 (m, 1H), 1.55–1.68 (m, 1H), 2.04–2.22 (m, 3H), 2.95–3.75 (m, 14H), 7.19 (t, 8.8 Hz, 2H), 7.32–7.44 (m, 5H), 7.47 (dd, 5.2 Hz, 8.8 Hz, 1H).

ESI-Mass; 440 (MH+).

Example 50

Synthesis of 1-[(4-Cyano-5-methyl-4-phenyl)hexyl]-4-[2-(4-fluorophenylsulfonyl)ethyl]piperazine 50-1) 1-[2-(4-Fluorophenylsulfonyl)ethyl]-4-[t-butoxycarbonyl)piperazine

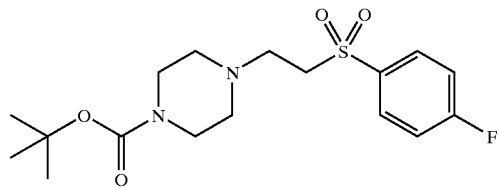

2-Chloroethyl-4-fluorophenyl sulfone (2.5 g), N-(t-butoxycarbonyl)piperazine (2.3 g) and triethylamine (1.7 ml) were dissolved in tetrahydrofuran (30 ml) and stirred overnight at room temperature. The reaction mixture was diluted with ethyl acetate, washed with water, dried, and evaporated. The residue was purified by Cromatorex NH silica gel column chromatography (hexane/ethyl acetate system) to give the title compound (4.4 g, quantitatively) as a colorless oil.

$^1$H-NMR (400 MHz, CDCl$_3$); δ (ppm) 1.44 (s, 9H), 2.30 (t, J=5 Hz, 4H) 2.79 (t, J=7.2 Hz, 2H), 3.26–3.31 (m, 6H), 7.22–7.27 (m, 2H), 7.92–7.96 (m, 2H).

50-2) 1-[(4-Cyano-5-methyl-4-phenyl)hexyl]-4-[2-(4-fluorophenylsulfonyl)ethyl]piperazine

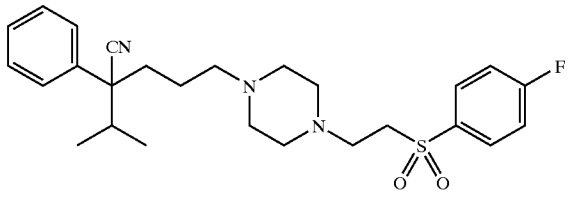

1-[2-(4-Fluorophenylsulfonyl)ethyl]-4-(t-butoxycarbonyl)piperazine (4.4 g) was dissolved in ethanol (20 ml), and 5 N HCl (10 ml) was added thereto, and the mixture was stirred at 50° C. for 2 hours. The reaction mixture was evaporated, basified with 5 N aqueous NaOH, and extracted with ethyl acetate. The organic layer was washed with water, dried, and evaporated. The free compound (80 mg, 46%) of the title compound was obtained as a colorless oil from a part (101 mg) of the residue (2.567 g) and 2-(1-methylethyl)-5-oxo-2-phenyl pentane nitrile (80 mg).
Free Compound;
$^1$H-NMR (400 MHz, CDCl$_3$); δ (ppm) 0.76 (d, J=6.8 Hz, 3/2H), 0.79 (d, 6.8 Hz, 3/2H), 1.01–1.13 (m, 1H), 1.19 (d, J=6.8 Hz, 3/2H), 1.21 (d, 6.8 Hz, 3/2H), 1.45–1.56 (m, 1H), 1.85 (ddd, J=4.4 Hz, 12 Hz, 13.6 Hz, 1/2H), 1.98 (ddd, J=4.4 Hz, 12 Hz, 13.6 Hz, 1/2H), 2.06–2.38 (m, 12H), 2.74 (t, J=7.4 Hz, 2H), 3.27 (t, J=7.4 Hz, 2H), 6.98 (t, J=8.6 Hz, 2H), 7.89–7.98 (m, 2H).

The above free compound was treated in a usual manner to give the hydrochloride (35 mg) of the title compound.
Hydrochloride;
$^1$H-NMR (400 MHz, DMSO-d$_6$); δ (ppm) 0.64 (d, J=6.4 Hz, 3H), 0.91–1.33 (m, 5H), 1.55–1.68 (m, 1H), 2.03–2.23 (m, 4H), 2.95–3.52 (m, 10H), 4.85–4.92 (m, 2H), 7.29–7.45 (m, 5H), 7.52 (t, J=8.8 Hz, 2H), 7.98 (dd, 7.8 Hz, 8.8 Hz, 2H).
ESI-Mass; 472 (MH+).

Example 51

Synthesis of 1-[(4-Cyano-5-methyl-4-phenyl)hexyl]-4-[2-(4-fluorophenylamino)ethyl]-piperazine 51-1) 1-[2-(4-Fluorophenylamino)ethyl]-4-benzylpiperazine

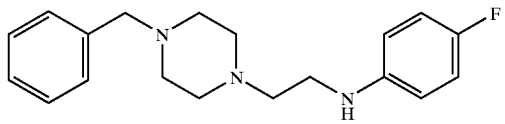

1-Benzyl-4-[N-(4-fluorophenyl)carbamoylmethyl] (12.05 g) was dissolved in tetrahydrofuran (120 ml), then lithium aluminum hydride (1.39 g) was added thereto, and the mixture was heated under reflux. After the reaction mixture was cooled, water (1.4 ml), 5 N NaOH (1.4 ml) and water (4.2 ml) were added thereto in this order, and insolubles were filtered through Celite and evaporated. The residue was purified by Cromatorex NH silica gel column chromatography (hexane/ethyl acetate system) to give the title compound (10.2 g, 89%) as a yellow oil.
$^1$H-NMR (400 MHz, CDCl$_3$); δ (ppm) 2.40–2.58 (br-s, 8H), 2.62 (t, J=6 Hz, 2H), 3.52 (s, 2H), 4.15–4.24 (br-s, 1H), 6.56 (dd, J=4.4 Hz, 8.8 Hz, 2H), 6.88 (t, J=8.8 Hz, 2H), 7.23–7.32 (m, 5H).

51-2) 1-[2-(4-Fluorophenylamino)ethyl]piperazine

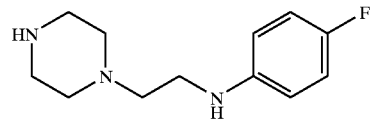

The title compound (1.45 g, quantitative) was obtained as a colorless oil from 1-[2-(4-fluorophenylamino)ethyl]-4-benzylpiperazine (2.05 g) in the same manner as in Example 65-2).

$^1$H-NMR (400 MHz, CDCl$_3$); δ (ppm) 2.40–2.55 (br-s, 4H), 2.61 (t, J=5.8 Hz, 2H), 2.90 (t, J=5 Hz, 4H), 3.11 (t, J=5.8 Hz, 2H), 4.13–4.30 (br-s, 1H), 6.56 (dd, J=4.4 Hz, 8.8 Hz, 2H), 6.89 (t, J=8.8 Hz, 2H).

51-3) 1-[(4-Cyano-5-methyl-4-phenyl)hexyl]-4-[2-(4-fluorophenylamino)ethyl]piperazine

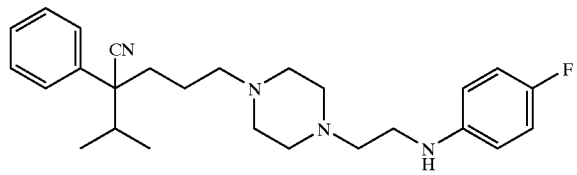

The free compound (411 mg, 69%) of the title compound was obtained as a colorless oil from 2-(1-methylethyl)-5-oxo-2-phenyl pentane nitrile (302 mg) and 1-[2-(4-fluorophenylamino)ethyl]piperazine (313 mg) in the same manner as in Example 1.

Free Compound;

$^1$H-NMR (400 MHz, CDCl$_3$); δ (ppm) 0.77 (d, J=6.8 Hz, 3H), 1.06–1.16 (m, 1H), 1.20 (d, J=6.4 Hz, 3H), 1.50–1.62 (m, 1H), 1.89 (ddd, J=4.4 Hz, 12 Hz, 13.6 Hz, 1H), 2.08–2.50 (m, 12H), 2.59 (t, J=5.8 Hz, 2H), 3.05–3.12 (m, 2H), 4.10–4.20 (br-s, 1H), 6.53–6.57 (m, 2H), 6.85–6.91 (m, 2H), 7.26–7.37 (m, 5H).

The above free compound (95 mg) was treated in a usual manner to give the hydrochloride (73 mg) of the title compound.

Hydrochloride;

$^1$H-NMR (400 MHz, DMSO-d$_6$); δ (ppm) 0.65 (d, J=6.8 Hz, 3H), 1.09 (d, J=6.4 Hz, 3H), 1.20–1.32 (m, 1H), 1.56–1.70 (m, 1H), 2.06–2.21 (m, 3H), 3.05–3.75 (m, 14H), 6.73–6.80 (m, 2H), 6.99 (t, J=8.8 Hz, 2H), 7.31–7.43 (m, 5H).

ESI-Mass; 423 (MH+).

Example 52

Synthesis of 1-[(4-Cyano-5-methyl-4-phenyl)hexyl]-4-{2-[N-(4-fluorophenyl)-N-methylamino]ethyl}piperazine

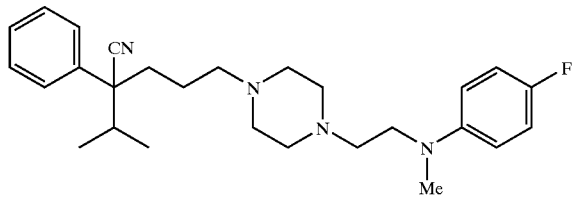

1-[(4-Cyano-5-methyl-4-phenyl)hexyl-4-[2-(4-fluorophenylamino)ethyl]piperazine (121 mg) and p-formaldehyde (87 mg) were dissolved in acetic acid (5 ml), then sodium triacetoxy borohydride (246 mg) was added thereto, and the mixture was stirred overnight at room temperature. Saturated sodium bicarbonate was added thereto, and the product was extracted with ethyl acetate, washed with water, dried, and evaporated. The residue was purified by Cromatorex NH silica gel column chromatography (hexane/ethyl acetate system) to give the free compound (61 mg, 48%) of the title compound as a colorless oil.

Free Compound;

$^1$H-NMR (400 MHz, CDCl$_3$); δ (ppm) 0.77 (d, J=6.8 Hz, 3H), 1.05–1.17 (m, 1H), 1.20 (d, J=6.8 Hz, 3H), 1.50–1.61 (m, 1H), 1.88 (ddd, J=4.4 Hz, 12 Hz, 13.6 Hz, 1H), 2.08–2.50 (m, 14H), 2.89 (s, 3H), 3.39 (t, J=7.6 Hz, 2H), 6.61–6.64 (m, 2H), 6.88–6.94 (m, 2H), 7.27–7.37 (m, 5H).

The above free compound was treated in a usual manner to give the hydrochloride (57 mg) of the title compound.

Hydrochloride;

$^1$H-NMR (400 MHz, DMSO-d$_6$); δ (ppm) 0.63 (d, J=6.4 Hz, 3H), 1.09 (d, J=6.4 Hz, 3H), 1.21–1.31 (m, 1H), 1.58–1.68 (m, 1H), 2.06–2.22 (m, 3H), 2.86 (s, 3H), 3.03–3.73 (m, 14H), 6.88 (dd, J=4.4 Hz, 8.8 Hz, 2H), 7.52 (t, J=8.8 Hz, 2H), 7.32–7.43 (m, 5H).

ESI-Mass; 437 (MH+).

Example 53

Synthesis of 1-[(4-Cyano-5-methyl-4-phenyl)hexyl]-4-{2-[N-(4-fluorophenyl)-N-acetylamino]ethyl}piperazine

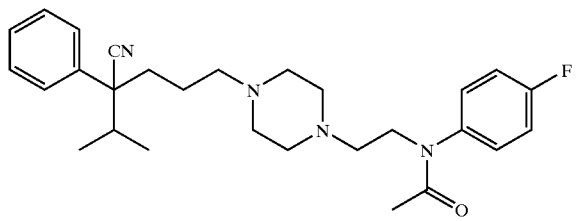

1-[(4-Cyano-5-methyl-4-phenyl)hexyl-4-[2-(4-fluorophenylamino)ethyl]piperazine (97 mg) and triethylamine (0.06 ml) were dissolved in tetrahydrofuran (4 ml), and acetyl chloride (0.03 ml) was added thereto under ice-cooling, and the mixture was stirred for 1 hour. Saturated sodium bicarbonate was added thereto, and the product was extracted with ethyl acetate, washed with water, dried, and evaporated. The residue was purified by Cromatorex NH silica gel column chromatography (hexane/ethyl acetate system) to give the title compound (97 mg, 91%) as a colorless oil.

Free Compound;

$^1$H-NMR (400 MHz, CDCl$_3$); δ (ppm) 0.77 (d, J=6.4 Hz, 3H), 1.06–1.14 (m, 1H), 1.19 (d, J=6.8 Hz, 3H), 1.48–1.59 (m, 1H), 1.80 (s, 3H), 1.88 (ddd, J=4.4 Hz, 12 Hz, 13.6 Hz, 1H), 2.07–2.48 (m, 14H), 3.78 (dt, J=2.4 Hz, 6.8 Hz, 2H), 7.08 (t, J=8.8 Hz, 2H), 7.20 (dd, J=4.8 Hz, 8.8 Hz, 2H), 7.27–7.36 (m, 5H).

The above free compound was treated in a usual manner to give the hydrochloride (62 mg) of the title compound.

Hydrochloride;

$^1$H-NMR (400 MHz, DMSO-d$_6$); δ (ppm) 0.65 (d, J=6.4 Hz, 3H), 1.09 (d, J=6.4 Hz, 3H), 1.20–1.35 (m, 1H), 1.58–1.60 (m, 1H), 1.71 (s, 3H), 2.05–2.21 (m, 3H), 3.00–4.00 (m, 14H), 7.28 (t, J=8.6 Hz, 2H), 7.32–7.43 (m, 5H), 7.63 (dt, J=4.8 Hz, 8.6 Hz, 2H).

ESI-Mass; 465 (MH+).

Example 54

Synthesis of 1-[(4-Cyano-5-methyl-4-phenyl)hexyl]-4-{2-[N-(4-fluorophenyl)-N-methanesulfonylamino]ethyl}piperazine

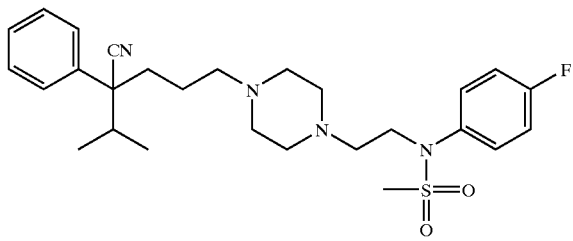

1-[(4-Cyano-5-methyl-4-phenyl)hexyl]-4-[2-(4-fluorophenylamino)ethyl]piperazine (98 mg) and triethylamine (0.2 ml) were dissolved in tetrahydrofuran (4 ml), and methane sulfonyl chloride (0.1 ml) was added thereto under ice-cooling, and the mixture was stirred for 1 hour. Saturated sodium bicarbonate was added thereto, and the product was extracted with ethyl acetate, washed with water, dried, and evaporated. The residue was purified by Cromatorex NH silica gel column chromatography (hexane/ethyl acetate system) to give the free compound (103 mg, 91%) of the title compound as a colorless oil.

Free Compound;

$^1$H-NMR (400 MHz, CDCl$_3$); δ (ppm) 0.77 (d, J=6.8 Hz, 3H), 1.04–1.16 (m, 1H), 1.19 (d, J=6.4 Hz, 3H), 1.48–1.59 (m, 1H), 1.88 (ddd, J=4.4 Hz, 12 Hz, 13.6 Hz, 1H), 2.06–2.46 (m, 12H), 2.96 (s, 3H), 3.73 (t, J=6.8 Hz, 2H), 7.08 (t, J=8.4 Hz, 2H), 7.27–7.36 (m, 7H).

The above free compound was treated in a usual manner to give the hydrochloride (63 mg) of the title compound.

Hydrochloride;

$^1$H-NMR (400 MHz, DMSO-d$_6$); δ (ppm) 0.65 (d, J=6.4 Hz, 3H), 1.08 (d, J=6.4 Hz, 3H), 1.20–1.30 (m, 1H), 1.55–1.68 (m, 1H), 2.05–2.21 (m, 3H), 3.05 (s, 3H), 3.10–3.70 (m, 12H), 4.03 (t, J=6.8 Hz, 2H), 7.27 (t, J=8.8 Hz, 2H), 7.31–7.37 (m, 1H), 7.40–7.43 (m, 4H), 7.52 (dt, J=5 Hz, 8.8 Hz, 2H).

ESI-Mass; 501 (MH+).

Example 55

Synthesis of 1-[(4-Cyano-5-methyl-4-phenyl)hexyl]-4-[2-benzylamino)ethyl]piperazine 55-1) 1-(2-Aminoethyl)-4-(t-butoxycarbonyl)piperazine

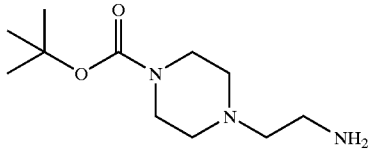

N-(2-Aminoethyl)piperazine (24.4 g) and benzaldehyde (26.9 ml) were dissolved in toluene (250 ml), and a Dean-Stark device was attached thereto, and the mixture was heated under reflux for 3 hours. After cooled to room temperature, a part (10 ml) of the reaction mixture was removed and concentrated to give N-[2-(benzylidene) aminoethyl]piperazine (1.4 g). Di (t-butyl) dicarbonate (45 g) was added to the remainder (about 240 ml) of the reaction mixture, and the mixture was stirred overnight at room temperature. 1 N aqueous potassium hydrogen sulfate (220 ml) was added thereto, and the mixture was vigorously stirred for 5 hours at room temperature, and the aqueous layer was partitioned by adding diethyl ether. The aqueous layer was basified by adding sodium hydroxide (solid), and the organic layer was partitioned by adding chloroform, washed with water, dried, and evaporated to give the title compound (14.9 g).

55-2) 1-[(4-Cyano-5-methyl-4-phenyl)hexyl]-4-[2-(benzylamino)ethyl]piperazine

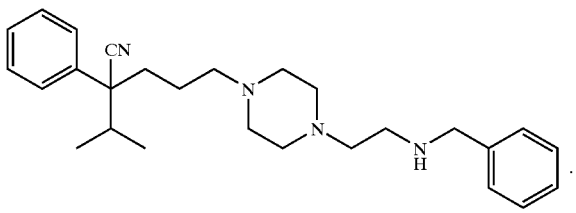

The previously obtained N-[2-(benzylidene)aminoethyl]piperazine (1.4 g), 2-(1-methylethyl)-5-oxo-2-phenyl pentane nitrile (808 mg) and acetic acid (0.9 ml) were dissolved in dichloroethane (10 ml) and sodium triacetoxy borohydride (2.5 g) was added thereto, and the title compound (311 mg, 20%) was obtained as a colorless oil in the same manner as in Example 1.
Free Compound;
$^1$H-NMR (400 MHz, CDCl$_3$); δ (ppm) 0.77 (d, J=6.8 Hz, 3H), 1.05–1.17 (m, 1H), 1.20 (d, J=6.8 Hz, 3H), 1.50–1.60 (m, 1H), 1.88 (m, 3H), 2.05–2.19 (m, 2H), 2.24–2.44 (m, 9H), 2.47 (t, J=6.0 Hz, 2H), 2.68 (t, J=6.0 Hz, 2H), 3.78 (s, 2H), 7.22–7.37 (m, 10H).

The above free compound (300 mg) was treated in a usual manner to give the hydrochloride (379 mg) of the title compound as a colorless amorphous.
Hydrochloride;
$^1$H-NMR (400 MHz, DMSO-d$_6$); δ (ppm) 0.67 (d, J=6.6 Hz, 3H), 1.11 (d, J=6.6 Hz, 3H), 1.66 (m, 1H), 1.64 (m, 1H), 1.91–2.16 (m, 2H), 2.22 (t, J=6.8 Hz, 1H), 3.05–3.10 (m, 6H), 3.35–3.44 (m, 2H), 3.71 (br-s, 7H), 4.16 (s, 2H), 7.34–7.40 (m, 2H), 7.42–7.44 (m, 6H), 7.56–7.59 (m, 2H), 9.39 (br-s, 2H).
ESI-Mass; 419 (MH+).

Example 56

Synthesis of 1-[(4-Cyano-5-methyl-4-phenyl)hexyl]-4-[2-(N-acetyl-N-benzylamino)ethyl]piperazine

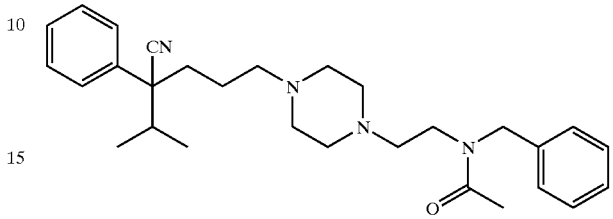

1-[(4-Cyano-5-methyl-4-phenyl)hexyl-4-[2-(benzylamino)ethyl]piperazine (51 mg) and triethylamine (0.2 ml) were dissolved in tetrahydrofuran (5 ml), and acetyl chloride (0.1 ml) was added thereto, and the mixture was stirred overnight at room temperature. The organic layer was partitioned by adding water (5 ml) and ethyl acetate, washed with water, dried, and evaporated. The residue was purified by Cromatorex NH silica gel column chromatography (ethyl acetate) to give the title compound (55 mg, 98%) as a colorless oil.
Free Compound;
$^1$H-NMR (400 MHz, CDCl$_3$); δ (ppm) 0.77 (d, J=6.8 Hz, 3H), 1.11 (m, 1H), 1.19 (d, J=6.8 Hz, 3H), 1.54 (m, 1H), 1.81–1.96 (m, 2H), 2.11 (s, 3H), 2.25 (m, 3H), 2.30 (m, 3H), 2.39 (m, 3H), 2.42 (t, J=7.2 Hz, 2H), 2.48 (t, J=6.8 Hz, 2H), 3.30 (t, J=7.0 Hz, 1H), 3.46 (m, 1H), 4.60 (t, J=17.6 Hz, 2H), 7.15–7.36 (m, 10H).

The above free compound (20 mg) was treated in a usual manner to give the hydrochloride (23 mg) of the title compound as a colorless amorphous.
Hydrochloride;
$^1$H-NMR (400 MHz, DMSO-d$_6$); δ (ppm) 0.67 (d, J=6.4 Hz, 3H), 0.86 (m, 1H), 1.11 (d, J=6.4 Hz, 3H), 1.23 (m, 1H), 1.31 (d, J=6.0 Hz, 3H), 1.62 (m, 1H), 2.11 (m, 1H), 2.22 (m, 1H), 2.67–3.44 (m, 12H), 4.35 (s, 2H), 7.37 (m, 1H), 7.44 (m, 9H), 7.70 (m, 2H).
ESI-Mass; 462 (MH+).

Example 57

Synthesis of 1-[(4-Cyano-5-methyl-4-phenyl)hexyl]-4-phenyl)hexyl]-4-[2-(N-methanesulfonyl-N-benzylamino)ethyl]piperazine

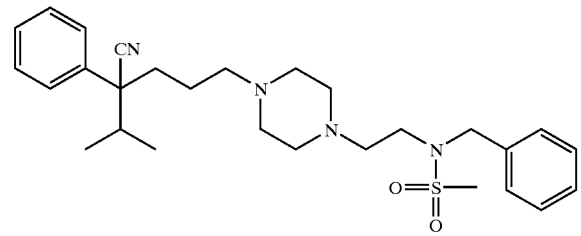

1-[(4-Cyano-5-methyl-4-phenyl)hexyl-4-[2-(benzylamino)ethyl]piperazine (53 mg) and triethylamine (0.2 ml) were dissolved in tetrahydrofuran (5 ml), and methane sulfonyl chloride (0.1 ml) was added thereto, and the mixture was stirred overnight. The organic layer was partitioned by adding water (50 ml) and ethyl acetate, washed with water, dried, and evaporated. The residue was purified by Cromatorex NH silica gel column chromatography (ethyl acetate) to give the title compound (61 mg, 97%) as a colorless oil.
Free Compound;
$^1$H-NMR (400 MHz, CDCl$_3$); δ (ppm) 0.77 (d, J=6.6 Hz, 3H), 1.12 (m, 1H), 1.19 (d, J=6.6 Hz, 3H), 1.49–1.58 (m, 1H), 1.73 (m, 1H), 1.85–1.90 (m, 1H), 2.07–2.30 (m, 8H), 2.29–2.40 (m, 5H), 2.98 (s, 3H), 3.28 (t, J=6.4 Hz, 2H), 4.11 (s, 2H), 7.25–7.40 (m, 10H).

The above free compound (20 mg) was treated in a usual manner to give the hydrochloride (23 mg) of the title compound as a colorless amorphous.
Hydrochloride;
$^1$H-NMR (400 MHz, DMSO-d$_6$); δ (ppm) 0.77 (d, J=6.8 Hz, 3H), 1.19–1.23 (m, 3H), 0.83–2.33 (m, 7H), 2.93 (s, 3H), 3.04–3.51 (m, 7H), 3.69–3.80 (m, 5H), 4.40 (s, 2H), 7.30–7.46 (m, 10H).
ESI-Mass; 497 (MH+).

Example 58

Synthesis of 1-[(4-Cyano-5-methyl-4-phenyl)hexyl]-4-[2-(N-benzyl-N-isopropylamino)ethyl]piperazine

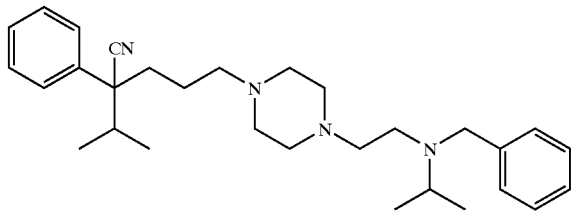

1-[(4-Cyano-5-methyl-4-phenyl)hexyl-4-[2-(benzylamino)ethyl]piperazine (67 mg) and isopropyl bromide (29.6 ml) were dissolved in dimethylformamide (10 ml), then potassium carbonate (33.2 mg) was added thereto, and the mixture was heated at 100° C. overnight. After the reaction mixture was cooled to room temperature, the organic layer was partitioned by adding aqueous saturated sodium bicarbonate (7 ml) and ethyl acetate, washed with water, dried, and evaporated. The residue was purified by Cromatorex NH silica gel column chromatography (hexane/ethyl acetate system) to give the title compound (15 mg, 20%) as a colorless oil.
Free Compound;
$^1$H-NMR (400 MHz, CDCl$_3$); δ (ppm) 0.77 (d, J=6.8 Hz, 3H), 0.89 (m, 1H), 0.99 (d, J=6.8 Hz, 6H), 1.10 (m, 1H), 1.19 (d, J=6.8 Hz, 3H), 1.26 (m, 1H), 1.53 (m, 1H), 1.69 (m, 2H), 1.87 (td, J=4.4 Hz, 12.8 Hz, 1H), 2.07–2.16 (m, 2H), 2.23–2.26 (m, 2H), 2.28–2.37 (m, 6H), 2.53–2.57 (m, 2H), 2.90 (quintet, J=6.6 Hz, 1H), 3.57 (s, 2H), 7.20 (m, J=7.0 Hz, 1H), 7.26–7.36 (m, 9H).

The above free compound (15 mg) was treated in a usual manner to give the hydrochloride (18 mg) of the title compound as a colorless amorphous.
Hydrochloride;
$^1$H-NMR (400 MHz, DMSO-d$_6$); δ (ppm) 0.67 (d, J=6.4 Hz, 3H), 0.86 (m, 1H), 1.11 (d, J=6.4 Hz, 3H), 1.23 (m, 1H), 1.31 (d, J=6.0 Hz, 6H), 1.62 (m, 1H), 2.11 (m, 1H), 2.22 (m, 1H), 2.67–3.44 (m, 13H), 4.35 (s, 2H), 7.37 (m, 1H), 7.44 (m, 9H), 7.70 (m, 2H).
ESI-Mass; 462 (MH+).

Example 59

Synthesis of 1-[(4-Cyano-5-methyl-4-phenyl)hexyl]-4-[2-(4-fluorobenzoyl)ethyl]piperazine 59-1) 1-[(4-Cyano-5-methyl-4-phenyl)hexyl]-4-(t-butoxycarbonyl)piperazine

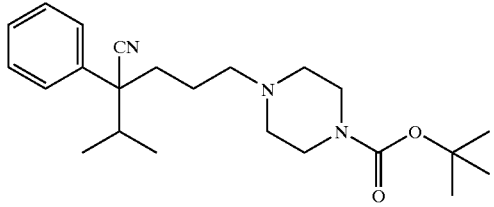

The title compound (671 mg, 89%) was obtained as a colorless oil from 2-(1-methylethyl)-5-oxo-2-phenyl pentane nitrile (400 mg) and N-(t-butoxycarbonyl)piperazine (346 mg) in the same manner as in Example 1.
$^1$H-NMR (400 MHz, CDCl$_3$); δ (ppm) 0.76 (d, J=6.8 Hz, 3H), 1.08–1.18 (m, 1H), 1.20 (d, J=6.8 Hz, 3H), 1.44 (s, 9H), 1.50–1.60 (m, 1H), 1.87–1.95 (m, 1H), 2.08–2.31 (m, 8H), 3.35–3.40 (m, 4H), 7.16–7.31 (m, 5H).

59-2) 1-[(4-Cyano-5-methyl-4-phenyl)hexyl] piperazine

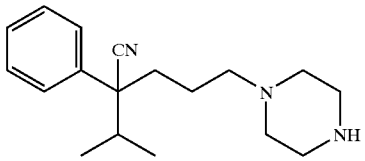

4 N HCl/ethyl acetate (20 ml) was added to 1-[(4-cyano-5-methyl-4-phenyl)hexyl]-4-(t-butoxycarbonyl)piperazine (671 mg), and the mixture was stirred at 50° C. for 3 hours. The reaction mixture was evaporated, then saturated sodium bicarbonate was added thereto, and the product was extracted with ethyl acetate. The organic layer was washed with water, dried, and evaporated. The residue was purified by Cromatorex NH silica gel column chromatography (hexane/ethyl acetate system) to give the title compound (377 mg, 76%) as a colorless oil.
$^1$H-NMR (400 MHz, CDCl$_3$); δ (ppm) 0.77 (d, J=6.8 Hz, 3H), 1.07–1.17 (m, 1H), 1.20 (d, J=6.8 Hz, 3H), 1.50–1.60 (m, 1H), 1.89 (ddd, J=4.4 Hz, 12 Hz, 13.6 Hz, 1H), 2.07–2.32 (m, 8H), 2.83 (t, J=5 Hz, 4H), 7.27–7.38 (m, 5H).

59-3) 1-[(4-Cyano-5-methyl-4-phenyl)hexyl]-4-[2-(4-fluorobenzoyl)ethyl]piperazine

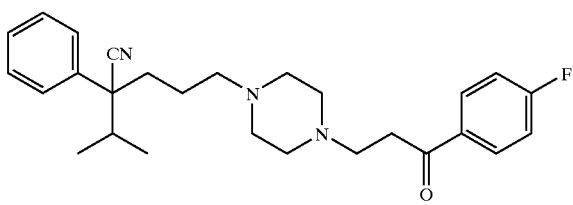

1-[(4-Cyano-5-methyl-4-phenyl)hexyl]piperazine (114 mg), 3-chloro-4-fluoropropiophenone (75 mg) and triethylamine (0.06 ml) were dissolved in tetrahydrofuran (3 ml), and the mixture was stirred overnight at room temperature. The reaction mixture was diluted with ethyl acetate, washed with water, dried, and evaporated. The residue was purified by Cromatorex NH silica gel column chromatography (hexane/ethyl acetate system) to give the free compound (99 mg, 56%) of the title compound as a colorless oil.

Free Compound;

$^1$H-NMR (400 MHz, CDCl$_3$); δ (ppm) 0.77 (d, J=6.8 Hz, 3H), 1.06–1.18 (m, 1H), 1.20 (d, J=6.8 Hz, 3H), 1.50–1.60 (m, 1H), 1.89 (ddd, J=4.4 Hz, 12 Hz, 13.6 Hz, 1H), 2.08–2.56 (m, 12H), 2.80 (t, J=7.6 Hz, 2H), 3.14 (t, J=7.6 Hz, 2H), 7.13 (t, J=8.4 Hz, 2H), 7.26–7.37 (m, 5H), 7.97 (dd, J=5.4 Hz, 8.4 Hz, 2H).

The above free compound (30 mg) was treated in a usual manner to give the hydrochloride (39 mg) of the title compound.

Hydrochloride;

$^1$H-NMR (400 MHz, DMSO-d$_6$); δ (ppm) 0.66 (d, J=6.8 Hz, 3H), 1.10 (d, J=6.8 Hz, 3H), 1.55–1.65 (m, 1H), 2.00–2.25 (m, 3H), 3.25–3.70 (m, 14H), 7.33–7.44 (m, 7H), 8.05 (dd, 5.8 Hz, 8.2 Hz, 2H).

ESI-Mass; 436 (MH+).

Example 60

Synthesis of 1-[(4-Cyano-5-methyl-4-phenyl)hexyl]-4-[-hydroxy-3-(4-flurophenyl)propyl]piperazine

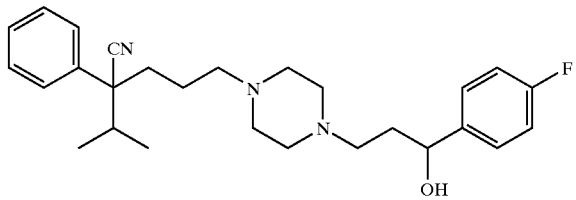

1-[(4-Cyano-5-methyl-4-phenyl)hexyl]-4-[2-(4-fluorobenzoyl)ethyl]piperazine (64 mg) was dissolved in ethanol (1 ml), then sodium borohydride (65 mg) was added thereto, and the mixture was stirred for 1 hour at room temperature. The reaction mixture was diluted with ethyl acetate, washed with water, dried, and evaporated. The residue was purified by Cromatorex NH silica gel column chromatography (hexane/ethyl acetate system) to give the free compound of the title compound (64 mg, quantitative) as a colorless oil.

Free Compound;

$^1$H-NMR (400 MHz, CDCl$_3$); δ (ppm) 0.77 (d, J=6.8 Hz, 3H), 1.08–1.18 (m, 1H), 1.20 (d, J=6.4 Hz, 3H), 1.50–1.60 (m, 1H), 1.79 (dd, J=6.6 Hz, 11 Hz, 2H), 3.76 (dt, J=4 Hz, 13 Hz, 1H), 2.08–2.76 (m, 14H), 4.88 (t, J=5.6 Hz, 1H), 7.01 (t, J=8.8 Hz, 2H), 7.27–7.37 (m, 7H).

The above free compound was treated in a usual manner to give the hydrochloride (60 mg) of the title compound.

Hydrochloride;

$^1$H-NMR (400 MHz, DMSO-d$_6$); δ (ppm) 0.65 (d, J=6.8 Hz, 3H), 1.09 (d, J=6.4 Hz, 3H), 1.15–1.28 (m, 1H), 1.52–1.67 (m, 1H), 1.90–2.22 (m, 5H), 2.95–3.80 (m, 12H), 4.64 (q, 4 Hz, 1H), 7.15 (t, J=8.8 Hz, 2H), 7.33–7.45 (m, 7H).

ESI-Mass; 438 (MH+).

Example 61

Synthesis of 1-[(4-Cyano-5-methyl-4-phenyl)hexyl]-4-[2-(4-fluorophenoxyl)acetyl]piperazine

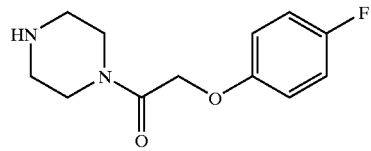

Thionyl chloride (4 ml) was added to 4-fluorophenoxy acetic acid (3.52 g) and heated under reflux for 1 hour. The reaction mixture was evaporated, and the residual tetrahydrofuran (5 ml) solution was added under ice-cooling to a solution of 1-benzyl piperazine (3.65 g) and triethylamine (2.9 ml) in tetrahydrofuran (15 ml), followed by stirring for 1 hour at room temperature. The reaction mixture was diluted with ethyl acetate, washed with water, dried, and evaporated. The residue was dissolved in ethanol (60 ml), then conc. hydrochloric acid (3 ml) and 10% palladium/carbon catalyst (1.3 g) were added thereto, and the mixture was stirred overnight at room temperature in a hydrogen atmosphere. After the catalyst was filtered off, the filtrate was evaporated, basified with 2 N aqueous NaOH, and extracted with ethyl acetate. The organic layer was washed with water, dried, and evaporated. The residue was purified by Cromatorex NH silica gel column chromatography (hexane/ethyl acetate system) to give the title compound (4.09 g, 83%) as a pale brown oil.

$^1$H-NMR (400 MHz, CDCl$_3$); δ (ppm) 2.82–2.87 (m, 4H), 3.54 (t, J=5.2 Hz, 2H), 3.60 (t, J=5.2 Hz, 2H), 4.66 (s, 2H), 6.88–7.00 (m, 4H).

61-2) 1-[(4-Cyano-5-methyl-4-phenyl)hexyl]-4-[2-(4-fluorophenoxy)acetyl]piperazine

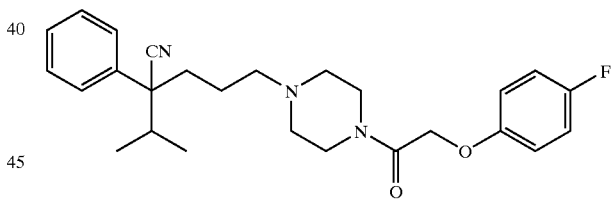

The free compound (140 mg, 98%) of the title compound was obtained as a colorless oil from 2-(1-methylethyl)-5-oxo-phenyl) pentane nitrile (70 mg) and 2-(4-fluorophenoxy)acetylpiperazine (78 mg) in the same manner as in Example 1.

Free Compound;

$^1$H-NMR (400 MHz, CDCl$_3$); δ (ppm) 0.77 (d, J=6.6 Hz, 3H), 1.06–1.17 (m, 1H), 1.20 (d, J=6.6 Hz, 3H), 1.48–1.60 (m, 2H), 1.89 (dt, J=4.4 Hz, 13.2 Hz, 1H), 2.07–2.20 (m, 3H), 2.22–2.32 (m, 4H), 3.48–3.64 (m, 4H), 4.63 (s, 2H), 6.70–6.80 (m, 2H), 6.85–7.00 (m, 2H), 7.28–7.34 (m, 1H), 7.34–7.38 (m, 4H).

The above free compound (140 mg) was treated in a usual manner to give the hydrochloride (142 mg) of the title compound.

Hydrochloride;

$^1$H-NMR (400 MHz, DMSO-d$_6$); δ (ppm) 0.67 (d, J=6.6 Hz, 3H), 1.12 (d, J=6.6 Hz, 3H), 1.20–1.30 (m, 1H), 1.55–1.70 (m, 1H), 2.00–2.30 (m, 3H), 2.78–2.90 (m, 1H), 2.90–3.18 (m, 3H), 3.40–3.53 (m, 1H), 3.95 (br-d, J=12.6 Hz, 1H), 4.33 (br-d, J=12.6 Hz, 1H), 4.75–4.90 (m, 2H), 6.90–6.97 (m, 2H), 7.07–7.15 (m, 2H), 7.33–7.41 (m, 1H), 7.41–7.50 (m, 4H), 10.6 (m, 1H). ESI-Mass; 438 (MH+).

Example 62

Synthesis of 1-[(4-Cyano-5-methyl-4-phenyl) hexyl-4-[2-hydroxy-3-(4-fluorophenoxyl)propyl]piperazine 62-1) 4-Fluorophenoxy Glycidyl Ether

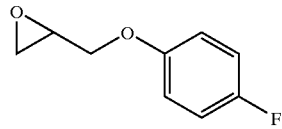

4-Fluorophenol (3.0 g) was dissolved in dimethylformamide (50 ml), then sodium hydride (1.28 g, 50%) was added thereto, and the mixture was stirred for 45 minutes in an ice bath. Epibromohydrin (2.3 ml) was added to the reaction mixture, and the mixture was stirred for 3 hours in the ice bath. The organic layer was partitioned by adding water and diethyl ether, and the resulting organic layer was washed with water and brine, dried, and evaporated. The residue was purified by silica gel column chromatography (hexane/ethyl acetate system) to give the free compound (3.4 g, 75%) of the title compound as a colorless oil.

Free Compound;

$^1$H-NMR (4 00 MHz, CDCl$_3$); δ (ppm) 2.75 (dd, J=5.6, 3.2 Hz, 1H), 2.88–2.92 (m, 1H), 3.32–3.37 (m, 1H), 3.91 (dd, J=5.6, 11.2 Hz, 1H), 4.20 (dd, J=3.2, 11.2 Hz, 1H).

62-2) 1-(t-Butoxy)carbonyl-4-[2-hydroxy-3-fluorophenoxy)propyl]piperazine

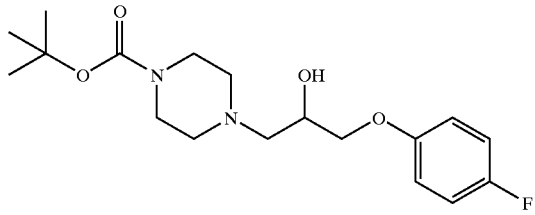

1-(t-Butoxycarbonyl)piperazine (1.8 g) and 4-fluorophenoxy glycidyl ether (1.6 g) were dissolved in 2-propanol (50 ml) and stirred for 2 hours under reflux. The solvent was evaporated, and the residue was purified by silica gel column chromatography (hexane/ethyl acetate system) to give the free compound (2.48 g, 74%) of the title compound as a colorless solid.

Free Compound;

$^1$H-NMR (400 MHz, CDCl$_3$); δ (ppm) 1.47 (s, 9H), 2.35–2.45 (m, 2H), 12.50–2.58 (m, 2H), 2.58–2.66 (m, 2H), 3.36–3.56 (m, 2H), 3.72–4.00 (m, 2H), 4.06–4.14 (m, 1H), 6.84–6.90 (m, 2H), 6.94–7.01 (m, 2H).

62-3) 1-[2-Hydroxy-3-(4-fluorophenoxy)propyl]piperazine Trifluoacetate

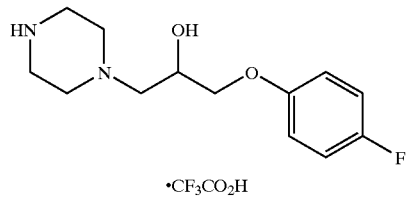

1-(t-Butoxycarbonyl)-4-[2-hydroxy-3-(4-fluorophenoxy)propyl]piperazine (520 mg) was dissolved in dichloromethane (5 ml), and trifluoroacetic acid (0.5 ml) was added thereto under ice-cooling, and the mixture was stirred for 2 hours. After the solvent was concentrated, toluene was added thereto, and the reaction mixture was evaporated again to give the trifluoroacetate (450 mg) of the title compound.

Trifluoroacetate;

$^1$H-NMR (400 MHz, DMSO-d$_6$); δ (ppm) 3.20–3.60 (m, 12H), 3.95 (d, J=4.8 Hz, 2H), 4.26 (m, 1H), 6.95–7.01 (m, 2H), 7.12–7.18 (m, 2H).

62-4) 1-[(4-Cyano-5-methyl-4-phenyl)hexyl]-4-[2-hydroxy-3-(4-fluorophenoxy)propyl]piperazine The free compound (124 mg, 74%) of the title compound was obtained as a colorless oil in the same manner as in Example 1 from 2-(t-methylethyl)-5-oxo-2-phenyl pentane nitrile (80 mg), 1-[2-hydroxy-3-(4-fluorophenoxy)propyl] piperazine, and the trifluoroacetate (274 mg) obtained in item 3) above.

Free Compound;

$^1$H-NMR (400 MHz, CDCl$_3$); δ (ppm) 0.77 (d, J=6.6 Hz, 3H), 1.05–1.20 (m, 1H), 1.21 (d, J=6.6 Hz, 3H), 1.50–1.80 (m, 3H), 1.80–2.20 (m, 3H), 2.20–2.60 (m, 7H), 2.60–2.70 (m, 2H), 3.92 (d, J=5.6 Hz, 2H), 4.04 (m, 1H), 6.83–6.88 (m, 2H), 6.92–7.00 (m, 2H), 7.27–7.33 (m, 1H), 7.34–7.40 (m, 4H).

The above free compound (124 mg) was treated in a usual manner to give the hydrochloride (110 mg) of the title compound.

Hydrochloride;

$^1$H-NMR (400 MHz, DMSO-d$_6$); δ (ppm) 0.67 (d, J=5.6 Hz, 3H), 1.11 (d, J=5.6 Hz, 3H), 1.60–1.70 (m, 1H), 2.00–2.15 (m, 3H), 3.00–3.90 (m, 12H), 3.90–4.00 (2H, m), 4.28 (m, 1H), 6.94–7.02 (m, 2H), 7.08–7.18 (m, 2H), 7.30–7.50 (m, 5H).

ESI-Mass; 454 (MH+).

Example 63

Synthesis of 1-[(4-Cyano-5-methyl-4-phenyl)hexyl]-4-[2-(4-fluorophenylaminocarbonyl)ethyl]piperazine

63-1) N-Acryloyl-4-fluoroaniline

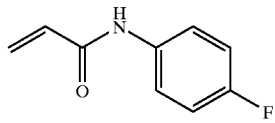

4-Fluoroaniline (7 ml) and acryloyl chloride (7.2 ml) were dissolved in tetrahydrofuran (100 ml), then triethylamine (15 ml) was added thereto, and the mixture was stirred overnight at room temperature. The organic layer was partitioned by adding aqueous saturated sodium bicarbonate and ethyl acetate, and the organic layer was washed with water and dried over sodium sulfate anhydrous, and after the drying agent was filtered off, the filtrate was evaporated, whereby the title compound (12.2g, 100%) was obtained as pale yellow solid.

$^1$H -NMR (400 MHz, CDCl$_3$); δ (ppm) 5.76–5.79 (m, 1H), 6.24 (dd, J=10.4, 16.8 Hz, 1H), 6.14–6.50 (m, 1H), 7.01–7.06 (m, 2H), 7.14 (m, 1H), 7.53–7.54 (m, 2H).

63-2) 1-Benzyl-4-[2-(4-fluorophenylaminocarbonyl)ethyl]piperazine

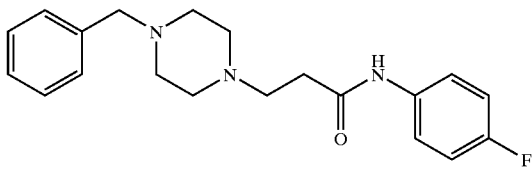

N-Acryloyl-4-fluoroaniline (12.2 g) and 1-benzyl piperazine (19.7 g) were dissolved in methanol (150 ml), and the mixture was stirred overnight at room temperature. The reaction mixture was evaporated, and the residue was purified by Cromatorex NH silica gel column chromatography (hexane/ethyl acetate system) to give the title compound (25 g, 100%) as a colorless oil.

$^1$H-NMR (400 MHz, CDCl$_3$); δ (ppm) 2.51 (t, J=5.8 Hz, 2H), 2.63 (br-s, 8H), 2.72 (t, J=5.8 Hz, 2H), 3.59 (s, 2H), 7.01 (m, J=8.8 Hz, 2H), 7.25–7.35 (m, 5H), 7.46–7.50 (m, 2H), 11.1 (br-s, 1H).

63-3) [2-(4-Fluorophenylaminocarbonyl)ethyl]piperazine

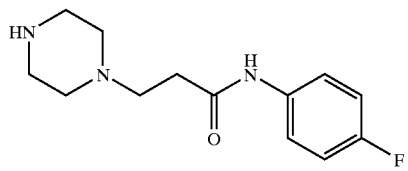

1-Benzyl-4-[2-(4-fluorophenylaminocarbonyl)ethyl]piperazine (2.9 g) was dissolved in acetic acid (100 ml), then 10% palladium carbon (7.2 g) was added thereto, and the mixture was stirred overnight in a hydrogen atmosphere. The 10% palladium carbon was filtered off, and the filtrate was evaporated, and water was added to the residue which was then basified by adding 1 N aqueous sodium hydroxide and subjected to extraction with chloroform, and the organic layer was washed with water, dried, and evaporated, whereby the title compound (1.5 g, 70%) was obtained as colorless oil.

$^1$H-NMR (400 MHz, CDCl$_3$); δ (ppm) 1.84 (br-s, 2H), 2.53 (t, J=5.8 Hz, 2H), 2.60 (m, 4H), 2.72 (t, J=5.8 Hz, 2H), 3.01 (t, J=4.8 Hz, 2H), 7.00 (m, J=8.8 Hz, 2H), 7.48–7.52 (m, 2H), 11.1 (br-s, 1H).

63-4) 1-[(4-Cyano-5-methyl-4-phenyl)hexyl]-4-[2-(4-fluorophenylaminocarbonyl)ethyl]piperazine

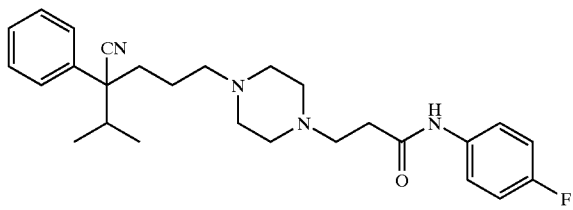

The title compound (163 mg, 62%) was obtained as a colorless oil from 2-(1-methylethyl)-5-oxo-2-phenyl pentane nitrile (126 mg) and [2-(4-fluorophenylaminocarbonyl)ethyl]piperazine (176 mg) in the same manner as in Example 66.

Free Compound;

$^1$H-NMR (400 MHz, CDCl$_3$); δ (ppm) 0.78 (d, J=6.8 Hz, 3H), 1.18 (m, 1H) 1.21 (d, J=6.8 Hz, 3H), 1.58 (m, 1H), 1.78 (m, 1H), 1.92 (td, J=13.0 Hz, 4.4 Hz, 1H), 2.13 (quintet, J=6.8 Hz, 1H), 2.15–2.21 (m, 1H), 2.26–2.38 (m, 3H), 2.44 (br-s, 3H), 2.50 (t, J=6.0 Hz, 2H), 2.58 (br-s, 3H), 2.70 (t, J=6.0 Hz, 2H), 6.99 (m, J=8.8 Hz, 2H), 7.30 (m, 1H), 7.35–7.39 (m, 4H), 7.46 (dd, J=4.8 Hz, 6.8 Hz, 1H), 7.47 (dd, J=4.8 Hz, 7.0 Hz, 1H), 11.1 (br-s, 1H).

The above free compound (100 mg) was treated in a usual manner to give the hydrochloride (189 mg) of the title compound.

Hydrochloride;

$^1$H-NMR (400 MHz, DMSO-d$_6$); δ (ppm) 0.67 (d, J=6.8 Hz, 3H), 1.11 (d, J=6.8 Hz, 3H), 1.26 (m, 1H), 1.59–2.45 (m, 5H), 2.23 (t, J=6.8 Hz, 1H), 2.54–3.86 (m, 13H), 7.15 (t, J=8.8 Hz, 2H), 7.37 (m, 1H), 7.44–7.46 (m, 4H), 7.58–7.62 (m, 2H).

ESI-Mass; 451 (MH+).

Example 64

Synthesis of 1-[(4-Cyano-5-methyl-4-phenyl)hexyl]-4-[2-(4-fluorobenzoylamino)ethyl]piperazine

64-1) 1-[2-(4-fluorobenzoylamino)]-4-(t-butoxycarbonyl)piperazine

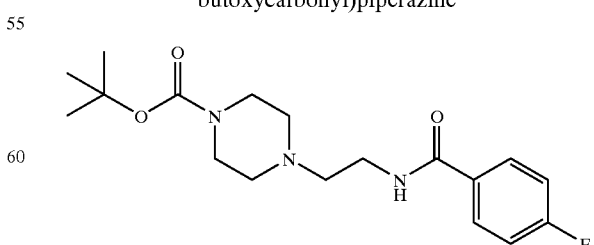

The 1-(2-aminoethyl)-4-(t-butoxycarbonyl)piperazine (1.33 g) obtained in Example 58 and 4-fluorobenzoyl chloride (1.1 g) were dissolved in tetrahydrofuran (20 ml), then triethylamine (1.6 ml) was added thereto, and the mixture was stirred overnight at room temperature. The organic layer was partitioned by adding aqueous saturated sodium bicarbonate and ethyl acetate, and the organic layer was washed with water, dried, and evaporated. The residue was purified by Cromatorex NH silica gel column chromatography (hexane/ethyl acetate system), whereby the title compound (1.42 g, 70%) was obtained as a colorless oil.

$^1$H-NMR (400 MHz, CDCl$_3$); δ (ppm) 1.47 (s, 9H), 2.44–2.26 (m, 4H), 2.62 (t, J=6.0 Hz, 2H), 3.46 (t, J=5.0 Hz, 4H), 3.54–3.56 (m, 2H), 6.71 (m, 1H), 7.12 (m, J=8.6 Hz, 2H), 7.77–7.81 (m, 2H).

64-2) 1-[(4-Cyano-9-methyl-4-phenyl)hexyl]-4-[2-(4-fluorobenzoylamino)ethyl]piperazine

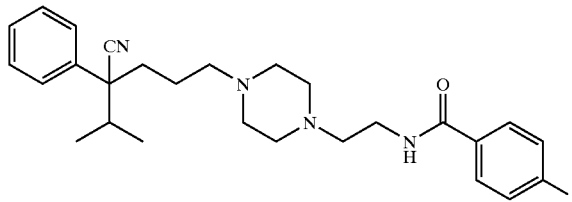

The title compound (102 mg, 40%) was obtained as a colorless oil from 1-[2-(4-fluorobenzenesulfonylamino)ethyl]-4-(t-butoxycarbonyl)piperazine (159 mg) in the same manner as in Example 66.

Free Compound;
$^1$H-NMR (400 MHz, CDCl$_3$); δ (ppm) 0.78 (d, J=6.8 Hz, 3H), 1.13 (m, 1H), 1.20 (d, J=6.8 Hz, 3H), 1.56 (m, 1H), 1.78–1.94 (m, 3H), 2.09–2.19 (m, 2H), 2.23–2.33 (m, 2H), 2.34 (m, 3H), 2.48 (m, 3H), 2.58 (t, J=6.2 Hz, 2H), 3.51 (t, J=5.6 Hz, 2H), 6.76 (br-s, 1H), 7.11 (m, J=8.8 Hz, 2H), 7.29 (m, 1H), 7.32–7.38 (m, 4H), 7.75–7.80 (m, 2H).

The above free compound (100 mg) was treated in a usual manner to give the hydrochloride (116 mg) of the title compound.

Hydrochloride;
$^1$H-NMR (400 MHz, DMSO-d$_6$); δ (ppm) 0.67 (d, J=6.8 Hz, 3H), 1.12 (d, J=6.8 Hz, 3H), 1.24–1.27 (m, 1H), 2.09–2.19 (m, 2H), 2.22 (d, J=6.6 Hz, 1H), 3.42 (br-s, 17H), 3.65 (m, 1H), 7.32 (t, J=8.8 Hz, 2H), 7.37 (m, 1H), 7.43–7.46 (m, 4H), 7.95–7.99 (m, 2H).

ESI-Mass; 451 (MH+).

Example 65

Synthesis of 1-[(4-Cyano-5-methyl-4-phenyl)hexyl]-4-[N-(4-fluorophenyl)carbamoylmethyl]piperazine 65-1) 1-Benzyl-4-[N-(4-fluorophenyl)carbamoylmethyl]piperazine

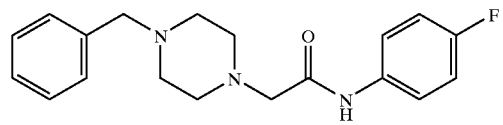

N-Chloroacetyl-4-fluoroaniline (15.18 g), 1-benzyl piperazine (18.94 g) and triethylamine (15 ml) were dissolved in dimethylformamide (200 ml), and the mixture was stirred overnight at room temperature. The reaction mixture was evaporated, and ethyl acetate was added thereto. The organic layer was washed with water, dried, and evaporated. The residue was purified by Cromatorex NH silica gel column chromatography (hexane/ethyl acetate system) to give the title compound (23.32 g, 86%) as pale brown solid.

$^1$H-NMR (400 MHz, CDCl$_3$); δ (ppm) 2.48–2.60 (m, 4H), 2.62–2.68 (m, 4H), 3.13 (s, 2H), 3.55 (s, 2H), 7.02 (t, J=8.8 Hz, 2H), 7.24–7.34 (m, 5H), 7.53 (dd, J=4.8 Hz, 8.8 Hz, 2H), 9.10–9.15 (br-s, 1H).

65-2) 4-[N-(4-Fluorophenyl)carbamoylmethyl]piperazine

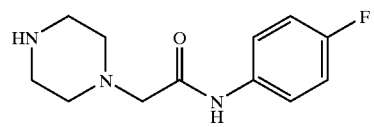

1-Benzyl-4-[N-(4-fluorophenyl)carbamoylmethyl]piperazine (6.07 g) was dissolved in ethanol (100 ml), then 10% palladium/carbon catalyst (1.3 g) was added thereto, and the mixture was stirred overnight at room temperature in a hydrogen atmosphere. After the catalyst was filtered off, the filtrate was evaporated, and the residue was purified by Cromatorex NH silica gel column chromatography (hexane/ethyl acetate system), whereby the title compound (4.21 g, 96%) was obtained as a pale brown oil.

$^1$H-NMR (400 MHz, CDCl$_3$); δ (ppm) 2.59 (t, J=1.8 Hz, 4H), 2.96 (t, J=4.8 Hz, 4H), 3.11 (s, 2H), 7.03 (t, J=8.8 Hz, 2H), 7.53 (dd, J=4.8 Hz, 8.8 Hz, 2H), 9.10–9.16 (br-s, 1H).

65-3) 1-(4-Cyano-5-methyl-4-phenyl)hexyl]-4-[N-(4-fluorophenyl)carbamoylmethyl]piperazine

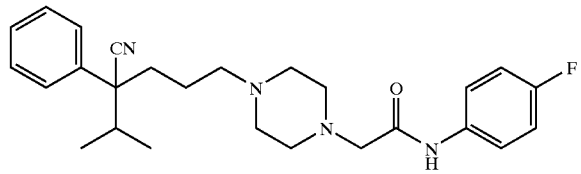

The free compound (183 mg, 84%) of the title compound was obtained as a colorless oil from 2-(1-methylethyl)-5-oxo-2-phenyl pentane nitrile (109 mg) and 4-[N-(4-fluorophenyl)carbamoylmethyl]piperazine (120 mg) in the same manner as in Example 1.

Free Compound;
$^1$H-NMR (400 MHz, CDCl$_3$); δ (ppm) 0.78 (d, J=6.4 Hz, 3H), 1.09–1.19 (m, 1H), 1.21 (d, J=6.8 Hz, 3H), 1.50–1.61 (m, 1H), 1.91 (ddd, J=4.4 Hz, 12.2 Hz, 13.4 Hz, 1H), 2.09–2.45 (m, 8H), 2.56–2.63 (br-s, 4H), 3.10 (m, 2H), 7.01 (t, 8.8 Hz, 2H), 7.27–7.38 (m, 5H), 7.51 (dd, J=4.8 Hz, 8.8 Hz, 2H), 9.07 (s, 1H).

The above free compound was treated in a usual manner to give the hydrochloride (182 mg) of the title compound.

Hydrochloride;
$^1$H-NMR (400 MHz, DMSO-d$_6$); δ (ppm) 0.66 (d, J=6.4 Hz, 3H), 1.10 (d, J=6.8 Hz, 3H), 1.18–1.30 (m, 1H), 1.56–1.68 (m, 1H), 2.03–2.23 (m, 3H), 3.00–3.90 (m, 13H), 7.16 (t, J=8.8 Hz, 2H), 7.33–7.44 (m, 5H), 7.61 (dd, J=5.2 Hz, 8.8 Hz, 2H).

ESI-Mass; 437 (MH+).

Example 66

Synthesis of 1-[(4-Cyano-5-methyl-4-phenyl)hexyl]-4-[2-(4-fluorobenzenesulfonylamino)ethyl]piperazine 66-1) 1-[2-(4-Fluorobenzenesulfonylamino)ethyl]-4-t-butoxycarbonyl)piperazine

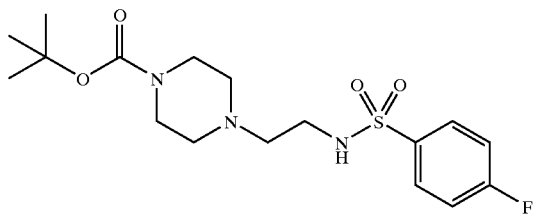

The 1-(2-aminoethyl)-4-(t-butoxycarbonyl)piperazine (2.01 g) obtained in Example 58 and 4-fluorobenzene sulfonyl chloride (2.05 g) were dissolved in tetrahydrofuran (20 ml), and triethylamine (2.4 ml) was added thereto, and the mixture was stirred overnight at room temperature. Water (50 ml) was added to the reaction mixture which was then extracted with ethyl acetate, and the organic layer was washed with water, dried, and evaporated. The residue was purified by Cromatorex NH silica gel column chromatography (hexane/ethyl acetate system), whereby the title compound (2.61 g, 77%) was obtained as a colorless oil.

$^1$H-NMR (400 MHz, CDCl$_3$); δ (ppm) 1.45 (s, 9H), 2.23 (t, J=5.2 Hz, 4H), 2.42–2.45 (m, 2H), 2.99–3.03 (m, 2H), 3.35 (t, J=5.2 Hz, 4H), 5.17 (m, 1H), 7.20 (m, J=8.6 Hz, 2H), 7.22–7.37 (m, 2H).

66-2) 1-[(4-Cyano-5-methyl-4-phenyl)hexyl]-4-[2-(4-fluorobenzenesulfonylamino)ethyl]piperazine

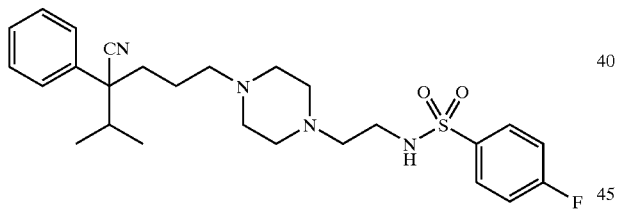

1-[2-(4-Fluorobenzenesulfonylamino)ethyl]-4-(t-butoxycarbonyl)piperazine (260 mg) was dissolved in dichloromethane (2.0 ml), and trifluoroacetic acid (2 ml) was added thereto under stirring at 0° C., and the mixture was stirred at 0° C. for 1 hour. The reaction mixture was evaporated. The residue was dissolved in dichloroethane (10 ml), and 2-(1-methylethyl)-5-oxo-2-phenyl pentane nitrile (177 mg), acetic acid (0.10 ml) and sodium triacetoxy borohydride (261 mg) were added thereto, and the title compound (247 mg, 62%) was obtained as a colorless oil in the same manner as in Example 1.
Free Compound;

$^1$H-NMR (400 MHz, CDCl$_3$) δ (ppm) 0.78 (d, J=6.8 Hz, 3H), 1.11 (m, 1H), 1.21 (d, J=6.8 Hz, 3H), 1.53 (m, 1H), 1.74–1.91 (m, 2H), 1.96–2.19 (m, 2H), 2.25–2.45 (m, 10H), 2.39 (t, J=5.8 Hz, 2H), 2.98 (t, J=5.8 Hz, 2H), 7.16–7.23 (m, 2H), 7.29 (m, 1H), 7.34–7.39 (m, 4H), 7.85–7.91 (m, 2H).

The above free compound (166 mg) was treated in a usual manner to give the hydrochloride (191 mg) of the title compound as a colorless amorphous.

Hydrochloride;

$^1$H-NMR (400 MHz, DMSO-d$_6$); δ (ppm) 0.67 (d, J=6.4 Hz, 3H), 1.11 (d, J=6.4 Hz, 3H), 1.25 (m, 1H), 1.62 (m, 1H), 2.06–2.24 (m, 3H), 3.17–3.21 (m, 6H), 3.33–3.51 (m, 10H), 7.33–7.39 (m, 1H), 7.41–7.49 (m, 6H), 7.89 (dd, J=5.2 Hz, 6.8 Hz, 1H), 7.91 (dd, J=5.2 Hz, 7.2 Hz, 1H), 8.12 (br-s, 1H).
ESI-Mass; 487 (MH+).

Example 67

Synthesis of 1-[(4-Cyano-5-methyl-4-phenyl)hexyl]-4-{2-[N-(4-fluorophenyl)sulfamoyl]ethyl}piperazine 67-1) 1-{2-[N-(4-fluorophenyl)sulfamoyl]ethyl}-4-(t-butoxycarbonyl)piperazine

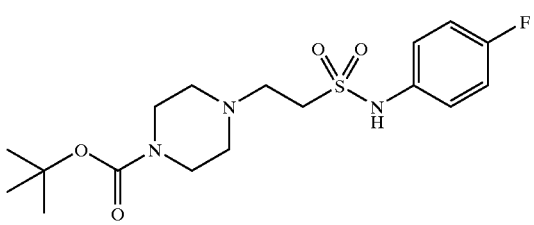

A solution of 4-fluoroaniline (3.41 g) and triethylamine (4.5 ml) in tetrahydrofuran (20 ml) was added dropwise to a solution of 2-chloroethane sulfonyl chloride (5 g) in tetrahydrofuran (50 ml) under ice-cooling, and the mixture was stirred for 1 hour at room temperature. 5 N aqueous NaOH was added thereto, followed by extraction with ethyl acetate. The organic layer was washed with water, dried, and evaporated. A part (3.81 g) of the residue (5.56 g) and N-(t-butoxycarbonyl)piperazine (2.3 g) were dissolved in methylene chloride (20 ml) and stirred at room temperature for 2 hours. The reaction mixture was evaporated and purified by Cromatorex NH silica gel column chromatography (hexane/ethyl acetate system), whereby the title compound (6.01 g, 82%) was obtained as a pale yellow oil.

$^1$H-NMR (400 MHz, CDCl$_3$); δ (ppm) 1.46 (s, 9H), 2.46 (t, J=5 Hz, 4H), 2.92 (t, J=6.4 Hz, 2H), 3.23 (t, J=6.4 Hz, 2H), 3.44 (t, J=5 Hz, 4H), 7.05 (t, J=8.6 Hz, 2H), 7.17–7.21 (m, 2H).

67-2) 1-{2-[N-(4-Fluorophenyl]ethyl}piperazine

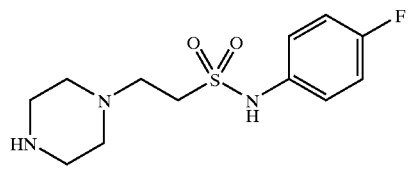

1-{2-[N-(4-Fluorophenyl)sulfonyl]ethyl}-4-(t-butoxycarbonyl)piperazine (6.01 g) was dissolved in ethanol (10 ml), then 4 N HCl/ethyl acetate (40 ml) was added thereto, and the mixture was stirred at 50° C. for 4 hours. The reaction mixture was evaporated, neutralized with 5 N aqueous NaOH, and extracted with chloroform. The organic layer was washed with water, dried, and evaporated, whereby the title compound (3.52 g, 79%) was obtained as a pale brown solid.

$^1$H-NMR (400 MHz, DMSO-d$_6$); δ (ppm) 2.20–2.30 (m, 4H), 2.60–2.66 (m, 6H), 3.19 (t, J=7.4 Hz, 2H), 7.15 (t, J=9.2 Hz, 2H), 7.22 (dd, J=4.8 Hz, 9.2 Hz, 2H).

67-3) 1-[(4-Cyano-5-methyl-4-phenyl)hexyl ]-4-{2-]N-(4-fluorophenyl)sulfonyl)ethyl}piperazine

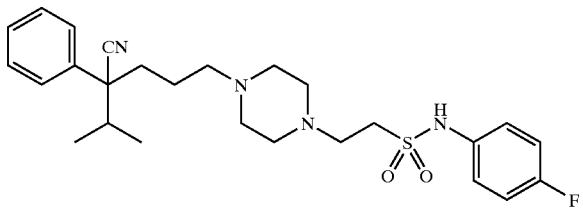

The free compound (179 mg, 80%) of the title compound was obtained as a pale yellow oil from 2-(1-methylethyl)-5-oxo-2-phenyl pentane nitrile (100 mg) and 1-[2-(4-fluorophenyl)propyl]piperazine (133 mg) in the same manner as in Example 1.

Free Compound;
$^1$H-NMR (400 MHz, CDCl$_3$); δ (ppm) 0.77 (d, J=6.4 Hz, 3H), 1.05–1.16 (m, 1H), 1.20 (d, J=6.8 Hz, 3H), 1.49–1.60 (m, 1H), 1.88 (ddd, J=4.4 Hz, 12 Hz, 13.6 Hz, 1H), 2.08–2.56 (m, 12H), 2.88 (t, J=6.4 Hz, 2H), 3.19 (t, J=6.4 Hz, 2H), 7.02 (t, J=8.6 Hz, 2H), 7.19 (dt, 4.4 Hz, 8.6 Hz, 2H), 7.27–7.38 (m, 5H).

The above free compound (119 mg) was treated in a usual manner to give the hydrochloride (120 mg) of the title compound.

Hydrochloride;
$^1$H-NMR (400 MHz, DMSO-d$_6$); δ (ppm) 0.65 (d, J=6.8 Hz, 3H), 1.09 (d, J=6.8 Hz, 3H), 1.15–1.28 (m, 1H), 1.53–1.65 (m, 1H), 2.00–2.25 (m, 3H), 2.95–3.75 (m, 14H), 7.17 (t, J=8.8 Hz, 2H), 7.25 (dt, J=4.8 Hz, 8.8 Hz, 2H), 7.32–7.43 (m, 5H), 10.00 (s, 1H).

ESI-Mass; 487 (MH+).

Example 68

Synthesis of 1-[(4-Cyano-5-methyl-4-phenyl)hexyl]-4-{2-[N-(4-fluorophenyl)-N-methylsulfamoyl]ethyl}piperazine

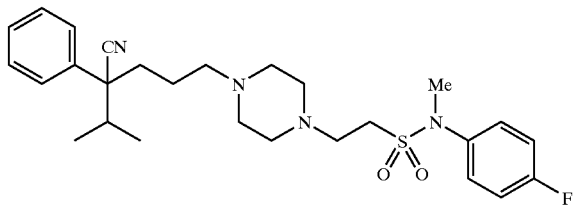

60% sodium hydride (10 mg) was added to a solution of 1-[(4-cyano-5-methyl-4-phenyl)hexyl]-4{2-[N-(4-fluorophenyl)sulfonyl]ethyl}piperazine (60 mg) in dimethylformamide (2 ml) under ice-cooling, and the mixture was stirred for 30 minutes at room temperature. The reaction mixture was again ice-cooled, and methyl iodide (0.01 ml) was added thereto, and the mixture was stirred for 1 hour. The reaction mixture was diluted with ethyl acetate, washed with water, dried, and evaporated. The residue was purified by Cromatorex NH silica gel column chromatography (hexane/ethyl acetate system) to give the free compound (51 mg, 81%) of the title compound as a pale yellow oil.

Free Compound;
$^1$H-NMR (400 MHz, CDCl$_3$); δ (ppm) 0.77 (d, J=6.6 Hz, 3H), 1.05–1.16 (m, 1H), 1.20 (d, J=6.6 Hz, 3H), 1.50–1.58 (m, 1H), 1.88 (ddd, J=4.4 Hz, 12 Hz, 13.6 Hz, 1H), 2.08–2.48 (m, 12H), 2.79–2.82 (m, 2H), 3.12–3.15 (m, 2H), 3.31 (s, 3H), 7.02 (t, J=8.6 Hz, 2H), 7.16 (t, 8.6 Hz, 2H), 7.27–7.38 (m, 7H).

The above free compound was treated in a usual manner to give the hydrochloride (38 mg) of the title compound.

Hydrochloride;
$^1$H-NMR (400 MHz, DMSO-d$_6$); δ (ppm) 0.65 (d, J=6.8 Hz, 3H), 1.09 (d, J=6.8 Hz, 3H), 1.18–1.3 (m, 1H), 1.55–1.68 (m, 1H), 2.03–2.23 (m, 3H), 2.95–3.20 (m, 4H), 3.25 (s, 3H), 3.35–3.80 (m, 10H), 7.24 (t, J=8.8 Hz, 2H), 7.32–7.43 (m, 5H), 7.49 (dd, J=4.8 Hz, 8.8 Hz, 2H).

ESI-Mass; 501 (MH+).

Example 69

Synthesis of 1-[(4-cyano-5-methyl-4-phenyl)hexyl]-4-[2-(N-methyl-4-fluorobenzenesulfonylamino)ethyl]piperazine

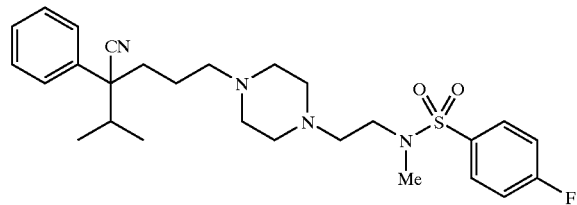

1-[(4-Cyano-5-methyl-4-phenyl)hexyl]-4[2-(4-fluorobenzenesulfonylamino)ethyl]piperazine (31 mg) was dissolved in dimethylformamide (5.0 ml), and sodium hydride (5.1 mg) and methyl iodide (0.01 ml) were added thereto at 0° C. under stirring, and the mixture was stirred overnight at room temperature. The reaction mixture was acidified by adding 5 M hydrochloric acid and then evaporated. The residue was dissolved in dimethylformamide (5 ml), and thiourea (7.3 mg) was added thereto, and the mixture was heated overnight under reflux. After the reaction mixture was cooled to room temperature, the organic layer was partitioned by adding water and ethyl acetate, and the organic layer was washed with water, dried, and evaporated. The residue was purified by Cromatorex NH silica gel column chromatography (hexane/ethyl acetate system) to give the title compound (13 mg, 41%) as a colorless oil.

Free Compound;
$^1$H-NMR (400 MHz, CDCl$_3$); δ (ppm) 0.77 (d, J=6.8 Hz, 3H), 1.08–1.14 (m, 1H), 1.20 (d, J=6.8 Hz, 3H), 1.25–1.55 (m, 3H), 1.88 (td, J=4.6,13.0 Hz, 1H), 2.08–2.18 (m, 2H), 2.21–2.27 (m, 2H), 2.27–2.38 (br-s, 3H), 2.38–2.48 (br-s, 3H), 2.52 (t, J=7.0 Hz, 2H), 2.78 (s, 3H), 3.13 (m, 2H), 7.19 (m, J=8.4 Hz, 2H), 7.29 (m, 1H), 7.34–7.41 (m, 4H), 7.84–7.79 (m, 2H).

The above free compound (13 mg) was treated in a usual manner to give the hydrochloride (14.8 mg) of the title compound as a colorless amorphous.

Hydrochloride;
$^1$H-NMR (400 MHz, CDCl$_3$); δ (ppm) 0.77–0.81 (m, 3H), 0.86–0.90 (m, 1H), 1.19–1.23 (m, 3H), 1.24–2.43 (m, 9H), 2.66–3.91 (m, 9H), 2.85 (m, 3H), 7.26–7.42 (m, 7H), 7.84 (m, 2H).

ESI-Mass; 501.1 (MH+).

Example 70

Synthesis of 1-[(4-Cyano-5-methyl-4-phenyl)hexyl]-4-{2-[(4-fluorophenylthio)carbonyloxy]ethyl}piperazine

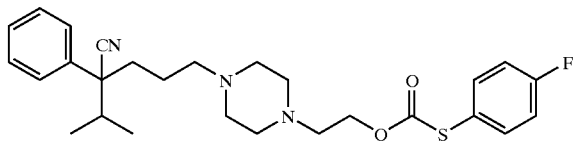

The free compound (228 mg, 84%) of the title compound was obtained as a colorless oil from 2-(1-methylethyl)-5-oxo-2-phenyl pentane nitrile (120 mg) and S-(4-fluorophenyl) thiocarbonate.1-(1-piperazinyl)ethyl (159 mg) in the same manner as in Example 1.
Free Compound;
$^1$H-NMR (400 MHz, CDCl$_3$); δ (ppm) 0.78 (d, J=6.8 Hz, 3H), 1.06–1.18 (m, 1H), 1.20 (d, J=6.8 Hz, 3H), 1.49–1.60 (m, 1H), 1.90 (ddd, J=4.4 Hz, 12 Hz, 13.6 Hz, 1H), 2.08–2.28 (m, 8H), 3.09 (t, J=6.8 Hz, 2H), 3.28–3.44 (m, 4H), 4.20 (t, J=6.8 Hz, 2H), 6.99 (t, J=8.6 Hz, 2H), 7.26–7.41 (m, 5H).

The above free compound was treated in a usual manner to give the hydrochloride (88 mg) of the title compound.
Hydrochloride;
$^1$H-NMR (400 MHz, DMSO-d$_6$); δ (ppm) 0.65 (d, J=6.4 Hz, 3H), 1.10 (d, J=6.4 Hz, 3H), 1.16–1.26 (m, 1H), 1.54–1.66 (m, 1H), 2.04–2.24 (m, 3H), 2.78–3.37 (m, 13H), 4.10–4.18 (m, 2H), 7.17 (t, J=9 Hz, 2H), 7.33–7.37 (m, 1H), 7.40–7.46 (m, 6H).
ESI-Mass; 484 (MH+).

Example 71

Synthesis of 1-[(4-Cyano-5-methyl-4-phenyl)hexyl]-4-[2-(2-pyridyloxy)ethyl]piperazine

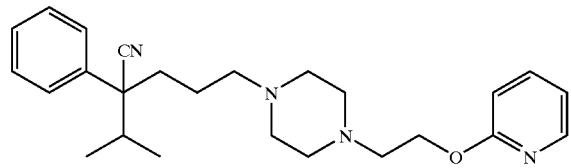

1-[(4-Cyano-5-methyl-4-phenyl)hexyl]-4-(2-hydroxyethyl)piperazine (225 mg) and 2-bromopyridine (0.10 ml) were dissolved in dimethylformamide (20 ml), then sodium hydride (45 mg) was added thereto at room temperature, and the mixture was stirred at 40° C. overnight. Sodium hydride (45 mg) and 2-bromopyridine (0.20 ml) were further added to the reaction mixture, and the mixture was heated at 75° C. The reaction mixture was poured into aqueous sodium bicarbonate, extracted with ethyl acetate, washed with water and brine, and dried. After evaporated, the residue was purified by Cromatorex NH silica gel column chromatography (hexane/ethyl acetate system), whereby the free compound of the title compound was obtained as an oil.
Free Compound;
$^1$H-NMR (400 MHz, CDCl$_3$); δ (ppm) 0.77 (d, J=6.8 Hz, 3H), 1.20 (d, J=6.8 Hz, 3H), 1.25–1.27 (m, 1H), 2.04–2.34 (m, 4H), 2.80–3.60 (m, 14H), 6.71–6.76 (m, 1H), 6.85–6.91 (m, 1H), 7.27–7.34 (m, 1H), 7.35–7.42 (m, 4H), 7.54–7.61 (m, 1H), 8.10–8.14 (m, 1H).

The above free compound was dissolved in methanol, and 4 N hydrogen chloride/ethyl acetate solution was added thereto. The solvent and excess hydrogen chloride were evaporated and recrystallized from methanol/ether, whereby the hydrochloride (55 mg) of the title compound was obtained.
Hydrochloride;
$^1$H-NMR (400 MHz, DMSO-d$_6$); δ (ppm) 0.68 (d, J=6.6 Hz, 3H), 1.11 (d, J=6.6 Hz, 3H), 1.20–1.33 (m, 1H), 1.56–1.70 (m, 1H), 2.04–2.30 (m, 3H), 3.00–3.82 (m, 14H), 4.61 (br-s, 2H), 6.86–6.90 (m, 1H), 7.02–7.07 (m, 1H), 7.34–7.40 (m, 1H), 7.42–7.48 (m, 4H), 7.73–7.79 (m, 1H), 8.17–8.20 (m, 1H).
ESI-Mass; 407 (MH+).

Example 72

Synthesis of 1-(3-Cyclohexyl-3-cyano-3-phenyl)propionyl-4-[2-(4-fluorophenoxy)ethyl]piperazine

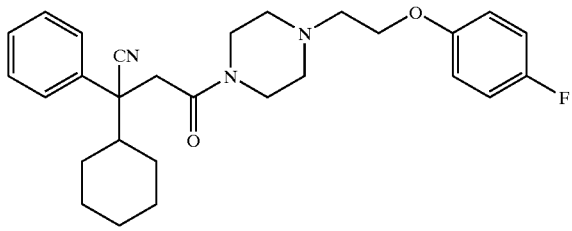

Cyclohexyl phenyl acetonitrile (1.99 g) synthesized according to J.M.C., 35, 2210–2214, 1992, and sodium hydride (370 mg, 65%) were dissolved in dimethylformamide (35 ml), and the mixture was stirred at 60° C. for 3 hours. The reaction mixture was allowed to reach room temperature, and ethyl brome acetate (1.67 g) and tetrahydrofuran (4 ml) were added thereto, and the mixture was stirred overnight at 60 to 70° C. The organic layer was partitioned by adding water and an ether/hexane mixed solvent, washed with water, dried, and evaporated. The residue was purified by silica gel column chromatography (hexane/ethyl acetate system), whereby ethyl 3-cyano-3-phenyl-3-cyclohexyl propionate (1.13 g) was obtained as a colorless oil.

Ethanol (16 ml) and 8 N sodium hydroxide (2.0 ml) were added thereto, and the mixture was stirred overnight at room temperature. After neutralized with 5 N hydrochloric acid, the organic layer was partitioned by adding ether/ethyl acetate, washed with water, dried, and evaporated to give 3-cyano-3-phenyl-3-cyclohexyl propionic acid (940 mg).

This carboxylic acid (205 mg) was dissolved in tetrahydrofuran (4.0 ml), and dimethylformamide (2 drops) and oxazalyl chloride (120 mg) were added thereto, and the mixture was stirred for 10 minutes at room temperature and then evaporated. The residue was dissolved in tetrahydrofuran (3.0 ml) and added to a solution of previously prepared 1-[2-(4-fluorophenoxy)ethyl]piperazine (215 mg) and triethylamine (120 mg) in tetrahydrofuran (5.0 ml). After stirred for 3 hours, the organic layer was partitioned by adding aqueous saturated sodium bicarbonate and ethyl acetate, washed with water, dried, and evaporated. The residue was purified by silica gel column chromatography (hexane-ethyl acetate/methanol system), whereby the title compound (160 mg) was obtained as a colorless oil.
Free Compound;
$^1$H-NMR (400 MHz, CDCl$_3$); δ (ppm) 1.05–1.40 m, 5H), 1.60–1.70 (m, 3H), 1.83–1.90 (m, 1H), 1.95–2.15 (m, 2H), 2.30–2.45 (m, 4H), 2.77 (t, J=5.8 Hz, 2H), 3.01 (d, J=5 Hz, 2H), 3.13 (d, J=5 Hz, 2H), 3.20–3.35 (m, 2H), 3.42–3.50 (m, 2H), 4.04 (t, J=5.8 Hz, 2H), 6.80–6.85 (m, 2H), 6.91–6.99 (m, 2H), 7.22–7.43 (m, 4H).

Example 73

Synthesis of 1-(2-Hydroxy-4-cyano-5-methyl-4-phenyl)hexyl-4-[2-(4-fluorophenoxy)ethyl]piperazine 73-1) (3-Methyl-2-cyano-2-phenyl)butyl Oxirane

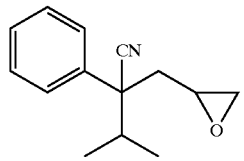

3-Methyl-2-phenylbutyronitrile (4.19 g) synthesized according to J.Chem.Soc. Perkin Trans, 1, 2845–2850, 1996, and 65% oily sodium hydride (1.05 g) were dissolved in dimethylformamide (90 ml), and the mixture was stirred at 60° C. for 3 hours. The reaction mixture was allowed to reach room temperature, and allyl bromide (2.9 g) and tetrahydrofuran (3.0 ml) were added thereto, and the mixture was stirred overnight at 60° C. The organic layer was partitioned by adding water and an ether/hexane mixed solvent, washed with water, dried, and evaporated. The residue was purified by silica gel column chromatography (hexane/ethyl acetate system), whereby (5-methyl-4-cyano-4-phenyl)-1-hexene (4.5 g, 86 %) was obtained as a colorless oil.

This product (2.5 g) was dissolved in dichloromethane (60 ml), and sodium bicarbonate (2.35 g) and m-chloroperbenzoic acid (2.76 g) were added thereto under ice-cooling, and the .mixture was stirred overnight at room temperature. Ethanol (16 ml) and 8 N sodium hydroxide (2.0 ml) were added thereto, and the mixture was stirred overnight at room temperature. Aqueous saturated sodium bicarbonate and dichloromethane were added to the reaction mixture, and the organic layer was partitioned, washed with water, dried, and evaporated. The residue was purified by silica gel column chromatography (hexane/ethyl acetate system), whereby the early eluted diastereomer (800 mg, 30%) of the title compound and the late eluted diastereomer (390 mg, 14%) of the title compound were obtained.

Diastereomer 1 (eluted early)

¹H-NMR (400 MHz, CDCl₃); δ (ppm) 0.81 (d, J=6.8 Hz, 3H), 1.19 (d, J=6.8 Hz, 3H), 2.05 (dd, J=7.2 Hz, 14 Hz, 1H), 2.16–2.24 (m, 1H), 2.44 (dd, J=12.8 Hz, 17.2 Hz, 1H), 2.58–2.64 (m, 1H), 2.64–2.68 (m, 1H), 2.70–2.74 (m, 1H), 7.30–7.50 (m, 5H).

Diastereomer 2 (eluted late)

¹H-NMR (400 MHz, CDCl₃); δ (ppm) 0.81(d, J=6.8 Hz, 3H), 1.22 (d, J=6.8 Hz, 3H), 1.92 (dd, J=6.4Hz, 14.4 Hz, 1H), 2.17–2.26 (m, 1H), 2.48–2.78 (m, 1H), 2.64–2.68 (m, 2H), 2.810–2.874 (m, 1H), 7.30–7.50 (m, 5H).

73-2) 1-(4-Hydroxy-4-cyano-5-methyl-4-phenyl)hexyl-4-[2-(4-fluorophenoxyl)ethyl]piperazine

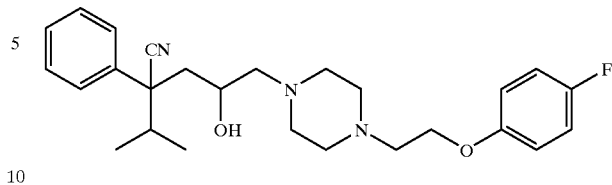

The early eluted diastereomer 1 (390 mg), 1-[2-(4-fluorophenoxy)ethyl]piperazine (450 mg), and ytterbium III trifluoromethane sulfonic acid monohydrate (90 mg) were added to dichloromethane (2.5 ml), and the mixture was stirred overnight at room temperature. The solvent was evaporated, and the residue was purified by silica gel column chromatography (hexane/ethyl acetate/methanol system) to give the title compound (320 mg, 40%).

¹H-NMR (400 MHz, CDCl₃); δ (ppm) 0.76 (d, J=6.8 Hz, 3H), 1.21 (d, J=6.8 Hz, 3H), 2.10–2.24(m, 3H), 2.27–2.43 (m, 3H), 2.43–2.51 (m, 7H), 2.73 (t, J=6.0 Hz, 2H), 3.48–3.55 (m, 1H), 4.03 (t, J=6.0 Hz, 2H), 6.79–6.85(m, 2H), 6.92–6.98 (m, 2H), 7.26–7.34 (m, 1H), 7.34–7.40 (m, 4H).

Example 74

Systhesis of 1-[(4-Cyano-5-methyl-4-phenyl)hexyl]-4-[2-(2-benzylphenoxy)ethyl]piperazine

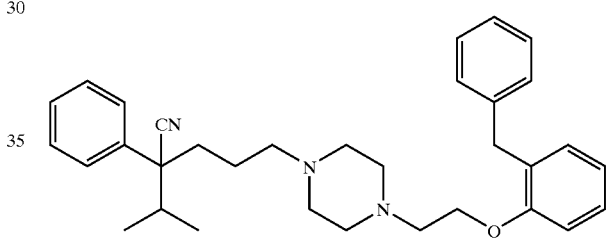

N-[2-(Benzylphenoxy)ethyl]piperazine (169.9 mg), 2-(1-methylethyl)-5-oxo-2-phenyl pentane nitrile (103 mg), and acetic acid(0.05 ml) were dissolved in dichloroethane (5 ml), then sodium triacetoxy borohydride (160 mg) was added thereto, and the mixture was treated in the same manner as in Example 1, whereby the free compound (96 mg, 41%) of the title compound was obtained as a colorless oil.

Free Compound;

¹H-NMR (400 MHz, CDCl₃); δ (ppm) 0.78 (d, J=6.2 Hz, 3H), 1.06–1.53 (m, 1H), 1.20 (d, J=6.2 Hz, 3H), 1.50–1.61 (m, 1H), 1.77 (m, 1H), 1.88 (td, J=4.4 Hz, 12.6 Hz, 1H), 1.95–2.31 (m, 7H), 2.50 (br-s, 4H), 2.75 (t, J=5.6 Hz, 2H), 3.06 (s, 2H), 4.06 (t, J=5.6 Hz, 2H), 6.83 (d, J=8.4 Hz, 1H), 6.88 (t, J=7.4 Hz, 1H), 7.08–7.32 (m, 8H), 7.34–7.39 (m, 4H).

The above free compound (96 mg) was treated in a usual manner to give the hydrochloride (110 mg) of the title compound as a colorless amorphous.

Hydrochloride;

¹H-NMR (400 MHz, CDCl₃); δ (ppm) 0.79(d, J=6.4 Hz, 3H), 1.24 (d, J=6.4 Hz, 3H), 1.25 (m, 1H), 1.43 (m, 1H), 1.78 (m, 1H), 2.04 (m, 1H), 2.16 (m, 2H), 2.33 (m, 1H), 2.87 (m, 1H), 2.90–3.10 (m, 2H), 3.25 (m, 1H), 3.35 (m, 2H), 3.46 (m, 2H), 3.70 (m, 2H), 4.00 (s, 2H), 4.43 (m, 2H), 6.84 (d, J=6.8 Hz, 1H), 7.00–7.07 (m, 5H), 7.19–7.20 (m, 2H), 7.36–7.44 (m, 6H).

ESI-Mass; 496 (MH+).

91

Figure 8:
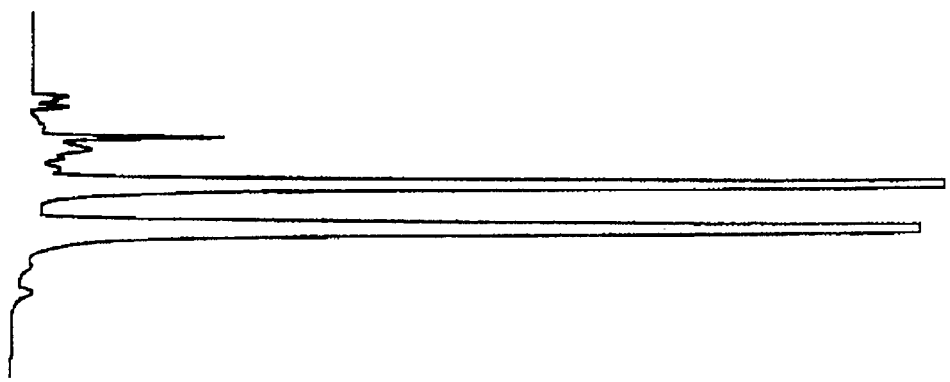
FIG. 8 is a HPLC chart showing that the compound obtained in Example 1 was optically resoluted by optically active column HPLC (the above (former) main peak shows the compound of Example 75 and the below (latter) shows the compound of Example 76).

Finally, experimental examples where the compound in Example 1 was optically resoluted by optically active column HPLC are described as Preparatory Examples for obtaining optically active substances in the present invention. (Refer to FIG. 8).

HPLC analysis conditions

| | |
|---|---|
| Solid phase: | chiralcel OJ (0.46 cm × 25 cm, Daicel Chemical) |
| Mobile phase: | n-hexane:isopropyl alcohol:ethanol = 850:100:50 |
| Flow rate: | 0.5 ml/min |
| Temperature: | 25° C. |
| Detector: | UV 210 nm |

Example 75

(−)-1-[(4-Cyano-5-methyl-4-phehnyl)hexyl]-4-[2-fluorophenoxyl)ethyl]piperazine hydrochloride The title compound was obtained as the early eluted fraction in the HPLC experimental example described above.

$[\alpha]^{29}{}_D = -5.18$ (C=1.0, ethanol)

Example 76

(+)-1-[(4-Cyano-5-methyl-4-phenyl)hexyl]-4-[2-(4-fluorophenoxyl)ethyl]piperazine Hydrochloride The title compound was obtained as the late eluted fraction in the HPLC experimental example described above.

$[\alpha]^{30}{}_D = +6.23$ (C=1.0, ethanol)

In the same manner, optically active substances were separated from the compound of Example 25.

Example 77

(−)-1-[(3-Cyano-4-methyl-3-phenyl)pentyl]-4-[2-(4-fluorophenoxyl)ethyl]piperazine Hydrochloride $[\alpha]^{27.8}{}_D = -6.552$ (C=0.250, ethanol)

Example 78

(+)-1-[(3-Cyano-4-methyl-3-phenyl)pentyl]-4-[2-(4-fluorophenoxyl)ethyl]piperazine Hydrochloride $[\alpha]^{27.6}{}_D = +4.118$ (C=0.267, ethanol)

In the same manner, optically active substances were separated from the compound of Example 38.

Example 79

(−)-1-[(4-Cyano-4-cyclohexyl-4-phenyl)butyl]-4-[2-(4-fluorophenoxyl)ethyl]piperazine Hydrochloride $[\alpha]27.4_D = -5.717$ (C=1.833, ethanol)

Example 80

(+)-1-[(4-Cyano-4-cyclohexyl-4-phenyl)butyl]-4-[2-(4-fluorophenoxyl)ethyl]piperazine Hydrochloride $[\alpha]^{28.2}{}_D = +4.792$ (C=0.250, ethanol)

92

Example 81

Synthesis of 1-[(4-Cyano-5-hydroxy-5-methyl-4-phenyl)hexyl]-4-[2-(4-fluorophenoxyl)ethyl] piperazine 81-1) Ethyl 5-Benzyloxy-2-cyano-2-phenylpetanoate

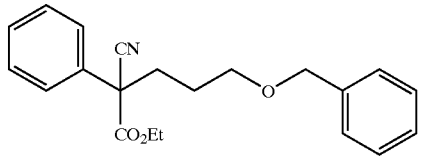

Sodium hydride was added to a solution of ethyl phenyl-cyanoacetate 3 g in dimethylformaldehyde 20 ml under ice-cooling, and the mixture was stirred at room temperature for 1 hour. It was ice-cooled again, benzyl-3-bromopropyl ether (4.2 ml) was added thereto, and the mixture was stirred at room temperature for 3 hours. After the reaction mixture was evaporated, water was added thereto and the product was extractedwithethylacetate. The organic layer was washed with water, dried, and evaporated. The residue was purified by silica gel column chromatography (hexane/ethyl acetate system), whereby the title compound (2.892 g, 54%) was obtained as a colorless oil.

$^1$H-NMR (400 MHz, CDCl$_3$); δ (ppm) 1.22 (t, J=7.2 Hz, 3H), 1.65–1.84 (m, 2H), 2.23–2.31 (m, 1H), 2.44–2.51 (m, 1H), 3.49 (t, J=6.2 Hz, 2H), 4.14–4.26(m, 2H), 4.46 (s, 2H), 7.23–7.41 (m, 8H), 7.54–7.56 (m, 2H).

81-2) 5-Benzyloxy-2-(1-hydroxy-1-methylethyl)-2-phenylpentanenitrile

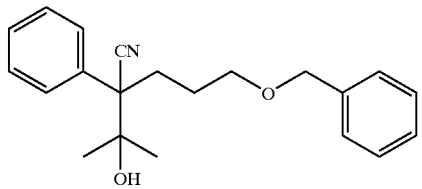

3M-methyl magnesium bromide in ether 8 ml was added dropwise to a solution of ethyl 5-benzyloxy-2-cyano-2-phenyl pentanoate 2.892 g in ether 30 ml under ice-cooling, and the mixture was stirred for 1 hour. Aqueous saturated ammonium chloride was added to the reaction mixture which was then extracted with ethyl acetate. The organic layer was washed with brine, dried, and evaporated. The residue was purified by silica gel column chromatography (hexane/ethyl acetate system) whereby the title compound (1.658 g, 60%) was obtained as a colorless oil.

$^1$H-NMR (400 MHz, CDCl$_3$); δ (ppm) 1.22 (s, 3H), 1.35–1.45 (m, 1H), 1.37 (s, 3H), 1.67–1.77 (m, 1H), 2.17–2.25 (m, 1H), 2.38–2.45 (m, 1H), 3.47 (t, J=6.2 Hz, 2H), 4.45 (s, 2H), 7.24–7.39 (m, 8H), 7.46–7.51 (m, 2H).

81-3) 2-(1-Hydroxy-1-methylpthyl)-5-ioin-2-phenylpentanenitrile

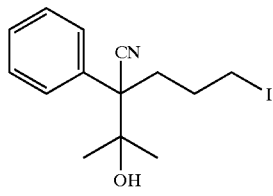

10%-palladium/carbon catalyst 250 mg was added to a tes o lution of 5-benzyloxy-2-(1-hydroxy-1-methylethyl)-2-phenylpentanenitrile 1.658 g in ethanol 20 ml, and the mixture was stirred in a hydrogen atmosphere for 5 hours. After the catalyst was filtered off, the filtrate was evaporated. The residue and triethylamine 1.1 ml were dissolved in tetrahydrofuran 15 ml, and methane sulfonyl chloride 0.6 ml was added thereto under ice-cooling, and the mixture was stirred at room temperature for 30 minutes. Water was added to the reaction mixture which was then extracted with ethyl acetate, and the organic layer was washed with water, dried, and evaporated. The residue was dissolved in acetone 40 ml, and sodium iodide 3.9 g was added thereto, and the mixture was heated under reflux for 2 hours. The reaction mixture was evaporated, water was added thereto, and the product was extracted with ethyl acetate. The organic layer was washed with water, dried, and evaporated, and the residue was purified by silica gel column chromatography (hexane/ethyl acetate system), whereby the title compound 1.493 g, 85% was obtained as a yellowish brown oil.

$^1$H-NMR (400 MHz, CDCl$_3$); δ (ppm) 1.25 (s, 3H), 1.42 (s, 3H), 1.50–1.60 (m, 1H), 1.91–2.01 (m, 1H), 2.20–2.27 (m, 1H), 2.45–2.52 (m, 1H), 3.12–3.26 (m, 2H), 7.36–7.44 (m, 1H), 7.47–7.51 (m, 2H).

81-4) 1-[(4-Cyano-5-hydroxy-5-methyl-4-phenyl)hexyl]-4-[2-fluorophenoxyl)ethyl]piperazine

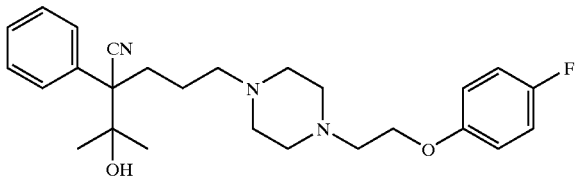

1-[2-(4-fluorophenoxy)ethyl]piperazine 359 mg and triethylamine 0.22 ml were added to a solution of 2-(1-hydroxy-1-methylethyl)-5-iodo-2-phenylpentanenitrile 545 mg in tetrahydrofuran 7 ml, and the mixture was stirred at room temperature overnight. The reaction mixture was diluted with ethyl acetate, washed with water, dried, and evaporated. The residue was purified by Chromatorex NH silica gel column chromatography (hexane/ethyl acetate system), whereby the title compound (406 mg, 56%) was obtained as a colorless oil.

Free Compound;
$^1$H-NMR (400 MHz, CDCl$_3$); δ (ppm) 1.24 (s, 3H), 1.39 (s, 1H), 1.57–1.72 (m, 2H), 2.12–2.19 (m, 1H), 2.28–2.70 (m, 11H), 2.78 (t, J=6 Hz, 2H), 4.04 (t, J=6 Hz, 2H), 6.81–6.85 (m, 2H), 6.93–6.99 (m, 2H), 7.32–7.42 (m, 3H), 7.46–7.50 (m, 2H).

The above free compound 125 mg was treated in a usual manner to give the hydrochloride 131 mg of the title compound.
Hydrochloride;
ESI-Mass; 440 (MH+).

Example 82

Synthesis of 1-[5-(4-Cyano-5-methyl-4-phenyl)hexenyl]-4-[2-(4-fluorophenoxyl)ethyl]piperazine

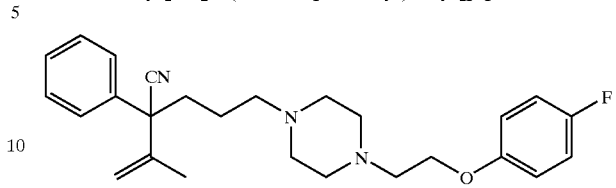

1-[(4-Cyano-5-hydroxy-5-methyl-4-phenyl)hexyl]-4-[2-(4-fluorophenoxy)ethyl]piperazine 145 mg was dissolved in thionyl chloride 1 ml and heated under reflux for 5 minutes. The reaction mixture was added dropwise to 5N-NaOH 10 ml and then extracted with ethyl acetate. The organic layer was washed with water, dried, and evaporated. The residue was purified by Chromatorex NH silica gel column chromatography (hexane/ethyl acetate system), whereby the title compound 98 mg, 70% was obtained as a colorless oil.

Free Compound;
$^1$H-NMR (400 MHz, CDCl$_3$); δ (ppm) 1.40–1.52 (m, 1H), 1.62 (s, 3H), 1.62–1.72 (m, 1H), 2.05–2.22 (m, 2H), 2.36 (t, J=7.4 Hz, 2H), 2.36–2.66 (m, 8H), 2.78 (t, J=5.8 Hz, 2H), 4.05 (t, J=5.8 Hz, 2H), 5.13 (s, 1H), 5.35 (s, 1H), 6.81–6.85 (m, 2H), 6.93–6.98 (m, 2H), 7.28–7.42 (m, 5H).

The above free compound 98 mg was treated in a usual manner to give the hydrochloride 81 mg of the title compound.
Hydrochloride;
ESI-Mass; 422 (MH+).

Example 83

Synthesis of 1-[4-Cyano-5-methyl-4-(4-hydroxyphenyl)hexyl]-4-[2-(4-fluorophenoxy)ethyl]piperazine

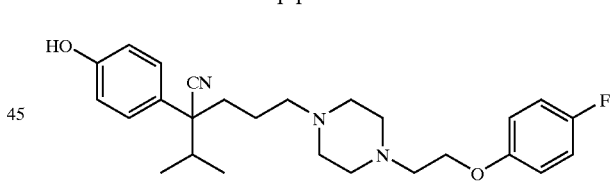

1-[4-Cyano-5-methyl-4-(4-methoxyphenyl)hexyl]-4-[2-(4-fluorophenoxy)ethyl]piperazine 85 mg obtained in Example 11 was dissolved in dichloromethane 3 ml, and 1M-boron tribromide (dichloromethane solution, 0.5 ml) was added dropwise thereto under ice-cooling. After haeting the mixture under reflux for 5 hours, it was cooled to room temperature and basified with aqueous saturated sodium bicarbonate under ice-cooling. The mixture was extracted with ethyl acetate, and the organic layer was washed with water, dried over sodium sulfate anhydride, and evaporated. The residue was purified by silica gel column chromatography (hexane/ethyl acetate system), whereby the title compound 30 mg, 36% was obtained as a colorless oil.

Free Compound;
$^1$H-NMR (400 MHz, CDCl$_3$); δ (ppm) 0.77 (d, J=6.6 Hz, 3H), 1.16 (d, J=6.6 Hz, 3H), 1.19–1.30 (m, 1H), 1.61–1.66 (m, 1H), 1.68–1.71 (m, 1H), 1.80 (td, J=4.4 Hz, 13.6 Hz, 1H), 1.99–2.05 (m, 1H), 2.08 (td, J=4.4 Hz, 12.8 Hz, 1H), 2.27–2.60 (m, 9H), 2.77 (t, J=5.6 Hz, 2H), 3.71 (m, 1H), 4.03 (t, J=5.6 Hz, 2H), 6.64–6.66 (m, 2H), 6.80 (t, J=4.4 Hz, 1H), 6.81 (dd, J=4.4 Hz, 9.2 Hz, 1H), 6.94 (tm, J=8.8 Hz, 2H), 7.13 (m, 1H), 7.15 (m, 1H).

ESI-Mass; 440 (MH+).

Oxalic acid (equivalent) was added at room temperature to a solution of the above free compound 13 mg in methanol. After the mixture was stirred for 10 minutes, the solvent was evaporated, whereby the oxalate 16.1 mg of the title compound was obtained. Oxalate; ESI-Mass; 440 (MH+).

Example 84

Synthesis of 1-[(4-Cyano-5-methyl-4-phenyl)hexyl]-4-[2-(2-hydroxy-4-fluorophenoxy)ethyl]piperazine 84-1) Ethyl(2-acetyl-4-fluorophenoxy)acetate

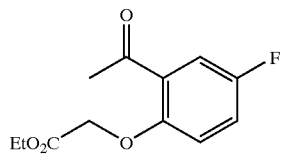

5'-Fluoro-2'-hydroxyacetophenone 2.0 g, ethyl iodoacetate 4.16 g and potassium carbonate 2.7 g were added to acetone 43 ml in a nitrogen atmosphere, and the mixture was stirred overnight under reflux with heating. After cooled to room temperature, the potassium carbonate was filtered off through Celite, and the filtrate was partitioned by adding water and ethyl acetate. The organic layer was washed with water and then with brine, dried over magnesium sulfate anhydride, and evaporated. The residue was purified by silica gel column chromatography (hexane/ethyl acetate system), whereby the title compound 3.07 g, 99% was obtained as a colorless oil.

$^1$H-NMR (400 MHz, CDCl$_3$); δ (ppm) 1.31 (t, J=7.0 Hz, 3H), 2.72 (s, 3H), 4.28 (q, J=7.0 Hz, 3H), 4.70 (s, 2H), 6.81 (dd, J=4.0 Hz, 9.2 Hz, 1H), 7.14 (ddd, J=3.2 Hz, 7.2 Hz, 9.2 Hz, 1H), 7.48 (dd, J=3.2 Hz, 8.8 Hz, 1H).

84-2) Ethyl (2-Acetoxy-4-fluorophenoxy)acetate

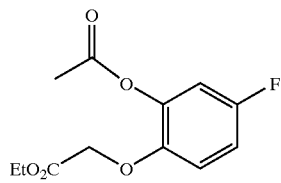

Ethyl (2-acetyl-4-fluorophenoxy) acetate 500 mg, sodium bicarbonate 505 mg and methachloroperbenzoic acid 1.80 g were added to dichloromethane 10 ml in a nitrogen atmosphere and stirred for 1 day under reflux with heating. The reaction mixture was cooled to room temperature, and 1M aqueous sodium thiosulf ate 5 ml was added thereto and stirred, and the mixture was partitioned by adding water and dichloromethane. The organic layer was washed with water and then with brine, dried over magnesium sulfate anhydride, and evaporated. The residue was purified by silica gel column chromatography (hexane/ethyl acetate system), whereby the title compound 333 mg, 74% was obtained as a colorless oil.

$^1$H-NMR (400 MHz, CDCl$_3$); δ (ppm) 1.30 (t, J=7.1 Hz, 3H), 2.34 (s, 3H), 4.26 (q, J=7.1 Hz, 2H), 4.57 (s, 2H), 6.82–6.92 (m, 3H).

84-3) 1-(2-Hydroxy-4-fluorophenoxyacetyl) pyrrolidine

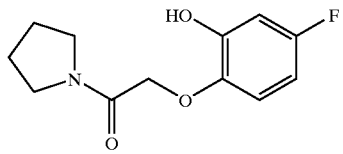

Pyrrolidine 1.87 g was added to ethyl (2-acetoxy-4-fluorophenoxy) acetate and stirred overnight. The reaction solution was partitioned by adding water and ethyl acetate. The organic layer was washed with water and then with saturated saline, dried over magnesium sulfate anhydride, and evaporated, whereby the title compound (1.20 mg, 96%) was obtained as a brown oil.

$^1$H-NMR (400 MHz, CDCl$_3$); δ (ppm) 1.82–2.04 (m, 4H), 3.26–3.32 (m, 2H), 3.50–3.56 (m, 2H), 4.50 (s, 2H), 6.46 (dt, J=3.1 Hz, 8.9 Hz, 1H), 6.67 (dd, J=3.1 Hz, 10.0 Hz, 1H), 6.91 (dd, J=5.5 Hz, 8.9 Hz, 1H).

84-4) 1-(2-Benzyloxy-4-fluorophenoxyacetyl) pyrrolidene

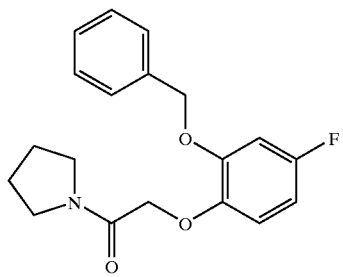

1-(2-Hydroxy-4-fluorophenoxyacetyl) pyrrolidine 82 mg was dissolved in N,N-dimethylformamide 12 ml in a nitrogen atmosphere, and sodium hydride 21 mg, 60% oil was added thereto, and the mixture was stirred for 15 minutes, and benzyl bromide 89 mg was added thereto, and the mixture was stirred at room temperature. After 45 minutes, aqueous saturated ammonium chloride was added thereto and stirred, and the mixture was partitioned by adding water and ethyl acetate. The organic layer was washed with water and then with brine, dried over magnesium sulfate anhydride, and evaporated. The residue was purified by silica gel column chromatography (diethyl ether) whereby the title compound 100 mg, 97% was obtained as a pale yellow oil.

$^1$H-NMR (400 MHz, CDCl$_3$); δ (ppm) 1.75–1.90 (m, 4H), 3.48 (t, J=6.8 Hz, 4H), 4.63 (s, 2H), 5.09 (s, 2H), 6.58 (ddd, J=2.8 Hz, 8.8 Hz, 11.2 Hz, 1H), 6.69 (dd, J=2.8 Hz, 10.0 Hz, 1H), 6.94 (dd, J=5.6 Hz, 8.8 Hz, 1H).

84-5) 1-[(4-Cyano-4-methyl-4-phnyl)hexyl]-4-[2-(2-fluorophenoxy)ethyl]piperazine

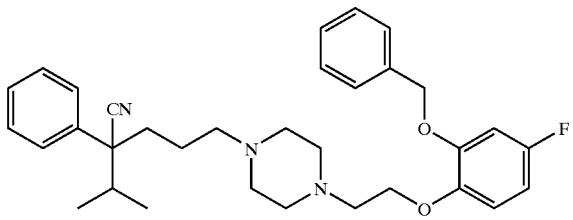

1-(2-Benzyloxy-4-fluorophenoxyacetyl) pyrrolidine 100 mg was dissolved in toluene 10 ml in a nitrogen atmosphere, and 3.4M bis(2-methoxyethoxy)aluminum sodium hydride in toluene (0.09 ml, trade name; Red-Al) was added thereto, and after the mixture was stirred for 1 hour, acetone 0.1 ml was added thereto, and the mixture was stirred at room temperature. After 15 minutes, 1N hydrochloric acid 1 ml was added thereto and the mixture was stirred, and then partitioned by adding water and ethyl acetate. The organic layer was washed with water, aqueous saturated sodium bicarbonate and brine in this order, dried over magnesium sulfate anhydride and evaporated to give an aldehyde 65 mg. This product 65 mg, acetic acid 0.06 ml, and 1-[(4-cyano-5-methyl-4-phenyl)hexyl]piperazine 71 mg was dissolved in dichloroethane 12.5 ml, and sodium triacetoxyborohydride 107 mg was added thereto, and the mixture was stirred at room temperature for 5 hours. The reaction mixture was partitioned by adding aqueous saturated sodium bicarbonate and ethyl acetate. The organic layer was washed with water and then with brine, dried over magnesium sulfate anhydride, and evaporated. The residue was purified by NH silica gel column chromatography (hexane/ethyl acetate system), whereby the title compound 66 mg, 49% was obtained as a pale yellow oil.

$^1$H-NMR (400 MHz, CDCl$_3$); δ (ppm) 0.77 (d, J=6.8 Hz, 3H), 1.10–1.20 (m, 1H), 1.20 (d, J=6.6 Hz, 3H), 1.45–1.60 (m, 1H), 1.82–1.93 (m, 1H), 2.05–2.20 (m, 2H), 2.20–2.40 (m, 6H), 2.45–2.65 (m, 4H), 2.77 (t, J=5.9 Hz, 2H), 4.08 (t, J=5.9 Hz, 2H), 5.06 (s, 2H), 6.57 (brdt, J=3.2 Hz, 8.8 Hz, 1H), 6.67 (dd, J=3.2 Hz, 10.0 Hz, 1H), 6.83 (dd, J=5.6 Hz, 8.8 Hz, 1H), 7.25–7.45 (m, 10H).

ESI-Mass; 530 (MH+).

84-6) 1-[(4-Cyano-5-methyl-4-phenyl)hexyl]-4-[2-(2-hydroxy-4-fluorophenoxy)ethyl]piperazine

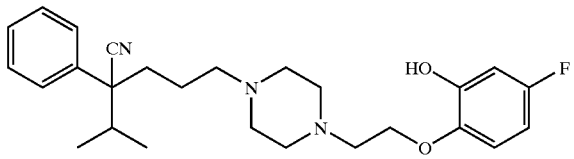

1-[(4-Cyano-5-methyl-4-phenyl)hexyl]-4-[2-(2-benzyloxy-4-fluorophenoxy)ethyl]piperazine 66 mg and 1,4-cyclohexadiene 0.23 ml were dissolved in ethanol 4 ml, and 10% palladium/carbon 6 mg was added thereto, and the mixture was stirred for 3 hours under reflux with heating. The reaction mixture was filtered through Celite and evaporated. The residue was purified by NH silica gel column chromatography (hexane/ethyl acetate system), whereby the free form (13 mg, 24%) of the title compound was obtained as a colorless oil.

Free Compound;
$^1$H-NMR (400 MHz, CDCl$_3$); δ (ppm) 0.78 (d, J=6.8 Hz, 3H), 1.05–1.20 (m, 1H), 1.20 (d, J=6.6 Hz, 3H), 1.50–1.63 (m, 1H), 1.80–1.93 (m, 1H), 2.05–2.20 (m, 2H), 2.28–2.35 (m, 2H), 2.35–2.70 (m, 8H), 2.56 (t, J=5.2 Hz, 2H), 4.03 (t, J=5.2 Hz, 2H), 6.43 (brdt, J=3.2 Hz, 8.8 Hz, 1H), 6.60 (dd, J=3.2 Hz, 10.4 Hz, 1H), 6.91 (dd, J=6.6 Hz, 8.8 Hz,$_1$H), 7.26–7.33 (m, 1H), 7.34–7.39 (m, 4H).

This product 13 mg was treated in a usual manner to give the hydrochloride 11 mg of the title compound.
Hydrochloride;
$^1$H-NMR (400 MHz, DMSO-d$_6$); δ (ppm) 0.67 (d, J=6.8 Hz, 3H), 1.11 (d, J=6.4 Hz, 3H), 1.20–1.35 (m, 1H), 1.58–1.70 (m, 1H), 2.05–2.35 (m, 3H), 3.30–3.80 (m, 12H), 4.26 (brs, 2H), 6.50–6.60 (m, 1H), 6.66 (dd, J=3.2 Hz, 10.0 Hz, 1H), 6.97 (dd, J=5.8 Hz, 9.0 Hz, 1H), 7.25–7.50 (m, 5H).
ESI-Mass; 440 (MH+).

Example 85

Synthesis of 1-[(4-Cyano-4-fluoro-4-phenyl)butyl]-4-[2-fluorophenoxy)ethyl]piperazine

85-1) 4-(1,3-Dioxolan-2-yl)-2-fluoro-2-phenylbutyonitrile

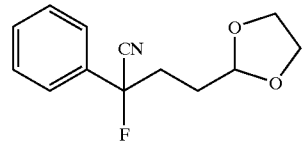

4-(1,3-Dioxolan-2-yl)-2-phenylbutyronitrile 1.00 g synthesized according to Heterocyclic Chem., 21, 307 (1990) was dissolved in tetrahydrofuran 10 ml, and 1.0 M lithium bis(trimethylsilyl)amide in tetrahydrofuran 5.52 ml was introduced into it in a nitrogen atmosphere at −78° C. The temperature was raised for 30 minutes to −20° C. and then cooled again to −78° C., and a solution of N-fluorobenzene sulfonimide 2.18 g in tetrahydrofuran 10 ml was introduced into it. The temperature was raised for 1 hour to −30° C., and aqueous saturated ammonium chloride was added thereto, and the solution was extracted with ethyl acetate and further washed with brine. It was dried over magnesium sulfate anhydride and evaporated. The residue was crystallized from ethanol, the insolubles were filtered off, and the filtrate was evaporated. The residue was purified by silica gel column chromatography (hexane/ethyl acetate system), whereby the title compound 0.55 g, 51% was obtained.

$^1$H-NMR (400 MHz, CDCl$_3$); δ (ppm) 1.86–2.02 (m, 2H), 2.25–2.45 (m, 2H), 3.84–4.00 (m, 4H), 4.93 (t, J=4.0 Hz, 1H), 7.40–7.52 (m, 5H).

85-2) 1-[(4-Cyano-4-fluoro-4-phenyl)butyl]-4-[2-(4-fluorophenoxy)ethyl]piperazine

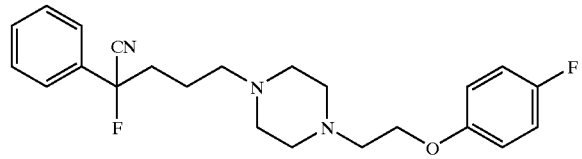

4-(1,3-Dioxolan-2-yl)-2-fluoro-2-phenylbutyronitrile was hydrolyzed with acid to be converted into 2-fluoro-5-oxo- 2-phenylpentanenitrile 0.12 g, and this product, alongwith 1-[2-(4-fluorophenyl)ethyl]piperazine 0.14 g, was treated in the same manner as in Example 1, whereby the free form (0.14 g, 56%) of the title oily compound was obtained.

Free Compound;

$^1$H-NMR (400 MHz, CDCl$_3$); δ (ppm) 1.62–1.90 (m, 2H), 2.15–2.35 (m, 2H), 2.37 (t, J=7.2 Hz, 2H), 2.45 (bs, 4H), 2.58 (bs, 4H), 2.79 (t, J=6.0 Hz, 2H), 4.05 (t, J=6.0 Hz, 2H), 6.80–6.86 (m, 2H), 6.93–7.00 (m, 2H), 7.42–7.55 (m, 5H).

This free compound 0.14 g was treated in a usual manner to give the hydrochloride 0.15 g of the title compound.

Hydrochloride; ESI-Mass; 400 (MH+).

Example 86

Synthhesis of 1-[(4-Cyano-5-methyl-4-pheny)hexyl]-4-[2-(2-ethoxycarhonylmethoxy-4-fluorophenoxy)ethyl]piperazine 8-1) 2-(2-Acetyl-4-fluorophenoxy)ethanol

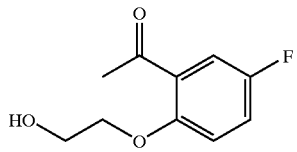

5'-Fluoro-2'-hydroxyacetophenone 5.0 g, 2-bromoethanol 6.08 g, potassium carbonate 13.4 g and sodium iodide 7.28 g were dissolved in N,N-dimethylformamide 108 ml and stirred at 100° C. overnight. The reaction mixture was cooled and then partitioned by adding water and ethyl acetate. The organic layer was washed with water and then with brine, dried over magnesium sulfate anhydride, and evaporated. The residue was purified by silica gel column chromatography (hexane/ethyl acetate system), whereby the title compound 1.66 g, 26% was obtained as a brown oil.

$^1$H-NMR (400 MHz, CDCl$_3$); δ (ppm) 2.36–2.40 (m, 1H), 2.64 (s, 3H), 3.96–4.02 (m, 2H), 4.16–4.20 (m, 2H), 6.95 (dd, J=4.0 Hz, 9.2 Hz, 1H), 7.16 (ddd, J=3.2 Hz, 7.6 Hz, 9.2 Hz, 1H), 7.43 (dd, J=3.2 Hz, 8.8 Hz, 1H).

86-2) 2-(2-Acetoxy-4-fluorophenoxy)ethanol

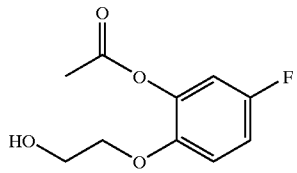

The title compound compound (96 mg, 68%) was obtained as a colorless oil from 2-(2-acetyl-4-fluorophenoxy)ethanol 141 mg, sodium bicarbonate 107 mg, and m-chloroperbenzoic acid 379 mg in the same manner as in Example 84–2).

$^1$H-NMR (400 MHz, CDCl$_3$); δ (ppm) 2.45–2.52 (m, 1H), 2.33 (s, 3H), 3.84–3.90 (M, 2H), 4.12–4.16 (m, 2H), 6.80–6.86 (m, 1H), 6.90–6.96 (m, 2H).

86-3) 2-(2-Hydroxy-4-fluorophenoxy)ethanol

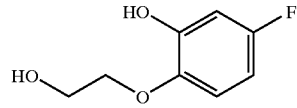

2-(2-Acetoxy-4-fluorophenoxy)ethanol 1.53 g was dissolved in a mixed solvent of tetrahydrofuran 10 ml and water 5 ml, then lithium hydroxide monohydride 294 mg was added thereto, and the mixture was stirred at 90° C. After stirred for 10 hours, the reaction mixture was cooled and partitioned by adding water and ethyl acetate. The organic layer was washed with water and then with brine, dried over magnesium sulfate anhydride and evaporated. The residue was purified by silica gel column chromatography (hexane/ethyl acetate system), whereby the title compound (1.07 g, 80%) was obtained as a colorless oil.

$^1$H-NMR (400 MHz, CDCl$_3$); δ (ppm) 2.30–2.40 (m, 1H), 3.96–4.02 (M, 2H), 4.10–4.14 (m, 2H), 6.51 (ddd, J=3.0 Hz, 8.4 Hz, 8.8 Hz, 1H), 6.69 (dd, J=3.0 Hz, 9.6 Hz, 1H), 6.83 (dd, J=5.2 Hz, 8.8 Hz, 1H), 6.90–6.63 (m, 1H).

86-4) 2-(2-Hydroxy-4-fluorophenoxy)ethanol

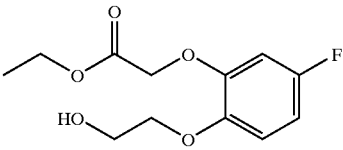

2-(2-Hydroxy-4-fluorophenoxy)ethanol 245 mg and ethyl bromoacetate 214 mg were dissolved in N,N-dimethylformamide 5 ml in a nitrogen atmosphere, and sodium hydride 51 mg, 60% oil was added thereto. The mixture was stirred at 90° C. for 1 hour and then partitioned by adding water and ethyl acetate. The organic layer was washed with water and then with brine, dried over magnesium sulfate anhydride, and evaporated. The residue was purified by NH silica gel column chromatography (hexane/ethyl acetate system), whereby the title compound 68 mg, 31% was obtained as a colorless oil.

$^1$H-NMR (400 MHz, CDCl$_3$); δ (ppm) 1.31 (t, J=7.2 Hz, 3H), 3.00–3.10 (m, 1H), 3.85–3.92 (m, 2H), 4.10–4.14 (m, 2H), 4.28 (q, J=7.2 Hz, 2H), 4.63 (s, 2H), 6.60 (dd, J=2.8 Hz, 9.6 Hz, 1H), 6.64–6.70 (m, 1H), 6.93 (dd, J=5.6 Hz, 9.2 Hz, 1H).

86-5) 1-[(4-Cyano-5-methyl-4-phenyl)hexyl]-4-[2 (2-ethoxycarbonylmethoxy-4-fluorophenoxy)ethyl] piperazine

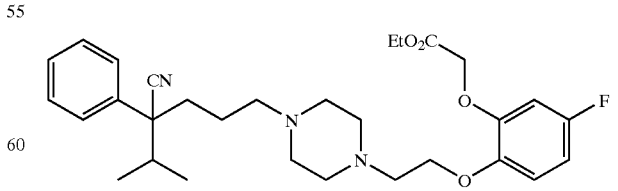

2-(2-Ethoxycarbonylmethoxy-4-fluorophenoxy)ethanol 68 mg and triethylamine 0.11 ml were dissolved in acetonitrile 5 ml in a nitrogen atmosphere, and methane sulfonyl chloride 36 mg was added thereto. After the mixture was stirred for 1 hour, sodium iodide 47 mg and 1-[(4-cyano-5-methyl-4-phenyl)hexyl]piperazine 90 mg in acetonitrile 5 ml was added thereto, and the mixture was stirred for 2 hours under reflux with heating. The reaction mixture was partitioned by adding water and ethyl acetate. The organic layer was washed with water and then with brine, dried over magnesium sulfate anhydride, and evaporated. The residue was purified by silica gel column chromatography (diethyl ether), whereby the title compound 82 mg, 59% was obtained as a colorless oil.

Free Compound;

$^1$H-NMR (400 MHz, CDCl$_3$); δ (ppm) 0.77 (d, J=6.8 Hz, 3H), 1.05–1.20 (m, 1H), 1.20 (d, J=6.8 Hz, 3H), 1.27–1.33 (m, 3H), 1.50–1.63 (m, 1H), 1.70–1.90 (m, 1H), 2.05–2.20 (m, 2H), 2.25–2.30 (m, 2H), 2.30–2.60 (m, 8H), 2.78 (t, J=6.0 Hz, 2H), 3.15 (s, 2H), 4.10 (t, J=6.0 Hz, 2H), 4.55–4.60 (m, 2H), 6.55–6.68 (m, 2H), 6.82–6.92 (m, 1H), 7.26–7.32 (m, 1H), 7.32–7.39 (m, 4H).

This product 28 mg was treated in a usual manner to give the hydrochloride 25 mg of the title compound.

Hydrochloride;

ESI-Mass; 526 (MH+).

Example 87

1-[(4-Cyano-5-methyl-4-phenyl)hexyl]-4-[2-(2-hydroxyethoxy-4-fluorophenoxy)ethyl]piperazine

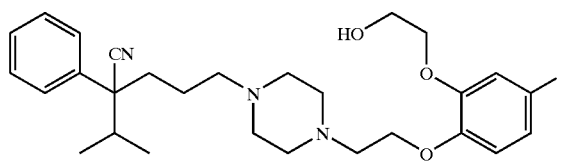

1 M lithium aluminum hydride in tetrahydrofuran 0.38 ml was added to 1-[(4-cyano-5-methyl-4-phenyl)hexyl]-4-[2-(2-ethoxycarbonylmethoxy-4-fluorophenoxy )ethyl] piperazine 20 mg in tetrahydrofuran 4 ml in an ice bath in a nitrogen atmosphere. After the reaction mixture was stirred for 40 minutes, water and 2N aqueous sodium hydroxide were added thereto. After the precipitates were filtered off through Celite, the filtrate was evaporated. The residue was purified by NH silica gel column chromatography (ethyl acetate), whereby the title compound 15 mg, 81% was obtained as a colorless oil.

Free Compound;

$^1$H-NMR (400 MHz, CDCl$_3$); δ (ppm) 0.77 (d, J=6.8 Hz, 3H), 1.05–1.20 (m, 1H), 1.20 (d, J=6.6 Hz, 3H), 1.45–1.63 (m, 1H), 1.82–1.93 (m, 1H), 2.05–2.20 (m, 2H), 2.25–2.35 (m, 2H), 2.40–2.50 (m, 4H), 2.55–2.70 (m, 4H), 2.82(t, J=6.0 Hz, 2H), 3.60–3.70 (m, 2H), 4.00–4.20 (m, 4H), 6.58–6.67 (m, 1H), 6.68 (dd, J=2.8 Hz, 9.8 Hz, 1H), 6.86 (dd, J=5.6 Hz, 8.8 Hz, 1H), 7.26–7.32 (m, 1H), 7.33–7.39 (m, 4H).

This product 15 mg was treated in a usual manner to give the hydrochloride 14 mg of the title compound.

Hydrochloride;

ESI-Mass; 484 (MH+).

Example 88

Synthesis of 1-[(4-Cyano-5-methyl-4-phenyl)hexyl]-4-[2-(2-methoxy-4-fluorophenoxy)ethyl]piperazine 88-1) 1-(2-Methoxy-4-fluorophenoxyacetyl) pyrrolidine

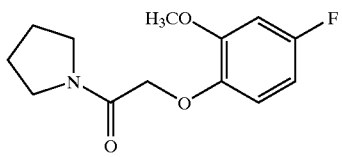

The title compound (90 mg, 69%) was obtained as a colorless crystalline from 1-(2-hydroxy-4-fluorophenoxy) acetyl pyrrolidine 123 mg and methyl iodide 0.05 ml in the same manner as in Example 84-1).

$^1$H-NMR (400 MHz, CDCl$_3$); δ (ppm) 1.80–1.90 (m, 2H), 1.90–2.00 (m, 2H), 3.48–3.58 (m, 4H), 3.86(s, 3H), 4.06 (s, 2H), 6.56 (brdt, J=3.2 Hz, 8.8 Hz, 1H), 6.64 (dd, J=3.2 Hz, 10.0 Hz, 1H), 6.90 (dd, J=5.6 Hz, 8.8 Hz, 1H).

88-2) 1-[(4-(Cyano-5-methyl-4-phenyl)hexyl]-4-[2-(2-methoxy-4-fluorophenoxy)ethyl]piperazine

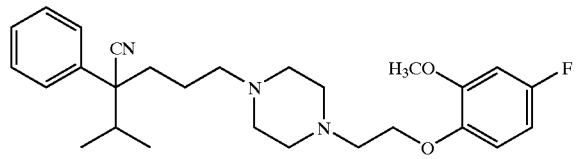

The title compound 39 mg, 24% was obtained as a pale yellow oil from 1-(2-methoxy-4-fluorophenoxyacetyl) pyrrolidine 90 mg, 3.4M bis(2-methoxyethoxy)aluminum sodium hydride in toluene 0.1 ml, and 1-[(4-cyano-5-methyl-4-phenyl)hexyl]piperazine 100 mg.

Free Compound;

$^1$H-NMR (400 MHz, CDCl$_3$); δ (ppm) 0.77 (d, J=6.8 Hz, 3H), 1.05–1.20 (m, 1H), 1.20 (d, J=6.8 Hz, 3H), 1.50–1.63 (m, 1H), 1.82–1.93 (m, 1H), 2.05–2.20 (m, 2H), 2.25–2.35 (m, 2H), 2.30–2.65 (m, 8H), 2.80 (t, J=6.0 Hz, 2H), 3.82 (s, 3H), 4.08 (t, J=6.0 Hz, 2H), 6.55 (brdt, J=2.8 Hz, 5.2 Hz, 1H), 6.62 (dd, J=2.8 Hz, 10.4 Hz, 1H), 6.81 (dd, J=5.2 Hz, 8.8 Hz, 1H), 7.26–7.33 (m, 1H), 7.32–7.39 (m, 4H).

This free compound 39 mg was treated in a usual manner to give the hydrochloride 33 mg of the title compound.

Hydrochloride;

$^1$H-NMR (400 MHz, DMSO-d$_6$); δ (ppm) 0.68 (d, J=6.6 Hz, 3H), 1.21 (d, J=6.6 Hz, 3H), 1.20–1.32 (m, 1H), 1.58–1.72 (m, 1H), 2.05–2.35 (m, 3H), 3.30–3.25 (2H), 3.25–3.70 (m, 10H), 3.78 (s, 3H), 4.33 (brs, 2H), 6.71 (brdt, J=3.0 Hz, 8.6 Hz, 1H), 6.95 (dd, J=3.0 Hz, 10.6 Hz, 1H), 6.77 (dd, J=5.5 Hz, 8.6 Hz, 1H), 7.34 (m, 1H), 7.42–7.48 (m, 4H).

ESI-Mass; 454 (MH+).

Example 89

Synthesis of 1-[(4-Cyano-5-methyl-4-phenyl)hexyl]-4-[2-(N-ispropylanilino)ethyl]piperazine

89-1) 2-(N-Isopropylanilino)ethanol

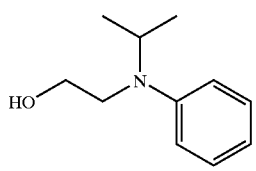

N-isopropyl aniline 1.0 g, ethyl bromoacetate 2.47 g, potassium carbonate 5.11 g and sodium iodide 5.55 g were dissolved in N,N-dimethylformamide 14 ml in a nitrogen atmosphere and stirred under reflux with heating. After 1 hour, the reaction mixture was cooled to room temperature and then partitioned by adding water and diethyl ether, and the organic layer was washed with water and then with brine, dried over magnesium sulfate anhydride, and evaporated. The residue was purified by silica gel column chromatography (hexane/diethyl ethersystem) to give N-ethoxycarbonylmethyl-N-isopropyl aniline 1.62 g. A part 550 mg of this product was dissolved in tetrahydrofuran 10 ml, and 1M lithium aluminum hydride in tetrahydrofuran 2.5 ml was added thereto under cooling in an ice bath in a nitrogen atmosphere. The mixture was stirred in the ice bath for 40 minutes, and water 0.1 ml, 2N aqueous sodium hydroxide 0.1 ml, water 0.3 ml, and diethyl ether 5 ml were added in this order and stirred. The insolubles were filtered off through Celite, and the filtrate was evaporated. The residue was purified by silica gel column chromatography (hexane/ethyl acetate system), whereby the title compound 383 mg, 86% was obtained as a colorless oil.

$^1$H-NMR (400 MHz, CDCl$_3$); δ (ppm) 1.16 (d, J=6.8 Hz, 6H), 1.84–1.91 (m, 1H), 3.32 (t, J=6.0 Hz, 2H), 3.64–3.91 (m, 2H), 3.97 (sept, J=6.8 Hz, 1H), 6.78–6.83 (m, 1H), 6.88–6.92 (m, 2H), 7.21–7.27 (m, 2H).

89-2) 1-[(4-Cyano-5-methyl-4-phenyl)hexyl]-4-[2-(N-isopropylanilino)ethyl]piperazine

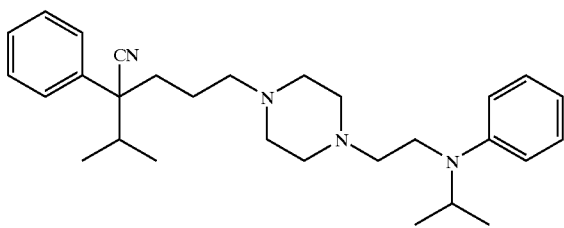

In a nitrogen atmosphere, methane sulfonyl chloride 80 mg was added to a solution of 2-(N-isopropylanilino)ethanol 125 mg and triethylamine 0.24 ml in acetonitrile 7 ml. After the mixture was stirred for 1 hour, sodium iodide 157 mg and a solution of 1-[(4-cyano-5-methyl-4-phenyl)hexyl]piperazine 100 mg in acetonitrile 3 ml were added thereto and stirred for 4 hours under reflux with heating. The reaction solution was partitioned by adding water and ethyl acetate, and the organic layer was washed with water and then with brine, dried over magnesium sulfate anhydride and evaporated. The residue was purified by NH silica gel column chromatography (hexane/ethyl acetate system), whereby the title compound 80 mg, 25% was obtained as a colorless oil.

Free Compound;
$^1$H-NMR (400 MHz, CDCl$_3$); δ (ppm) 0.77(d, J=6.8 Hz, 3H), 1.05–1.15 (m, 1H), 1.16 (d, J=6.4 Hz, 6H), 1.20 (d, J=6.4 Hz, 3H), 1.50–1.60 (m, 1H), 1.88 (dt, J=4.8 Hz, 13.2 Hz, 1H), 2.07–2.18 (m, 2H), 2.21–2.57 (m, 12H), 3.30 (brt, J=8.0 Hz, 2H), 3.99–4.09 (m, 1H), 6.64–6.70 (m, 1H), 6.74–6.78 (m, 2H), 7.18–7.23 (m, 2H), 7.27–7.31 (m, 1H), 7.34–7.38 (m, 4H).

This free product 80 mg was treated in a usual manner to give the hydrochloride 70 mg of the title compound.
Hydrochloride;
ESI-Mass; 447 (MH+).

Example 90

Synthesis of 1-[(4-Cyano-5-methyl-4-phenyl)hexyl]-4-[2-(N-cyclohexylanilino)ethyl]piperazine

90-1) 2-(N-cylohexylanilino)ethanol

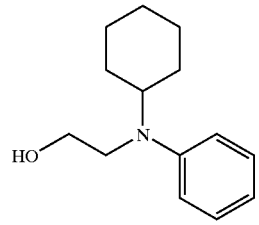

N-ethoxycarbonylmethyl-N-cyclohexyl aniline 1.89 g was obtained from N-cyclohexyl aniline 1.30 g in the same manner as in the above example. This product 860 mg was reduced to give the title compound (300 mg, 42%).

$^1$H-NMR (400 MHz, CDCl$_3$); δ (ppm) 1.05–1.18 (m, 1H), 1.26–1.44 (m, 4H), 1.63–1.71 (m, 1H), 1.80–1.87 (m, 5H), 3.67 (t, J=6.7 Hz, 2H), 3.42 (m, 1H), 3.64–3.70 (m, 2H), 6.76–6.81 (m, 1H), 6.86–6.90 (m, 2H), 7.20–7.26 (m, 2H).

90-2) 1-[(4-Cyano-5-methyl-4-phenyl)hexyl]-4-[2-(N-cyclohexylanilino)ethyl]piperazine

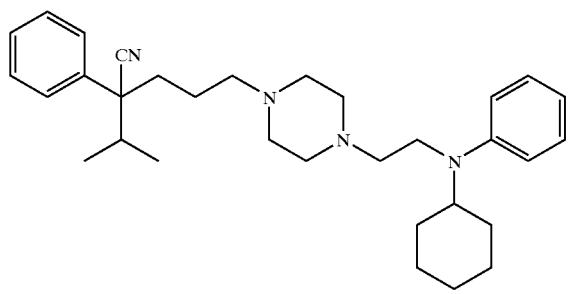

In a nitrogen atmosphere, methane sulfonyl chloride (80 ml) was added to a solution of 2-(N-cylohexylanilino)ethanol 153 mg and triethylamine 0.24 ml in acetonitrile 7 ml. After the mixture was stirred for 1 hour, sodium iodide 157 mg and a solution of 1-[(4-cyano-5-methyl-4-phenyl)hexyl]piperazine 100 mg in acetonitrile 3 ml were added thereto and stirred at 70° C. overnight. The mixture was partitioned by adding water and ethyl acetate, and the organic layer was washed with water and then with brine, dried over magnesium sulfate anhydride, and evaporated. The residue was purified by NH silica gel column chromatography (hexane/ethyl acetate system), whereby the title compound 172 mg, 50% was obtained as a colorless oil.

Free Compound;
¹H-NMR (400 MHz, CDCl₃); δ (ppm) 0.77 (d, J=6.6 Hz, 3H), 1.03–1.19 (m, 1H), 1.20 (d, J=6.8 Hz, 3H), 1.30–1.45 (m, 3H), 1.48–1.60 (m, 1H), 1.64–1.72 (m, 1H), 1.78–1.94 (m, 4H), 2.06–2.20 (m, 2H), 2.20–2.58 (m, 12H), 3.34 (brt, J=8.0 Hz, 2H), 3.50–3.56 (m, 1H), 6.61–6.68 (m, 1H), 6.71–6.76 (m, 2H), 7.17–7.23 (m, 2H), 7.27–7.31 (m, 1H), 7.34–7.38 (m, 4H).

This free compound 172 mg was treated in a usual manner to give the hydrochloride 160 mg of the title compound.
Hydrochloride;
ESI-Mass; 487 (MH+).

Example 91

Synthesis of 1-[(4-Cyano-5-methyl-4-phenyl)hexyl]-4-{2-[N-methyl(4-isopropylanilino)ethyl]}piperazine 91-1) 2-[N-methyl(4-Isopropylanilino)]Ethanol

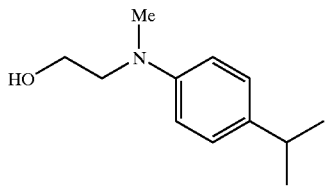

Methyl chloroformate 1.43 ml was added to a solution of 4-isopropylaniline 2.5 g and N,N-diisopropylethylamine 6.45 ml in tetrahydrofuran 60 ml in a nitrogen atmosphere. After stirred for 3 hours, the reaction solution was partitioned by adding water and ethyl acetate. The organic layer was washed with water and then with brine, dried over magnesium sulfate anhydride, and evaporated. The residue was dissolved in N,N-dimethylformamide 30 ml, and sodium hydride 951 mg, 60% oil was added thereto in a nitrogen atmosphere under cooling in an ice bath. After the mixture was stirred in the ice bath for 45 minutes, a solution of ethyl bromoacetate 4.63 g in N,N-dimethylformamide 10 ml was added thereto. The reaction mixture was cooled to room temperature, stirred overnight, and partitioned by adding water and ethyl acetate. The organic layer was washed with water and then with brine, dried over magnesium sulfate anhydride, and evaporated to give residues 5.53 g. A part 1.5 g of the residues was dissolved in tetrahydrofuran 5 ml and added dropwise to a previously prepared suspension of lithium aluminum hydride 305 mg in tetrahydrofuran 10 ml in an ice bath in a nitrogen atmosphere. After this addition was finished, the mixture was heated for 2 hours under reflux. After the reaction mixture was cooled to room temperature, water 0.3 ml, 2N aqueous sodium hydroxide 0.3 ml, water 0.9 ml and diethyl ether 15 ml were added thereto in this order under stirring. The insolubles were removed by filtration through Celite, and the filtrate was evaporated. The residue was purified by silica gel column chromatography (hexane/ethyl acetate system), whereby the title compound 900 mg was obtained as a colorless oil.

¹H-NMR (400 MHz, CDCl₃); δ (ppm) 1.22 (d, J=7.0 Hz, 6H), 1.80–1.90 (m, 1H), 2.83 (sept, J=6.8 Hz, 1H), 2.80–2.85 (m, 1H), 2.92 (s, 3H), 3.43 (t, J=5.5 Hz, 2H), 3.78–3.84 (m, 2H), 6.78 (d, J=8.6 Hz, 2H), 7.11 (d, J=8.6 Hz, 2H).

91-2) 1-[(4-Cyano-5-methyl-4-phenyl)hexyl]-4-{2-[N-methyl (4-isopropylanilino)ethyl]}piperazine

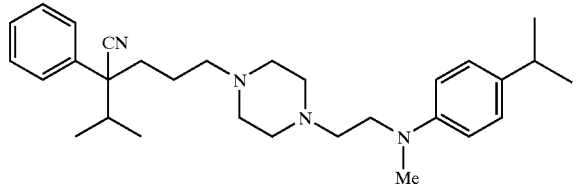

In a nitrogen atmosphere, methane sulfonyl chloride 80 mg was added to a solution of 2-[N-methyl(4-isopropylanilino)]ethanol 135 mg in triethylamine (0.24 ml)/acetonitrile (7 ml). After stirring for about 2 hours, sodium iodide 157 mg and a solution of 1-[(4-cyano-5-methyl-4-phenyl)hexyl]piperazine 100 mg in acetonitrile 3 ml were added thereto and stirred at 70° C. overnight. It was partitioned by adding water and ethyl acetate. The organic layer was washed with water and then with brine, dried over magnesium sulfate anhydride and evaporated. The residues were purified by silica gel column chromatography (methanol/ethyl acetate system), whereby the title compound 78 mg, 48% was obtained as a colorless oil.

Free Compound;
¹H-NMR (400 MHz, CDCl₃); δ (ppm) 0.77 (d, J=6.6 Hz, 3H), 1.04–1.18 (m, 1H), 1.20 (d, J=6.6 Hz, 3H), 1.21 (d, J=6.9 Hz, 6H), 1.48–1.62 (m, 1H), 1.84–1.94 (m, 1H), 2.06–2.20 (m, 2H), 2.22–2.56 (m, 12H), 2.74–2.86 (m, 1H), 2.90 (s, 3H), 3.42 (t, J=7.6 Hz, 2H), 6.65 (brd, J=8.7 Hz, 2H), 7.08 (brd, J=8.7 Hz, 2H), 7.26–7.32 (m, 1H). 7.33–7.38 (m, 4H).

This free compound 78 mg was treated in a usual manner to give the hydrochloride 70 mg of the title compound.
Hydrochloride;
ESI-Mass; 461 (MH+).

Example 92

Synthesis of 1-[(4-Cyano)-5-methyl -4-phenyl) hexyl]-4-{2-[N-methyl (3-Isopropylanilino)ethyl]}piperazine 92-1) 2-[N-methyl (3-Isopropylanilino)]ethanol

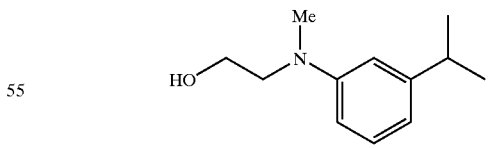

The title compound 900 mg was obtained from 3-Isopropylaniline 2.5 g in the same manner as in the above example.

¹H-NMR (400 MHz, CDCl₃); δ (ppm) 1.25 (d, J=6.8 Hz, 6H), 1.78–1.81 (m, 1H), 2.80–2.85 (m, 1H), 2.96 (s, 3H), 3.47 (t, J=5.7 Hz, 2H), 3.78–3.84 (m, 2H), 6.63–6.99 (m, 4H), 7.18 (brt, J=7.8 Hz, 1H).

92-2) 1-[(4-Cyano-5-methyl-4-phenyl)hexyl]-4-{2-[N-methyl(3-Isopropylanilino)ethyl]}piperazine

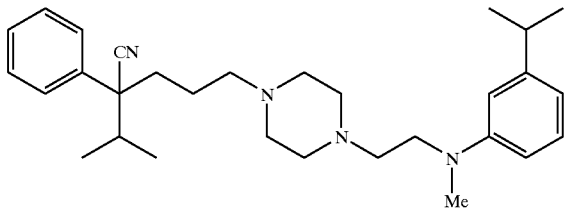

93-2) 1-[(4-(Cyano-5-methyl-4-phenyl)hexyl]-4-{2-[N-methyl(2-Isopropylanilino)ethyl]}piperazine

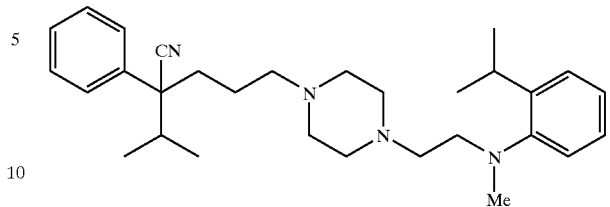

In a nitrogen atmosphere, methane sulfonyl chloride 80 mg was added to a solution of 2-[N-methyl(3-Isopropylanilino)]ethanol 135 mg and triethylamine 0.24 ml in acetonitrile 7 ml. After stirring for about 2 hours, sodium iodide 157 mg and a solution of 1-[(4-cyano-5-methyl-4-phenyl)hexyl]piperazine 100 mg in acetonitrile 3 ml were added thereto and stirred at 70° C. overnight. It was partitioned by adding water and ethyl acetate. The organic layer was washed with water and brine, dried over magnesium sulfate anhydride and evaporated. The residue was purified by silica gel column chromatography (methanol/ethyl acetate system), whereby the title compound 100 mg, 61% was obtained as a colorless oil.

Free Compound;

$^1$H-NMR (400 MHz, CDCl$_3$); δ (ppm) 0.77 (d, J=6.8 Hz, 3H), 1.04–1.20 (m, 1H), 1.20 (d, J=6.8 Hz, 3H), 1.23 (d, J=6.8 Hz, 6H), 1.48–1.62 (m, 1H), 1.89 (dt, J=4.4 Hz, 13.6 Hz, 1H), 2.07–2.20 (m, 2H), 2.26–2.32 (m, 2H), 2.32–2.57 (m, 10H), 2.78–2.88 (m, 1H), 2.93 (s, 3H), 3.42–3.48 (m, 2H), 6.51–6.60 (m, 2H), 7.14 (brt, J=8.0 Hz, 1H), 7.23–7.31 (m, 2H), 7.35–7.38 (m, 4H).

This free compound 100 mg was treated in a usual manner to give the hydrochloride 98 mg of the title compound.
Hydrochloride;
ESI-Mass; 461 (MH+).

Example 93

Synthesis of 1-[(4-Cyano-5-methyl-4-phenyl)hexyl]-4-{2-[N-methyl(2-Isopropylanilino)ethyl]}piperazine 93-1) 2-(N-methyl-2-Isopropylanilino)ethanol

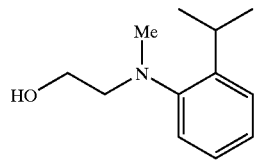

The title compound 950 mg was obtained from 2-Isopropylaniline 2.5 g in the same manner as in the above example.

$^1$H-NMR (400 MHz, CDCl$_3$); δ (ppm) 1.22 (d, J=7.0 Hz, 6H), 2.50–2.57 (m, 1H), 2.80–2.85 (m, 1H), 2.65 (s, 3H), 3.09 (t, J=5.4 Hz, 2H), 3.51–3.62 (m, 1H), 3.62–3.70 (m, 2H), 7.01 (m, 4H), 7.18 (brt, J=7.8 Hz, 1H).

In a nitrogen atmosphere, methane sulfonyl chloride 80 mg was added to a solution of 2-(N-methyl-2-Isopropylanilino) ethanol 135 mg and triethylamine 0.24 ml in acetonitrile 7 ml. After stirring for about 2 hours, the solution was added to sodium iodide 157 mg and 1-[(4-cyano-5-methyl-4-phenyl)hexyl]piperazine 100 mg in acetonitrile 3 ml, and stirred at 70° C. overnight. It was partitioned by adding water and ethyl acetate, and the organic layer was washed with water and then with brine, dried over magnesium sulfate anhydride, and evaporated. The residue was purified by NH silica gel column chromatography (hexane/ethyl acetate system), whereby the title compound 154 mg, 95% was obtained as a colorless oil.

Free Compound;

$^1$H-NMR (400 MHz, CDCl$_3$); δ (ppm) 0.76 (d, J=6.4 Hz, 3H), 1.04–1.20 (m, 1H), 1.16–1.23 (m, 9H), 1.48–1.60 (m, 1H), 1.87 (dt, J=4.4 Hz, 13.6 Hz, 1H), 2.07–2.17 (m, 2H), 2.22–2.48 (m, 12H), 2.65 (s, 3H), 2.99–3.04 (m, 1H), 3.46–3.58 (m, 2H), 7.10–7.17 (m, 3H), 7.23–7.31 (m, 2H), 7.34–7.37 (m, 4H).

This free compound 154 mg was treated in a usual manner to give the hydrochloride 145 mg of the title compound.
Hydrochloride;
ESI-Mass; 461 (MH+).

Example 94

Synthesis of 1-[(4-Cyano-5-methyl-4-phenyl)hexyl]-4-{2-[3,4-(methylenedioxy)phenoxy]ethyl}piperazine 94-1) 2-[3,4-(Methylenedioxy)phenoxy]ethylbromide

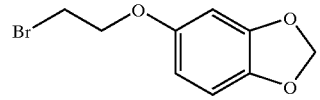

Sodium hydroxide 0.15 g was dissolved in water 6 ml, and Sesamol 0.50 g and 1,2-dibromoethane 0.37 ml were added thereto and heated under reflux for 12 hours. After cooling, water was added thereto, and the product was extracted with ethyl acetate and further washed with brine. The product was dried over magnesium sulfate anhydride and evaporated. The residue was purified by (NH) silica gel column chromatography (hexane/ethyl acetate system), whereby the title compound 0.30 g, 34% was obtained.

$^1$H-NMR (400 MHz, CDCl$_3$); δ (ppm) 3.59 (t, J=6.4 Hz, 2H), 4.21 (t, J=6.4 Hz, 2H), 5.92 (s, 2H), 6.33 (dd, J=2.4 Hz, J=8.4 Hz, 1H), 6.51 (d, J=2.4 Hz, 1H), 6.70 (d, J=8.4 Hz, 1H).

109

94-2) 1-[(4-Cyano)-5-methyl-4-phenyl)hexyl]-4-{2-[3,4-(methylenedioxy)phenoxy]ethyl}piperazine

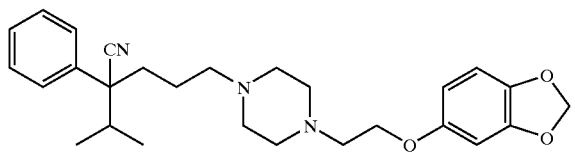

The free compound 0.12 g, 59% of the title compound was obtained as an oil by treating 1-[(4-cyano-5-methyl-4-phenyl)hexyl]piperazine 0.13 g and 2-[3,4-(methylenedioxy)phenoxy]ethylbromide 0.11 g in the same manner as in Example 59-3).

Free Compound;

$^1$H-NMR (400 MHz, CDCl$_3$); δ (ppm) 0.77 (d, J=6.8 Hz, 3H), 1.06–1.18 (m, 1H), 1.20 (d, J=6.8 Hz, 3H), 1.50–1.62 (m, 1H), 1.89 (dt, J=4.4 Hz, J=12.4 Hz, 1H), 2.07–2.19 (m, 2H), 2.27 (t, J=7.2 Hz, 2H), 2.36 (bs, 4H), 2.54 (bs, 4H), 2.74 (t, J=6.0 Hz, 2H), 4.00 (t, J=6.0 Hz, 2H), 5.90 (s, 2H), 6.30 (dd, J=2.4 Hz, J=8.4 Hz, 1H), 6.49 (d, J=2.4 Hz, 1H), 6.68 (d, J=8.4 Hz, 1H), 7.25–7.33 (m, 1H), 7.35–7.38 (m, 4H).

The above free compound 0.12 g was treated in a usual manner to give the hydrochloride 0.14 g of the title compound.

Hydrochloride;
 ESI-Mass; 450 (MH+).

Example 95

Synthesis of 1-[(4-Cyano-5-methyl-4-phenyl)hexyl]-4-[2-(6-quinolyloxy)ethyl]piperazine

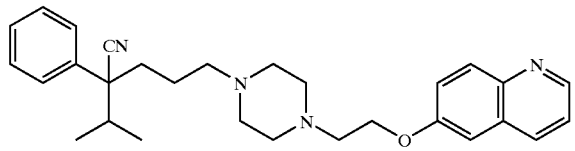

The free form 0.10 g, 63% of the title compound was obtained as an oil from 1-[(4-cyano-5-methyl-4-phenyl)hexyl]-4-(2-chloroethyl)piperazine 0.12 g and 6-hydroxyquinoline 0.25 g in the same manner as in Example 99.

Free Compound;

$^1$H-NMR (400 MHz, CDCl$_3$); δ (ppm) 0.77 (d, J=6.8 Hz, 3H), 1.06–1.20 (m, 1H), 1.20 (d, J=6.8 Hz, 3H), 1.50–1.62 (m, 1H), 1.89 (dt, J=4.4 Hz, J=12.4 Hz, 1H), 2.03–2.20 (m, 2H), 2.28 (t, J=7.2 Hz, 2H), 2.39 (bs, 4H), 2.60 (bs, 4H), 2.86 (t, J=6.0 Hz, 2H), 4.21 (t, J=6.0 Hz, 2H), 7.06 (d, J=2.4 Hz, 1H), 7.25–7.40 (m, 7H), 7.99 (d, J=9.2 Hz, 1H), 8.02 (d, J=8.4 Hz, 1H), 8.74–8.78 (m, 1H).

The free compound 0.10 g was treated in a usual manner to give the hydrochloride 0.12 g of the title compound.

Hydrochloride;
 ESI-Mass; 457 (MH+).

Example 96

Synthesis of 1-[(4-Cyano-5-methyl-4-phenyl)hexyl]-4-[2-(5-isoquinolyloxy)ethyl]piperazine

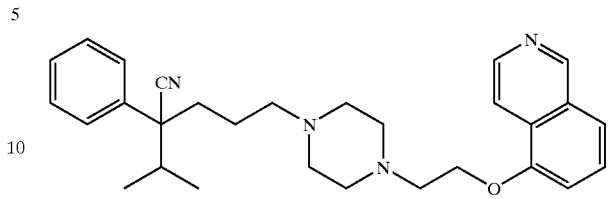

The free form 0.08 g, 51% of the title compound was obtained as an oil from 1-[(4-cyano-5-methyl-4-phenyl)hexyl]-4-(2-chloroethyl)piperazine 0.12 g and 5-hydroxyquinoline 0.25 g in the same manner as in Example 99.

Free Compound;

$^1$H-NMR (400 MHz, CDCl$_3$); δ (ppm) 0.77 (d, J=6.8 Hz, 3H), 1.06–1.20 (m, 1H), 1.20 (d, J=6.8 Hz, 3H), 1.50–1.62 (m, 1H), 1.89 (dt, J=4.4 Hz, J=12.4 Hz, 1H), 2.04–2.20 (m, 2H), 2.28 (t, J=6.8 Hz, 2H), 2.38 (bs, 4H), 2.64 (bs, 4H), 2.95 (t, J=5.6 Hz, 2H), 4.27 (t, J=5.6 Hz, 2H), 6.98 (d, J=7.6 Hz, 1H), 7.25–7.33 (m, 1H), 7.33–7.38 (m, 4H), 7.48 (t, J=8.0 Hz, 1H), 7.52 (t, J=8.0 Hz, 1H), 7.98 (d, J=6.0 Hz, 1H), 8.52 (d, J=6.0 Hz, 1H), 9.20 (s, 1H).

The above free compound 0.08 g was treated in a usual manner to give the hydrochloride 0.10 g of the title compound.

Hydrochloride;
 ESI-Mass; 457 (MH+).

Example 97

Synthesis of 1-[{2-(5-Cyano-6-methyl-5-phenyl)heptyl}]4-[2-(4-fluorophenoxy)ethyl]piperazine 97-1) 4-Cyano-5-methyl-4-phenylhexanoic Acid

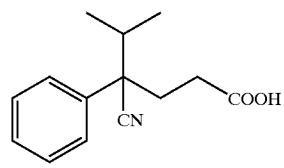

2-(1-Methylethyl)-5-oxo-2-phenylpentane nitrile, 6.00 g 27.9 mmol, was dissolved in a mixed solvent of water 55 ml/t-butyl alcohol 200 ml, and sodium dihydrogen phosphate 4.35 g 27.9 mmol and 2-methyl-2-butene 14.8 ml 139 mmol were further added thereto. Sodium chlorite 10.0 g 111 mmol in limited amounts was added thereto and stirred for 2 hours. The reaction mixture was ice-cooled and acidified by 2N hydrochloric acid. Then, it was extracted with ether, washed with dilute hydrochloric acid, dried over magnesium sulfate, and evaporated. The residue was purified by silica gel column chromatography (ethyl acetate/hexane system), whereby the title compound, 4.10 g 17.7 mmol, 63.4%, was obtained as a white solid.

$^1$H-NMR (400 MHz, CDCl$_3$); δ (ppm) 0.79 (d, J=6.78 Hz, 3H), 1.23 (d, J=6.59 Hz, 3H), 1.94–2.06 (m, 1H), 2.08–2.23 (m, 2H), 2.38–2.54 (m, 2H), 7.29–7.42 (m, 5H).

ESI-MS; 230 (MH−). m.p. 82–84° C.

97-2) N,O-dimethyl-4cyano-5-methyl-4-phenylhexanoic Acid Hydroxylamine Amide

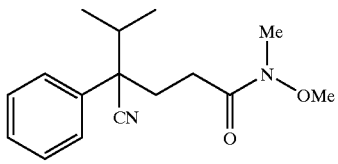

4-Cyano-5-methyl-4-phenylhexanoic acid, 2.80 g 12.1 mmol, was dissolved in tetrahydrofuran 70.0 ml containing a small amount of N,N-dimethylformamide. Under ice-cooling, oxalyl chloride 1.16 ml was added dropwise added thereto and the temperature was raised to room temperature. The reaction mixture was evaporated and dissolved again in tetrahydrofuran 15.0 ml. Under ice-cooling, previously prepared N,O-dimethyl hydroxylamine hydrochloride 6.00 g was added thereto and the mixture was added dropwise to a mixed solution of ether and 5N aqueous NaOH. The reaction mixture was washed with brine, dried over magnesium sulfate, and evaporated. The residue was purified by Chromatorex NH silica gel column chromatography (ethyl acetate/hexane system), whereby the title compound, 2.72 g 9.90 mmol, 81.9%, was obtained as a pale yellow oil.

$^1$H-NMR (400 MHz, CDCl$_3$); δ (ppm) 0.80 (d, J=6.78, 3H), 1.23 (d, J=6.78, 3H), 1.95–2.08 (m, 1H), 2.08–2.22 (m, 1H), 2.22–2.34 (m, 1H), 2.42–2.63 (m, 2H), 3.11 (s, 3H), 3.52 (s, 3H), 7.26–7.42 (m, 5H).

97-3) 5-Cyano-6-methyl-5-phenylhepatan-2-one

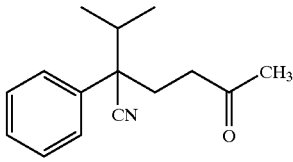

The above amide, 140 mg 0.51 mmol, was dissolved in tetrahydrofuran 4.00 ml. Under ice-cooling, solution of 1.05 M methyl lithium in ether 0.77 ml was added dropwise thereto. The reaction mixture was partitioned by adding aqueous saturated ammonium chloride and ethyl acetate, and the organic layer was washed with brine, dried over magnesium sulfate and evaporated. The residue was purified by silica gel column chromatography (ethyl acetate/hexane system), whereby the title compound, 110 mg 0.48 mol, 94.1%, was obtained as a colorless oil.

$^1$H-NMR (400 MHz, CDCl$_3$); δ (ppm) 0.78 (d, J=6.78, 3H), 1.22 (d, J=6.59, 3H), 2.00–2.23 (m, 6H), 2.37–2.46 (m, 1H), 2.53–2.63 (m, 1H), 7.29–7.42 (m, 5H).

97-4) 1-[{2-(5-Cyano-6-methyl-5-phenyl)heptyl}]-4-[2-(4-fluorophenoxy)ethyl]piperazine

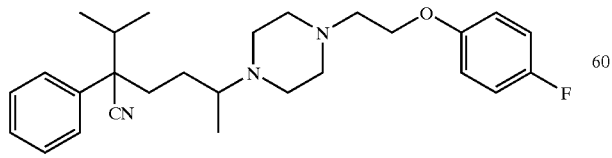

110 mg (0.48 mmol) of 5-cyano-6-methyl-5-phenylhepata-2-one, 129 mg 0.58 mmol of 1-[2-(4-fluorophenoxy)ethyl]piperazine, and acetic acid 60.0 μl were dissolved in dichloroethane 3.00 ml. After 5 minutes, sodium triacetoxyborohydride 153 mg was added thereto. After 19 hours, the reaction mixture was partitioned by adding aqueous saturated sodium bicarbonate and ethyl acetate. The organic layer was washed again with aqueous saturated sodium bicarbonate and then with brine, dried over magnesium sulfate, and evaporated. The residue was purified by silica gel column chromatography (ethyl acetate/methanol system), whereby the title compound (20 mg 46 umol, 9.52%) was obtained as a colorless oil.

$^1$H-NMR (400 MHz, DMSO-d$_6$); δ (ppm) 0.77 (d, J=6.78 Hz, 3H), 0.85–1.16 (m, 4H), 1.18–1.23 (m, 3H), 1.28–1.61 (m, 1H), 1.77–1.88 (m, 1H), 2.26–2.66 (m, 9H), 2.70–2.80 (m, 2H), 4.00–4.07 (m, 2H), 6.81–6.86 (m, 2H), 6.92–6.99 (m, 2H), 7.26–7.33 (m, 1H), 7.33–7.39 (m, 4H).

ESI-MS; 438 (MH+).

Example 98

Synthesis of 1-{[4-(7-Cyano-8-methyl-7-phenyl)nonyl]}-4-[2-(4-fluorophenoxy)ethyl]piperazine

98-1) 4-Cyano-5-methyl-5-phenylhexanal

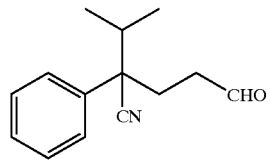

212 mg 0.92 mmol of 4-Cyano-5-methyl-4-phenylhexanol disclosed in Example 2 or 3 of JP 11-70613-A was dissolved in dichloromethane 9 ml. Molecular sieves 4A 100 mg and N-methylmorpholine-N-oxide 162 mg were added thereto and stirred. After 13 minutes, tetra-n-propylammonium perruthenate ((n-C$_3$H$_7$)$_4$NRuO$_4$, 32.3 mg) was added thereto. After 1 hour, the reaction mixture was evaporated. The residue was purified by silica gel column chromatography (ethyl acetate/hexane system), whereby the title compound, (92 mg 0.43 mmol, 46.4%) was obtained as a colorless oil.

$^1$H-NMR (400 MHz, CDCl$_3$); δ (ppm) 0.80 (d, J=6.78, 3H), 1.24 (d, J=6.59, 3H), 2.08–2.24 (m, 3H), 2.43–2.53 (m, 1H), 2.56–2.66 (m, 1H), 7.30–7.43 (m, 5H), 9.65 (s, 1H).

98-2) 7-Cyano-8-methyl-7-phenylnonane-4-ol

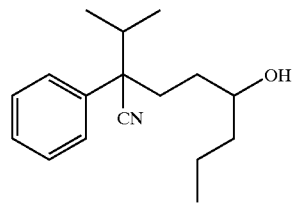

4-Cyano-5-methyl-5-phenylhexanal, 92 mg 0.43 mmol, 46.4%, was dissolved in tetrahydrofuran 2 ml. The reaction mixture was ice-cooled, and a solution of 2.0 M propyl magnesium chloride in ether 0.5 ml was added thereto. The reaction mixture was partitioned by adding aqueous saturated ammonium chloride and ethyl acetate. The organic layer was washed with brine, dried over magnesium sulfate, and evaporated. The residue was purified by silica gel column chromatography (ethyl acetate/hexane system), whereby the title compound, 70 mg 0.27 mmol, 62.8%, was obtained as a colorless syrup.

¹H-NMR (400 MHz, CDCl₃); δ (ppm) 0.79 (d, J=6.59, 3H), 0.84–0.91 (m, 3H), 0.94–1.58 (m, 8H), 1.83–1.92 and 2.34–2.44 (m, total 1H), 2.08–2.19 (m, 2H), 3.43–3.62 (m, 1H), 7.27–7.40 (m, 5H).

98-3) 7-Cyano-8-methyl-7-phenylnonane-4-one

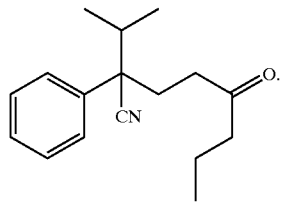

7-Cyano-8-methyl-7-phenylnonane-4-ol, 70 mg 0.27 mmol, was dissolved in dimethyl sulfoxide 3.00 ml and triethylamine 0.70 ml. A sulfur trioxide-pyridine complex 64.7 mg was added thereto. After 1 hour, an additional sulfur trioxide-pyridine complex 80.0 mg was added thereto. The reaction mixture was partitioned by adding aqueous saturated sodium bicarbonate and ethyl acetate. The organic layer was washed with aqueous ammonium chloride and then with brine, dried over magnesium sulfate and evaporated. The residue was purified by silica gel column chromatography (ethyl acetate/hexane system), whereby the title compound, 50 mg 0.19 mmol, 72.0%, was obtained as a colorless syrup.

¹H-NMR (400 MHz, CDCl₃); δ (ppm) 0.78 (d, J=6.78, 3H), 0.83 (t, J=7.42, 3H), 1.22 (d, J=6.78,3H), 1.44–1.56 (m, 2H), 1.96–2.06 (m, 1H), 2.08–2.33 (m, 4H), 2.36–2.46 (m, 1H), 2.48–2.59 (m, 1H), 7.27–7.42 (m, 5H).

98-4) 1-{[4-(7-Cyano-8-methyl-7-phenyl)nonyl]}-4-[2-(4-fluorophenoxy)ethyl]piperazine

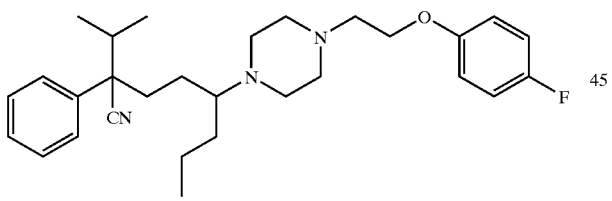

50 mg 0.19 mmol of 7-cyano-8-methyl-7-phenylnonane-4-one, 51.1 mg 0.23 mmol of 1-[2-(4-fluorophenoxy)ethyl]piperazine, and acetic acid 21.8 μl were dissolved in dichloroethane 2.00 ml. After 5 minutes, sodium triacetoxyborohydride 80.5 mg was added thereto. After 14 hours, additional acetic acid 0.20 ml was added thereto, and after 2 hours, additional dichloroethane 2.00 ml and sodium triacetoxyborohydride 40.0 mg were added thereto. After 23 hours, the reaction mixture was partitioned by adding aqueous saturated sodium bicarbonate and ethyl acetate. The organic layer was washed with saturated sodium bicarbonate and then with brine, dried over magnesium sulfate, and evaporated. The residue was purified by Chromatorex NH silica gel column chromatography (ethyl acetate/hexane system), whereby the title compound, 3.00 mg 6.44 μmol, 3.39% was obtained as a colorless oil.

¹H-NMR (400 MHz, DMSO-d₆); δ (ppm) 0.72–1.60 (m, 14H), 1.80–2.86 (m, 15H), 4.06 (t, J=5.86 Hz, H), 6.81–6.87 (m, 2H), 6.93–7.00 (m, 2H), 7.28–7.40 (m, 5H).

Example 99

Synthesis of 1-[(4-Cyano-5-methyl-4-phenyl)hexyl]-4-[2-(4-pyridyloxy)ethyl]piperazine 99-1) 4-Cyano-5-methyl-4-phenylhexyl Iodide

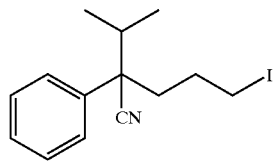

5.00 g 23.0 mmol of 4-Cyano-5-methyl-4-phenylhexanol disclosed in Example 2 or 3 of JP 11-70613-A was added to and dissolved in acetonitrile 150 ml and triethylamine 3.53 ml. Mesyl chloride, 1.96 ml 25.3 mmol, was added thereto. After 25 minutes, sodium iodide 20.7 g was added thereto. The reaction mixture was partitioned by adding brine and ethyl acetate. The organic layer was washed with aqueous sodium thiosulfate and then with brine, dried over magnesium sulfate, and evaporated. The residue was purified by silica gel column chromatography (ethyl acetate/hexane system), whereby the title compound, 5. 89 g 18.0 mmol, 78.2%, was obtained as a pale yellow oil.

¹H-NMR (400 MHz, CDCl₃); δ (ppm) 0.79 (d, J=6.78, 3H), 1.22 (d, J=6.59, 3H), 1.37–1.49 (m, 1H), 1.82–1.94 (m, 1H), 1.98–2.26 (m, 3H), 3.04–3.18 (m, 2H), 7.28–7.42 (m, 5H).

99-2) 1-[(4-Cyano-5-methyl-4-phenyl)hexyl]-4-(2-hydroxyethyl)piperazine

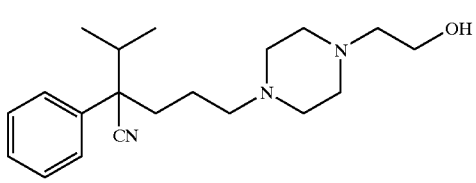

The above iodide, 2.07 g 6.32 mmol, was dissolved in acetonitrile 40 ml. Triethylamine 0.88 ml and 1-ethanol piperazine, 1.07 g 8.22 mmol, were added thereto, and the mixture was heated at 50° C. The reaction mixture was partitioned by adding brine and ethyl acetate. The organic layer was washed with aqueous 1N-aqueous NaOH and then with brine, dried over magnesium sulfate, and evaporated. The residue was purified by Chromatorex NH silica gel column chromatography (ethyl acetate), whereby the title compound, 1.92 g 5.83 mmol, 92.2%, was obtained as a pale yellow oil.

¹H-NMR (400 MHz, CDCl₃); δ (ppm) 0.77 (d, J=6.78, 3H), 1.06–1.18 (m, 1H) 1.20 (d, J=6.59, 3H), 1.49–1.62 (m, 1H), 1.84–1.94 (m, 1H), 2.06–2.62 (m, 14H), 3.61 (t, J=5.40, 2H), 7.26–7.40 (m, 5H).

99-3) 1-[(4-Cyano-5-methyl-4-phenyl)hexyl]-4-(2-chloroethyl)piperazine

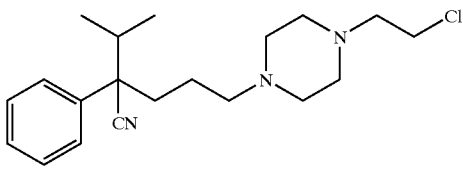

1-[(4-Cyano-5-methyl-4-phenyl)hexyl]-4-(2-hydroxyethyl)piperazine, 900 mg 2.73 mmol, was dissolved in dichloromethane 10 ml. Thionyl chloride 0.60 ml was added thereto. The mixture was left for 2 hours, and then heated under reflux, and 15 minutes thereafter, additional thionyl chloride 2.00 ml was added. The reaction solution was poured little by little into ice-water, then adjusted to pH 11 with 1N-aqueous NaOH, and partitioned by adding ethyl acetate. The organic layer was washed with aqueous dilute NaOH and then with brine, dried over magnesium sulfate, and evaporated. The residue was purified by Chromatorex NH silica gel column chromatography (ethyl acetate/hexane system), whereby the title compound, 728 mg 2.09 mmol, 76.6%, was obtained as a pale yellow oil.

$^1$H-NMR (400 MHz, CDCl$_3$); δ (ppm) 0.77 (d, J=6.59, 3H), 1.06–1.23 (m, 1H), 1.20 (d, J=6.59, 3H), 1.48–1.67 (m, 1H), 1.84–1.94 (m, 1H), 2.07–2.58 (m, 12H), 2.71 (t, J=7.05, 2H), 3.56 (t, J=7.05, 2H), 7.26–7.40 (m, 5H).

99-4) 1-[(4-Cyano)-5-methyl-4-phenyl)hexyl]-4-[2-(4-pyridyloxy)ethyl]piperazine

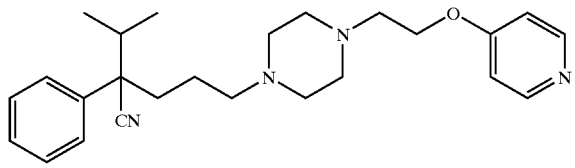

4-Hydroxypyridine, 205 mg 2.16 mmol, was suspended in toluene (4 ml), and sodium hydride, 86.4 mg 2.16 mmol, was added thereto. The mixture was heated at 100° C., and a solution of 150 mg 0.43 mmol of 1-[(4-cyano-5-methyl-4-phenyl)hexyl]-4-(2-chloroethyl)piperazine in toluene 1 ml was added thereto. After 25 minutes, additional dimethyl sulfoxide 2.00 ml was added thereto. After brine was added and the reaction mixture was adjusted to pH 11 with 1N-aqueous NaOH, it was partitioned by adding ethyl acetate. The organic layer was washed with aqueous dilute NaOH and brine, dried over magnesium sulfate, and evaporated. The residue was purified by Chromatorex NH silica gel column chromatography (ethyl acetate/hexane system), whereby the title compound, 43.0 mg 0.11 mmol, 24.6%, was obtained as a pale yellow syrup.

$^1$H-NMR (400 MHz, CDCl$_3$); δ (ppm) 0.77 (d, J=6.78, 3H), 1.05–1.20 (m, 1H), 1.20 (d, J=6.78, 3H), 1.50–1.62 (m, 1H), 1.83–1.93 (m, 1H), 2.06–2.65 (m, 12H), 2.80 (t, J=5.86, 2H), 4.12 (t, J=5.86, 2H), 6.78 (dd, J=1.65, 4.76, 2H), 7.25–7.39 (m, 5H), 8.41 (dd, J=1.47, 4.76, 2H).

ESI-MS; 407 (MH+).

Example 100

Synthesis of 1-[(4-Cyano-5-methyl-4-phenyl)hexyl]-4-[2-(3-pyridyloxy)ethyl]piperazine

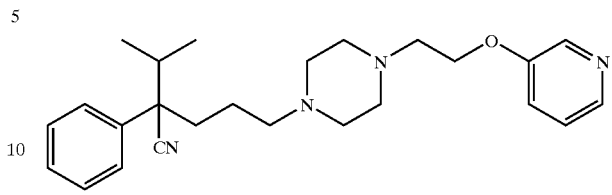

3-Hydroxypyridine, 205 mg 2.16 mmol, was suspended in toluene 2 ml. Sodium hydride, 86.4 mg 2.16 mmol, was added thereto, and the mixture was heated at 100° C., and then a solution of 150 mg 0.43 mmol of 1-[(4-cyano-5-methyl-4-phenyl)hexyl]-4-(2-chloroethyl)piperazine in toluene 1 ml was added thereto. After 25 minutes, additional dimethyl sulfoxide 1.00 ml was added thereto. After brine was added to the reaction mixture and the mixture was adjusted to pH 11 with 1N-aqueous NaOH, it was partitioned by adding ethyl acetate. The organic layer was washed with aqueous dilute NaOH and then with brine, dried over magnesium sulfate, and evaporated. The residue was purified by Chromatorex NH silica gel column chromatography (ethyl acetate/hexane system), whereby the title compound, 93.0 mg 0.23 mmol, 53.2%, was obtained as a pale yellow syrup.

$^1$H-NMR (400 MHz, CDCl$_3$); δ (ppm) 0.77 (d, J=6.78, 3H), 1.05–1.20 (m, 1H), 1.20 (d, J=6.59, 3H), 1.50–1.63 (m, 1H), 1.82–1.95 (m, 1H), 2.06–2.70 (m, 12H), 2.81 (t, J=5.77, 2H), 4.12 (t, J=5.77, 2H), 4.12 (t, J=5.86, 2H), 7.16–7.40 (m, 7H), 8.20–23 (m, 2H), 8.29–8.33 (m, 2H).

ESI-MS; 407 (MH+).

Example 101

Synthesis of 1-[(4-Cyano-5-methyl-4-phenyl)hexyl]-4-[2-(5-quinolyloxy)ethyl]piperazine

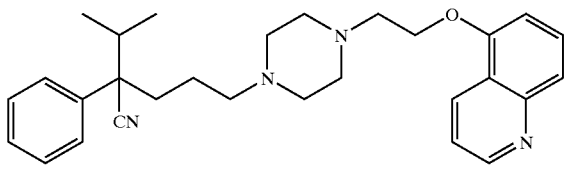

5-Hydroxyquinoline, 313 mg 2.16 mmol, was dissolved in dimethyl sulfoxide 8 ml. Sodium hydride, 86.4 mg 2.16 mmol, was added thereto, and the mixture was heated at 100° C., and then a solution of 150 mg 0.43 mmol of 1-[(4-cyano-5-methyl-4-phenyl)hexyl]-4-(2-chloroethyl)piperazine in toluene 1 ml was added thereto. After brine was added to the reaction mixture and the mixture was adjusted to pH 11 with 1N-aqueous NaOH, it was partitioned by adding ethyl acetate. The organic layer was washed with aqueous dilute NaOH and brine, dried over magnesium sulfate, and evaporated. The residue was purified by Chromatorex NH silica gel column chromatography (ethyl acetate/hexane system), whereby the title compound (77.0 mg 0.11 mmol, 24.6%) was obtained as a pale yellow syrup.

$^1$H-NMR (400 MHz, CDCl$_3$); δ (ppm) 0.77 (d, J=6.59, 3H), 1.05–1.20 (m, 1H), 1.20 (d, J=6.59, 3H), 1.50–1.63 (m, 1H), 1.83–1.94 (m, 1H), 2.05–2.75 (m, 12H), 2.94 (t, J=5.68, 2H), 4.27 (t, J=5.68, 2H), 6.84 (d, J=7.69, 1H), 7.24–7.40 (m, 5H), 8.41 (dd, J=1.47, 4.76, 2H).

ESI-MS; 457 (MH+).

Example 102

Synthesis of 1-[(4-Cyano-5-methyl-4-phenyl)hexyl]-4-[2-(4-trifluoromethylphenoxy)ethyl]piperazine

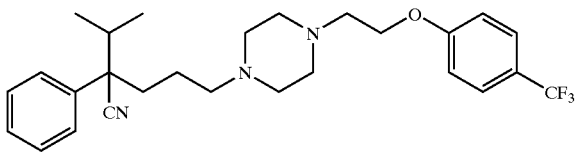

1-[(4-Cyano-5-methyl-4-phenyl)hexyl]-4-(2-hydroxyethyl)piperazine, 466 mg 1.41 mmol, was dissolved in N,N-dimethylformamide 15 ml. Potassium t-butoxide, 316 mg 2.82 mmol, was added thereto. After stirring for 5 minutes, 4-fluorobenztrifluoride, 0.32 ml 2.54 mmol, was added thereto. After brine was added to the reaction mixture and the mixture was adjusted to pH 11 with 1N-aqueous NaOH, it was partitioned by adding ethyl acetate. The organic layer was washed with aqueous dilute NaOH and brine, dried over magnesium sulfate, and evaporated. The residue was purified by Chromatorex NH silica gel column chromatography (ethyl acetate/hexane system) whereby the title compound, (432 mg 0.91 mmol, 64.7%) was obtained as a colorless syrup.

$^1$H-NMR (400 MHz, CDCl$_3$); δ (ppm) 0.77 (d, J=6.78, 3H), 1.05–1.20 (m, 1H), 1.20 (d, J=6.78, 3H), 1.49–1.62 (m, 1H), 1.82–1.93 (m, 1H), 2.05–2.65 (m, 12H), 2.80 (t, J=5.86, 2H), 4.11 (t, J=5.86, 2H), 6.95 (d, J=8.42, 2H), 7.26–7.39 (m, 5H), 7.53 (d, J=8.61, 2H).

ESI-MS; 474 (MH+).

Example 103

Synthesis of 1-[(4-Cyano-5-methyl-4-phenyl)hexyl]-4-[2-(1-naphthyloxy)ethyl]piperazine

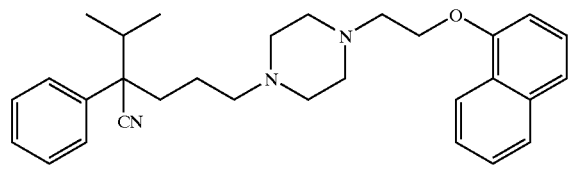

383 mg 2.66 mmol of 1-naphthol, 438 mg 1.33 mmol of 1-[(4-cyano-5-methyl-4-phenyl)hexyl]-4-(2-hydroxyethyl)piperazine and 420 mg 1.60 mmol of triphenyl phosphine were dissolved in tetrahydrofuran 15 ml. Diethyl azodicarboxylate, 0.25 ml 1.60 mmol, was added thereto. After brine was added to the reaction mixture and the mixture was adjusted to pH 11 with 1N-aqueous NaOH, it was partitioned by adding ethyl acetate. The organic layer was washed with aqueous dilute NaOH and brine, dried over magnesium sulfate, and evaporated. The residue was purified by Chromatorex NH silica gel column chromatography (ethyl acetate/hexane system), whereby the title compound, 123 mg 0.27 mmol, 20.3%, was obtained as a colorless syrup.

$^1$H-NMR (400 MHz, CDCl$_3$); δ (ppm) 0.77 (d, J=6.78, 3H), 1.05–1.20 (m, 1H), 1.20 (d, J=6.78, 3H), 1.50–1.70 (m, 1H), 1.84–1.95 (m, 1H), 2.05–2.75 (m, 12H), 2.96 (t, J=5.68, 2H), 4.28 (t, J=5.68, 2H), 6.79 (dd, J=0.92, 6.591H), 7.24–7.52 (m, 9H), 7.76–7.82 (m, 1H), 8.20–8.27 (m, 1H).

ESI-MS; 456 (MH+).

Example 104

Synthesis of 1-[(4-Cyano-5-methyl -4-phenyl) hexyl]-4-[2-ethyl-2-(4-fluorophenoxy)ethyl] piperazine

104-1) 1-Benzyl-4-[2-vinyl-2-(4-fluorophenoxy)ethyl]piperazine

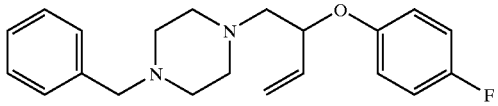

Butadiene monoxide 5.0 g and 1-benzyl piperazine 10.5 g were dissolved in methylene chloride 60 ml, and ytterbium triflate hydrate 3.7 g was added thereto and stirred for 2 hours. Water was added to the reaction mixture which was then extracted with chloroform, dried over sodium sulfate anhydride, and evaporated to give residue 9.05 g. The residue 720 mg, 4-fluorophenoxy 654 mg and triphenyl phosphine 1.53 g were dissolved in tetrahydrofuran 10 ml, and diethyl azodicarboxylate 0.92 ml was added thereto in an ice bath, and the mixture was stirred overnight. The mixture was partitioned by adding water and ethyl acetate. The organic layer was washed with water and brine successively, dried over magnesium sulfate anhydride, and evaporated. The residue was purified by NH silica gel column chromatography (hexane/ethyl acetate system), whereby the title compound, 919 mg, 92%, w as obtained as a colorless oil.

$^1$H-NMR (400 MHz, CDCl$_3$); δ (ppm) 2.40–2.50 (m, 4H), 2.50–2.65 (m, 4H), 2.60 (dd, J=4.0 Hz, 13.4 Hz, 1H), 2.78 (dd, J=7.5 Hz, 13.4 Hz, 1H), 3.49 (s, 2H), 4.48–4.72 (m, 1H), 5.21 (md, J=10.6 Hz, 1H), 5.26 (md, J=17.3 Hz, 1H), 5.86 (ddd, J=5.9 Hz, 10.6 Hz, 17.3 Hz, 1H), 6.80–6.88 (m, 2H), 6.90–6.97 (m, 2H), 7.20–7.35 (m, 5H).

104-2) 1-Benzyl-4-[2-(4-fluorophenoxy)butyl] piperazine

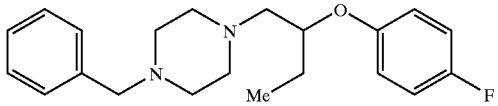

1-Benzyl-4-[2-vinyl-2-(4-fluorophenoxy)ethyl] piperazine 919 mg was dissolved in ethanol 20 ml, and palladium hydroxide/carbon 50 mg, 51.5% wet was added thereto, and the mixture was reduced for 8 hours under hydrogen pressure at about 3 kg/cm$^3$. After the insolubles were filtered off, the filtrate was evaporated, and the residue was purified by NH silica gel column chromatography (hexane/ethyl acetate system), whereby the title compound, 717 mg, 77%, was obtained as a colorless oil.

$^1$H-NMR (400 MHz, CDCl$_3$); δ (ppm) 0.95 (t, J=7.5 Hz, 3H), 1.60–1.72 (m, 2H), 2.40–2.60 (m, 8H), 2.51 (dd, J=4.6 Hz, 13.3 Hz, 1H), 2.63 (dd, J=6.5 Hz, 13.3 Hz, 1H), 3.49 (s, 2H), 4.18–4.25 (m, 1H), 6.84–6.88 (m, 2H), 6.90–6.96 (m, 2H), 7.21–7.29 (m, 1H), 7.29–7.33 (m, 4H).

104-3) 1-[2-(4-Fluorophenoxy)butyl]piperazine

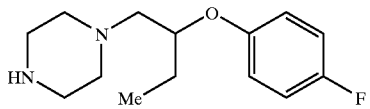

1-Benzyl-4-[2-(4-fluorophenoxy)butyl]piperazine 717 mg was dissolved in dichloroethane 10 ml, and 1-chloroethyl chloroformate 598 mg was added thereto, and the mixture was stirred for 2 hours under reflux with heating. After the reaction mixture was concentrated, methanol 10 ml was added thereto, and the mixture was stirred for 1 hour under reflux with heating. After the mixture was evaporated, it was partitioned by adding ether and 2N hydrochloric acid, and the aqueous layer was neutralized with 2N sodium hydroxide followed by extracting with ethyl acetate. The organic layer was washed with water and brine successively, dried over magnesium sulfate anhydride and evaporated, whereby the title compound 168 mg, 32% was obtained as a colorless oil.

$^1$H-NMR (400 MHz, CDCl$_3$); δ (ppm) 0.96 (t, J=7.5 Hz, 3H), 1.60–1.80 (m, 2H), 2.40–2.50 (m, 4H), 2.49 (dd, J=4.4 Hz, 13.4 Hz, 1H), 2.63 (dd, J=6.6 Hz, 13.4 Hz, 1H), 2.83–2.90 (m, 4H), 4.20–4.28 (m, 1H), 6.85–6.90 (m, 2H), 6.91–6.97 (m, 2H).

104-4) 1-[(4-Cyano-5-methyl-4-phenyl)hexyl]-4-[2-(4-fluorophenoxy)butyl]piperazine

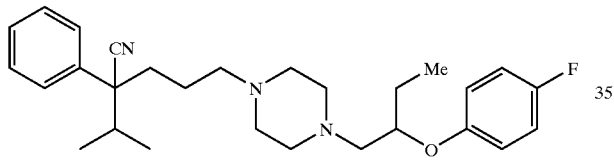

In a nitrogen atmosphere, 2-[1-methyl(ethyl)]-2-phenyl-5-hydroxypentanenitrile 142 mg and triethylamine 0.27 ml were dissolved in acetonitrile 10 ml, and methane sulfonyl chloride 0.06 ml was added thereto. After the mixture was stirred for 1 hour, sodium iodide 490 mg and a solution of 1-[2-ethyl-2-(4-fluorophenoxy)ethyl]piperazine 165 mg in acetonitrile 5 ml were added thereto and stirred at 70° C. overnight. The reaction mixture was partitioned by adding water and ethyl acetate. The organic layer was washed with water and brine successively, dried over magnesium sulfate anhydride and evaporated. The residue was purified by NH silica gel column chromatography (hexane/ethyl acetate system), whereby the title compound 130 mg, 44% was obtained as a colorless oil.

Free Compound;
$^1$H-NMR (400 MHz, CDCl$_3$); δ (ppm) 0.76 (d, J=6.6 Hz, 3H), 0.94 (t, J=7.5 Hz, 3H), 1.05–1.15 (m, 1H), 1.19 (d, J=6.4 Hz, 3H), 1.55–1.75 (m, 2H), 1.87 (dt, J=4.2 Hz, 13.2 Hz, 1H), 2.05–2.18 (m, 2H), 2.20–2.37 (m, 6H), 2.40–2.50 (m, 5H), 2.61 (dd, J=6.4 Hz, 13.6 Hz, 1H), 4.15–4.22 (m, 1H), 6.82–6.88 (m, 2H), 6.91–6.97 (m, 2H), 7.23–7.30 (m, 1H), 7.30–7.38 (m, 4H).

This free compound 130 mg was treated in a usual manner to give the hydrochloride 135 mg of the title compound.
Hydrochloride;
$^1$H-NMR (400 MHz, DMSO-d$_6$); δ (ppm) 0.67 (d, J=6.6 Hz, 3H) 0.86 (t, J=7.4 Hz, 3H), 1.11 (d, J=6.6 Hz, 3H), 1.20–1.35 (m, 2H), 1.55–1.70 (m, 3H), 2.05–2.25 (m, 3H), 3.00–4.00 (m, 11H), 4.75–4.90 (m, 1H), 7.05–7.12 (m, 2H), 7.12–7.17 (m, 2H), 7.35–7.40 (m, 1H), 7.50–7.70 (m, 4H).
ESI-Mass; 452 (MH+).

Example 105

Synthesis of 1-[(4-Cyano-5-methyl-4-phenyl)hexyl]-4-[2-(4-quinazolinyloxy)ethyl]piperazine

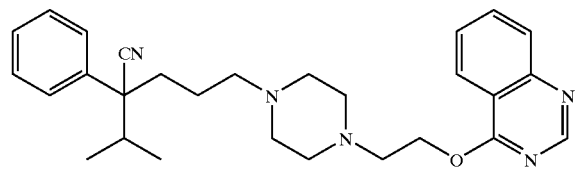

The free form 0.059 g, 45% of the title oily compound was obtained from 1-[(4-cyano-5-methyl-4-phenyl)hexyl]-4-(2-chloroethyl)piperazine 0.10 g and 4-hydroxyquinazoline 0.21 g in the same manner as in Example 99.

Free Compound;
$^1$H-NMR (400 MHz, CDCl$_3$); δ (ppm) 0.77 (d, J=6.8 Hz, 3H), 1.04–1.18 (m, 1H), 1.20 (d, J=6.8 Hz, 3H), 1.47–1.60 (m, 1H), 1.88 (dt, J=4.4 Hz, J=12.4 Hz, 1H), 2.04–2.18 (m, 2H), 2.25 (t, J=7.6 Hz, 2H), 2.31 (bs, 4H), 2.49 (bs, 4H), 2.69 (t, J=6.0 Hz, 2H), 4.07 (t, J=6.0 Hz, 2H), 7.25–7.32 (m, 1H), 7.32–7.38 (m, 4H), 7.47–7.53 (m, 1H), 7.68–7.78 (m, 1H), 8.04 (s, 1H), 8.29–8.32 (m, 1H).

The above free compound 0.059 g was treated in a usual manner to give the hydrochloride 0.05 g of the title compound.
Hydrochloride;
ESI-Mass; 458 (MH+).

Example 106

Synthesis of 1-[(4-Cyano-9-methyl-4-phenyl)hexyl]-4-{2-[4-(3-pyridyl)phenoxy]ethyl}piperazine

106-1) 2-[4-(3-Pyridyl)phenoxy]ethanol

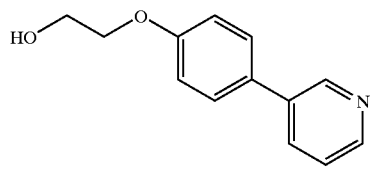

In a nitrogen atmosphere, 2-(4-bromophenoxy)ethanol 500 mg, diethyl (3-pyridyl) borane 509 mg, finely pulverized potassium hydroxide 388 mg, tetra-n-butyl ammonium bromide 74 mg and a tetrakis-triphenyl phosphine palladium complex 133 mg were added to tetrahydrofuran 10 ml and stirred under reflux with heating. After stirring for 2 hours, the mixture was cooled to room temperature and partitioned by adding water and ethyl acetate. The organic layer was washed with water and then with brine, dried over magnesium sulfate anhydride, and evaporated. The residue was purified by silica gel column chromatography (hexane/ethyl acetate system), whereby the title compound (233 mg, 50%) was obtained as a pale yellow crystalline.

$^1$H-NMR (400 MHz, CDCl$_3$) δ (ppm) 2.45 (t, J=6.2 Hz, 1H), 3.97–4.02 (m, 2H) 4.12–4.17 (m, 2H), 7.02 (brd, J=8.8 Hz, 2H), 7.32–7.36 (m, 1H), 7.51 (brd, J=8.8 Hz, 2H), 7.80–7.85 (m, 1H), 8.53–8.56 (m, 1H), 8.78–8.82 (m, 1H).
ESI-Mass; 216 (MH+).

106-2) 1-[(4-Cyano-5-methyl-4-phenyl)hexyl]-4-{2-[4-(3-pyridyl)phenoxy]ethyl}piperazine

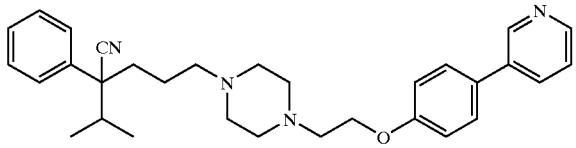

In a nitrogen atmosphere, 2-[4-(3-pyridyl)phenoxy]ethanol 68 mg and triethylamine 0.13 ml were dissolved in acetonitrile 6 ml in an ice bath, and methane sulfonyl chloride 40 mg was added thereto. After stirring for 3 hours, sodium iodide 142 mg and a solution of 1-[(4-cyano-5-methyl-4-phenyl)hexyl]piperazine 90 mg in acetonitrile 3 ml were added thereto, and the mixture was stirred for 5 hours under reflux with heating. After cooling, the reaction solution was partitioned by adding water and ethyl acetate. The organic layer was washed with water and brine, dried over magnesium sulfate anhydride and evaporated. The residue was purified by NH silica gel column chromatography (hexane/ethyl acetate system), whereby the title compound 17 mg, 11% was obtained as a colorless oil.

Free Compound;
$^1$H-NMR (400 MHz, CDCl$_3$); δ (ppm) 0.77 (d, J=6.8 Hz, 3H), 1.05–1.20 (m, 1H), 1.20 (d, J=6.6 Hz, 3H), 1.50–1.60 (m, 1H), 1.82–1.92 (m, 1H), 2.05–2.20 (m, 2H), 2.25–2.30 (m, 2H), 2.30–2.45 (m, 4H), 2.50–2.65 (m, 4H), 2.82 (t, J=5.9 Hz, 2H), 4.14 (t, J=5.9 Hz, 2H), 7.00 (d, J=8.8 Hz, 2H), 7.20–7.40 (m, 6H), 7.50 (d, J=8.8 Hz, 2H), 7.80–7.84 (m, 1H), 8.50–8.55 (m, 1H), 8.80–8.81 (m, 1H).

This free compound 17 mg was treated in a usual manner to give the hydrochloride 13 mg of the title compound.
Hydrochloride;
$^1$H-NMR (400 MHz, DMSO-d$_6$); δ (ppm) 0.67 (d, J=6.8 Hz, 3H), 1.11 (d, J=6.6 Hz, 3H), 1.20–1.30 (m, 1H), 1.55–1.70 (m, 1H), 2.05–2.30 (m, 3H), 3.00–3.25 (m, 2H), 3.25–3.80 (m, 10H), 4.45–4.50 (m, 2H), 7.19 (d, J=8.8 Hz, 2H), 7.33–7.40 (m, 1H), 7.40–7.50 (m, 4H), 7.86 (d, J=8.8 Hz, 2H), 7.96 (dd, J=5.5 Hz, 8.1 Hz, 1H), 8.68 (brd, J=8.1 Hz, 1H), 8.77 (dd, J=1.1 Hz, 5.5 Hz, 1H), 9.15 (d, J=2.0 Hz, 1H).
ESI-Mass; 483 (MH+).

Example 107

Synthesis of 1-[(4-Cyano-5-methyl-4-phenyl)hexyl]-4-{2-[3-(3-pyridyl)phenoxy]ethyl}piperazine

107-1) 2-[3-(3-Pyridyl)phenoxy]ethanol

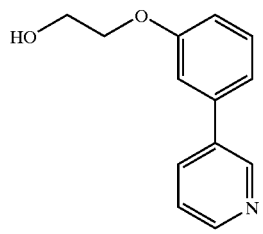

The title compound 435 mg, 88% was obtained as a pale yellow crystalline from 2-(3-bromophenoxy)ethanol 500 mg in the same manner as in the above example.

$^1$H-NMR (400 MHz, CDCl$_3$); δ (ppm) 2.13 (t, J=6.2 Hz, 1H), 3.98–4.04 (m, 2H), 4.14–4.20 (m, 2H), 6.95–7.00 (m, 1H), 7.12–7.15 (m, 1H), 7.17–7.22 (m, 1H), 7.34–7.44 (m, 2H), 7.84–7.90 (m, 1H), 8.58–8.62 (m, 1H), 8.82–8.86 (m, 1H).

ESI-Mass; 216 (MH+).

107-2) 1-[(4-Cyano-5-methyl-4-phenyl)hexyl]-4-{2-[3-(3-pyridyl)phenoxy]ethyl}piperazine

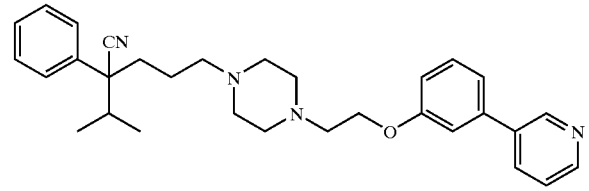

In a nitrogen atmosphere, 2-[3-(3-pyridyl)phenoxy]ethanol 68 mg and triethylamine 0.13 ml were dissolved in acetonitrile 6 ml in an ice bath, and methane sulfonyl chloride 40 mg was added thereto. After stirring for 3 hours, sodium iodide 142 mg and a solution of 1-[(4-cyano-5-methyl-4-phenyl)hexyl]piperazine 90 mg in acetonitrile 3 ml were added thereto, and the mixture was stirred for 5 hours under reflux with heating. After cooling, the reaction mixture was partitioned by adding water and ethyl acetate. The organic layer was washed with water and brine, dried over magnesium sulfate anhydride, and evaporated. The residue was purified by NH silica gel column chromatography (hexane/ethyl acetate system), whereby the title compound (44 mg, 29%) was obtained as a colorless oil.

Free Compound;

$^1$H-NMR (400 MHz, CDCl$_3$); δ (ppm) 0.77 (d, J=6.8 Hz, 3H), 1.05–1.20 (m, 1H), 1.20 (d, J=6.8 Hz, 3H), 1.50–1.60 (m, 1H), 1.82–1.92 (m, 1H), 2.05–2.20 (m, 2H), 2.25–2.30 (m, 2H), 2.30–2.45 (m, 4H), 2.45–2.65 (m, 4H), 2.82 (t, J=5.9 Hz, 2H), 4.15 (t, J=5.9 Hz, 2H), 6.91–6.98 (m, 1H), 7.10–7.12 (m, 1H), 7.14–7.18 (m, 1H), 7.25–7.32 (m, 1H), 7.32–7.40 (m, 6H), 7.83–7.87 (m, 1H), 8.56 (dd, J=1.5 Hz, 4.8 Hz, 1H), 8.23 (dd, J=0.7 Hz, 2.4 Hz, 1H).

This free compound 29 mg was treated in a usual manner to give the hydrochloride 23 mg of the title compound.

Hydrochloride;

$^1$H-NMR (400 MHz, DMSO-d$_6$); δ (ppm) 0.67 (d, J=6.8 Hz, 3H), 1.11 (d, J=6.6 Hz, 3H), 1.20–1.35 (m, 1H), 1.58–1.73 (m, 1H), 2.05–2.25 (m, 3H), 3.00–3.85 (m, 12H), 4.50–4.56 (m, 2H), 7.13–7.18 (m, 1H), 7.33–7.40 (m, 1H), 7.42–7.54 (m, 7H), 7.97 (dd, J=5.5 Hz, 8.2 Hz, 1H), 8.70 (brd, J=8.2 Hz, 1H), 8.82 (dd, J=1.3 Hz, 5.5 Hz, 1H), 9.20 (d, J=1.8 Hz, 1H).

ESI-Mass; 483 (MH+).

Example 108

Synthesis of 1-[(4-Cyano-5-methyl-4-phenyl)hexyl]-4-[2-(4-bromophenoxy)ethyl]piperazine

108-1) 2-(4-Bromophenoxy)ethanol

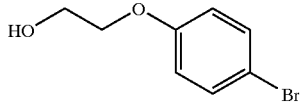

In a nitrogen atmosphere, 4-bromophenol 5.0 g, 2-bromoethanol 5.42 g, and potassium carbonate 12.0 g were added to N,N-dimethylformamide 30 ml, and the mixture was stirred at 100° C. After 1 hour, the mixture was cooled to room temperature and partitioned by adding water and diethyl ether. The organic layer was washed with water and brine, dried over magnesium sulfate anhydride and evaporated. The residue was purified by silica gel column chromatography (hexane/ethyl acetate system), whereby the title compound 5.15 g, 82% was obtained as a colorless crystalline.

$^1$H-NMR (400 MHz, CDCl$_3$); δ (ppm) 1.95–2.00 (m, 1H), 3.94–3.99 (m, 2H), 4.04–4.07 (m, 2H), 6.81 (brd, J=9.2 Hz, 2H), 7.38 (brd, J=9.2 Hz, 2H).

108-2) 1-[(4-Cyano-5-methyl-4-phenyl)hexyl]-4-[2-(4-bromophenoxy)ethyl]piperazine

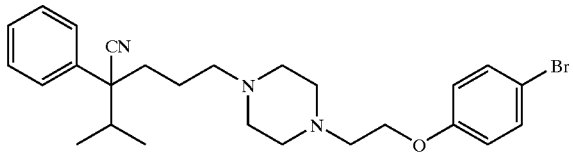

In a nitrogen atmosphere, 2-(4-bromophenoxy)ethanol 350 mg and triethylamine 0.68 ml were dissolved in acetonitrile 16 ml, and methane sulfonyl chloride 221 mg was added thereto. After stirring for 1 hour, sodium iodide 725 mg and a solution of 1-[(4-cyano-5-methyl-4-phenyl)hexyl]piperazine 460 mg in acetonitrile 8 ml were added thereto, and the mixture was stirred for 3 hours under reflux with heating. After cooling, the reaction mixture was partitioned by adding water and ethyl acetate, and the organic layer was washed with water and brine. It was dried over magnesium sulfate anhydride and evaporated. The residue was purified by NH silica gel column chromatography (hexane/ethyl acetate system), whereby the title compound 587 mg, 75% was obtained as a colorless oil.

Free Compound;
$^1$H-NMR (400 MHz, CDCl$_3$); δ (ppm) 0.77 (d, J=6.6 Hz, 3H), 1.05–1.20 (m, 1H), 1.20 (d, J=6.8 Hz, 3H), 1.50–1.60 (m, 1H), 1.82–1.92 (m, 1H), 2.05–2.20 (m, 2H), 2.25–2.30 (m, 2H), 2.30–2.43 (m, 4H), 2.43–2.60 (m, 4H), 2.77 (t, J=5.9 Hz, 2H), 4.04 (t, J=5.9 Hz, 2H), 6.77 (d, J=8.8 Hz, 2H), 7.25–7.32 (m, 1H), 7.32–7.38 (m, 6H).

This free compound 55 mg was treated in a usual manner to give the hydrochloride 50 mg of the title compound.

Hydrochloride;
$^1$H-NMR (400 MHz, DMSO-d$_6$); δ (ppm) 0.67 (d, J=6.6 Hz, 3H), 1.11 (d, J=6.6 Hz, 3H), 1.20–1.30 (m, 1H), 1.55–1.70 (m, 1H), 2.05–2.30 (m, 3H), 3.00–3.80 (m, 12H), 4.34 (brs, 2H), 6.97 (d, J=8.8 Hz, 2H), 7.33–7.40 (m, 1H), 7.42–7.46 (m, 4H), 7.48 (d, J=8.8 Hz, 2H).

ESI-Mass; 484 (M[$_{79}$Br]H+), 486 (M[$_{81}$Br]H+).

Example 109

Synthesis of 1-[(4-Cyano-5-methyl-4-phenyl)hexyl]-4-[2-(3-bromophenoxy)ethyl]piperazine

109-1) 2-(3-Bromophenoxy)ethanol

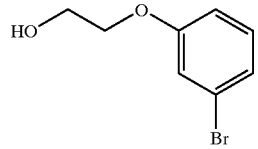

In a nitrogen atmosphere, 3-bromophenol 5.0 g, 2-bromoethanol 5.42 g, and potassium carbonate 12.0 g were added to N,N-dimethylformamide 30 ml, and the mixture was stirred at 100° C. After 1 hour, the reaction mixture was cooled to room temperature and partitioned by adding water and diethyl ether. The organic layer was washed with water and then with brine, dried over magnesium sulfate anhydride and evaporated. The residue was purified by silica gel column chromatography (hexane/ethyl acetate system), whereby the title compound (4.85 g, 77%) was obtained as a colorless oil.

$^1$H-NMR (400 MHz, CDCl$_3$); δ (ppm) 1.95–2.00 (m, 1H), 3.94–3.99 (m, 2H), 4.04–4.09 (m, 2H), 6.84–6.88 (m, 1H), 7.07–7.17 (m, 3H).

109-2) 1-[(4-Cyano-5-methyl-4-phenyl)hexyl]-4-[2-(3-bromophenoxy)ethyl]piperazine

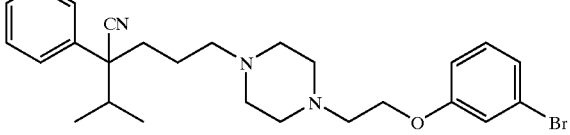

In a nitrogen atmosphere, 2-(3-bromophenoxy)ethanol 350 mg and triethylamine 0.68 ml were dissolved in acetonitrile 16 ml, and methane sulfonyl chloride 221 mg was added thereto. After the mixture was stirred for 1 hour, sodium iodide 725 mg and a solution of 1-[(4-cyano-5-methyl-4-phenyl)hexyl]piperazine 460 mg in acetonitrile 8 ml were added thereto, and the mixture was stirred for 3 hours under reflux with heating. After cooling, the reaction mixture was partitioned by adding water and ethyl acetate. The organic layer was washed with water and then with brine, dried over magnesium sulfate anhydride and evaporated. The residue was purified by NH silica gel column chromatography (hexane/ethyl acetate system), whereby the title compound (659 mg, 84%) was obtained as a colorless oil.

Free Compound;
$^1$H-NMR (400 MHz, CDCl$_3$); δ (ppm) 0.77 (d, J=6.8 Hz, 3H), 1.10–1.20 (m, 1H), 1.20 (d, J=6.6 Hz, 3H), 1.50–1.60 (m, 1H), 1.83–1.95 (m, 1H), 2.05–2.20 (m, 2H), 2.25–2.30 (m, 2H), 2.30–2.45 (m, 4H), 2.45–2.65 (m, 4H), 2.77 (t, J=5.9 Hz, 2H), 4.05 (t, J=5.9 Hz, 2H), 6.80–6.84 (m, 1H), 7.04–7.18 (m, 3H), 7.26–7.32 (m, 1H), 7.35–7.38 (m, 4H).

This free product 71 mg was treated in a usual manner to give the hydrochloride 60 mg of the title compound.

Hydrochloride;
¹H-NMR (400 MHz, DMSO-d₆); δ (ppm) 0.67 (d, J=6.4 Hz, 3H), 1.11 (d, J=6.4 Hz, 3H), 1.20–1.30 (m, 1H), 1.55–1.70 (m, 1H), 2.05–2.30 (m, 3H), 3.00–3.80 (m, 12H), 4.38 (brs, 2H), 6.98–7.04 (m, 1H), 7.15–7.30 (m, 3H), 7.33–7.40 (m, 1H), 7.42–7.50 (m, 4H).
ESI-Mass; 484 (M[₇₉Br]H+), 486 (M[₈₁Br]H+).

Example 110

Synthesis of 1-[(4-Cyano-5-methyl-4-phenyl)hexyl]-4-[2-(2-bromophenoxy)ethyl]piperazine 110-1) 2-(2-Bromophenoxy)ethanol

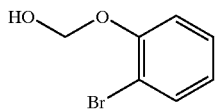

In a nitrogen atmosphere, 2-bromophenol 5.0 g, 2-bromoethanol 5.42 g, and potassium carbonate 12.0 g were added to N,N-dimethylformamide 30 ml, and the mixture was stirred at 100° C. After about 2.5 hours, the reaction mixture was cooled to room temperature and partitioned by adding water and diethyl ether. The organic layer was washed with water and then with brine, dried over magnesium sulfate anhydride and evaporated. The residue was purified by silica gel column chromatography (hexane/ethyl acetate system), whereby the title compound 5.09 g, 81% was obtained as a colorless oil.
¹H-NMR (400 MHz, CDCl₃); δ (ppm) 2.25 (t, J=6.6 Hz, 1H), 3.96–4.03 (m, 4H), 4.12–4.18 (m, 4H), 6.89 (ddd, J=1.5 Hz, 7.5 Hz, 7.9 Hz, 1H), 6.93 (dd, J=1.5 Hz, 8.2 Hz, 1H), 7.27 (ddd, J=1.7 Hz, 7.5 Hz, 8.2 Hz, 1H), 7.55 (dd, J=1.7 Hz, 7.9 Hz, 1H).

110-2) 1-[(4-Cyano-5-methyl-4-phenyl)hexyl]-4-[2-(2-bromophenoxy)ethyl]piperazine

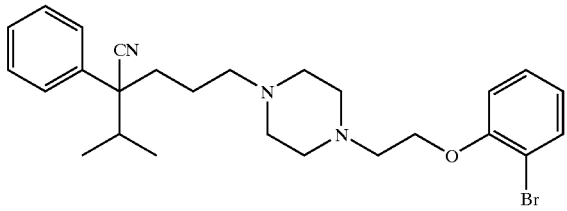

In a nitrogen atmosphere, 2-(2-bromophenoxy)ethanol 350 mg and triethylamine 0.68 ml were dissolved in acetonitrile 16 ml, and methane sulfonyl chloride 221 mg was added thereto. After the mixture was stirred for 1 hour, sodium iodide 725 mg and a solution of 1-[(4-cyano-5-methyl-4-phenyl)hexyl]piperazine 460 mg in acetonitrile 8 ml were added thereto, and the mixture was stirred for 3 hours under reflux with heating. After cooling, the reaction mixture was partitioned by adding water and ethyl acetate, and the organic layer was washed with water and then with brine, dried over magnesium sulfate anhydride and evaporated. The residue was purified by NH silica gel column chromatography (hexane/ethyl acetate system), whereby the title compound 470 mg, 60% was obtained as a colorless oil.
Free Compound;
¹H-NMR (400 MHz, CDCl₃); δ (ppm) 0.77 (d, J=6.6 Hz, 3H), 1.05–1.20 (m, 1H), 1.20 (d, J=6.8 Hz, 3H), 1.50–1.60 (m, 1H), 1.80–1.95 (m, 1H), 2.05–2.20 (m, 2H), 2.23–2.30 (m, 2H), 2.30–2.45 (m, 4H), 2.50–2.70 (m, 4H), 2.86 (t, J=5.8 Hz, 2H), 4.14 (t, J=5.8 Hz, 2H), 6.80–6.90 (m, 2H), 7.21–7.32 (m, 2H), 7.33–7.38 (m, 4H), 7.52 (dd, J=1.5 Hz, 7.9 Hz, 1H).
This free product 61 mg was treated in a usual manner to give the hydrochloride 50 mg of the title compound.
Hydrochloride;
¹H-NMR (400 MHz, DMSO-d₆); δ (ppm) 0.67 (d, J=6.8 Hz, 3H), 1.11 (d, J=6.8 Hz, 3H), 1.20–1.35 (m, 1H), 1.58–1.70 (m, 1H), 2.05–2.35 (m, 3H), 3.00–3.85 (m, 12H), 4.67 (brs, 2H), 6.92–6.98 (m, 1H), 7.14–7.18 (m, 1H), 7.34–7.40 (m, 2H), 7.42–7.48 (m, 4H), 7.60 (dd, J=1.6 Hz, 8.0 Hz, 1H).
ESI-Mass; 484 (M[₇₉Br]H+), 486 (M[₈₁Br]H+).

Example 111

Synthesis of 1-[(4-Cyano-5-methyl-4-phenyl)hexyl]-4-{2-[4-(imidazol-1-yl)phenoxy]ethyl}piperazine

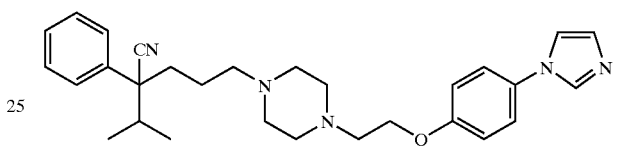

The free compound 0.05 g, 34% of the title compound was obtained as an oil from 1-[(4-cyano-5-methyl-4-phenyl)hexyl]-4-(2-chloroethyl)piperazine 0.11 g and 4-(imidazole-1-yl) phenol 0.25 g in the same manner as in Example 99.
Free Compound;
¹H-NMR (400 MHz, CDCl₃); δ (ppm) 0.78 (d, J=6.8 Hz, 3H), 1.06–1.20 (m, 1H), 1.21 (d, J=6.8 Hz, 3H), 1.50–1.63 (m,₁H), 1.89 (dt, J=4.4 Hz, J=12.4 Hz, 1H), 2.05–2.20 (m, 2H), 2.29 (t, J=7.2 Hz, 2H), 2.38 (bs, 4H), 2.57 (bs, 4H), 2.81 (t, J=6.0 Hz, 2H), 4.12 (t, J=6.0 Hz, 2H), 6.98 (d, J=8.8 Hz, 2H), 7.19 (d, J=8.8 Hz, 2H), 7.26–7.33 (m, 3H), 7.33–7.40 (m, 4H), 7.75 (s, 1H).
The above free compound 0.05 g was treated in a usual manner to give the hydrochloride 0.052 g of the title compound.
Hydrochloride;
ESI-Mass; 472 (MH+).

Example 112

Synthesis of 1-[(4-Cyano-5-methyl-4-phenyl)hexyl]-4-[2-(2-pyrimidinyloxy)ethyl]piperazine

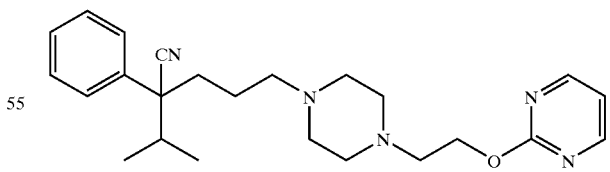

The free compound 0.03 g, 26% of the title compound was obtained as an oil from 1-[(4-cyano-5-methyl-4-phenyl)hexyl]-4-(2-chloroethyl)piperazine (0.10 g) and 2-hydroxypyrimidine 0.19 g in the same manner as in Example 99.
Free Compound;
¹H-NMR (400 MHz, CDCl₃); δ (ppm) 0.77 (d, J=6.8 Hz, 3H), 1.05–1.18 (m, 1H), 1.19 (d, J=6.8 Hz, 3H), 1.48–1.60

(m, 1H), 1.89 (dt, J=4.4 Hz, J=12.0 Hz, 1H), 2.07–2.37 (m, 8H), 2.46 (bs, 4H), 2.70 (t, J=6.0 Hz, 2H), 3.96 (t, J=6.0 Hz, 2H), 6.26 (dd, J=4.0 Hz, J=6.4 Hz, 1H), 7.26–7.33 (m, 1H), 7.33–7.49 (m, 4H), 7.66 (dd, J=2.8 Hz, J=6.4 Hz, 1H), 8.56 (dd, J=2.8 Hz, J=4.0 Hz, 1H).

The above free compound 0.03 g was treated in a usual manner to give the hydrochloride 0.03 g of the title compound.
Hydrochloride;
ESI-Mass; 408 (MH+).

Example 113

Synthesis of 1-[(4-Cyano-5-methyl-4-phenyl)hexyl]-4-{2-[(3-pyridyl)phenoxy]ethyl}piperazine 113-1) 2-[2-(3-Pyridyl)phenoxy]ethanol

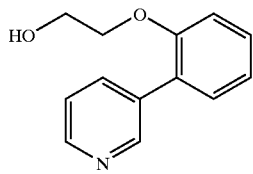

The title compound 111 mg, 22% was obtained as a pale yellow crystalline from 2-(2-bromophenoxy)ethanol 500 mg in the same manner as in the above example.
$^1$H-NMR (400 MHz, CDCl$_3$); δ (ppm) 3.89 (brt, J=4.4 Hz, 2H), 4.11 (brt, J=4.4 Hz, 2H), 7.03 (brd, J=8.6 Hz, 1H), 7.06–7.12 (m, 1H), 7.30–7.40 (m, 3H), 7.86 (brd, J=7.9 Hz, 1H), 8.40–8.60 (m, 1H), 8.65–8.90 (m, 1H).
ESI-Mass 216 (MH+).

113-2) 1-[(4-Cyano-5-methyl-4-phenyl)hexyl]-4-{2-[2-(3-pyridyl)phenoxy]ethyl}piperazine

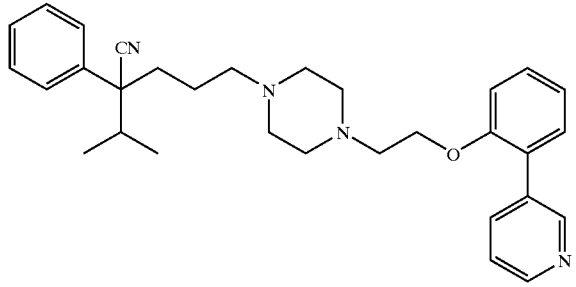

In a nitrogen atmosphere, 2-[2-(3-pyridyl)phenoxy] ethanol 80 mg and triethylamine 0.13 ml were dissolved in acetonitrile 6 ml in an ice bath, and methane sulfonyl chloride 40 mg was added thereto. After stirring the mixture for 3hours, sodium iodide 142 mg and a solution of 1-[(4-cyano-5-methyl-4-phenyl)hexyl]piperazine 90 mg in acetonitrile 3 ml were added thereto and stirred for 5 hours under reflux conditions. After cooling, the reaction solution was partitioned by adding water and ethyl acetate. The organic layer was washed with water and then with brine, dried over magnesium sulfate anhydride and evaporated. The residue was purified by silica gel column chromatography (methanol/ethyl acetate system), whereby the title compound (46 mg, 26%) was obtained as a pale yellow oil.
Free Compound;
$^1$H-NMR (400 MHz, CDCl$_3$); δ (ppm) 0.77 (d, J=6.8 Hz, 3H), 1.05–1.20 (m, 1H), 1.20 (d, J=6.9 Hz, 3H), 1.50–1.60 (m, 1H), 1.82–1.92 (m, 1H), 2.05–2.20 (m, 2H), 2.30–2.40 (m, 6H), 2.40–2.55 (m, 4H), 2.71 (t, J=5.9 Hz, 2H), 4.09 (t, J=5.9 Hz, 2H), 6.98 (brd, J=8.1 Hz), 7.02–7.08 (m, 1H), 7.25–7.38 (m, 8H), 7.86–7.92 (m, 1H), 8.53 (dd, J=1.6 Hz, 4.9 Hz, 1H), 8.76 (dd, J=0.7 Hz, 2.2 Hz, 1H).

This free compound 46 mg was treated in a usual manner to give the hydrochloride 30 mg of the title compound.
Hydrochloride;
$^1$H-NMR (400 MHz, DMSO-d$_6$); δ (ppm) 0.67 (d, J=6.6 Hz, 3H), 1.10 (d, J=6.6 Hz, 3H), 1.20–1.35 (m, 1H), 1.55–1.70 (m, 1H), 2.05–2.25 (m, 3H), 3.00–3.85 (m, 12H), 4.43–4.50 (m, 2H), 7.15–7.22 (m, 1H), 7.34–7.40 (m, 1H), 7.42–748 (m, 4H), 7.50–7.56 (m, 2H), 8.00–8.08 (m, 1H), 8.66–8.74 (m, 1H), 8.78–8.84 (m, 1H), 9.14 (brs, 1H).
ESI-Mass; 483 (MH+).

Example 114

Synthesis of 1-[4-Cyano-5-methyl-4-(2-cyano-5-thienyl)hexyl]-4-[2-(4-fluorophenoxy)ethyl] piperazine 114-1) 3-Methyl-2-(2-thienyl)butane Nitrile

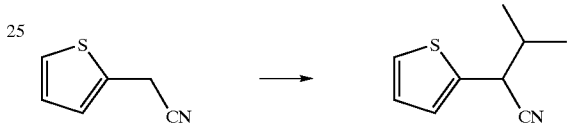

2-Thienyl acetonitrile, 15 g 0.12 mol, was dissolved in tetrahydrofuran 125 ml and added dropwise to a suspension of sodium amide 4.75 g 0.12 mol in tetrahydrofuran 250 ml under ice-cooling. After stirring for 5 minutes, a solution of 2-bromopropane 11.4 ml 0.12 mol in tetrahydrofuran 125 ml was added dropwise thereto. Aqueous saturated ammonium chloride was added to the reaction mixture which was then extracted with ethyl acetate. The extract was washed with brine, dried over magnesium sulfate and evaporated. The residue was purified by silica gel column chromatography (ethyl acetate/hexane system), whereby the title compound, 5.56 g 33.6 mmol, 28.0% was obtained as a yellow oil.
$^1$H-NMR (400 MHz, CDCl$_3$); δ (ppm) 1.08 (d, J=6.80 Hz, 3H), 1.12 (d, J=6.80 Hz, 3H), 2.14–2.24 (m, 1H), 3.95 (d, J=6.00 Hz, 1H), 6.99 (dd, J=4.00 Hz, 5.20 Hz, 1H), 7.05–7.08 (m, 1H), 7.27 (dd, J=1.20 Hz, 5.20 Hz, 1H).

114-2) Ethyl 4-Cyano-5-methyl-4-(2-thienyl) hexanoate

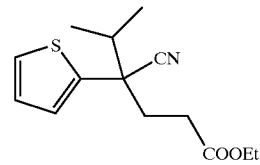

3-Methyl-2-(2-thienyl)butane nitrile 5.56 g 33.6 mmol and ethyl acrylate 4.00 ml 37.0 mmol were dissolved in tetrahydrofuran 100 ml. Potassium t-butoxide, 566 mg 5.04 mmol, was added little by little thereto at room temperature. Generation of heat continued during this step. After stirring for 1 hour, brine 100 ml and aqueous saturated ammonium chloride 150 ml were added thereto successively, and the mixture was extracted with ether 1 L. The organic layer was washed with brine 500 ml and water 500 ml successively, dried over magnesium sulfate anhydride and evaporated. The residue was purified by silica gel column chromatography (ethyl acetate/hexane system), whereby the title compound (5.57 g 21.0 mmol, 62.5%) was obtained as a yellow oil.

$^1$H-NMR (400 MHz, CDCl$_3$); δ (ppm) 0.92 (d, J=6.78 Hz, 3H), 1.22 (d, J=7.14 Hz, 3H), 1.23 (t, J=7.14, 3H), 2.01–2.19 (m, 3H), 2.41–2.58 (m, 2H), 4.01–4.15 (m, 2H), 6.96 (dd, J=3.60 Hz, 5.13 Hz1H), 7.12 (dd, J=1.20 Hz, 3.60 Hz, 1H), 7.29 (dd, J=1.20 Hz, 5.13 Hz, 1H).

114-3) 4-Cyano-5-methyl-4-(2-thienyl)hexanol

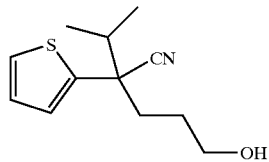

The above ester, 5.50 g 20.7 mmol, was dissolved in tetrahydrofuran 100 ml and cooled to −30 to −40° C. A solution of 1 M lithium aluminum hydride in tetrahydrofuran 150 ml was added dropwise thereto and the temperature was raised for 1 hour to 0° C. The reaction mixture was cooled again, and water 0.60 ml, 5 N aqueous sodium hydroxide 0.60 ml and water 1.80 ml were added thereto successively, and the mixture was filtered through Celite and evaporated. The residue was purified by silica gel column chromatography (ethyl acetate/hexane system), whereby the title compound, 3.99 g 17.9 mmol, 86.3%, was obtained as a yellow oil.

$^1$H-NMR (400 MHz, CDCl$_3$); δ (ppm) 0.92 (d, J=6.78 Hz, 3H), 1.19 (d, J=6.78 Hz, 3H), 1.33–1.46 (m, 1H), 1.65–1.77 (m, 1H), 1.80–1.90 (m, 1H), 2.08 (sept, J=6.78 Hz, 1H), 2.27 (ddd, J=4.40 Hz, 12.0 Hz, 13.2 Hz, 1H), 3.63 (brd-s, 2H), 6.96 (dd, J=3.60 Hz, 5.20 Hz, 1H), 7.11–7.14 (m, 1H), 7.27 (dd, J=1.20 Hz, 5.20 Hz, 1H).

114-4) [4-Cyano-5-methyl-4-(2-thienyl)hexyloxy]-t-butyldimethyl Silane

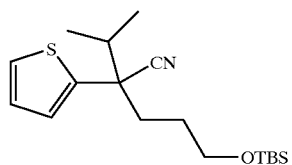

(wherein TBS represents t-butyldimethylsilyl group)

4-Cyano-5-methyl-4-(2-thienyl)hexanol, 2.00 g 8.95 mmol, was dissolved in N,N-dimethylformamide 50 ml. At room temperature, imidazole 1.83 g 26.9 mmol and t-butyl dimethyl chlorosilane 1.55 g 10.3 mmol were added thereto successively. Brine was added to the reaction mixture which was then extracted with ethyl acetate. The organic layer was washed with brine, dried over magnesium sulfate anhydride and evaporated. The residue was purified by silica gel column chromatography (ethyl acetate/hexane system), whereby the title compound (2.83 g 8.95 mmol, 100%) was obtained as a colorless oil.

$^1$H-NMR (400 MHz, CDCl$_3$); δ (ppm) 0.01 (s, 3H), 0.02 (s, 3H), 0.88 (s, 9H), 0.92 (d, J=6.78 Hz, 3H), 1.18 (d, J=6.78 Hz, 3H), 1.27–1.41 (m, 1H), 1.59–1.71 (m, 1H) 1.83 (ddd, J=4.40 Hz, 12.4 Hz, 13.2 Hz, 1H), 2.07 (sept, J=6.78 Hz, 1H), 2.22 (ddd, J=4.40 Hz, 12.4 Hz, 13.2 Hz, 1H), 3.59 (t, J=6.04 Hz, 2H), 6.95 (dd, J=3.60 Hz, 5.20 Hz, 1H), 7.11 (dd, J=1.20 Hz, 3.60 Hz, 1H), 7.26 (dd, 1.20 Hz, 5.20 Hz, 1H).

114-5) [4-Cyano-5-methyl-4-(2-bromo-5-thienyl)hexyloxy]-t-butyldimethyl Silane

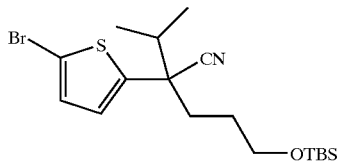

[4-Cyano-5-methyl-4-(2-thienyl)hexyloxy]-t-butyldimethyl silane, 2.72 g 8.95 mmol, was dissolved in N,N-dimethylformamide 7 ml. N-bromosucciimide 1.75 g 9.83 mmol was added thereto at room temperature and heated at 80° C. Brine was added to the reaction mixture which was then extracted with ethyl acetate. The organic layer was washed with brine, dried over magnesium sulfate anhydride and evaporated. The residue was purified by silica gel column chromatography (ethyl acetate/hexane system), whereby the title compound, 2.56 g 6.15 mmol, 68.7%, was obtained as a colorless oil.

$^1$H-NMR (400 MHz, CDCl$_3$); δ (ppm) 0.02 (s, 3H), 0.03 (s, 3H), 0.88 (s, 9H), 0.94 (d, J=6.78 Hz, 3H), 1.17 (d, J=6.59 Hz, 3H), 1.32–1.44 (m, 1H), 1.59–1.80 (m, 2H), 1.95–2.06 (m, 1H), 2.15–2.25 (m, 1H), 3.60 (t, J=5.86 Hz, 2H), 6.88 (d, J=3.60 Hz, 1H), 6.91 (d, J=3.60 Hz, 1H).

114-6) [4-Cyano-5-methyl-4-(2-formyl-5-thienyl)hexyloxy]-t-butyldimethyl Silane

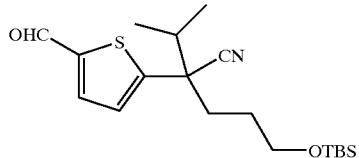

A solution of [4-cyano-5-methyl-4-(2-bromo-5-thienyl)hexyloxy]-t-butyldimethyl silane, 1.42 g 3.41 mmol, in tetrahydrofuran 20 ml was cooled to −70° C. A solution of 1.53 M butyl lithium in hexane 1.52 ml was added dropwise thereto and stirred for 10 minutes. N,N-dimethylformamide 1.52 ml was added thereto, and the temperature was raised to room temperature. Aqueous saturated ammonium chloride and brine were added to the reaction mixture which was then extracted with ether. The organic layer was washed with brine, dried over magnesium sulfate anhydride and evaporated. The residue was purified by silica gel column chromatography (ethyl acetate/hexane system), whereby the title compound, 515 mg 1.41 mmol, 41.3%, was obtained as a yellow syrup.

$^1$H-NMR (400 MHz, CDCl$_3$); δ (ppm) 0.01 (s, 3H), 0.02 (s, 3H), 0.87 (s, 9H), 0.93 (d, J=6.59 Hz, 3H), 1.21 (d, J=6.59 Hz, 3H), 1.22–1.36 (m, 1H), 1.60–1.73 (m, 1H), 1.80–1.90 (m, 1H), 2.11 (sept, J=6.59 Hz, 1H), 2.24–2.34 (m, 1H), 3.59 (t, J=5.86 Hz, 2H), 7.26 (d, J=3.60 Hz, 1H), 7.65 (d, J=3.60 Hz, 1H), 9.89 (s, 1H).

114-7) [4-Cyano-5-methyl-4-(2-cyano-5-thienyl) hexyloxy]-t-butyldimethyl Silane

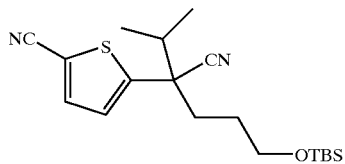

[4-Cyano-5-methyl-4-(2-formyl-5-thienyl)hexyloxy]-t-butyldimethyl silane, 510 mg 1.39 mmol, was dissolved in ethanol 5 ml, and a solution of hydroxylamine hydrochloride 145 mg 2.09 mmol and sodium acetate 228 mg 2.78 mmol in water 1.25 ml was added thereto, and the mixture was heated at 80° C. Brine was added to the reaction mixture and then extracted with ether. The organic layer was washed with brine, dried over magnesium sulfate anhydride, and evaporated to give an oxime compound. This oxime compound was dissolved in N,N-dimethylformamide 10 ml and cooled at 0° C., followed by adding carbodiimidazole. Thereafter, the mixture was heated at 60° C., and 20 minutes later, triethylamine was added thereto. Under cooling, brine was added to the reaction mixture which was then extracted with ether. The organic layer was washed with brine, dried over magnesium sulfate anhydride, and evaporated. The residue was purified by silica gel column chromatography (ethyl acetate/hexane system), whereby the title compound, 452 mg 1.25 mmol, 89.9%, was obtained as a yellow oil.

$^1$H-NMR (400 MHz, CDCl$_3$); δ (ppm) 0.02 (s, 3H), 0.03 (s, 3H), 0.88 (s, 9H), 0.93 (d, J=6.59 Hz, 3H), 1.20 (d, J=6.59 Hz, 3H), 1.23–1.36 (m, 1H), 1.60–1.73 (m, 1H), 1.80–1.90 (m, 1H), 2.08 (sept, J=6.59 Hz, 1H), 2.22–2.32 (m, 1H), 3.60 (t, J=5.60 Hz, 2H), 7.14 (d, J=3.60 Hz, 1H), 7.51 (d, J=3.60 Hz, 1H).

114-8) 4-Cyano-5-methyl-4-(2-cyano-5-thienyl) hexanol

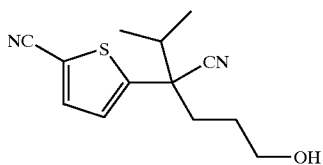

[4-Cyano-5-methyl-4-(2-cyano-5-thienyl)hexyloxy]-t-butyldimethylsilane, 452 mg 1.25 mmol, was dissolved in 10 ml tetrahydrofuran and cooled at 0° C. A solution of 1 M tetrabutylammonium fluoride in tetrahydrofuran 1.38 ml was added dropwise thereto, and then the temperature was raised to room temperature. Aqueous saturated ammonium chloride and brine were added to the reaction mixture which was then extracted with ether. The organic layer was washed with brine, dried over magnesium sulfate anhydride, and evaporated. The residue was purified by silica gel column chromatography (ethyl acetate/hexane system), whereby the title compound, 273 mg 1.10 mmol, 87.9%, was obtained as a yellow syrup.

$^1$H-NMR (400 MHz, CDCl$_3$); δ (ppm) 0.94 (d, J=6.59 Hz, 3H), 1.22 (d, J=6.78 Hz, 3H), 1.28–1.42 (m, 1H), 1.66–1.78 (m, 1H), 1.83–1.93 (m, 1H), 2.03–2.16 (m, 1H), 2.32 (ddd, J=4.40 Hz, 12.4 Hz, 13.2 Hz, 1H), 3.58–3.74 (m, 2H), 7.16 (d, J=3.60 Hz, 1H), 7.52 (d, J=3.60 Hz, 1H).

114-9) 1-[4-Cyano-5-methyl-4-(2-cyano-5-thienyl) hexyl]-4-[2-(4-fluorophenoxy)ethyl]piperazine

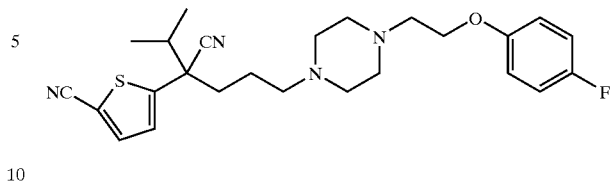

4-Cyano-5-methyl-4-(2-cyano-5-thienyl)hexanol, 273 mg 1.10 mmol, was dissolved in acetonitrile 5.00 ml and cooled at 0° C. Triethylamine 0.16 ml and methane sulfonyl chloride 0.10 ml 1.21 mmol were added thereto and the temperature was raised to room temperature. After 1 hour, the mixture was partitioned by adding ether and brine. The organic layer was washed with aqueous saturated sodium bicarbonate, dried over magnesium sulfate anhydride and evaporated. A half about 0.55 mmol of the residues was dissolved in N,N-dimethylformamide 5.00 ml, and 500 mg 3.34 mmol of sodium iodide, 76.0 mg 0.55 mmol of potassium carbonate, and 202 mg 0.90 mmol of 1-[2-(4-fluorophenoxy)ethyl]piperazine were added thereto, and the mixture was heated at 60° C. Brine was added to the reaction mixture which was then extracted with ethyl acetate. The organic layer was washed with brine, dried over magnesium sulfate anhydride, and evaporated. The residue was purified by Chromatorex NH silica gel column chromatography (ethyl acetate/hexane system), whereby the title compound, 215 mg 0.47 mmol, 86.0%, was obtained as a yellow syrup.

$^1$H-NMR (400 MHz, CDCl$_3$); δ (ppm) 0.92 (d, J=6.78 Hz, 3H), 1.21 (d, J=6.59 Hz, 3H), 1.18–1.32 (m, 1H), 1.58–1.71 (m, 1H), 1.72–1.82 (m, 1H), 2.01–2.12 (m, 1H), 2.17–2.27 (m, 1H), 2.28–2.68 (m, 10H), 2.79 (t, J=5.86 Hz, 2H), 4.05 (t, J=5.86 Hz, 2H), 6.80–6.87 (m, 2H), 6.92–6.99 (m, 2H), 7.15 (d, J=3.80 Hz, 1H), 7.51 (d, J=3.80 Hz, 1H).

ESI-MS; 455 (MH+).

Example 115

Synthesis of 1-[4-Cyano-5-methyl-4-(2-cyano-5-thienyl)hexyl]-4-[2-(3-fluorophenoxy)ethyl] piperazine

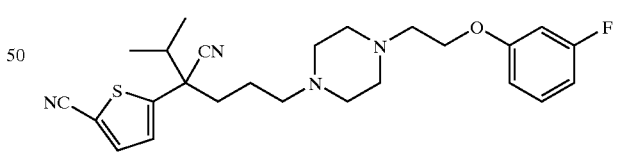

The title compound was obtained by using 1-[2-(3-fluorophenoxy)ethyl]piperazine in the same manner as in the above example.

$^1$H-NMR (400 MHz, CDCl$_3$); δ (ppm) 0.92 (d, J=6.78 Hz, 3H), 1.21 (d, J=6.78 Hz, 3H), 1.18–1.32 (m, 1H), 1.58–1.71 (m, 1H), 1.72–1.82 (m, 1H), 2.06 (sept, J=6.78 Hz, 1H), 2.17–2.27 (m, 1H), 2.28–2.68 (m, 10H), 2.80 (t, J=5.86 Hz, 2H), 4.07 (t, J=5.86 Hz, 2H), 6.68–6.71 (m, 3H), 7.15 (d, J=4.00 Hz, 1H), 7.17–7.24 (m, 1H), 7.51 (d, J=4.00 Hz, 1H).

ESI-MS; 455 (MH+).

Example 116

Synthesis of 1-[4-Cyano-5-methyl-4-(2-thienyl)hexyl]-4-[2-(3-fluorophenoxy)ethyl]piperazine

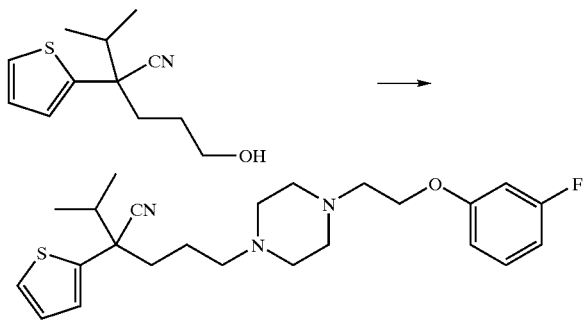

The title compound (yield, 86.9%; 336 mg) was obtained from 1-[2-(3-fluorophenoxy)ethyl]piperazine 323 mg and 4-cyano-5-methyl-4-(2-thienyl)hexanol 200 mg in the same manner as in Example 114.

$^1$H-NMR (400 MHz, CDCl$_3$); δ (ppm) 0.90 (d, J=6.59 Hz, 3H), 1.18 (d, J=6.59 Hz, 3H), 1.25–1.38 (m, 1H), 1.58–1.70 (m, 1H), 1.72–1.82 (m, 1H), 2.06 (sept, J=6.59 Hz, 1H), 2.11–2.21 (m, 1H), 2.27–2 2.64 (m, 10H), 2.79 (t, J=5.86 Hz, 2H), 4.07 (t, J=5.86 Hz, 2H), 6.58–6.70 (m, 3H), 6.94 (dd, J=3.60 Hz, 5.20 Hz, 1H), 7.11 (dd; J=1.2 Hz, 3.6 Hz, 1H), 7.16–7.24(m, 1H), 7.25 (dd, J=1.20 Hz, 5.20 Hz).

ESI-MS; 430 (MH+).

Example 117

Synthesis of 1-[(4-Cyano-5-methyl-4-phenyl)hexyl]-4-{2-[3-(3-thienyl)phenoxy]ethyl}piperazine

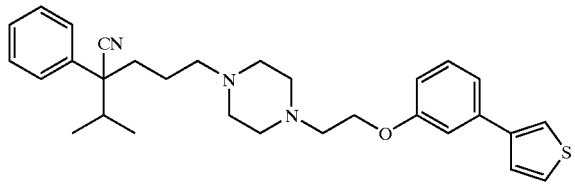

In a nitrogen atmosphere, 1-[(4-cyano-5-methyl-4-phenyl)hexyl]-4-[2-(3-bromophenoxy)ethyl]piperazine 100 mg, thiophene-3-boric acid 53 mg, and a tetrakistriphenyl phosphine palladium complex 24 mg were dissolved in toluene 4.0 ml, and 10% aqueous sodium bicarbonate was added thereto, and the atmosphere was replaced by nitrogen, and the mixture was heated for 4 hours under reflux with heating. The reaction mixture was cooled and then partitioned by adding water and ethyl acetate. The organic layer was washed with water and then with brine, dried over magnesium sulfate anhydride and evaporated. The residue was purified by NH silica gel column chromatography (hexane/ethyl acetate system), whereby the title compound (21 mg, 21%) was obtained as a colorless oil.

Free Compound;

$^1$H-NMR (400 MHz, CDCl$_3$); δ (ppm) 0.77 (d, J=6.8 Hz, 3H), 1.05–1.20 (m, 1H), 1.20 (d, J=6.8 Hz, 3H), 1.50–1.63 (m, 1H), 1.83–1.95 (m, 1H), 2.05–2.20 (m, 2H), 2.23–2.30 (m, 2H), 2.30–2.45 (m, 4H), 2.45–2.60 (m, 4H), 2.81 (t, J=6.0 Hz, 2H), 4.13 (t, J=6.0 Hz, 2H), 6.80–6.84 (m, 1H), 7.12–7.14 (m, 1H), 7.16–7.20 (m, 1H), 7.25–7.32 (m, 2H), 7.33–7.38 (m, 2H), 7.42–7.45 (m, 6H), 7.42–7.45 (m, 1).

This free compound 21 mg was treated in a usual manner to give the hydrochloride 17 mg of the title compound.

Hydrochloride;

$^1$H-NMR (400 MHz, DMSO-d$_6$); δ (ppm) 0.67 (d, J=6.4 Hz, 3H), 1.11 (d, J=6.8 Hz, 3H), 1.20–1.30 (m, 1H), 1.55–1.70 (m, 1H), 2.05–2.30 (m, 3H), 3.20–3.80 (m, 12H), 4.42 (brs, 2H), 6.90–6.95 (m, 1H), 7.30–7.40 (m, 4H), 7.40–7.50 (m, 4H), 7.55–7.58 (m, 1H), 7.62–7.66 (m, 1H), 7.88–7.92 (m, 1H).

ESI-Mass; 488 (MH+).

Example 118

Synthesis of 1-[(4-Cyano-5-methyl-4-phenyl)hexyl]-4-{2-[2-(6-methyl-2-pyridyl)vinylphenoxyl]ethyl}piperazine

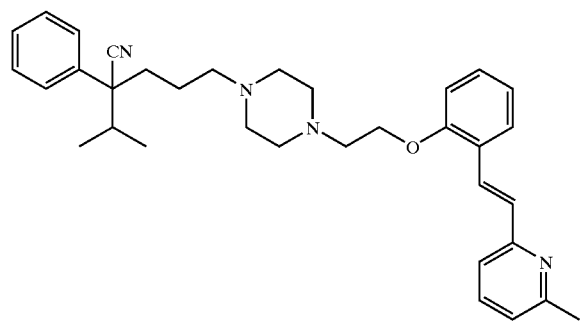

In a nitrogen atmosphere, 1-[(4-cyano-5-methyl-4-phenyl)hexyl)-4-(2-(2-bromophenoxy)ethyl]piperazine 100 mg, 6-vinyl-2-methylpyridine 49 mg, palladium acetate 4.6 mg and tris(2-methylphenyl) phosphine 12.5 mg were dissolved in N,N-dimethylformamide 4.0 ml, and triethylamine 1 ml was added thereto, and the mixture was stirred for 10 hours under reflux with heating. The reaction mixture was cooled, filtered through Celite, and partitioned by adding water and diethyl ether. The organic layer was washed with water and then with brine, dried over magnesium sulfate anhydride and evaporated. The residues were purified by NH silica gel column chromatography (hexane/ethyl acetate system), whereby the title compound (115 mg, 100%) was obtained as a colorless oil.

Free Compound;

$^1$H-NMR (400 MHz, CDCl$_3$); δ (ppm) 0.77 (d, J=6.6 Hz, 3H), 1.05–1.20 (m, 1H), 1.20 (d, J=6.6 Hz, 3H), 1.50–1.60 (m, 1H), 1.83–1.93 (m, 1H), 2.05–2.20 (m, 2H), 2.20–2.30 (m, 2H), 2.30–2.45 (m, 4H), 2.50–2.70 (m, 4H), 2.56 (s, 3H), 2.89 (t, J=5.9 Hz, 2H), 4.16 (t, J=5.9 Hz, 2H), 6.88 (d, J=8.4 Hz, 1H), 6.94–7.00 (m, 2H), 7.18–7.38 (m, 6H), 7.52 (t, J=7.7 Hz, 1H), 7.62–7.66 (m, 1H), 7.87 (d, J=16.7 Hz, 1H).

This free compound 115 mg was treated in a usual manner to give the hydrochloride 110 mg of the title compound.

Hydrochloride;

ESI-Mass; 523 (MH+).

Example 119

Synthesis of 1-[(4-Cyano-5-methyl-4-phenyl)hexyl]-4-[2-(3-cyanophenoxy)ethyl]piperazine

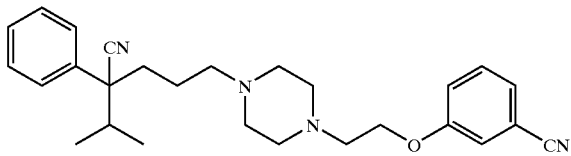

In a nitrogen atmosphere, 1-[(4-cyano-5-methyl-4-phenyl)hexyl]-4-[2-(3-bromophenoxy)ethyl]piperazine 100 mg, zinc cyanide 24 mg, and a tetrakistriphenyl phosphine palladium complex 24 mg were dissolved in N,N-dimethylformamide 4.0 ml and heated and stirred for 9 hours under reflux. The reaction mixture was cooled, filtered through Celite, and partitioned by adding water and diethyl ether. The organic layer was washed with water and then with brine, dried over magnesium sulfate anhydride and evaporated. The residue was purified by NH silica gel column chromatography (hexane/ethyl acetate system), whereby the title compound (63 mg, 71%) was obtained as a colorless oil.

Free Compound;
$^1$H-NMR (400 MHz, CDCl$_3$); δ (ppm) 0.77 (d, J=6.8 Hz, 3H), 1.05–1.20 (m, 1H), 1.20 (d, J=6.6 Hz, 3H), 1.50–1.60 (m, 1H), 1.83–1.95 (m, 1H), 2.05–2.20 (m, 2H), 2.25–2.30 (m, 2H), 2.30–2.48 (m, 4H), 2.48–2.65 (m, 4H), 2.80 (t, J=5.7 Hz, 2H), 4.09 (t, J=5.7 Hz, 2H), 7.10–7.17 (m, 2H), 7.21–7.39 (m, 7H).

This free compound 63 mg was treated in a usual manner to give the hydrochloride 58 mg of the title compound.
Hydrochloride;
ESI-Mass; 431 (MH+).

Example 120

Synthesis of 1-[(4-Cyano-5-methyl-4-phenyl)hexyl]-4-[2-(3-phenylphenoxy)ethyl]piperazine

120-1) 2-(3-Phenylphenoxy)ethanol

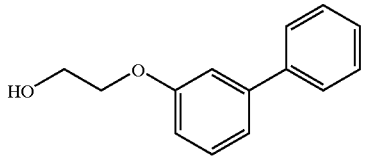

In a nitrogen atmosphere, 3-phenylphenol 2.65 g, 2-bromoethanol 2.92 g and potassium carbonate 6.51 g were dissolved in N,N-dimethylformamide 16 ml and stirred at 100° C. After 5 hours, the reaction mixture was cooled to room temperature and partitioned by adding water and diethyl ether. The organic layer was washed with water and then with brine, dried over magnesium sulfate anhydride, and evaporated. The residue was purified by silica gel column chromatography (hexane/ethyl acetate system), whereby the title compound (1.78 g, 53%) was obtained as a colorless crystalline.

$^1$H-NMR (400 MHz, CDCl$_3$); δ (ppm) 2.18–2.24 (m, 1H), 3.96–4.00 (m, 2H), 4.14 (t, J=4.8 Hz, 2H), 6.88–6.92 (m, 1H), 7.13–7.16 (m, 1H), 7.18–7.22 (m, 1H), 7.32–38 (m, 2H), 7.40–7.45 (m, 2H), 7.55–7.59 (m, 2H).

120-2) 1-[(4-Cyano-5-methyl-4-phenyl)hexyl]-4-[-2-(3-phenylphenoxy)ethyl]piperazine

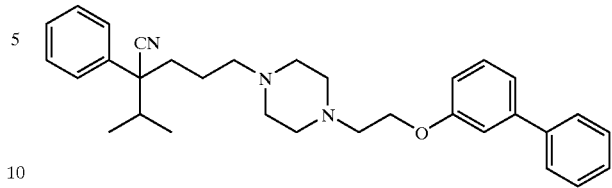

In a nitrogen atmosphere, 2-(3-phenylphenoxy)ethanol 68 mg and triethylamine 0.13 ml were dissolved in acetonitrile 6 ml in an ice bath, and methane sulfonyl chloride 40 mg was added thereto. After the mixture was stirred for 3 hours, sodium iodide 142 mg and a solution of 1-[(4-cyano-5-methyl-4-phenyl)hexyl]piperazine 90 mg in acetonitrile 3 ml were added thereto, and the mixture was stirred for 15 hours under reflux with heating. After cooling, the reaction mixture was partitioned by adding water and ethyl acetate. The organic layer was washed with water and then with brine, dried over magnesium sulfate anhydride and evaporated. The residue was purified by NH silica gel column chromatography (hexane/ethyl acetate system), whereby the title compound (127 mg, 84%) was obtained as a colorless oil.

Free Compound;
$^1$H-NMR (400 MHz, CDCl$_3$); δ (ppm) 0.77 (d, J=6.8 Hz, 3H), 1.05–1.20 (m, 1H), 1.20 (d, J=6.8 Hz, 3H), 1.50–1.60 (m, 1H), 1.82–1.92 (m, 1H), 2.05–2.20 (m, 2H), 2.25–2.30 (m, 2H), 2.30–2.45 (m, 4H), 2.45–2.65 (m, 4H), 2.81 (t, J=5.9 Hz, 2H), 4.14 (t, J=5.9 Hz, 2H), 6.85–6.90 (m, 1H), 7.11–7.14 (m, 1H), 7.15–7.19 (m, 1H), 7.25–7.45 (m, 9H), 7.55–7.60 (m, 2H).

This free compound 127 mg was treated in a usual manner to give the hydrochloride 115 mg of the title compound.
Hydrochloride;
ESI-Mass; 482 (MH+).

Example 121

Synthesis of 1-[(4-Cyano-5-methyl-4-phenyl)hexyl]-4-{2-[3-(2-cyanovinyl)phenoxy]ethyl}piperazine

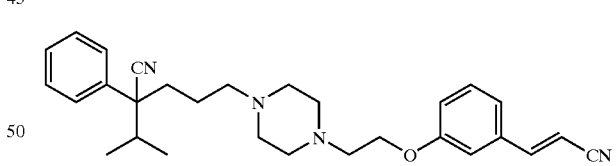

1-[(4-Cyano-5-methyl-4-phenyl)hexyl]-4-[2-(2-bromophenoxy)ethyl]piperazine 200 mg, acrylonitrile 0.08 ml, palladium acetate 9.3 mg, and tris(2-methylphenyl) phosphine 25 mg were dissolved in N,N-dimethylformamide 8.0 ml, and triethylamine 2.0 ml was added thereto, and the mixture was heated in a sealed vessel at 100° C. for 12 hours. The reaction mixture was cooled and then filtered through Celite, and partitioned by adding water and ethyl acetate. The organic layer was washed with water and then with brine, dried over magnesium sulfate anhydride, and evaporated. The residue was purified by NH silica gel column chromatography (hexane/ethyl acetate system), whereby the title compound (65 mg, 35%) was obtained as a colorless oil.

Free Compound;
¹H-NMR (400 MHz, CDCl₃); δ (ppm) 0.77 (d, J=6.6 Hz, 3H), 1.05–1.20 (m, 1H), 1.20 (d, J=6.6 Hz, 3H), 1.50–1.60 (m, 1H), 1.82–1.92 (m, 1H), 2.05–2.20 (m, 2H), 2.25–2.30 (m, 2H), 2.30–2.45 (m, 4H), 2.45–2.65 (m, 4H), 2.79 (t, J=5.9 Hz, 2H), 4.09 (t, J=5.9 Hz, 2H), 5.85 (d, J=16.8 Hz, 1H), 6.64–7.40 (m, 10H).

This free compound 32 mg was treated in a usual manner to give the hydrochloride 30 mg of the title compound.
Hydrochloride;
ESI-Mass; 457 (MH+).

Example 122

Synthesis of 1-[(4-Cyano-5-methyl-4-phenyl)hexanoyl]-4-[2-(4-fluorophenoxy)ethyl]piperazine

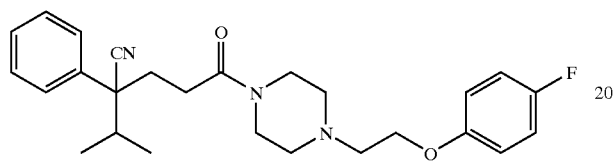

The title compound 8.53 g, 85% was obtained as a colorless oil from 4-cyano-5-methyl-4-phenylhexanoic acid 5.28 g and 1-[2-(4-fluorophenoxy)ethyl]piperazine 5.38 g in the same manner as in Example 97–2).
Free Comound;
¹H-NMR (400 MHz, CDCl₃); δ (ppm), 0.78 (d, J=6.8 Hz, 3H), 1.22 (d, J=6.6 Hz, 3H), 1.80–1.93 (m, 1H), 2.10–2.20 (m, 1H), 2.25–2.55 (m, 7H), 2.77 (t, J=5.5 Hz, 2H), 3.20–3.40 (m, 2H), 3.45–3.70 (m, 2H), 4.03 (t, J=5.5 Hz, 2H), 6.79–6.84 (m, 2H), 6.92–6.98 (m, 2H), 7.14–7.40 (m, 5H).
ESI-Mass; 438 (MH+).

Example 123

Synthesis of 1-[(4-Cyano-4-phenyl)butyl]-4-[2-(4-fluorophenoxy)ethyl]piperazine

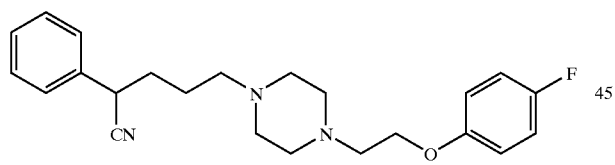

The title compound 874 mg, 67% was obtained as a pale yellow oil from (4-cyano-4-phenyl)butylaldehyde 720 mg and 1-[2-(4-fluorophenoxy)ethyl]piperazine 689 mg in the same manner as in Example 1.
Free Comound;
¹H-NMR (400 MHz, CDCl₃); δ (ppm) 1.60–1.70 (m, 2H), 1.86–2.00 (m, 2H), 2.37 (t, J=7.2 Hz, 2H), 2.40–2.54 (m, 4H), 2.54–2.66 (m, 4H), 2.76–2.82 (m, 2H), 3.84–3.88 (m, 1H), 4.02–4.08 (m, 2H), 6.81–6.86 (m, 2H), 6.93–6.98 (m, 2H), 7.30–7.40 (m, 5H).

This free product 874 mg was treated in a usual manner to give the hydrochloride 890 mg of the title compound.
Hydrochloride;
¹H-NMR (400 MHz, DMSO-d₆); δ (ppm) 1.75–1.85 (m, 2H), 1.85–2.02 (m, 2H), 3.12–3.22 (m, 2H), 3.22–3.82 (m, 10H), 4.28–4.38 (m, 3H), 7.01–7.06 (m, 2H), 7.13–7.20 (m, 2H), 7.34–7.38 (m, 1H), 7.40–7.46 (m, 4H).
ESI-Mass; 382 (MH+).

What is claimed is:
1. An N,N-substituted cyclic amine compound represented by the following formula (VIII):

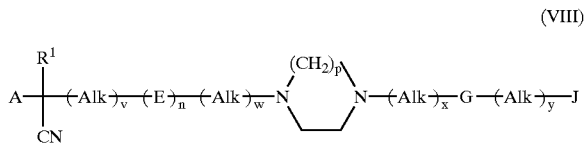

(VIII)

wherein

A represents an aryl group which may be substituted, a heteroaryl group which may be substituted, an aralkyl group which may be substituted, or a heteroaryl alkyl group which may be substituted;

E represents a group represented by the formula —CO— or a group represented by the formula —CHOH—;

G represents an oxygen atom, a sulfur atom, and a group represented by the formula —NR¹⁰—, wherein R¹⁰ represents a hydrogen atom, a lower alkyl group, a lower cycloalkyl, a lower acyl group or a lower alkyl sulfonyl group, a group represented by —CO—, a group represented by —COO—, a group represented by the formula —CONR¹¹, wherein R¹¹ represents a hydrogen atom or a lower alkyl group, a group represented by the formula —NR¹²CO—, _wherein R¹² represents a hydrogen atom or a lower alkyl group, a group represented by the formula —SO—, a group represented by the formula —SO₂—, a group represented by the formula —SONR¹³—, wherein R¹³ represents a hydrogen atom or a lower alkyl group, a group represented by the formula —NR¹⁴SO—, wherein R¹⁴ represents a hydrogen atom or a lower alkyl group, a group represented by the formula —SO₂NR¹⁵— wherein R¹⁵ represents a hydrogen atom or a lower alkyl group, a group represented by the formula —NR¹⁶SO₂—, wherein R¹⁶ represents a hydrogen atom or a lower alkyl group, a group represented by the formula >C=N—OR¹⁷, wherein R¹⁷ represents a hydrogen atom or a lower alkyl group, a group represented by the formula —NHCONH—, a group represented by the formula —NHCSNH—, a group represented by the formula —C(=NH)NH, a group represented by the formula —NHC(=NH)—, a group represented by the formula —OCOS—, a group represented by the formula —SCOO—, a group represented by the formula —OCOO—, a group represented by the formula —NHCOO—, a group represented by the formula —OCONH—, a group represented by the formula —CO(CH₂)ₛO—, a group represented by the formula —CHOH— or a group represented by the formula —CHOH(CH₂)ₛO—, wherein s represents 0 or an integer of 1 to 6;

J represents an aryl group which may be substituted or a heteroaryl group which may be substituted;

R¹ represents a hydrogen atom, a halogen atom, a hydroxy group, a lower alkyl group, a lower alkenyl group, a lower alkynyl group, a lower cycloalkyl group, a hydroxy lower alkyl group, a lower alkoxyalkyl group, a cyano-lower alkyl group, a halogenated lower alkyl group, an optionally N-substituted amino-lower alkyl group, a group represented by the formula —NR¹⁸R¹⁹, wherein R¹⁸ and R¹⁹ may be the same as or different from each other and each represents a hydrogen atom or a lower alkyl group, an aralkyl group, a morpholinyl group, a thiomorpholinyl group, a piperidyl group, a pyrrolidinyl group or a piperazinyl group;

Alk represents a linear or branched lower alkylene group; and n, v, x, w and y are independent of each other and each represents 0 or 1, and p represents 2 or 3, provided that x is 1 when G is —CO—, or a pharmacologically acceptable salt thereof.

2. A N,N-substituted cyclic amine compound represented by the following formula (I):

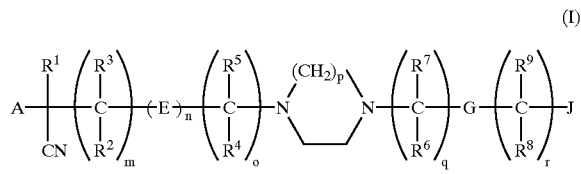

(I)

wherein

A represents an aryl group which may be substituted, a heteroaryl group which may be substituted, an aralkyl group which may be substituted or a heteroaryl alkyl group which may be substituted;

E represents a group represented by the formula —CO— or a group represented by the formula —CHOH—;

G represents an oxygen atom, a sulfur atom, and a group represented by the formula —$NR^{10}$—, wherein $R^{10}$ represents a hydrogen atom, a lower alkyl group, a lower acyl group or a lower alkyl sulfonyl group, a group represented by —OC—, a group represented by —COO—, a group represented by the formula —$CONR^{11}$, wherein $R^{11}$ represents a hydrogen atom or a lower alkyl group, a group represented by the formula —$NR^{12}CO$—, wherein $R^{12}$ represents a hydrogen atom or a lower alkyl group, a group represented by the formula —SO—, a group represented by the formula —$SO_2$—, a group represented by the formula —$SONR^{13}$ —, wherein $R^{13}$ represents a hydrogen atom or a lower alkyl group, a group represented by the formula —$NR^{14}SO$—, wherein $R^{14}$ represents a hydrogen atom or a lower alkyl group, a group represented by the formula —$SO_2NR^{15}$—, wherein $R^{15}$ represents a hydrogen atom or a lower alkyl group, a group represented by the formula —$NR^{16}SO_2$—, wherein $R^{16}$ represents a hydrogen atom or a lower alkyl group, a group represented by the formula $>C=N-OR^{17}$, wherein $R^{17}$ represents a hydrogen atom or a lower alkyl group, a group represented by the formula —NHCONH—, a group represented by the formula —NHCSNH—, a group represented by the formula —C(=NH)NH—, a group represented by the formula —NHC(=NH)—, a group represented by the formula —OCOS—, a group represented by the formula —SCOO—, a group represented by the formula —OCOO—, a group represented by the formula —NHCOO—, a group represented by the formula —OCONH—, a group represented by the formula —$CO(CH_2)_sO$—, a group represented by the formula —CHOH— or a group represented by the formula —$CHOH(CH_2)_sO$—, wherein s is 0 or an integer of 1 to 6;

J represents an aryl group which may be substituted or a heteroaryl group which may be substituted;

$R^1$ represents a lower alkyl group, a cycloalkyl group, a group represented by the formula —$NR^{18}R^{19}$, wherein $R^{18}$ and $R^{19}$ may be the same as or different from each other and each represents a hydrogen atom or a lower alkyl group, a morpholinyl group, a thiomorpholinyl group, a piperidyl group, a pyrrolidnyl group or a piperazinyl group;

$R^2$, $R^3$, $R^4$, $R^5$, $R^6$, $R^7$, $R^8$ and $R^9$ may be the same as or different from each other and each represents a hydrogen atom or a lower alkyl group; and m, o, q and r may be the same as or different from each other and each represents 0 or an integer of 1 to 6, n is 0 or 1, and p is 2 or 3, provided that q is an integer of 1 when G is —CO—, or a pharmacologically acceptable salt thereof.

3. The compound of claim 2 represented by the following formula (II):

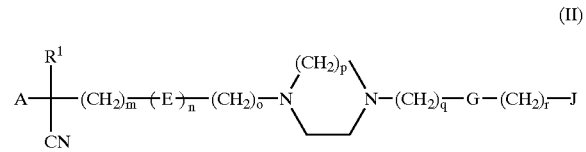

(II)

wherein A, E, G, J, $R^1$, m, n, o, p, q and r have the same meanings as defined above, or a pharmacologically acceptable salt thereof.

4. The compound of claim 2 represented by the following formula (III):

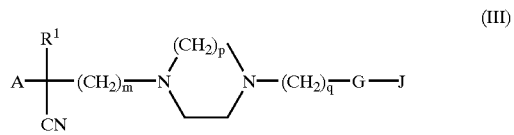

(III)

wherein A, G, J, $R^1$, m, p and q have the same meanings as defined above, or a pharmacologically acceptable salt thereof.

5. A N,N-substituted cyclic amine compound represented by the following formula (IV):

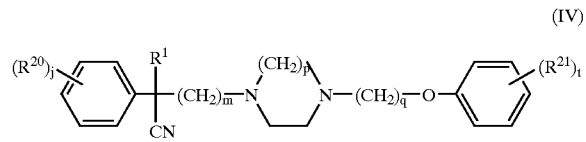

(IV)

wherein $R^1$ represents a hydrogen atom, a halogen atom, a hydroxy group, a lower alkyl group, a lower alkenyl group, a lower alkynyl group, a lower cycloalkyl group, a hydroxy lower alkyl group, a lower alkoxyalkyl group, a cyano-lower alkyl group, a halogenated lower alkyl group, an optionally N-substituted amino-lower alkyl group, a group represented by the formula —$NR^{18}R^{19}$, wherein $R^{18}$ and $R^{19}$ may be the same as or different from each other and each represents a hydrogen atom or a lower alkyl group, an aralkyl group, a morpholinyl group, a thiomorpholinyl group, a piperidyl group, a pyrrolidinyl group or a piperazinyl group;

m and q may be the same as or different from each other and each represents 0 or an integer of 1 to 6;

p is 2 or 3;

$R^{20}$ and $R^{21}$ are the same as or different from each other and each represents a hydrogen atom, a halogen atom, a hydroxy group, a mercapto group, a lower alkyl group, a lower alkoxy group, a hydroxymethyl group, a nitro group, an amino group which may be substituted, a cyano group, a carboxyl group, a lower alkoxy carbonyl group, a lower thioalkoxy group, a lower alkyl sulfonyl group, a lower acyl group, a halogenated lower alkyl group, an aryl group which may be substituted, a heteroaryl group which may be substituted, an aryloxy group, an aralkyloxy group, a lower alkoxycarbonylalkoxy group or a hydroxy lower alkoxy group, and $R^{20}$ groups or $R^{21}$ groups may form an alicyclic group which may be substituted, or a heterocylclic group or alkylene dioxy group which may be substituted; and j and t may be the same as or different from each other and each represents 0 or an integer of 0 or 1 to 5, or a pharmacologically acceptable salt thereof.

6. The compound of claim 1, 2, 3, 4, or 5, wherein said compound is selected from the group consisting of:

(1) 1-[(4-cyano-5-methyl-4-phenyl)hexyl]-4-[2-(4-fluorophenoxy)ethyl]piperazine, (2) 1-[(4-cyano-5-methyl-4-phenyl)hexyl]-4-[3-(4-fluorophenoxy)propyl]piperazine, (3) 1-[(4-cyano-5-methyl-4-phenyl)hexyl]-4-[2-(4-fluorophenoxy)ethyl]homopiperazine, (4) 1-[(3-cyano-4-methyl-3-phenyl)pentyl]-4-[2-(4-fluorophenoxy)ethyl]homopiperazine, (5) 1-[(3-cyano-4-methyl-3-phenyl)pentyl]-4-[3-(4-fluorophenoxy)propyl]piperazine, (6) 1-[(4-cyano-5-methyl-4-phenyl)hexyl]-4-(4-phenoxybutyl)piperazine, (7) 1-[(4-cyano-5-methyl-4-phenyl)hexyl]-4-(2-phenoxyethyl)piperazine, (8) 1-[(4-cyano-5-methyl-4-phenyl)hexyl]-4-[2-(4-nitrophenoxy)ethyl]piperazine, (9) 1-[4-cyano-5-methyl-4-(4-methylphenyl)hexyl]-4-[2-(4-fluorophenoxy)ethyl]piperazine,

(10) 1-[4-cyano-5-methyl-4-(4-chlorophenyl)hexyl]-4-[2-(4-fluorophenoxy)ethyl]piperazine,

(11) 1-[4-cyano-5-methyl-4-(4-methoxyphenyl)hexyl]-4-[2-(4-fluorophenoxy)ethyl]piperazine,

(12) 1-[4-cyano-5-methyl-4-(4-carbomethoxyphenyl)hexyl]-4-[2-(4-fluorophenoxy)ethyl]piperazine,

(13) 1-[4-cyano-5-methyl-4-(4-hydroxymethylphenyl)hexyl]-4-[2-(4-fluorophenoxy)ethyl]piperazine,

(14) 1-[4-cyano-5-methyl-4-(4-hydroxyiminomethylphenyl)hexyl]-4-[2-(4-fluorophenoxy)ethyl]piperazine,

(15) 1-[4-cyano-5-methyl-4-(4-cyanophenyl)hexyl]-4-[2-(4-fluorophenoxy)ethyl]piperazine,

(16) 1-[4-cyano-5-methyl-4-(4-nitrophenyl)hexyl]-4-[2-(4-fluorophenoxy)ethyl]piperazine,

(17) 1-[4-cyano-5-methyl-4-(4-aminophenyl)hexyl]-4-[2-(4-fluorophenoxy)ethyl]piperazine,

(18) 1-[4-cyano-5-methyl-4-(4-acetamidophenyl)hexyl]-4-[2-(4-fluorophenoxy)ethyl]piperazine,

(19) 1-[4-cyano-5-methyl-4-(4-dimethylaminophenyl)hexyl]-4-[2-(4-fluorophenoxy)ethyl]piperazine,

(20) 1-{[4-cyano-5-methyl-4-(2-thienyl)hexyl]}-4-[2-(4-fluorophenoxy)ethyl]piperazine,

(21) 1-{[4-cyano-5-methyl-4-(3-pyridyl)hexyl]}-4-[2-(4-fluorophenoxy)ethyl]piperazine,

(22) 1-{[4-cyano-5-methyl-4-(2-fluorophenyl)hexyl]}-4-[2-(4-fluorophenoxy)ethyl]piperazine,

(23) 1-{[4-cyano-5-methyl-4-(3-fluorophenyl)hexyl]}-4-[2-(4-fluorophenoxy)ethyl]piperazine,

(24) 1-{[4-cyano-5-methyl-4-(4-fluorophenyl)hexyl]}-4-[2-(4-fluorophenoxy)ethyl]piperazine,

(25) 1-[(3-cyano-4-methyl-3-phenyl)pentyl]-4-[2-(4-fluorophenoxy)ethyl]piperazine,

(26) 1-[(4-cyano-4-phenyl)pentyl]-4-[2-(4-fluorophenoxy)ethyl]piperazine,

(27) 1-[(4-cyano-4-phenyl)heptyl]-4-[2-(4-fluorophenoxy)ethyl]piperazine,

(28) 1-[(4-cyano-4-phenyl)hexyl]-4-[2-(4-fluorophenoxy)ethyl]piperazine,

(29) 1-[(4-cyano-4-phenyl)octyl]-4-[2-(4-fluorophenoxy)ethyl]piperazine,

(30) 1-[(4-cyano-6-methyl-4-phenyl)heptyl]-4-[2-(4-fluorophenoxy)ethyl]piperazine,

(31) 1-[(4-cyano-5-methyl-4-phenyl)hexyl]-4-[2-(2-fluorophenoxy)ethyl]piperazine,

(32) 1-[(4-cyano-5-methyl-4-phenyl)hexyl]-4-[2-(3-fluorophenoxy)ethyl]piperazine,

(33) 1-[(4-cyano-5-methyl-4-phenyl)hexyl]-4-[3-(4-fluorophenoxy)pentyl]piperazine,

(34) 1-[(4-cyano-5-methyl-4-phenyl)heptyl]-4-[3-(4-fluorophenoxy)ethyl]piperazine,

(35) 1-[(4-cyano-5-methyl-4-phenyl)hexyl]-4-[2-(3,4-difluorophenoxy)ethyl]piperazine,

(36) 1-[(4-cyano-5-methyl-4-phenyl)hexyl]-4-[2-(4-chlorophenoxy)ethyl]piperazine,

(37) 1-{[4-cyano-5-methyl-4-(3,4-dichlorophenyl)hexyl]}-4-[2-(4-fluorophenoxy)ethyl]piperazine,

(38) 1-[(4-cyano-4-cyclohexyl-4-phenyl)butyl]-4-[2-(4-fluorophenoxy)ethyl]piperazine,

(39) 1-[(4-cyano-5-methyl-4-phenyl)hexyl]-4-[2-(4-methoxyphenoxy)ethyl]piperazine,

(40) 1-[(4-cyano-5-methyl-4-phenyl)hexyl]-4-[2-(2,3-dimethoxyphenoxy)ethyl]piperazine,

(41) 1-[(4-cyano-5-methyl-4-phenyl)hexyl]-4-[2-(3,4-dimethoxyphenoxy)ethyl]piperazine,

(42) 1-[(4-cyano-5-methyl-4-phenyl)hexyl]-4-[2-(4-aminophenoxy)ethyl]piperazine,

(43) 1-[(4-cyano-5-methyl-4-phenyl)hexyl]-4-[2-(4-dimethylaminophenoxy)ethyl]piperazine,

(44) 1-[(4-cyano-5-methyl-4-phenyl)hexyl]-4-[2-(4-acetamidophenoxy)ethyl]piperazine,

(45) 1-[(4-cyano-5-methyl-4-phenyl)hexyl]-4-[2-(4-methylthiophenoxy)ethyl]piperazine,

(46) 1-[(4-cyano-5-methyl-4-phenyl)hexyl]-4-[2-(2-cyanophenoxy)ethyl]piperazine,

(47) 1-[(4-cyano-5-methyl-4-phenyl)hexyl]-4-[2-(4-cyanophenoxy)ethyl]piperazine,

(48) 1-[(4-cyano-5-methyl-4-phenyl)hexyl]-4-[2-(benzyloxy)ethyl]piperazine,

(49) 1-[(4-cyano-5-methyl-4-phenyl)hexyl]-4-[2-(4-fluorophenylthio)ethyl]piperazine,

(50) 1-[(4-cyano-5-methyl-4-phenyl)hexyl]-4-[2-(4-fluorophenylsulfonyl)ethyl]piperazine,

(51) 1-[(4-cyano-5-methyl-4-phenyl)hexyl]-4-[2-(4-fluorophenylamino)ethyl]piperazine,

(52) 1-[(4-cyano-5-methyl-4-phenyl)hexyl]-4-{2-[N-(4-fluorophenyl)-N-methylamino]ethyl}piperazine,

(53) 1-[(4-cyano-5-methyl-4-phenyl)hexyl]-4-{2-[N-(4-fluorophenyl)-N-acetylamino]ethyl}piperazine,

(54) 1-[(4-cyano-5-methyl-4-phenyl)hexyl]-4-{2-[N-(4-fluorophenyl)-N-methanesulfonylamino]ethyl}piperazine,

(55) 1-[(4-cyano-5-methyl-4-phenyl)hexyl]-4-[2-(benzylamino)ethyl]piperazine,

(56) 1-[(4-cyano-5-methyl-4-phenyl)hexyl]-4-[2-(N-acetyl-N-benzylamino)ethyl]piperazine,

(57) 1-[(4-cyano-5-methyl-4-phenyl)hexyl]-4-[2-(N-methanesulfonyl-N-benzylamino)ethyl]piperazine,

(58) 1-[(4-cyano-5-methyl-4-phenyl)hexyl]-4-[2-(N-benzyl-N-Isopropylamino)ethyl]piperazine,

(59) 1-[(4-cyano-5-methyl-4-phenyl)hexyl]-4-[2-(4-fluorobenzoyl)ethyl]piperazine,

(60) 1-[(4-cyano-5-methyl-4-phenyl)hexyl]-4-[3-hydroxy-3-(4-fluorophenyl)propyl]piperazine,

(61) 1-[(4-cyano-5-methyl-4-phenyl)hexyl]-4-[2-(4-fluorophenoxy)acetyl]piperazine,

(62) 1-[(4-cyano-5-methyl-4-phenyl)hexyl]-4-[2-hydroxy-3-(4-fluorophenoxy)propyl]piperazine,

(63) 1-[(4-cyano-5-methyl-4-phenyl)hexyl]-4-[2-(4-fluorophenylaminocarbonyl)ethyl]piperazine,

(64) 1-[(4-cyano-5-methyl-4-phenyl)hexyl]-4-[2-(4-fluorobenzoylamino)ethyl]piperazine,

(65) 1-[(4-cyano-5-methyl-4-phenyl)hexyl]-4-[N-(4-fluorophenyl)carbamoylmethyl]piperazine,

(66) 1-[(4-cyano-5-methyl-4-phenyl)hexyl]-4-[2-(4-fluorobenzenesulfonylamino)ethyl]piperazine,

(67) 1-[(4-cyano-5-methyl-4-phenyl)hexyl]-4-{2-[N-(4-fluorophenyl)sulfamoyl]ethyl}piperazine,

(68) 1-[(4-cyano-5-methyl-4-phenyl)hexyl]-4-{2-[N-(4-fluorophenyl)-N-methylsulfamoyl]ethyl}piperazine,

(69) 1-[(4-cyano-5-methyl-4-phenyl)hexyl]-4-[2-(N-methyl-4-fluorobenzenesulfonylamino)ethyl]piperazine,

(70) 1-[(4-cyano-5-methyl-4-phenyl)hexyl]-4-{2-[(4-fluorophenylthio)carbonyloxy]ethyl}piperazine,

(71) 1-[(4-cyano-5-methyl-4-phenyl)hexyl]-4-[2-(2-pyridyloxy)ethyl]piperazine,

(72) 1-(3-cyclohexyl-3-cyano-3-phenyl)propionyl-4-[2-(4-fluorophenoxy)ethyl]piperazine,

(73) 1-(2-hydroxy-4-cyano-5-methyl-4-phenyl)hexyl-4-[2-(4-fluorophenoxy)ethyl]piperazine,

(74) 1-[(4-cyano-5-methyl-4-phenyl)hexyl]-4-[2-(2-benzylphenoxy)ethyl]piperazine,

(75) 1-[(4-cyano-5-hydroxy-5-methyl-4-phenyl)hexyl]-4-[2-(4-fluorophenoxy)ethyl]piperazine,

(76) 1-[5-(4-cyano-5-methyl-4-phenyl)hexenyl]-4-[2-(4-fluorophenoxy)ethyl]piperazine,

(77) 1-[4-cyano-5-methyl-4-(4-hydroxyphenyl)hexyl]-4-[2-(4-fluorophenoxy)ethyl]piperazine,

(78) 1-[(4-cyano-5-methyl-4-phenyl)hexyl]-4-[2-(2-hydroxy-4-fluorophenoxy)ethyl]piperazine,

(79) 1-[(4-cyano-4-fluoro-4-phenyl)butyl]-4-[2-(4-fluorophenoxy)ethyl]piperazine,

(80) 1-[(4-Cyano-5-methyl-4-phenyl)hexyl]-4-[2-(2-ethoxycarbonylmethoxy-4-fluorophenoxy)ethyl]piperazine,

(81) 1-[(4-cyano-5-methyl-4-phenyl)hexyl]-4-[2-(2-hydroxyethoxy-4-fluorophenoxy)ethyl]piperazine,

(82) 1-[(4-cyano-5-methyl-4-phenyl)hexyl]-4-[2-(2-methoxy-4-fluorophenoxy)ethyl]piperazine,

(83) 1-[(4-cyano-5-methyl-4-phenyl)hexyl]-4-[2-(N-Isopropylanilino)ethyl]piperazine,

(84) 1-[(4-cyano-5-methyl-4-phenyl)hexyl]-4-[2-(N-cyclohexylanilino)ethyl]piperazine,

(85) 1-[(4-cyano-5-methyl-4-phenyl)hexyl]-4-{2-[N-methyl(4-Isopropylanilino)ethyl]}piperazine,

(86) 1-[(4-cyano-5-methyl-4-phenyl)hexyl]-4-{2-[N-methyl(3-Isopropylanilino)ethyl]}piperazine,

(87) 1-[(4-cyano-5-methyl-4-phenyl)hexyl]-4-{2-[N-methyl(2-Isopropylanilino)ethyl]}piperazine,

(88) 1-[(4-cyano-5-methyl-4-phenyl)hexyl]-4-{2-[3,4-(methylenedioxy)phenoxy]ethyl}piperazine,

(89) Synthesis of 1-[(4-cyano-5-methyl-4-phenyl)hexyl]-4-[2-(6-quinolyloxy)ethyl]piperazine,

(90) 1-[(4-cyano-5-methyl-4-phenyl)hexyl]-4-[2-(5-isoquinolyloxy)ethyl]piperazine,

(91) 1-[{2-(5-cyano-6-methyl-5-phenyl)heptyl}]-4-[2-(4-fluorophenoxy)ethyl]piperazine,

(92) 1-{[4-(7-cyano-8-methyl-7-phenyl)nonyl]}-4-[2-(4-fluorophenoxy)ethyl]piperazine,

(93) 1-[(4-cyano-5-methyl-4-phenyl)hexyl]-4-[2-(4-pyridyloxy)ethyl]piperazine,

(94) 1-[(4-cyano-5-methyl-4-phenyl)hexyl]-4-[2-(3-pyridyloxy)ethyl]piperazine,

(95) 1-[(4-cyano-5-methyl-4-phenyl)hexyl]-4-[2-(5-quinolyloxy)ethyl]piperazine,

(96) 1-[(4-cyano-5-methyl-4-phenyl)hexyl]-4-[2-(4-trifluoromethylphenoxy)ethyl]piperazine,

(97) 1-[(4-cyano-5-methyl-4-phenyl)hexyl]-4-[2-(1-naphthyloxy)ethyl]piperazine,

(98) 1-[(4-cyano-5-methyl-4-phenyl)hexyl]-4-[2-ethyl-2-(4-fluorophenoxy)ethyl]piperazine,

(99) 1-[(4-cyano-5-methyl-4-phenyl)hexyl]-4-[2-(4-quinazolinyloxy)ethyl]piperazine, (100) 1-[(4-cyano-5-methyl-4-phenyl)hexyl]-4-{2-[4-(3-pyridyl)phenoxy]ethyl}piperazine, (101) 1-[(4-cyano-5-methyl-4-phenyl)hexyl]-4-{2-[3-(3-pyridyl)phenoxy]ethyl}piperazine, (102) 1-[(4-cyano-5-methyl-4-phenyl)hexyl]-4-[2-(4-bromophenoxy)ethyl]piperazine, (103) 1-[(4-cyano-5-methyl-4-phenyl)hexyl]-4-[2-(3-bromophenoxy)ethyl]piperazine, (104) 1-[(4-cyano-5-methyl-4-phenyl)hexyl]-4-[2-(2-bromophenoxy)ethyl]piperazine, (105) 1-[(4-Cyano-5-methyl-4-phenyl)hexyl]-4-{2-[4-(imidazol-1-yl)phenoxy]ethyl}piperazine, (106) 1-[(4-cyano-5-methyl-4-phenyl)hexyl]-4-[2-(2-pyrimidinyloxy)ethyl]piperazine, (107) 1-[(4-cyano-5-methyl-4-phenyl)hexyl]-4-{2-[2-(3-pyridyl)phenoxy]ethyl}piperazine, (108) 1-[4-cyano-5-methyl-4-(2-cyano-5-thienyl)hexyl]-4-[2-(4-fluorophenoxy)ethyl]piperazine, (109) 1-[4-cyano-5-methyl-4-(2-cyano-5-thienyl)hexyl]-4-[2-(3-fluorophenoxy)ethyl]piperazine, (110) 1-[4-cyano-5-methyl-4-(2-thienyl)hexyl]-4-[2-(3-fluorophenoxy)ethyl]piperazine, (111) 1-[(4-cyano-5-methyl-4-phenyl)hexyl]-4-{2-[3-(3-thienyl)phenoxy]ethyl}piperazine, (112) 1-[(4-cyano-5-methyl-4-phenyl)hexyl]-4-{2-[2-(6-methyl-2-pyridyl)vinylphenoxy]ethyl}piperazine, (113) 1-[(4-cyano-5-methyl-4-phenyl)hexyl]-4-[2-(3-cyanophenoxy)ethyl]piperazine, (114) 1-[(4-cyano-5-methyl-4-phenyl)hexyl]-4-[2-(3-phenylphenoxy)ethyl]piperazine, (115) 1-[(4-cyano-5-methyl-4-phenyl)hexyl]-4-{2-[3-(2-cyanovinyl)phenoxy]ethyl}piperazine, (116) 1-[(4-cyano-5-methyl-4-phenyl)hexanoyl]-4-[2-(4-fluorophenoxy)ethyl]piperazine, and (117) 1-[(4-cyano-4-phenyl)butyl]-4-[2-(4-fluorophenoxy)ethyl]piperazine, or a pharmacologically acceptable salt thereof.

7. A pharmaceutical composition comprising:

the N,N-substituted cyclic amine compound as claimed in any of claims 1, 2 or 5 or a pharmacologically acceptable salt thereof; and a pharmaceutically acceptable carrier.

8. A method of treating and improving the diseases against which inhibitory action on P/Q type calcium channel is effective, comprising administering an effective amount of the N,N-substituted cyclic amine compound as claimed in any of claims 1, 2 or 5 or a pharmacologically acceptable salt thereof as the active ingredient to a patient in need thereof.

9. A method of treating and improving the diseases against which an inhibitory action on N type calcium channel is effective, comprising administering an effective amount of the N,N-substituted cyclic amine compound as claimed in any of claims 1, 2 or 5 or a pharmacologically acceptable salt thereof to a patient in need thereof.

10. A method for inhibiting the death of nerve cells or for protecting brain nerve cells, comprising administering an effective amount of the N,N-substituted cyclic amine compound as claimed in any of claims 1, 2 or 5 or a pharmacologically acceptable salt thereof to a patient in need thereof.

11. A method of treating or improving a nerve disease, comprising administering an effective amount of the N,N-substituted cyclic amine compound as claimed in any of claims 1, 2 or 5 or a pharmacologically acceptable salt thereof to a patient in need thereof.

12. The method as claimed in claim 11, wherein the nerve cell disease is one disease selected from the group consisting of acute ischemic stroke, cerebral apoplexy, cerebral infarction, head trauma, cerebral nerve cell death, Alzheimer disease, Parkinson disease, amyotrophic lateral sclerosis, Huntington disease, cerebral circulatory metabolism disturbance, cerebral function disturbance, pain, spasm, schizophrenia, migraine, epilepsy, maniac-depressive psychosis, nerve degenerative diseases, cerebral ischemia, AIDS dementia complications, edema, anxiety disorder (generalized anxiety disorder) and diabetic neuropathy.

13. A pharmaceutical composition comprising a pharmacologically effective amount of the N,N-substituted cyclic amine compound as claimed in any of claims 1, 2 or 5 or a pharmacologically acceptable salt thereof; a pharmacologically acceptable carrier; and at least one ingredient selected from the group consisting of a filler, a binder, a disintegrator, a lubricant, a coloring agent, and a taste and odor correctives.

14. A method of treating a disease against which calcium antagonism is effective, which comprises administering a pharmacologically effective amount of N,N-substituted cyclic amine compound as claimed in any of claims 1, 2 or 5 or a pharmacologically acceptable salt thereof to a patient in need thereof.

15. The compound according to claim 1, wherein said compound is one compound selected from the group consisting of 1-[(4-cyano-5-methyl-4-phenyl)hexyl]-4-[2-(4-fluorphenoxy)ethyl]piperazine, 1-[4-cyano-5-methyl-4-(4-methylphenyl)hexyl]-4-[2-(4-fluorophenoxy)ethyl]piperazine, 1-[4-cyano-5-methyl-4-(4-chlorophenyl)hexyl]-4-[2-(4-fluorophenoxy)ethyl]piperazine, 1-[4-cyano-5-methyl-4-(4-methoxyphenyl)hexyl]-4-[2-(4-fluorophenoxy)ethyl]piperazine, 1-{[4-cyano-5-methyl-4-(2-thienyl)hexyl]}-4-[2-(4-fluorophenoxy)ethyl]piperazine, 1-{[4-cyano-5-methyl-4-(2-fluorophenyl)hexyl]}-4-[2-(4-fluorophenoxy)ethyl]piperazine, 1-{[4-cyano-5-methyl-4-(3-fluorophenyl)hexyl]}-4-[2-(4-fluorophenoxy)ethyl]piperazine, 1-{[4-cyano-5-methyl-4-(4-fluorophenyl)hexyl]}-4-[2-(4-fluorophenoxy)ethyl]piperazine, 1-[(4-cyano-5-methyl-4-phenyl)hexyl]-4-[2-(4-chlorophenoxy)ethyl]piperazine, 1-[(4-cyano-5-methyl-4-phenyl)hexyl]-4-{2-[N-(4-fluorophenyl)-N-methylamino]ethyl}piperazine, 1-[(4-cyano-5-hydroxy-5-methyl-4-phenyl)hexyl]-4-[2-(4-fluorophenoxy)ethyl]piperazine, 1-[5-(4-cyano-5-methyl-4-phenyl)hexenyl]-4-[2-(4-fluorophenoxy)ethyl]piperazine, 1-[(4-cyano-4-fluoro-4-phenyl)butyl]-4-[2-(4-fluorophenoxy)ethyl]piperazine, 1-[(4-cyano-5-methyl-4-phenyl)hexyl]-4-{2-[N-methyl(3-Isopropylanilino)ethyl]}piperazine, 1-[(4-cyano-5-methyl-4-phenyl)hexyl]-4-{2-[3,4-(methylenedioxy)phenoxy]ethyl}piperazine, 1-{[4-(7-cyano-8-methyl-7-phenyl)nonyl]}-4-[2-(4-fluorophenoxy)ethyl]piperazine, 1-[(4-cyano-5-methyl-4-phenyl)hexyl]-4-[2-(5-quinolyloxy)ethyl]piperazine, 1-[(4-cyano-5-methyl-4-phenyl)hexyl]-4-[2-(2-bromophenoxy)ethyl]piperazine, 1-[(4-cyano-5-methyl-4-phenyl)hexyl]-4-{2-[2-(3-pyridyl)phenoxy]ethyl}piperazine, 1-[4-cyano-5-methyl-4-(2-cyano-5-thienyl)hexyl]-4-[2-(3-fluorophenoxy)ethyl]piperazine, 1-[(4-cyano-5-methyl-4-phenyl)hexanoyl]-4-[2-(4-fluorophenoxy)ethyl]piperazine.

16. The method of claim 8, wherein said pharmaceutical composition is administered at a dosage of 0.01 to 1000 mg per day.

* * * * *

UNITED STATES PATENT AND TRADEMARK OFFICE
CERTIFICATE OF CORRECTION

PATENT NO. : 6,737,425 B1
DATED : May 18, 2004
INVENTOR(S) : Yamamoto et al.

It is certified that error appears in the above-identified patent and that said Letters Patent is hereby corrected as shown below:

<u>Column 143,</u>
Lines 10-11, change "(58) 1-[(4-cyano-5-methyl-4-phenyl)hexyl]-4-[2-(N-benzyl-N-Isopropylamino)ethyl]piperazine," to
-- (58) 1-[(4-cyano-5-methyl-4-phenyl)hexyl]-4-[2-(N-benzyl-N-isopropylamino)ethyl]piperazine, --
Lines 59-61, change "(80) 1-[(4-Cyano-5-methyl-4-phenyl)hexyl]-4-[2-(-2-ethoxycarbonylmethoxy-4-fluorophenoxy)ethyl]piperazine," to
-- (80) 1-[(4-cyano-5-methyl-4-phenyl)hexyl]-4-[2-(2-ethoxycarbonylmethoxy-4-fluorophenoxy)ethyl]piperazine, --
Lines 66-67, change "(83) 1-[(4-cyano-5-methyl-4-phenyl)hexyl]-4-[2-(N-Isopropylanilino)ethyl]piperazine," to -- (83) 1-[(4-cyano-5-methyl-4-phenyl)hexyl]-4-[2-(N-isopropylanilino)ethyl]piperazine, --

<u>Column 146,</u>
Line 35, change "phenyl)hexyl]-4-{2-[N-methyl(3-Isopropylanilino)ethyl]}" to
-- phenyl)hexyl]-4-{2-[N-methyl(3-isopropylanilino)ethyl]} --

Signed and Sealed this

Twenty-sixth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,737,425 B1
DATED : May 18, 2004
INVENTOR(S) : Noboru Yamamoto et al.

Page 1 of 1

It is certified that error appears in the above-identified patent and that said Letters Patent is hereby corrected as shown below:

Column 144,
Lines 3-7, change "(85) 1-[(4-cyano-5-methyl-4-phenyl)hexyl]-4-{2-[N-methyl(4-Isopropylanilino)ethyl]}piperazine,
(86) 1-[(4-cyano-5-methyl-4-phenyl)hexyl]-4-{2-[N-methyl(3-Isopropylanilino)ethyl]}piperazine,
(87) 1-[(4-cyano-5-methyl-4-phenyl)hexyl]-4-{2-[N-methyl(2-Isopropylanilino)ethyl]}piperazine," to -- (85) 1-[(4-cyano-5-methyl-4-phenyl)hexyl]-4-{2-[N-methyl(4-isopropylanilino)ethyl]}piperazine,
(86) 1-[(4-cyano-5-methyl-4-phenyl)hexyl]-4-{2-[N-methyl(3-isopropylanilino)ethyl]}piperazine,
(87) 1-[(4-cyano-5-methyl-4-phenyl)hexyl]-4-{2-[N-methyl(2-isopropylanilino)ethyl]}piperazine, --.
Lines 12-13, change "(89) Synthesis of 1-[(4-cyano-5-methyl-4-phenyl)hexyl]-4-[2-(6-quinolyloxy)ethyl]piperazine," to -- (89) 1-[(4-cyano-5-methyl-4-phenyl)hexyl]-4-[2-(6-quinolyloxy)ethyl]piperazine, --.
Lines 46-47, change "(105) 1-[(4-Cyano-5-methyl-4-phenyl)hexyl]-4-{2-[4-(imidazol-1-yl)phenoxy]ethyl}piperazine," to -- (105) 1-[(4-cyano-5-methyl-4-phenyl)hexyl]-4-{2-[4-(imidazol-1-yl)phenoxy]ethyl}piperazine, --.

Signed and Sealed this

Twenty-third Day of May, 2006

JON W. DUDAS
*Director of the United States Patent and Trademark Office*